(12) United States Patent
Hindson et al.

(10) Patent No.: US 12,097,495 B2
(45) Date of Patent: Sep. 24, 2024

(54) METHODS AND COMPOSITIONS FOR DETECTING GENETIC MATERIAL

(71) Applicant: Bio-Rad Laboratories, Inc., Hercules, CA (US)

(72) Inventors: Benjamin J. Hindson, Livermore, CA (US); Serge Saxonov, Oakland, CA (US); Phillip Belgrader, Severna Park, MD (US); Kevin D. Ness, Pleasanton, CA (US); Michael Y. Lucero, San Francisco, CA (US); Billy W. Colston, Jr., San Ramon, CA (US); Shawn Paul Hodges, Newark, CA (US); Nicholas J. Heredia, Mountain House, CA (US); Jeffrey Clark Mellen, San Francisco, CA (US); Camille Bodley Troup, Livermore, CA (US); Paul Wyatt, Foster City, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 172 days.

(21) Appl. No.: 17/750,195

(22) Filed: May 20, 2022

(65) Prior Publication Data
US 2022/0362764 A1 Nov. 17, 2022

Related U.S. Application Data

(63) Continuation of application No. 17/486,667, filed on Sep. 27, 2021, which is a continuation of application (Continued)

(51) Int. Cl.
*B01L 3/00* (2006.01)
*B01F 23/41* (2022.01)
(Continued)

(52) U.S. Cl.
CPC .......... *B01L 3/50273* (2013.01); *B01F 23/41* (2022.01); *B01F 33/3011* (2022.01); (Continued)

(58) Field of Classification Search
CPC .......... B01F 23/41; B01F 25/14; B01F 25/23; B01F 33/3011; B01F 33/3021; (Continued)

(56) References Cited

U.S. PATENT DOCUMENTS

| 3,575,220 A | 4/1971 | Davis et al. |
| 4,051,025 A | 9/1977 | Ito |

(Continued)

FOREIGN PATENT DOCUMENTS

| CN | 2364458 Y | 2/2000 |
| DE | 102005037401 A1 | 2/2007 |

(Continued)

OTHER PUBLICATIONS

Schroeder, Groff M. et al., "Introduction to Flow Cytometry" version 5.1, 182 pgs. (2004).

(Continued)

*Primary Examiner* — Jennifer Wecker
(74) *Attorney, Agent, or Firm* — Withers Bergman LLP; Thomas C. Meyers

(57) ABSTRACT

The present disclosure provides methods and compositions for detecting polynucleotides in a sample and for quantifying polynucleotide load in a sample. The polynucleotides can be associated with a disease, disorder, or condition. In some applications, methylated DNA is quantified, e.g., in order to determine the load of polynucleotides in a sample. The present disclosure also provides methods and compositions for determining the load of fetal polynucleotides in a biological sample, e.g., the load of fetal polynucleotides (e.g., DNA, RNA) in maternal plasma. The present disclo- (Continued)

sure provides methods and compositions for detecting cellular processes such as cellular viability, growth rates, and infection rates. This disclosure also provides compositions and methods for detecting differences in copy number of a target polynucleotide. In some embodiments, the methods and compositions provided herein are useful for diagnosis of fetal genetic abnormalities, when the starting sample is maternal tissue (e.g., blood, plasma). The methods and materials described apply techniques for allowing detection of small, but statistically significant, differences in polynucleotide copy number.

18 Claims, 34 Drawing Sheets

Specification includes a Sequence Listing.

Related U.S. Application Data

No. 16/667,811, filed on Oct. 29, 2019, now Pat. No. 11,130,128, which is a continuation of application No. 15/707,908, filed on Sep. 18, 2017, now Pat. No. 10,512,910, which is a continuation of application No. 15/351,354, filed on Nov. 14, 2016, now Pat. No. 9,764,322, which is a continuation-in-part of application No. 13/400,030, filed on Feb. 17, 2012, now abandoned.

(60) Provisional application No. 61/490,040, filed on May 25, 2011, provisional application No. 61/488,667, filed on May 20, 2011, provisional application No. 61/478,777, filed on Apr. 25, 2011, provisional application No. 61/453,537, filed on Mar. 16, 2011, provisional application No. 61/449,580, filed on Mar. 4, 2011, provisional application No. 61/444,674, filed on Feb. 18, 2011.

(51) Int. Cl.
| | |
|---|---|
| *B01F 33/3011* | (2022.01) |
| *B01F 33/81* | (2022.01) |
| *B01L 9/00* | (2006.01) |
| *C12Q 1/686* | (2018.01) |
| *B01F 25/00* | (2022.01) |
| *B01F 25/23* | (2022.01) |
| *B01F 33/302* | (2022.01) |
| *G01N 35/08* | (2006.01) |

(52) U.S. Cl.
CPC ............ *B01F 33/813* (2022.01); *B01L 3/502* (2013.01); *B01L 3/502784* (2013.01); *B01L 3/52* (2013.01); *B01L 9/527* (2013.01); *C12Q 1/686* (2013.01); *B01F 25/14* (2022.01); *B01F 25/23* (2022.01); *B01F 33/3021* (2022.01); *B01L 3/502761* (2013.01); *B01L 2200/025* (2013.01); *B01L 2200/0636* (2013.01); *B01L 2200/0647* (2013.01); *B01L 2200/0673* (2013.01); *B01L 2200/14* (2013.01); *B01L 2200/16* (2013.01); *B01L 2300/0609* (2013.01); *B01L 2300/0681* (2013.01); *B01L 2300/0816* (2013.01); *B01L 2300/0829* (2013.01); *B01L 2300/0861* (2013.01); *B01L 2400/049* (2013.01); *G01N 35/08* (2013.01)

(58) Field of Classification Search
CPC ............ B01F 33/813; B01L 2200/025; B01L 2200/0636; B01L 2200/0647; B01L 2200/0673; B01L 2200/14; B01L 2200/16; B01L 2300/0609; B01L 2300/0681; B01L 2300/0816; B01L 2300/0829; B01L 2300/0861; B01L 2400/049; B01L 3/502; B01L 3/50273; B01L 3/502761; B01L 3/502784; B01L 3/52; B01L 9/527; G01N 35/08; C12Q 1/686; C12Q 1/6883; C12Q 2600/154

See application file for complete search history.

(56) References Cited

U.S. PATENT DOCUMENTS

| | | |
|---|---|---|
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,123,798 A | 9/2000 | Gandhi et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,176,962 B1 | 1/2001 | Soane et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |

(56) References Cited

U.S. PATENT DOCUMENTS

| | | |
|---|---|---|
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,915,679 B2 | 7/2005 | Chien et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,060,227 B2 | 6/2006 | Staats |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,160,687 B1 | 1/2007 | Kapur et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,351,376 B1 | 4/2008 | Quake et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 8,633,015 B2 | 1/2014 | Ness et al. |
| 9,328,376 B2 | 5/2016 | Hiddessen et al. |
| 9,417,190 B2 | 8/2016 | Hindson et al. |
| 9,500,664 B2 | 11/2016 | Ness et al. |
| 9,623,384 B2 | 4/2017 | Hindson et al. |
| 10,512,910 B2 | 12/2019 | Colston, Jr. et al. |
| 2001/0046701 A1 | 11/2001 | Schulte et al. |
| 2002/0003001 A1 | 1/2002 | Weigl et al. |
| 2002/0021866 A1 | 2/2002 | Everett et al. |
| 2002/0022261 A1 | 2/2002 | Anderson et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0089561 A1 | 7/2002 | Weitzel et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0168298 A1 | 11/2002 | Huhn et al. |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0006140 A1 | 1/2003 | Vacca et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0037739 A1 | 2/2004 | NcNeely et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0090168 A1 | 5/2004 | Kumar et al. |
| 2004/0109793 A1 | 6/2004 | McNeely et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2004/0228770 A1 | 11/2004 | Gandhi et al. |
| 2004/0261524 A1 | 12/2004 | Chesk |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0158739 A1* | 7/2005 | Jeddeloh ............... C12Q 1/683 |
| | | 435/6.12 |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0252773 A1 | 11/2005 | Mcbride et al. |
| 2005/0266582 A1 | 12/2005 | Modlin et al. |
| 2005/0277125 A1 | 12/2005 | Benn et al. |
| 2005/0282206 A1 | 12/2005 | Michael Corbett et al. |
| 2006/0014187 A1 | 1/2006 | Li et al. |
| 2006/0024831 A1 | 2/2006 | Kao et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2006/0234298 A1 | 10/2006 | Chiu et al. |
| 2006/0275893 A1 | 12/2006 | Ishii et al. |
| 2007/0003442 A1 | 1/2007 | Link et al. |
| 2007/0010974 A1 | 1/2007 | Nicoli et al. |
| 2007/0039866 A1 | 2/2007 | Schroeder et al. |
| 2007/0048756 A1 | 3/2007 | Mei et al. |
| 2007/0054199 A1 | 3/2007 | Wakabayashi |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0253868 A1 | 11/2007 | Beebe et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0056948 A1 | 3/2008 | Dale et al. |
| 2008/0070862 A1 | 3/2008 | Laster et al. |
| 2008/0090244 A1 | 4/2008 | Knapp et al. |
| 2008/0125727 A1 | 5/2008 | Seibold et al. |

(56) References Cited

U.S. PATENT DOCUMENTS

| | | |
|---|---|---|
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166720 A1 | 7/2008 | Hsieh et al. |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0223721 A1 | 9/2008 | Cohen et al. |
| 2008/0241841 A1 | 10/2008 | Murakawa et al. |
| 2008/0257438 A1 | 10/2008 | Wang et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0047713 A1 | 2/2009 | Handique |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0269248 A1 | 10/2009 | Falb et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0015606 A1 | 1/2010 | Davies et al. |
| 2010/0018584 A1 | 1/2010 | Bransky et al. |
| 2010/0020565 A1 | 1/2010 | Seward |
| 2010/0022414 A1 | 1/2010 | Link et al. |
| 2010/0022680 A1 | 1/2010 | Karnik et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0105049 A1* | 4/2010 | Ehrich ............... C12Q 1/6806 435/6.12 |
| 2010/0137152 A1 | 6/2010 | Gorfinkel et al. |
| 2010/0137163 A1 | 6/2010 | Link et al. |
| 2010/0173394 A1 | 7/2010 | Colston et al. |
| 2010/0184928 A1 | 7/2010 | Kumacheva |
| 2010/0217736 A1 | 8/2010 | Sarel |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0039724 A1* | 2/2011 | Lo ..................... C12Q 1/6827 435/6.12 |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0003755 A1 | 1/2012 | Chapin et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |
| 2017/0065979 A1 | 3/2017 | Ness et al. |
| 2017/0144116 A1 | 5/2017 | Ness et al. |
| 2017/0144160 A1 | 5/2017 | Ness et al. |
| 2017/0144161 A1 | 5/2017 | Hindson et al. |

FOREIGN PATENT DOCUMENTS

| | | |
|---|---|---|
| EP | 1522582 A2 | 4/2005 |
| EP | 1677094 A2 | 7/2006 |
| EP | 1522582 B1 | 4/2007 |
| GB | 1503163 A | 3/1978 |
| GB | 2097692 A | 11/1982 |
| JP | 295433 A | 4/1990 |
| JP | 08035971 A | 2/1996 |
| JP | 2002505439 A | 2/2002 |
| JP | 2006180810 A | 7/2006 |
| JP | 2007175002 A | 7/2007 |
| JP | 2009536313 A | 10/2009 |
| JP | 2009538123 A | 11/2009 |
| JP | 2010506136 A | 2/2010 |
| JP | 2011041925 A | 3/2011 |
| WO | 82/02562 A1 | 8/1982 |
| WO | 84/02000 A1 | 5/1984 |
| WO | 92/01812 A | 2/1992 |
| WO | 94/05414 A1 | 3/1994 |
| WO | 96/12194 A1 | 4/1996 |
| WO | 98/00231 A1 | 1/1998 |
| WO | 98/16313 A1 | 4/1998 |
| WO | 98/44151 A1 | 10/1998 |
| WO | 98/44152 A1 | 10/1998 |
| WO | 98/47003 A1 | 10/1998 |
| WO | 9944740 A1 | 9/1999 |
| WO | 0078455 A1 | 12/2000 |
| WO | 01/07159 A2 | 2/2001 |
| WO | 01/12327 A1 | 2/2001 |

(56) References Cited

FOREIGN PATENT DOCUMENTS

| | | |
|---|---|---|
| WO | 02/23163 A1 | 3/2002 |
| WO | 02/060584 A2 | 8/2002 |
| WO | 02063288 A1 | 8/2002 |
| WO | 02/068104 A1 | 9/2002 |
| WO | 02/081490 A2 | 10/2002 |
| WO | 02/081729 A2 | 10/2002 |
| WO | 03/016558 A1 | 2/2003 |
| WO | 03/042410 A1 | 5/2003 |
| WO | 03052428 A1 | 6/2003 |
| WO | 03/072258 A1 | 9/2003 |
| WO | 2004/040001 A1 | 5/2004 |
| WO | 2005/007812 A2 | 1/2005 |
| WO | 2005/010145 A2 | 2/2005 |
| WO | 2005/021151 A1 | 3/2005 |
| WO | 2005/023091 A2 | 3/2005 |
| WO | 2005/055807 A2 | 6/2005 |
| WO | 2005/073410 A2 | 8/2005 |
| WO | 2005/075683 A1 | 8/2005 |
| WO | 2006/023719 A2 | 3/2006 |
| WO | 2006/027757 A2 | 3/2006 |
| WO | 2006/038035 A2 | 4/2006 |
| WO | 2006/086777 A2 | 8/2006 |
| WO | 2006/095981 A1 | 9/2006 |
| WO | 2006128098 A2 | 11/2006 |
| WO | 2007081385 A2 | 7/2007 |
| WO | 2007/091228 A1 | 8/2007 |
| WO | 2007/091230 A1 | 8/2007 |
| WO | 2007/092473 A2 | 8/2007 |
| WO | 2007121489 A2 | 10/2007 |
| WO | 2007/133710 A2 | 11/2007 |
| WO | 2008/021123 A1 | 2/2008 |
| WO | 2008/024114 A1 | 2/2008 |
| WO | 2008/063227 A1 | 5/2008 |
| WO | 2008063227 A2 | 5/2008 |
| WO | 2008/070074 A2 | 6/2008 |
| WO | 2008/070862 A2 | 6/2008 |
| WO | 2008/109176 A2 | 9/2008 |
| WO | 2008/109878 A2 | 9/2008 |
| WO | 2008/112177 A2 | 9/2008 |
| WO | 2008109176 A3 | 9/2008 |
| WO | 2009/002920 A2 | 12/2008 |
| WO | 2008148200 A1 | 12/2008 |
| WO | 2009002920 A1 | 12/2008 |
| WO | 2009/015863 A1 | 2/2009 |
| WO | 2009/049889 A1 | 4/2009 |
| WO | 2009069034 A1 | 6/2009 |
| WO | 2009/085246 A1 | 7/2009 |
| WO | 2009152520 A2 | 12/2009 |
| WO | 2010/001419 A1 | 1/2010 |
| WO | 2010/018465 A2 | 2/2010 |
| WO | 2010036352 A1 | 4/2010 |
| WO | 2011/034621 A2 | 3/2011 |
| WO | 2011/079176 A2 | 6/2011 |

OTHER PUBLICATIONS

Swillens, Stéphane et al., "Instant evaluation of the absolute initial number of cDNA copies from a single real-time PCR curve," Nucleic Acids Research, vol. 32, No. 6, pp. 1-6, (2004).
Gullberg, Mats et al., "Cytokine detection by antibody-based proximity ligation," PNAS, vol. 101, No. 22, pp. 8420-8424, Jun. 1, 2004.
Zhang, Tianhao et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
Applied Biosystems, "Operator's Manual Tempo Nano LC Tempo NanaTano MDLC Systems", Jan. 1, 2005, 74 pages.
Chabert, Max et al., "Droplet fusion by alternating current (AC) field electrocoalescence in microchannels," Electrophoresis, vol. 26, pp. 3706-3715, (2005).
Musyanovych, Anna et al., "Miniemulsion Droplets as Single Molecule Nanoreactors for Polymerase Chain Reaction," Biomacromolecules, vol. 6, No. 4, pp. 1824-1828, (2005).

Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).
Wetmur, James G. et al., "Molecular haplotyping by linking emulsion PCR: analysis of paraoxonase 1 haplotypes and phenotypes," Nucleic Acids Research, vol. 33, No. 8, pp. 2615-2619, (2005).
Li, Paul C. H. et al., "Microfluidic Lab-on-a-Chip", (Book Chapter) Ewing's Analytical Instrumentation Handbook Third Edition, (2005), pp. 581-679.
Roach, L. Spencer et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Dorfman, Kevin D. et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
Margulies, Marcel et al., "Genome sequencing in microfabricated high-density picolitre reactors," Nature, vol. 437, 51 pgs., Sep. 15, 2005.
Garstecki, Piotr et al., "Formation of droplets and bubbles in a microfluidic T-junction—scaling and mechanism of break-up," Lab on a Chip, vol. 6, pp. 437-446, (2006).
Link, Darren R. et al., "Electric Control of Droplets in Microfluidic Devices," Angewandte Chemie Int. Ed., vol. 45, pp. 2556-2560, (2006).
Tan, Yung-Chieh et al., "Monodispersed microfluidic droplet generation by shear focusing microfluidic device", Sensors and Actuators B, vol. 114 (2006) pp. 350-356.
Thurecht, Kristofer J. et al., "Investigation of spontaneous microemulsion formation in supercritical carbon dioxide using high-pressure NMR," Journal of Supercritical Fluids, vol. 38, pp. 111-118, (2006).
Thurecht, Kristofer J. et al., "Kinetics of Enzymatic Ring-Opening Polymerization of $\epsilon$-Caprolactone in Supercritical Carbon Dioxide," Macromolecules, vol. 39, pp. 7967-7972, (2006).
Zhelev, Toshko et al., "Heat Integration in Micro-Fluidic Devices," 16th European Symposium on Computer Aided Process Engineering and 9th International Symposium on Process Systems Engineering, pp. 1863-1868 published by Elsevier B.V. (2006).
Fielden, Peter et al., "Micro-Droplet Technology for High Throughout Systems and Methods," 1 pg., Mar. 8, 2006.
Emerson, David et al., "Microfluidic Modelling Activities at C3M," Centre for Microfluidics & Microsystems Modelling, Daresbury Laboratory, pp. 1-26, May 15, 2006.
Leamon, John H. et al., "Overview: methods and applications for droplet compartmentalization of biology," Nature Methods, vol. 3, No. 7, pp. 541-543, Jul. 2006.
Williams, Richard et al., "Amplification of complex gene libraries by emulsion PCR," Nature Methods, vol. 3, No. 7, pp. 545-550, Jul. 2006.
Griffiths, Andrew D. et al., "Miniaturising the laboratory in emulsion droplets," Trends in Biotechnology, vol. 24, No. 9, pp. 395-402, Jul. 14, 2006.
"Mair, Dieudonne A. et al., ""Injection molded microfluidic chips featuring integrated interconnects""", Lab on a Chip, vol. 6, Jul. 31, 2006, pp. 1346-1354".
Fan, Jian-Bing et al., "Highly parallel genomic assays," Nature Reviews/Genetics, vol. 7, pp. 632-644, Aug. 2006.
Jarvius, Jonas et al., "Digital quantification using amplified single-molecule detection," Nature Methods, vol. 3, No. 9, 15 pgs, Sep. 2006.
Liu, Kan et al., "Droplet-based synthetic method using microflow focusing and droplet fusion," Microfluid Nanfluid, vol. 3, pp. 239-243, (2007), published online Sep. 22, 2006.
Glotsos, Dimitris et al., "Robust Estimation of Bioaffinity Assay Fluorescence Signals," IEEE Transactions on Information Technology in Biomedicine, vol. 10, No. 4, pp. 733-739, Oct. 2006.
Edgar, J. Scott et al., "Capillary Electrophoresis Separation in the Presence of an Immiscible Boundary for Droplet Analysis", Analytical Chemistry, vol. 78, No. 19, Oct. 1, 2006, pp. 6948-6954.
Chen, Delai L. et al., "Using Three-Phase Flow of Immiscible Liquids to Prevent Coalescence of Droplets in Microfluidic Chan-

(56) References Cited

OTHER PUBLICATIONS nels: Criteria to Identify the Third Liquid and Validation with Protein Crystallization," Langmuir, vol. 23, No. 4, pp. 2255-2260, (2007).
Diehl, Frank et al., "Digital quantification of mutant DNA in cancer patients," Current Opinion in Oncology, vol. 19, pp. 36-42, (2007).
Hori, Machiko et al., "Uniform amplification of multiple DNAs by emulsion PCR," Biochemical and Biophysical Research Communications, vol. 352, pp. 323-328, (2007).
Mohr, S. et al., "Numerical and experimental study of a droplet-based PCR chip," Microfluid Nanofluid, vol. 3, pp. 611-621, (2007).
Gustafsdottir, Sigrun M. et al., "In vitro analysis of DNA-protein interactions by proximity ligation," PNAS, vol. 104, No. 9, pp. 3067-3072, Feb. 27, 2007.
Diekema, Daniel J. et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Baroud, Charles N. et al., "Thermocapillary valve for droplet production and sorting," Physical Review E 75, 046302, pp. 046302-1-046302-5, Apr. 5, 2007.
Ge, Qinyu et al., "Emulsion PCR-based method to detect Y chromosome microdeletions," Analytical Biochemistry, vol. 367, pp. 173-178, May 10, 2007.
Zhang, Chunsun et al., "Miniaturized PCR chips for nucleic acid amplification and analysis: latest advances and future trends," Nucleic Acids Research, vol. 35, No. 13, pp. 4223-4237, Jun. 18, 2007.
Lo, Y. M. Dennis et al., "Digital PCR for the molecular detection of fetal chromosomal aneuploidy," PNAS, vol. 104, No. 32, pp. 13116-13121, Aug. 7, 2007.
Jin, Dayong et al., "Practical Time-Gated Luminescence Flow Cytometry. II: Experimental Evaluation Using UV LED Excitation," Cytometry Part A • 71A, pp. 797-808, Aug. 24, 2007.
Hobbs, Helen R. et al., "Homogeneous Biocatalysis in both Fluorous Biphasic and Supercritical Carbon Dioxide Systems," Angewandte Chemie, vol. 119, pp. 8006-8009, Sep. 6, 2007.
Blow, Nathan, "PCR's next frontier," Nature Methods, vol. 4, No. 10, pp. 869-875, Oct. 2007.
Pamme, Nicole, "continuous flow separations in microfluidic devices," Lab on a Chip, vol. 7, pp. 1644-1659, Nov. 2, 2007.
Becker, Holger et al., "Polymer microfabrication technologies for microfluidic systems", Analytical and Bioanalytical Chemistry, vol. 390, Nov. 8, 2007, pp. 89-111.
Beer, N. Reginald et al., "On-Chip, Real-Time, Single-Copy Polymerase Chain Reaction in Picoliter Droplets," Analytical Chemistry, vol. 79, No. 22, pp. 8471-8475, Nov. 15, 2007.
Zhao, Yuejun et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
Sigma-Aldrich, "Synthesis of Mesoporous Materials," Material Matters, 3.1, 17, (2008).
Nisisako, Takasi et al., "Microfluidic large-scale integration on a chip for mass production of monodisperse droplets and particles", Lab on a Chip, vol. 8, (2008), pp. 287-293.
Carroll, Nick J. et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Bécamel, Philippe, Authorized Officer, The International Bureau of WIPO, "International Preliminary Report on Patentability" in connection with related International App. No. PCT/US2011/030101, dated Sep. 25, 2012, 7 pgs.
Merriam-Webster Dictionary definition of "Gasket", included as an exhibit in IPR2018-00300 Petition filed Dec. 14, 2017, 1 page.
Bernoulli Pressure Lowering, http:\hyperphysics, pp. 1-4, included as an exhibit in IPR2018-00300, IPR2018-00301 and IPR2018-00302 Petitions filed Dec. 14, 2017 and IPR2018-00432, IPR2018-00433 and IPR2018-00434 Petitions filed Jan. 9, 2018, 4 pgs.
Falb, Peter W. et al., U.S. Appl. No. 61/047,377, filed Apr. 23, 2008, included as an exhibit in IPR2018-00300, IPR2018-00301 and IPR2018-00302 Petitions filed Dec. 14, 2017 and IPR2018-00432, IPR2018-00433 and IPR2018-00434 Petitions filed Jan. 9, 2018, 75 pgs.
Kumacheva, Eugenia, U.S. Appl. No. 60/924,921, filed Jun. 5, 2007, included as an exhibit in IPR2018-00300, IPR2018-00301 and IPR2018-00302 Petitions filed Dec. 14, 2017 and IPR2018-00432, IPR2018-00433 and IPR2018-00434 Petitions filed Jan. 9, 2018, 46 pgs.
www.smithbearing.com, Fractional, Letter & No. Drill Sizes, included as an exhibit in IPR2018-00301 Petition filed Dec. 14, 2017 and IPR2018-00433 Petition filed Jan. 9, 2018, 1 page.
European Patent Office, "Extended European Search Report" in connection with related European Patent Application No. 09816582.2, dated Feb. 27, 2018, 12 pgs.
Lin, H.-H et al., "On-Demand Double Emulsification Utilizing Pneumatically Actuated Multilayer PDMS Microstructures", 2009 International Solid-State Sensors, Actuators and Microsystems Conference, Denver, CO, USA, Jun. 21-25, 2009, IEEE, pp. 809-812.
Lin, Hsuan-Han et al., "On-demand double emulsification utlizing pneumatically actuated, selectively surface modified PDMS microdevices", Microfluid Nanofluid, vol. 9, No. 6, May 21, 2010, pp. 1091-1102.
Wu, Min-Hsien et al., "Development of microfluidic alginate microbead generator tunable by pulsed airflow injection or the microencapsulation of cells", Microfluid nanofluid, vol. 8, No. 6, Oct. 15, 2009, pp. 823-835.
Clausell-Tormos, Jenifer et al., "Droplet-Based Microfluidic Platforms for the Encapsulation and Screening of Mammalian Cells and Multicellular Organisms," Chemistry & Biology, vol. 15, pp. 427-437, May 2008.
Teh, Shia-Yen et al., "Droplet microfluidics," Lab on a Chip, vol. 8, pp. 198-220, Jan. 11, 2008.
Chloroform (Phenomenex), Solvent Miscibility Table, Internet Archive WayBackMachine, 3 pgs., Feb. 1, 2008.
Beer, N. Reginald et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Mehta, Somil C. et a., "Mechanism of Stabilization of Silicone Oil—Water Emulsions Using Hybrid Siloxane Polymers," Langmuir, vol. 24, No. 9, pp. 4558-4563, Mar. 26, 2008.
Shah, Rhutesh K. et al., "Polymers fit for function Making emulsions drop by drop," Materials Today, vol. 11, No. 4, pp. 18-27, Apr. 2008.
Abdelgawad, Mohamed et al., "All-terrain droplet actuation," Lab on a Chip, vol. 8, pp. 672-677, Apr. 2, 2008.
Hung, Lung-Hsin et al., "Rapid microfabrication of solvent-resistant biocompatible microfluidic devices," Lab on a Chip, vol. 8, pp. 983-987, Apr. 8, 2008.
Kumaresan, Palani et al., "High-Throughput Single Copy DNA Amplification and Cell Analysis in Engineered Nanoliter Droplets," Analytical Chemistry, 17 pgs., Apr. 15, 2008.
Luk, Vivienne N. et al., "Pluronic Additives: A Solution to Sticky Problems in Digital Microfluidics," Langmuir, vol. 24, No. 12, pp. 6382-6289, May 16, 2008.
Lin, Yen-Heng et al., "Droplet Formation Utilizing Controllable Moving-Wall Structures for Double-Emulsion Applications," Journal of Microelectromechanical Systems, vol. 17, No. 3, pp. 573-581, Jun. 2008.
Dube, Simant et al., "Mathematical Analysis of Copy Number Variation in a DNA Sample Using Digital PCR on a Nanofluidic Device," PloS One, vol. 3, Issue 8, pp. 1-9, Aug. 6, 2008.
Qin, Jian et al., "Studying copy number variations using a nanofluidic platform," Nucleic Acids Research, vol. 36, No. 18, pp. 1-8, Aug. 18, 2008.
Holtze, C. et al., "Biocompatible surfactants for water-in-fluorocarbon emulsions," Lab on a Chip, vol. 8, pp. 1632-1639, Sep. 2, 2008.
Shendure, Jay et al., "Next-generation DNA sequencing," Nature Biotechnology, vol. 26, No. 10, pp. 1135-1145, Oct. 2008.

(56) References Cited

OTHER PUBLICATIONS

Zimmermann, Bernhard G. et al., "Digital PCR: a powerful new tool for noninvasive prenatal diagnosis?," Prenatal Diagnosis, vol. 28 pp. 1087-1093, Nov. 10, 2008.
Kiss, Margaret Macris et al., "High-Throughput Quantitative Polymerase Chain Reaction in Picoliter Droplets," Analytical Chemistry, 8 pgs., downloaded Nov. 17, 2008.
Bransky, Avishay et al., "A microfluidic droplet generator based on a piezoelectric actuator," Lab on a Chip, vol. 9, pp. 516-520, Nov. 20, 2008.
Weitz, David A., "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Beer, Neil Reginald et al., "Monodisperse droplet generation and rapid trapping for single molecule detection and reaction kinetics measurement," Lab on a Chip, vol. 9, pp. 841-844, Dec. 5, 2008.
Abate, Adam R. et al., "Functionalized glass coating for PDMS microfluidic devices," Lab on a Chip Technology: Fabrication and Microfluidics, 11 pgs., (2009).
Cawthon, Richard M., "Telomere length measurement by a novel monochrome multiplex quantitative PCR method," Nucleic Acids Research, vol. 37, No. 3, pp. 1-7, (2009).
Chen, Chia-Hung et al., "Janus Particles Templated from Double Emulsion Droplets Generated Using Microfluidics," Langmuir, vol. 29, No. 8, pp. 4320-4323, Mar. 18, 2009.
Fidalgo, Luis M. et al., "Coupling Microdroplet Microreactors with Mass Spectrometry: Reading the Contents of Single Droplets Online," Angewandte Chemie, vol. 48, pp. 3665-3668, Apr. 7, 2009.
Garstecki, Piotr et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Mazutis, Linas et al., "A fast and efficient microfluidic system for highly selective one-to-one droplet fusion," Lab on a Chip, vol. 9, pp. 2665-2672, Jun. 12, 2009.
Mazutis, Linas et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Mccaughan, Frank et al., "Single-molecule genomics," Journal of Pathology, vol. 220, pp. 297-306, Nov. 19, 2009.
Young, Lee W., Authorized officer, International Searching Authority, International Search Report, PCT Application Serial No. PCT/US2009/05317; mailing date: Nov. 20, 2009.
Young, Lee W., Authorized officer, International Searching Authority, Written Opinion of the International Searching Authority, PCT Application Serial No. PCT/US2009/05317; mailing date: Nov. 20, 2009.
Eksigent, "Product Note Eksigent: NanoFlow Metering System", Jan. 1, 2010, 4 pages.
Weaver, Suzanne et al., "Taking qPCR to a higher level: Analysis of CNV reveals the power of high throughput qPCR to enhance quantitative resolution," Methods, vol. 50, pp. 271-276, Jan. 15, 2010.
Markey, Amelia L. et al., "High-throughput droplet PCR," Methods, vol. 50, pp. 277-281, Feb. 2, 2010.
Nam, Yoon Sung et al., "Nanosized Emulsions Stabilized by Semi-solid Polymer Interphase," Langmuir, ACS Publications, Jul. 23, 2010.
Schütze, Tatjana et al., "A streamlined protocol for emulsion polymerase chain reaction and subsequent purification," Analytical Biochemistry, vol. 410, pp. 155-157, Nov. 25, 2010.
Bhat, Somanath et al., "Effect of sustained elevated temperature prior to amplification on template copy number estimation using digital polymerase chain reaction," Analyst, vol. 136, pp. 724-732, (2011).
Wetmur, James G., et al., "Linking Emulsion PCR Haplotype Analysis," PCR Protocols, Methods in Molecular Biology, vol. 687, pp. 165-175, (2011).
Zhong, Qun et al., "Multiplex digital PCR: breaking the one target per color barrier of quantitative PCR," Lab on a Chip, vol. 11, pp. 2167-2174, (2011).
Thinxxs Microtechnology AG, "Emerald Biosystems: Protein Crystallization," 1 pg., downloaded Mar. 8, 2011.
Giffo-Schmitt, Beate, Authorized Officer, The International Bureau of WIPO, "International Preliminary Report on Patentability" in connection with related International Application No. PCT/US2009/005317, dated Mar. 29, 2011, 8 pgs.
Huang, Jiaqi et al., "Rapid Screening of Complex DNA Samples by Single-Molecule Amplification and Sequencing," PLoS One, vol. 6, Issue 5, pp. 1-4, May 2011.
Vulto, Paul et al., "Phaseguides: a paradigm shift in microfluidic priming and emptying," Lab on a Chip, vol. 11, No. 9, pp. 1561-1700, May 7, 2011.
Young, Lee W., Authorized Officer, International Searching Authority, Commissioner of Patents, "International Search Report" in connection with related International App. No. PCT/US2011/030101, dated Jun. 1, 2011, 2 pgs.
Young, Lee W., Authorized Officer, International Searching Authority, Commissioner of Patents, "International Search Report" in connection with related International App. No. PCT/US2011/030101, dated Jun. 1, 2011, 9 pgs.
Kekevi, Burcu et al., Synthesis and Characterization of Silicone-Based Surfactants as Anti-Foaming Agents, J. Surfact Deterg (2012), vol. 15, pp. 73-81, published online Jul. 7, 2011.
Pinheiro, Leonardo B. et al., "Evaluation of a Droplet Digital Polymerase Chain Reaction Format for DNA Copy Number Quantification," Analytical Chemistry, vol. 84, pp. 1003-1011, Nov. 28, 2011.
Solimini, Nicole L. et al., "Recurrent Hemizygous Deletions in Cancers May Optimize Proliferative Potential," Science, vol. 337, pp. 104-109, Jul. 6, 2012.
Labsmith, "CapTite™ Microfluidic Interconnects" webpage, downloaded Jul. 11, 2012.
Labsmith, "Microfluid Components" webpage, downloaded Jul. 11, 2012.
Tanner, Nathan A. et al., "Simultaneous multiple target detection in real-time loop-mediated isothermal amplification," BioTechniques, vol. 53, pp. 8-19, Aug. 2012.
Scherer, A., California Institute of Technology, "Polymerase Chain Reactors" PowerPoint presentation, 24 pgs., date unknown.
Eschenback Optik GMBH, Optics for Concentrated Photovoltaics (CPV), 1 pg., date unknown.
Smid-Korbar, J. et al., "Efficiency and usability of silicone surfactants in emulsions," International Journal of Cosmetic Science 12, pp. 135-139, (1990), presented at the 15th IFSCC International Congress, Sep. 26-29, 1988, London.
Chittofrati, A. et al., "Perfluoropolyether microemulsions," Progress in Colloid & Polymer Science 79, pp. 218-225, (1989).
Snow, Steven A. "Synthesis and Characterization of Zwitterionic Silicone Sulfobetaine Surfactants," Langmuir, vol. 6, No. 2, American Chemical Society, pp. 385-391, (1990).
Polydimethylsiloxane, 5 pgs., published in FNP 52 (1992).
Newman, D.A. et al., "Phase Behavior of Fluoroether-Functional Amphiphiles in Supercritical Carbon Dioxide," The Journal of Supercritical Fluids, vol. 6, No. 4, pp. 205-210, (1993).
Higuchi, Russell et al., "Kinetic PCR Analysis: Real-time Monitoring of DNA Amplification Reactions," Bio/Technology vol. II, pp. 1026-1030, Sep. 11, 1993.
Gasperlin, M. et al., "The structure elucidation of semisolid w/o emulsion systems containing silicone surfactant," International Journal of Pharmaceutics 107, pp. 51-56, (1994).
Sela, Y. et al., "Newly designed polysiloxane-graft-poly (oxyethylene) copolymeric surfactants: preparation, surface activity and emulsification properties," Colloid & Polymer Science 272, pp. 684-691, (1994).
Piatyszek, Mieczyslaw A. et al., "Detection of telomerase activity in human cells and tumors by a telomeric repeat amplification protocol (TRAP)," Methods in Cell Science 17, pp. 1-15, (1995).
Shuber, Anthony P. et al., "A Simplified Procedure for Developing Multiplex PCRs," Genome Research, published by Cold Spring Harbor Laboratory Press, pp. 488-493, (1995).

(56) References Cited

OTHER PUBLICATIONS

Yazdi, A. V. et al., "Highly Carbon Dioxide Soluble Surfactants, Dispersants and Chelating Agents," Fluid Phase Equilibria, vol. 117, pp. 297-303, (1996).
Avilion, Ariel A. et al., "Human Telomerase RNA and Telomerase Activity in Immortal Cell Lines and Tumor Tissues," Cancer Research 56, pp. 645-650, Feb. 1, 1996.
Brody, James P. et al., "Biotechnology at Low Reynolds Numbers", Biophysical Journal. vol. 71, Dec. 1996, pp. 3430-3441.
Kalinina, Olga et al., "Nanoliter scale PCR with TaqMan Detection," Nucleic Acids Research, vol. 25, No. 10 pp. 1999-2004, (1997).
Nie, Shuming et al., "Optical Detection of Single Molecules," Annu. Rev. Biophys. BiomoL Struct. vol. 26, pp. 567-596, (1997).
Singley, Edith J. et al., "Phase behavior and emulsion formation of novel fluoroether amphiphiles in carbon dioxide," Fluid Phase Equilibria 128, pp. 199-219, (1997).
Guo, Zhen et al., "Enhanced discrimination of single nucleotide polymorphisms by artificial mismatch hybridization," Nature Biotechnology vol. 15, pp. 331-335, Apr. 1997.
Ghenciu, E. G. et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.
Alexandridis, Paschalis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.
Duffy, David C. et al., Rapid Prototyping of Microfluidic Systems in Poly(dimethylsiloxane), Analytical Chemistry, vol. 70, No. 23, Dec. 1, 1998, pp. 4974-4984.
Da Rocha, Sandro R. P. et al., "Effect of Surfactants on the Interfacial Tension and Emulsion Formation between Water and Carbon Dioxide," Langmuir, vol. 15, No. 2, pp. 419-428, (1999), published on web Dec. 29, 1998.
De Mello, Andrew J. et al., "Chip technology for micro-separation", BioMethods, vol. 10, (1999), pp. 129-177.
Vogelstein, Bert et al., "Digital PCR," Proc. Natl. Acad. Sci. USA, vol. 96, pp. 9236-9241, Aug. 1999.
O'Lenick, Anthony J., Jr., "Silicone Emulsions and Surfactants—A Review," Silicone Spectator, Silitech LLC, May 2009 (original published May 2000).
O'Lenick, Anthony J. Jr., "Silicone Emulsions and Surfactants," Journal of Surfactants and Detergents, vol. 3, No. 3, Jul. 2000.
Garti, N. et al., "Water Solubilization in Nonionic Microemulsions Stabilized by Grafted Siliconic Emulsifiers," Journal of Colloid and Interface Science vol. 233, pp. 286-294, (2001).
Katsura, Shinji et al., "Indirect micromanipulation of single molecules in water-in-oil emulsion," Electrophoresis, vol. 22, pp. 289-293, (2001).
Kunieda, Hironobu et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).
Schneegaß, Ivonne et al., "Miniaturized flow-through PCR with different template types in a silicon chip thermocycler," Lab on a Chip, vol. 1, pp. 42-49, (2001).
Nagai, Hidenori et al., "Development of A Microchamber Array for Picoliter PCR," Analytical Chemistry, vol. 73, No. 5, pp. 1043-1047, Mar. 1, 2001.
Price, Christopher B., "Regular Review Point of Care Testing," BMJ, vol. 322, May 26, 2001.
Whitesides, George M. et al., "Flexible Methods for Microfluidics", Physics Today, Jun. 2001, pp. 42-48.
Chien, Ring-Ling et al., "Multiport flow-control system for lab-on-a-chip microfluidic devices", Fresenius Journal of Analytical Chemistry, vol. 371, Jul. 27, 2001, pp. 106-111.
3M Specialty Materials, "3M Fluorinert Electronic Liquid FC-3283," product information guide, issued Aug. 2001.
Galambos, Paul et al., "Precision Alignment Packaging for Microsystems with Multiple Fluid Connections", Proceedings of 2001 ASME: International Mechanical Engineering Conference and Exposition, Nov. 11-16, 2001 New York, NY, 8 pgs.
Cawthon, Richard M., "Telomere measurement by quantitative PCR," Nucleic Acids Research, vol. 30, No. 10, pp. 1-6, (2002).
Hill, Randla M., "Silicone surfactants—new developments," Current Opinion in Colloid & Interface Science 7, pp. 255-261, (2002).
Wang, Anfeng et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).
Kawai, A. et al., "Mass-Production System of Nearly Monodisperse Diameter Gel Particles Using Droplets Formation in a Microchannel", Micro Total Analysis Systems, vol. 1, 2002, pp. 368-370.
Dasgupta, Purnendu K. et al., "Light emitting diode-based detectors Absorbance, fluorescence and spectroelectrochemical measurements in a planar flow-through cell," Analytica Chimica Acta 500, pp. 337-364, (2003).
Landegren, Ulf et al., "Padlock and proximity probes for in situ and array-based analyses: tools for the post-genomic era," Comp. Funct. Genom, vol. 4, pp. 525-530, (2003).
Rutledge, R. G. et al., "Mathematics of quantitative kinetic PCR and the application of standard curves," Nucleic Acids Research, vol. 31, No. 16, pp. 1-6, (2003).
Anna, Shelley L. et al., "Formation of dispersions using "flow focusing" in microchannels," Applied Physics Letters, vol. 82, No. 3, Jan. 20, 2003.
Goldschmidt GMBH, "Abil® EM 90 Emulsifier for the formulation of cosmetic W/O creams and lotions," degussa. creating essentials brochure, pp. 1-7, May 2003.
Ding, Chunming et al., "Direct molecular haplotyping of long-range genomic DNA with M1-PCR," PNAS, vol. 100, No. 13, pp. 7449-7453, Jun. 24, 2003.
Dressman, Devin et al., "Transforming single DNA molecules into fluorescent magnetic particles for detection and enumeration of genetic variations," PNAS, vol. 100, No. 15, Jul. 22, 2003.
Pohl, Gudrun et al., "Principle and applications of digital PCR" review, www.future-drugs.com, Expert Rev. Mol. Diagn. 4(1), pp. 41-47, (2004).
Rutledge, R. G., "Sigmoidal curve-fitting redefines quantitative real-time PCR with the prospective of developing automated high-throughput applications," Nucleic Acids Research. vol. 32, No. 22, pp. 1-8, (2004).

* cited by examiner

Figure 19
Maximum Extension in Droplet Generation
Sample: Master Mix/ NTC
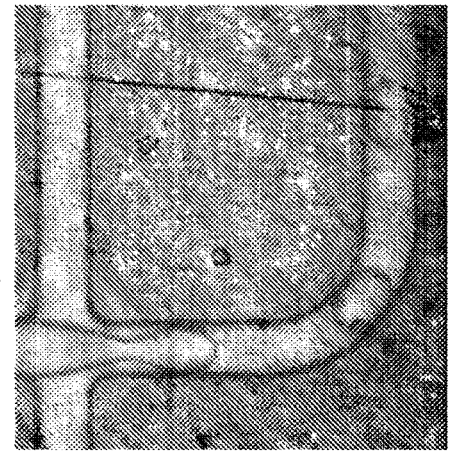
Oil/Sample Ratio = 2.2
1 psi nom
Oil/Sample Ratio = 1.4
1 psi

Figure 21

| sample # | 1 | 2 | 3 | 4 | 5 | 6 | 7 | 8 | Sample Type | Conc (ng/ul) |
|---|---|---|---|---|---|---|---|---|---|---|
| nom psi | 0.5 | 1 | 1.5 | 2 | 2.5 | 3 | 3.5 | 4 | | |
| 1 | J | J | J | J | J | J | J | J | Raji undig | 75 |
| 2 | N | N | E | E | J | J | J | J | Raji undig | 37.5 |
| 3 | E | E | E | J | J | J | J | J | Raji undig | 18.75 |
| 4 | N | N | N | N | N | N | N | N | Raji undig | 3.75 |
| 5 | E | E | E | J | J | J | J | J | Raji undig | 0 |
| 6 | J | J | J | J | J | J | J | J | 19205 undig | 75 |
| 7 | J | E | E | J | J | J | J | J | 19205 undig | 37.5 |
| 8 | E | E | N | N | N | N | E | air | 19205 undig | 18.75 |
| 9 | N | N | E | J | J | J | J | E | 19205 undig | 3.75 |
| 10 | E | E | E | E | E | J | E | J | 19205 undig | 0 |
| 11 | N | N | N | N | N | N | N | N | Raji digested | 75 |
| 12 | N | N | N | N | N | N | N | N | Raji digested | 37.5 |
| 13 | N | N | N | N | N | N | N | N | Raji digested | 18.75 |
| 14 | E | E | E | E | E | J | J | J | Raji digested | 3.75 |
| 15 | N | N | N | N | N | N | N | N | Raji digested | 0 |
| 16 | N | E | N | E | E | J | N | N | 19205 digested | 75 |
| 17 | N | N | N | N | N | N | N | N | 19205 digested | 37.5 |
| 18 | N | N | N | N | N | N | N | N | 19205 digested | 18.75 |
| 19 | N | N | N | N | N | N | N | N | 19205 digested | 3.75 |
| 20 | N | N | N | N | N | N | N | N | 19205 digested | 0 |

N = Normal    E = Extension    J = Jetting

Figure 22

Allele frequencies and the relative risks Type 2 Diabetes, Crohn's Disease, and Rheumatoid Arthritis.

| Disease | dbSNP rs iID | Relative risk[1] for RR | Relative risk[1] for RN | Frequency[2] of RR | Frequency[2] of RN |
|---|---|---|---|---|---|
| Type 2 Diabetes | rs10012946[3] | 1.1464 | 1.0239 | 0.5000 | 0.4667 |
| | rs10811661[4] | 1.3008 | 1.1282 | 0.6667 | 0.2500 |
| | rs1801282[4] | 1.4128 | 1.2417 | 0.8667 | 0.1167 |
| | rs4402960[4] | 1.1602 | 1.1233 | 0.1167 | 0.3500 |
| | rs4506565[5] | 1.6133 | 1.2738 | 0.0847 | 0.3729 |
| | rs5215[4] | 1.1681 | 1.0935 | 0.1000 | 0.6167 |
| | rs8050136[6] | 1.3609 | 1.1176 | 0.1167 | 0.6667 |
| | rs9494266[7] | 1.4909 | 1.2296 | 0.0169 | 0.0847 |
| Crohn's Disease | rs1000113[5] | 1.9102 | 1.5354 | 0.0000 | 0.0667 |
| | rs10210302[5] | 1.8433 | 1.1890 | 0.3000 | 0.5000 |
| | rs10761659[5] | 1.5461 | 1.2287 | 0.2333 | 0.6333 |
| | rs10883365[5] | 1.6154 | 1.1989 | 0.3000 | 0.4000 |
| | rs11805303[5] | 1.8525 | 1.3875 | 0.1000 | 0.3833 |
| | rs17221417[5] | 1.9118 | 1.2883 | 0.1000 | 0.5167 |
| | rs17234657[5] | 2.3053 | 1.5360 | 0.0667 | 0.2000 |
| | rs2542151[5] | 1.9997 | 1.2980 | 0.0500 | 0.2833 |
| | rs9858542[5] | 1.8316 | 1.0895 | 0.0333 | 0.4167 |
| Rheumatoid Arthritis | rs10118357[8] | 1.7278 | 1.3152 | 0.2712 | 0.5254 |
| | rs13207033[8] | 1.7559 | 1.3258 | 0.6667 | 0.3167 |
| | rs6457617[5] | 5.0847 | 2.3414 | 0.2167 | 0.5667 |
| | rs6679677[9] | 3.1672 | 1.6847 | 0.0000 | 0.2833 |
| | rs6920220[5] | 1.7023 | 1.1965 | 0.0000 | 0.3500 |

[1]The relative risks provided here were calculated using the GCI methodology, as described herein.
[2]The allele frequencies are taken from the HapMap project's CEU population.
[3]Sandhu et al., Nat Genet. 39: 951-3 (2007).
[4]Scott et al., Science. 316: 1341-5 (2007).
[5]Wellcome Trust Case Control Consortium, Nature. 447: 661-78 (2007).
[6]Zeggini et al., Science. 316: 1336-41 (2007).
[7]Salonen et al., Am J Hum Genet. 81: 338-45 (2007).
[8]Remmers et al., N Engl J Med. 357: 977-86 (2007).
[9]Kyogoku et al., Am J Hum Genet. 75: 504-7 (2004).

Figure 24
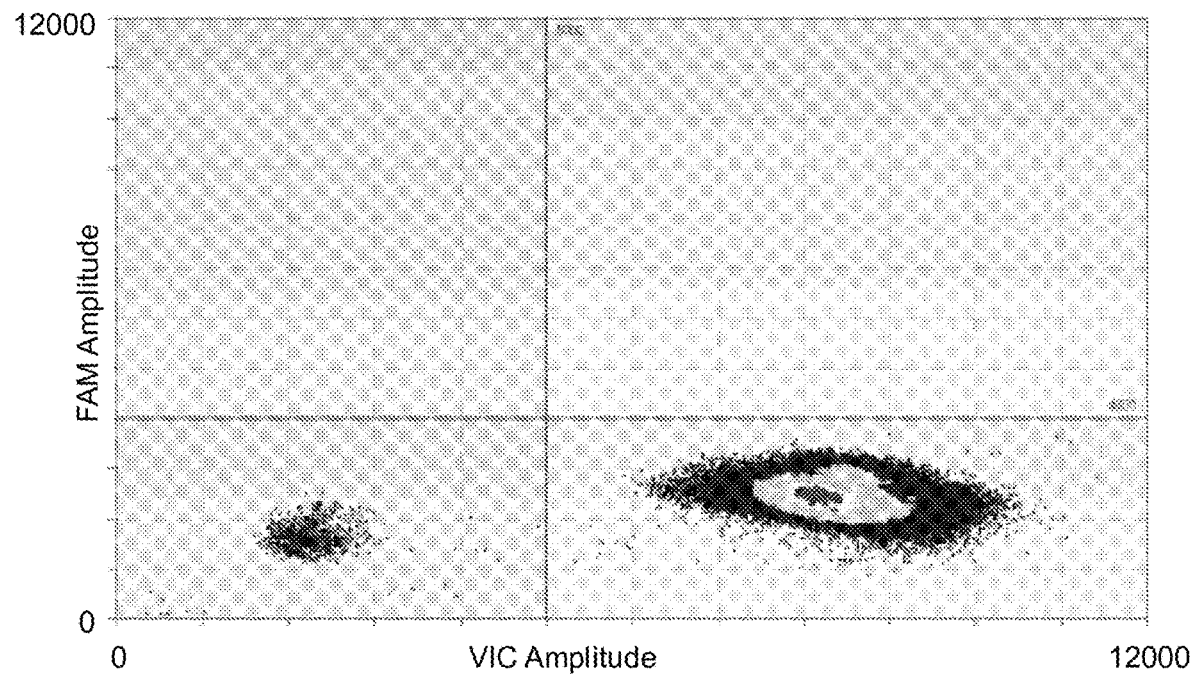
A   0% Mutant (Wild-type Only) - Undigested
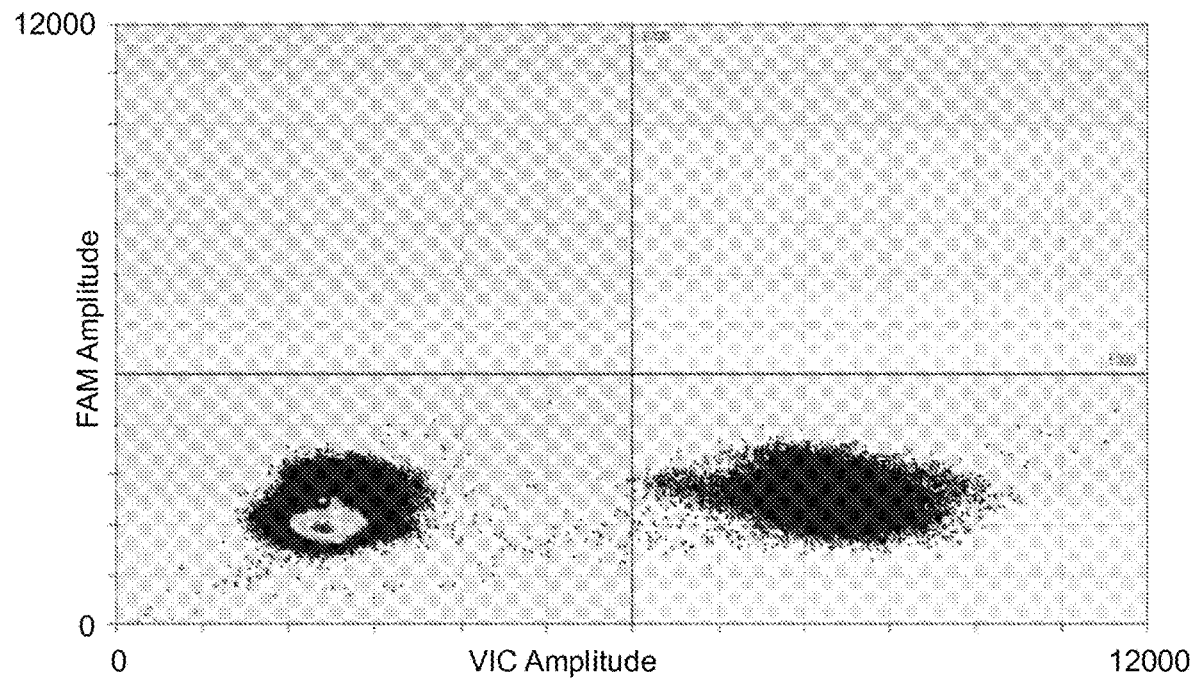
B   0% Mutant (Wild-type Only) - WT BRAF Digested

Figure 26
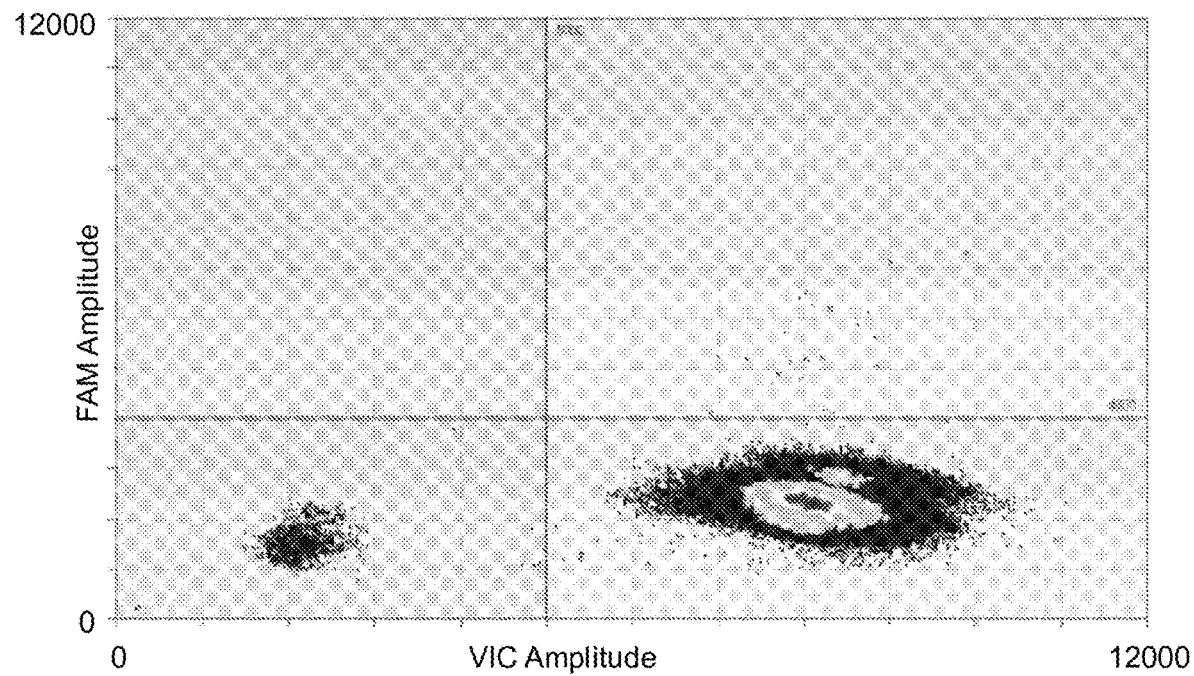
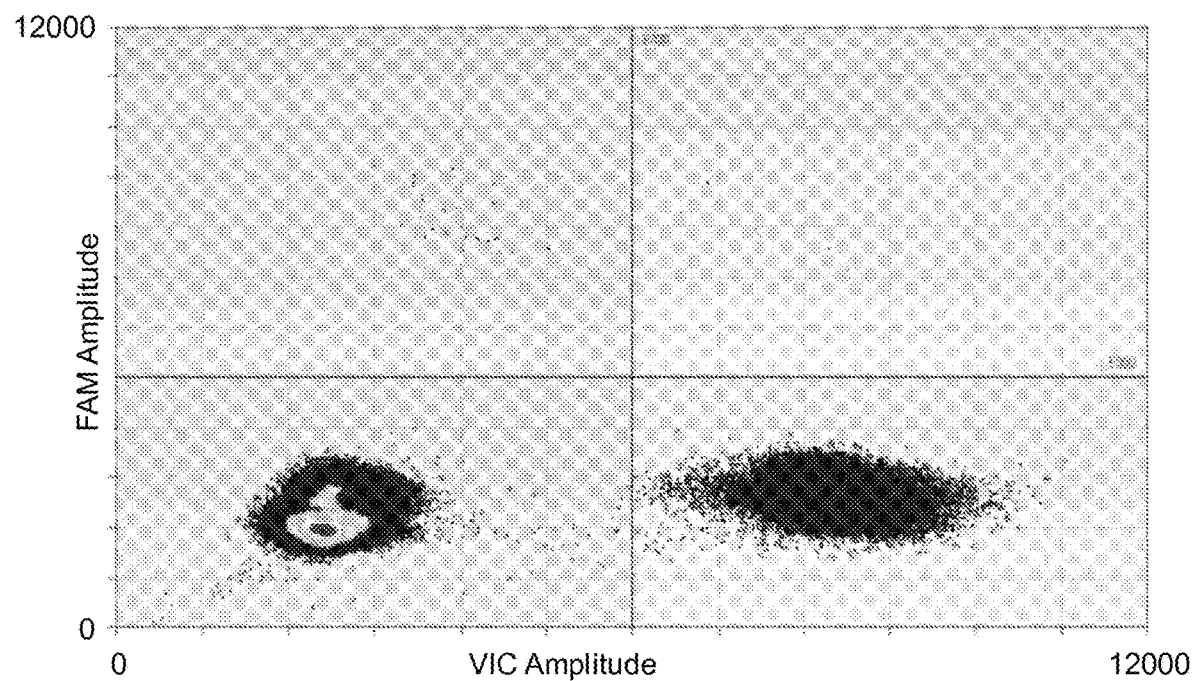

Figure 31

Table: Detection of BRAF mutant DNA in wild-type DNA background

Mutant (FAM Channel)

| Target mutant fraction (%) | Positive droplet counts | Negative droplet counts | Measured mass (ng) | Low (%;95% CI) | High (%;95% CI) |
|---|---|---|---|---|---|
| 0 | 0 | 104684 | 0.000 | 0.000 | 0.000 |
| 0.001 | 6 | 104533 | 0.030 | 0.006 | 0.055 |
| 0.005 | 23 | 108166 | 0.112 | 0.066 | 0.158 |
| 0.01 | 38 | 104898 | 0.191 | 0.130 | 0.252 |
| 0.1 | 357 | 103862 | 1.812 | 1.624 | 2.000 |
| 1.0 | 3753 | 98656 | 19.71 | 19.08 | 20.34 |

Wildtype (VIC Channel)

| Target mutant fraction (%) | Positive droplet counts | Negative droplet counts | Measured mass (ng) | Low (ng;95% CI) | High (ng;95% CI) | Measured mutant fraction (%) | Low (%;95% CI) | High (%;95% CI) |
|---|---|---|---|---|---|---|---|---|
| 0 | 103935 | 749 | 2608 | 2572 | 2647 | 0 | 0.0000 | 0.0000 |
| 0.001 | 103640 | 899 | 2511 | 2478 | 2547 | 0.0012 | 0.0012 | 0.0002 |
| 0.005 | 107243 | 946 | 2502 | 2470 | 2537 | 0.0045 | 0.0045 | 0.0027 |
| 0.01 | 104018 | 918 | 2502 | 2469 | 2537 | 0.0077 | 0.0076 | 0.0052 |
| 0.1 | 102807 | 1412 | 2271 | 2245 | 2299 | 0.0798 | 0.0798 | 0.0715 |
| 1.0 | 101652 | 757 | 2591 | 2555 | 2630 | 0.7608 | 0.7608 | 0.7341 |

SEQUENCE LISTING

<160> NUMBER OF SEQ ID NOS: 34

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 1
gacnnnnngt c                                                          11

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 2 cacnnnngtg                                                            10

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(6)
<223> OTHER INFORMATION: a, c, t, g, unknown or other

<400> SEQUENCE: 3
acnnnngtay c                                                          11

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 4
cgannnnnnt gc                                                         12

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (4)..(8)
<223> OTHER INFORMATION: a, c, t, g, unknown or other

<400> SEQUENCE: 5
gcnnnnnngg c                                                              11

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 6 gatnnnnatc                                                                10

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, t, g, unknown or other

<400> SEQUENCE: 7
ccnnnnnnng g                                                              11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 8
gcannnnntg c                                                              11

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 9
gacnnnnnng tc                                                             12

<210> SEQ ID NO 10
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgtaactata acggtcctaa ggtagcgaa                                          29

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tagggataac agggtaat                                                      18

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, t, g, unknown or other

<400> SEQUENCE: 12
gcnnnnnnng c                                                             11

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tggcaaacag ctattatggg tattatgggt                                         30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atctatgtcg ggtgcggaga aagaggtaat                                         30

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other
```

<400> SEQUENCE: 15 gacnnnngtc                                                                 10

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, t, g, unknown or other

<400> SEQUENCE: 16
ggccnnnnng gcc                                                             13

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agctggcacc cgctgg                                                          16

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtgtggggtt gcacgcg                                                         17

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
acccggctgg agcgt                                                           15

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgcttaacat agcagaagca                                                      20

<210> SEQ ID NO 21
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 21
agtttcgaac tctggcacct                                               20

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tgtcgcactc tccttgtttt tgaca                                         25

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcaaaggcga ggctctgt                                                 18

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgttccgaaa gttgccttttt atgg                                         24

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
accgccgaga ccgcgtc                                                  17

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccgaatagga acgttgagcc gt                                            22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
                                primer

<400> SEQUENCE: 27
gcaaatgtta tcgaggtccg gc                                              22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
ttggcagcct ttgccgcggc                                                 20

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
tctgccacct aagcggccgc ag                                              22

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctactgtttt cctttactta ctacacctca ga                                   32

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atccagacaa ctgttcaaac tgatg                                           25

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
tagctacaga gaaatc                                                     16

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 33
ctagctacag tgaaatc                                                17

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aacgcgtttc gcgagcg                                                17
```

METHODS AND COMPOSITIONS FOR DETECTING GENETIC MATERIAL

CROSS-REFERENCE

This application is a continuation of U.S. patent application Ser. No. 17/486,667, filed Sep. 27, 2021, which, in turn, is a continuation of U.S. patent application Ser. No. 16/667,811, filed Oct. 29, 2019, now U.S. Pat. No. 11,130,128, which, in turn, is a continuation of U.S. patent application Ser. No. 15/707,908, filed Sep. 18, 2017, now U.S. Pat. No. 10,512,910, which, in turn, is a continuation of U.S. patent application Ser. No. 15/351,354, filed Nov. 14, 2016, now U.S. Pat. No. 9,764,322, which, in turn, is a continuation-in-part of U.S. patent application Ser. No. 13/400,030, filed Feb. 17, 2012, now abandoned, which, in turn, is based upon and claims the benefit under 35 U.S.C. § 119(e) of the following U.S. provisional patent applications: Ser. No. 61/444,674, filed Feb. 18, 2011; Ser. No. 61/449,580, filed Mar. 4, 2011; Ser. No. 61/453,537, filed Mar. 16, 2011; Ser. No. 61/478,777, filed Apr. 25, 2011; Ser. No. 61/488,667, filed May 20, 2011; and Ser. No. 61/490,040, filed May 25, 2011. Each of these applications is incorporated herein by reference in its entirety.

This application is related to U.S. Patent Application Publication No. 20110159499, first inventor Hindson, filed Nov. 25, 2010, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, which was originally created on Mar. 28, 2012 in connection with parent application Ser. No. 13/400,030, was named 38938201.txt and is 9,541 bytes in size.

BACKGROUND

There is a general need in the art for adequate methods of detecting DNA and genetic variations present at low concentrations in biological samples. Furthermore, there is a need in the art for adequate methods and compositions for detecting and quantifying fetal DNA in circulating maternal plasma.

Prenatal diagnosis of fetal aneuploidies using invasive testing by amniocentesis or Chorionic Villus Sampling (CVS) is associated with a 0.5% to 2% procedure-related risk of pregnancy loss (D'Alton, M. E., (1994) Semin Perinatol 18:140-62; Caughey A B (2006) Obstet Gynecol 108:612-6). A potentially less-invasive method of analyzing fetal DNA would be to evaluate fetal DNA circulating in maternal plasma. However, such method is hampered by the low concentration of fetal DNA circulating in maternal plasma, particularly at earlier gestational ages, as well as the presence of circulating maternal DNA. It can be difficult to assess enough target counts to differentiate an aneupoloid fetus (e.g., trisomy of chromosome 21) from a euploid fetus (i.e., a fetus containing the normal number of chromosomes).

Improved methods and compositions for detecting other types of genetic variations in biological samples, not necessarily from maternal blood, would also be a useful contribution to the art. Examples of such genetic variations include single nucleotide polymorphisms (SNP's). Also useful would be improved methods and compositions for monitoring a certain aspect of a sample over time, such as growth rate.

SUMMARY

In one aspect, a method of detecting methylated DNA is provided, comprising: a. contacting a DNA sample with a methylation-sensitive reagent; b. partitioning said DNA sample into a plurality of spatially-isolated partitions; c. detecting a first locus within said DNA sample, wherein said first locus is hypermethylated in fetal DNA; and d. quantifying the amount of said first locus, thereby detecting methylated DNA. In some embodiments, said spatially-isolated partitions are emulsified droplets. In some embodiments, said first locus is selected from the group consisting of: RASSF1A, CASP8, RARB, SCGB3A1, DAB2IP, PTPN6, THY1, TMEFF2, APC, and PYCARD. In some embodiments, said methylation-sensitive reagent is a methylation-sensitive enzyme. In some embodiments, the method further comprises detecting a second locus within said DNA sample, wherein said second locus is present in both the maternal and fetal DNA and wherein said second locus is not significantly cleaved by said methylation-sensitive reagent (e.g., enzyme). In some embodiments, the method further comprises detecting a third locus within said DNA sample, wherein said third locus is present in both the maternal and fetal DNA and wherein said third locus is significantly cleaved by said methylation-sensitive reagent (e.g., enzyme). In some embodiments, the method further comprises amplifying a sequence associated with said first locus to produce a detectable signal. In some embodiment, said signal is a fluorescent signal.

In another aspect, a method of quantifying methylated DNA is provided, comprising: a. contacting a DNA sample with a methylation-sensitive reagent, wherein said DNA sample comprises a major population and a minor population; b. partitioning said DNA sample into a plurality of spatially-isolated partitions; c. detecting a first quantity of a first locus within said DNA sample; d. detecting a second quantity of a second locus within said DNA sample; and e. comparing said first and second quantities, to obtain a value indicative of a percentage of methylated DNA in the sample. In some embodiments, said plurality of spatially-isolated partitions are emulsified droplets. In some embodiments, said methylation-sensitive reagent is a methylation-sensitive enzyme. In some embodiments, said major population comprises maternal DNA and said minor population comprises fetal DNA. In some embodiments, said first locus is hypermethylated in fetal DNA. In some embodiments, said first locus comprises a sequence selected from the group consisting of: RASSF1A, CASP8, RARB, SCGB3A1, DAB2IP, PTPN6, THY1, TMEFF2, APC, and PYCARD. In some embodiments, said second locus does not comprise a restriction site recognized by said methylation-sensitive reagent. In some embodiments, said second locus is methylated in (a) maternal DNA and (b) fetal DNA. In some embodiments, said second locus comprises a sequence from the group consisting of: RNASE P and TERT. In some embodiments, said method further comprises detecting a signal associated with a third locus within said DNA sample. In some embodiments, said third locus is not significantly methylated in fetal DNA. In some embodiments, said third locus is cleaved by said methylation-sensitive enzyme. In some embodiments, said first locus and said third locus have an identical, or about identical, number of sites susceptible to cleavage by said methylation-sensitive enzyme. In some embodiments, said third locus comprises a sequence of a housekeeping gene. In some embodiments, said third locus comprises a sequence of BETA ACTIN. In some embodiments, said third locus comprises a sequence of the Y chromosome, a Rh blood type gene, a RhD blood type gene, a RhC blood type gene, a RhE blood type gene, an ABO blood type gene, or a HLA-type gene. In some embodiments, said third locus comprises a sequence of SRY. In some embodiments, said value indicative of the percentage of methylated DNA in said sample is adjusted by a value associated with the presence of said third locus within said DNA sample. In some embodiments, said method further comprises calculating the amount of total DNA in said sample. In some embodiments, said method further comprises prior to step (a), isolating a subsample from said DNA sample, wherein said subsample is not contacted with said methylation-sensitive reagent. In some embodiments, said method further comprises detecting said first or second locus in said subsample. In some embodiments, said method further comprises detecting a third locus within said subsample. In some embodiments, said methylation-sensitive reagent is selected from the group consisting of: bisulfite, hydrogen sulfite and disulfite. In some embodiments, said detecting of said first and second quantities comprises an amplification reaction. In some embodiments, said method further comprises partitioning said DNA subsample into a plurality of spatially isolated partitions. In some embodiments, said method further comprises comparing said value indicative of the percentage of methylated DNA in said DNA sample with a value at an earlier gestational timepoint, thereby detecting a pregnancy-associated disorder. In some embodiments, said pregnancy-associated disorder is selected from the group consisting of: preeclampsia, preterm labor, and intrauterine growth retardation (IUGR). In some embodiments, said value indicative of the percentage of methylated DNA in the sample is calculated using a detectable signal from at least a third locus within said DNA sample, wherein said third locus comprises a sequence that is not significantly cleaved by said methylation-sensitive reagent. In some embodiments, said method does not comprise performing real-time PCR. In some embodiments, said method is at least 1000-times more sensitive than a real-time PCR assay.

In another aspect, a method of quantifying methylated DNA is provided, comprising: a. splitting a DNA sample into a target portion and reference portion; b. contacting the target portion with a methylation-sensitive enzyme; c. partitioning each of the target portion and reference portion into a plurality of emulsified droplets; d. amplifying a locus within said target portion and a locus within said reference portion, wherein the amplification produces a detectable signal; and e. measuring a ratio of detectable signals from the target and reference portions, thereby quantifying methylated DNA. In some embodiments, said locus within said target portion is the same genetic locus as said locus within said reference portion. In some embodiments, said locus within the target portion is a different genetic locus than said locus within said reference portion. In some embodiments, said methylation-sensitive enzyme is activation-induced cytidine deaminase. In some embodiments, said methylation-sensitive enzyme is a restriction enzyme. In some embodiments, wherein the restriction enzyme is selected from the group consisting of: Aat II, Aci I, Acl I, Afe I, Age I, Asc I, Ava I, BmgB I, BsaA I, BsaH I, BspD I, Eag I, Fse I, Fau I, Hpa II, HinP1 I, Nar I, Hin6I, HapII and SnaB I. In some embodiments, said detecting comprises detecting at least one fluorescent molecule. In some embodiments, said at least one fluorescent molecule comprises a cleavable fluorescer-quencher pair. In some embodiments, said fluorescent molecule is detected within an emulsified droplet. In some embodiments, said method does not comprise a step prior to step (a), comprising increasing the relative concentration of fetal polynucleotides to total polynucleotides in said biological sample.

In another aspect, a method of determining the load of a fetal polynucleotide in a sample of maternal blood or plasma is provided, wherein the origin of said fetal polynucleotide is a female fetus, wherein the sensitivity of said determining is at least 75% equivalent to the sensitivity of determining a load of a polynucleotide originating from a male fetus in a sample of maternal blood or plasma.

In another aspect, a method of determining fetal sex is provided, comprising: a. dividing a sample of nucleic acids into a first and second subsample, wherein said sample comprises maternal and fetal nucleic acids; b. contacting said first subsample with a methylation-sensitive enzyme; c. partitioning each of said subsamples into a plurality of emulsified droplets; d. amplifying a first locus within the first subsample and a second and third loci within the second subsample, wherein the amplification produces a detectable signal; and e. computing a value reflecting both a first ratio and a second ratio, wherein said first ratio is computed using detectable signals from said first and second loci and said second ratio is computed using detectable signals from said first and third loci, thereby determining fetal sex. In some embodiments, said third locus is SRY. In some embodiments, said second locus is hypermethylated in fetal DNA compared to maternal DNA. In some embodiments said first ratio is positively correlated with the amount of fetal DNA in said sample. In some embodiments, said second ratio is positively correlated with the presence of male fetal DNA in said sample. In some embodiments, said fetal DNA is determined to be female when said first ratio is relatively high and indicates the presence of fetal DNA and when said second ratio is relatively low and indicates the absence of male fetal DNA. In some embodiments, said second locus is selected from the group consisting of: RASSF1A, CASP8, RARB, SCGB3A1, DAB2IP, PTPN6, THY1, TMEFF2, APC and PYCARD. In some embodiments, said first locus is not significantly cleaved by said methylation-sensitive reagent. In some embodiments, said first locus comprises a sequence of RNASE P. In some embodiments, a Pearson's correlation coefficient between said first and second ratios is greater than 85%.

Disclosed herein are methods of detecting methylated DNA, comprising: contacting a DNA sample with a methylation-sensitive reagent; partitioning said DNA sample into a plurality of emulsified droplets; amplifying a locus within said DNA sample, wherein the amplification produces a detectable signal; and, detecting said detectable signal, thereby detecting methylated DNA. In some embodiments, the locus is selected from the group consisting of: RASSF1A, CASP8, RARB, SCGB3A1, DAB2IP, PTPN6, THY1, TMEFF2, and PYCARD. In some embodiments, said methylation-sensitive reagent is a methylation-sensitive enzyme. In another embodiment, said DNA sample comprises fetal DNA.

In another aspect, provided herein is a method of quantifying methylated DNA comprising contacting a DNA sample with a methylation-sensitive reagent; partitioning said DNA sample into a plurality of emulsified droplets; detecting a first detectable signal, wherein the first detectable signal is correlated with the presence of a first locus in said DNA sample; detecting a second detectable signal, wherein the second detectable signal is correlated with the presence of a second locus in said DNA sample; and computing a ratio between said first detectable signal and said second detectable signal, thereby quantifying methylated DNA. In some embodiments, the method further comprises amplifying the first locus in the DNA sample and amplifying the second locus in the DNA sample. In some embodiments, said methylation-sensitive reagent is a methylation-sensitive enzyme. In some embodiments, the first locus is selected from the group consisting of: RASSF1A, CASP8, RARB, SCGB3A1, DAB2IP, PTPN6, THY1, TMEFF2, and PYCARD. In some embodiments, the second locus is selected from the group consisting of: RNASE P, Beta Actin, SRY, and TERT. In some embodiments, said methylation-sensitive reagent is selected from the group consisting of: bisulfite, hydrogen sulfite and disulfite. Some embodiments further comprise comparing the computed ratio to a ratio determined at an earlier gestational timepoint, thereby detecting a pregnancy-associated disorder. In some embodiments, the pregnancy-associated disorder is selected from the group consisting of: preeclampsia, preterm labor, and intrauterine growth retardation (IUGR). Also disclosed herein are methods of quantifying methylated DNA, comprising: splitting a DNA sample into a target portion and reference portion; contacting the target portion with a methylation-sensitive enzyme; partitioning each of the target portion and reference portion into a plurality of partitions; amplifying a locus within the target portion and a locus within the reference portion, wherein the amplification produces a detectable signal; and, measuring a ratio of detectable signals from the target and reference portions, thereby quantifying methylated DNA. In some embodiments, said locus within said target portion is the same genetic locus as said locus within said reference portion. In some embodiments, said locus within the target portion is a different genetic locus than said locus within said reference portion. In some embodiments, said methylation-sensitive enzyme is activation-induced cytidine deaminase. In some embodiments, said methylation-sensitive enzyme is a restriction enzyme. In some embodiments, the restriction enzyme is selected from the group consisting of: Aat II, Aci I, Acl I, Afe I, Age I, Asc I, Ava I, BmgB I, BsaA I, BsaH I, BspD I, Eag I, Fse I, Fau I, Hpa II, HinP1 I, Nar I, Hin6I, HapII and SnaB I. In some embodiments, the detectable signal comprises a fluorescent molecule. In some embodiments, the fluorescent molecule comprises a cleavable fluorescer-quencher pair, and said amplification results in cleavage of said fluorescent molecule. In some embodiments, the detectable signal is individually detected for each partition or emulsified droplet. In some embodiments, the DNA is obtained from a biological sample. In some embodiments, the biological sample is a blood or plasma sample. Some embodiments further comprise the step of measuring the detectable signal relative to the volume of the biological sample. In some embodiments, the method does not comprise a prior step comprising increasing the relative concentration of fetal polynucleotides to total polynucleotides in said biological sample. In some embodiments, said amplifying a locus comprises a plurality of targets within said locus.

Disclosed herein are methods of determining the load of a fetal polynucleotide in a sample of maternal blood or plasma, wherein the origin of said fetal polynucleotide is a female fetus. In some embodiments, the sensitivity of said determining is at least 75% equivalent to the sensitivity of determining the load a fetal polynucleotide in a sample of maternal blood or plasma, wherein the origin of said fetal polynucleotide is a male fetus. In some embodiments, the sensitivity of said determining is at least 85% equivalent to the sensitivity of determining the load a fetal polynucleotide in a sample of maternal blood or plasma, wherein the origin of said fetal polynucleotide is a male fetus. In some embodiments, the sensitivity of said determining is at least 95% equivalent to the sensitivity of determining the load a fetal polynucleotide in a sample of maternal blood or plasma, wherein the origin of said fetal polynucleotide is a male fetus. Disclosed herein are methods of determining fetal load, comprising: isolating a population of nucleic acids from a biological sample comprising a mixture of maternal and fetal nucleic acids; splitting said population of nucleic acids into two equal portions; contacting the first portion with a methylation-sensitive enzyme; partitioning each of the two equal portions into a plurality of partitions; amplifying a first locus within the first portion and a second locus within the second portion, wherein the amplification produces a detectable signal; and measuring a ratio of detectable signals from the target and reference portions, thereby determining fetal load.

Disclosed herein are methods of determining fetal sex, comprising: isolating a population of nucleic acids from a biological sample comprising a mixture of maternal and fetal nucleic acids; splitting said population of nucleic acids into two equal portions; contacting the first portion with a methylation-sensitive enzyme; partitioning each of the two equal portions into a plurality of partitions; amplifying a first locus within the first portion and a second and third loci within the second portion, wherein the amplification produces a detectable signal; and computing a third ratio of a first ratio to a second ratio, wherein the first ratio is computed using detectable signals from the first and second loci and the second ratio is computed using detectable signals from the first and third loci, thereby determining fetal sex. In some embodiments, the third locus is SRY. In some embodiments, if the third ratio is 1:0 the fetus is female. In some embodiments, if the third ratio is 1:1, the fetus is male. In some embodiments, the second locus is selected from the group consisting of: RASSF1A, CASP8, RARB, SCGB3A1, DAB2IP, PTPN6, THY1, TMEFF2, and PYCARD.

Disclosed herein are methods of determining fetal load, comprising: isolating a population of nucleic acids from a biological sample comprising a mixture of maternal and fetal nucleic acids; splitting said population of nucleic acids into a target portion and a reference portion; contacting said target portion with a methylation-sensitive enzyme; partitioning said target portion and said reference portion into a plurality of partitions; amplifying one or more target sequences within said target portion and one or more reference sequences within said reference portion, wherein said amplification produces a detectable target signal and a detectable reference signal; and measuring a ratio of said detectable target signal to said detectable reference signal, thereby determining fetal load. In some embodiments, said one or more target sequences and said one or more reference sequences comprise two or more sequences within a single gene. In some embodiments, the biological sample is a blood or plasma sample. In some embodiments, the volume of said target portion is equal to the volume of said reference portion. In some embodiments, the volume of said target portion is not equal to the volume of said reference portion. In some embodiments, said ratio is corrected for volume. In some embodiments, said methylation-sensitive reagent is selected from the group consisting of: bisulfite, hydrogen sulfite and disulfite. In some embodiments, said methylation-sensitive reagent is a methylation-sensitive enzyme. In some embodiments, said methylation-sensitive enzyme is activation-induced cytidine deaminase. In some embodiments, said methylation-sensitive enzyme is a restriction enzyme. In some embodiments, the restriction enzyme is selected from the group consisting of: Aat II, Aci I, Acl I, Afe I, Age I, Asc I, Ava I, BmgB I, BsaA I, BsaH I, BspD I, Eag I, Fse I, Fau I, Hpa II, HinP1 I, Nar I, Hin6I, HapII and SnaB I. In some embodiments, said one or more target sequences are the same as said one or more reference sequences. In some embodiments, said one or more target sequences and said one or more reference sequences comprise one or more of: RASSF1A, CASP8, RARB, SCGB3A1, DAB2IP, PTPN6, THY1, TMEFF2, or PYCARD. In some embodiments, said one or more target sequences are not the same as said one or more reference sequences. In some embodiments, said one or more target sequences comprise one or more of: RASSF1A, CASP8, RARB, SCGB3A1, DAB2IP, PTPN6, THY1, TMEFF2, or PYCARD. In some embodiments, said one or more reference sequences comprise one or more of: RNASE P, Beta Actin, SRY, or TERT. In some embodiments, said plurality of partitions is a plurality of emulsified droplets. In some embodiments, said detectable target signal and said detectable reference signal comprises a fluorescent molecule. In some embodiments, said fluorescent molecule comprises a cleavable fluorescer-quencher pair, and said amplification results in cleavage of said fluorescent molecule.

Disclosed herein are methods for detecting variations in a polynucleotide comprising: incubating a sample with a first restriction enzyme, wherein said sample comprises: a wild-type polynucleotide; and a mutant polynucleotide that is a mutant form of said wild-type polynucleotide; wherein said first restriction enzyme preferentially digests said wild-type polynucleotide over said mutant polynucleotide; and performing digital PCR on said sample in order to detect said mutant polynucleotide. In some embodiments, said wild-type polynucleotide is a first allele of a genetic marker and said mutant polynucleotide is a second allele of said genetic marker. In some embodiments, said genetic marker is associated with cancer. In some embodiments, said wild-type polynucleotide is a portion of a gene. Some embodiments further comprise incubating said sample with a second restriction enzyme, wherein said wild-type polynucleotide does not contain a recognition site of said second restriction enzyme and wherein said mutant polynucleotide does not contain a recognition site of said second restriction enzyme.

Disclosed herein are methods for detecting a target polynucleotide with an allele of interest comprising: incubating a sample with a first restriction enzyme, wherein said sample comprises: (i) a wild-type polynucleotide comprising a target sequence of a first allele of a genetic marker, and (ii) a target polynucleotide comprising a sequence of a second allele of said genetic marker; and wherein the target sequence comprising said first allele forms a recognition sequence of said first restriction enzyme, and the target sequence comprising said second allele does not form a recognition sequence of said first restriction enzyme; and detecting said target polynucleotide by performing digital PCR with said sample to amplify said target sequence. Some embodiments further comprise incubating said sample with a second restriction enzyme, wherein said target sequence does not contain a recognition site of said second restriction enzyme. In some embodiments, said digital PCR is microfluidic-based digital PCR. In some embodiments, said digital PCR is droplet digital PCR. In some embodiments, said detecting comprises hybridizing a first probe specific to said first allele and a second probe specific to said second allele. In some embodiments, said detecting comprises hybridizing a first probe specific to said wild-type polynucleotide and a second probe specific to said mutant polynucleotide. In some embodiments, said first probe comprises a first label and said second probe comprises a second label. In some embodiments, said first restriction enzyme is TspRI. In some embodiments, said second restriction enzyme is HAEIII. In some embodiments, said target sequence is a sequence of a human BRAF gene, EGFR gene, or c-KIT gene. In some embodiments, said wild-type polynucleotide is a sequence of a human BRAF gene, EGFR gene, or c-KIT gene. In some embodiments, said second allele of said genetic marker is V600E of human BRAF. In some embodiments, said mutant polynucleotide is V600E of human BRAF. In some embodiments, the copy number ratio between said target polynucleotide and said wild-type nucleotide is less than $1/10,000$, $1/1,000,000$, or $1/100,000,000$. In some embodiments, said digital PCR is performed for less than 30 cycles. In some embodiments, said digital PCR is performed in droplets with a size that is about or less than 1 nL.

Disclosed herein are methods for detecting variations in a polynucleotide comprising: incubating a sample with a first restriction enzyme, wherein said sample comprises: a wild-type polynucleotide; and a mutant polynucleotide that is a mutant form of said wild-type polynucleotide, wherein the number of copies of said mutant polynucleotide is less than 0.1% of the total copies of polynucleotides in the sample; and performing digital PCR on said sample in order to detect said mutant polynucleotide. In some embodiments, said number of copies of said mutant polynucleotide is less than 0.01% of the total copies of polynucleotides in the sample. In some embodiments, said mutant polynucleotide is detected with an accuracy of greater than 60%. In some embodiments, said mutant polynucleotide is detected with an accuracy of greater than 80%. In some embodiments, said mutant polynucleotide is detected with an accuracy of greater than 90%.

Disclosed herein are methods for detecting variations in a polynucleotide comprising: incubating a sample with a first restriction enzyme, wherein said sample comprises: a wild-type polynucleotide; and a mutant polynucleotide that is a mutant form of said wild-type polynucleotide; wherein said first restriction enzyme preferentially digests said wild-type polynucleotide over said mutant polynucleotide; and performing digital PCR on said sample in order to detect said mutant polynucleotide. In some embodiments, said sample is obtained from maternal blood or plasma.

Disclosed herein are methods for detecting variations in a polynucleotide comprising: incubating a sample with a reagent, wherein said sample comprises: a wild-type polynucleotide; and a mutant polynucleotide that is a mutant form of said wild-type polynucleotide; wherein said reagent preferentially digests said wild-type polynucleotide over said mutant polynucleotide; and performing digital PCR on said sample in order to detect said mutant polynucleotide.

Disclosed herein are methods for detecting a target polynucleotide with an allele of interest, the method comprising: a. incubating a sample with an endonuclease that recognizes and cleaves non-perfectly matched double stranded DNA, wherein the sample comprises: i. a background polynucleotide comprising a sequence of a first allele of a genetic marker, ii. a target polynucleotide comprising a sequence of a second allele of the genetic marker, and iii. a digestion probe that is perfectly complementary to the sequence of the second allele of the genetic marker; and b. detecting the target polynucleotide by subjecting the sample to digital PCR. In some embodiments, the detecting step comprises performing a Taqman assay with a detection probe that is perfectly complementary to at least a portion of the target polynucleotide. In some embodiments, the detection probe comprises an LNA modification. In some embodiments, the LNA modification does not locate at the 5' end of the detection probe. In some embodiments, the endonuclease comprises T7 endonuclease I. In some embodiments, the digestion probe is not perfectly complementary to the sequence of the first allele of the genetic marker.

Disclosed herein are populations of at least 5,000, 10,000, 50,000, or 100,000 emulsified droplets comprising polynucleotides obtained from a maternal sample wherein said maternal sample comprises: fetal DNA comprising a mutant polynucleotide; and maternal DNA comprising a wild-type form of said mutant polynucleotide; and wherein greater than 50% of said emulsified droplets comprise said mutant polynucleotide and wherein each of said emulsified droplets comprises on average one copy of said mutant polynucleotide. In some embodiments, each of said emulsified droplets comprises on average less than 5, 4, 3, 2, or 1 copy of said mutant polynucleotide. In some embodiments, about, or at least about 5, 10, 25, 50, 75, 100, 125, 150, 175, or 200 droplets have zero DNA.

Disclosed herein are methods for measuring the growth rate of a cellular population comprising: removing a first portion from said cellular population; measuring a quantity of polynucleotides within said first portion of said cellular population using digital PCR; after said removing of step a, removing a second portion from said cellular population; measuring a quantity of polynucleotides within said second cellular population using digital PCR; and comparing said quantity of polynucleotides obtained in step b with said quantity of polynucleotides obtained in step d. In some embodiments, said digital PCR of step b is droplet digital PCR. In some embodiments, said digital PCR of step d is droplet digital PCR. In some embodiments, said removing of step c occurs at least five minutes after said removing of step a. Some embodiments further comprise treating the cellular population with a test agent. In one embodiment, the test agent is a chemical compound. In one embodiment, the cellular population is a population of microbes. In some embodiments, the cellular population is a population of eukaryotic cells. In some embodiments, the cellular population is contaminated with other material.

INCORPORATION BY REFERENCE

All publications, patents, and patent applications mentioned in this specification are herein incorporated by reference in their entirety and to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the methods, compositions, and kits described herein, representative illustrative methods and materials are now described.

Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Stryer, L. (1995) Biochemistry (4th Ed.) Freeman, New York; Gait, "Oligonucleotide Synthesis: A Practical Approach" 1984, IRL Press, London, Nelson and Cox (2000), Lehninger, (2004) Principles of Biochemistry $4^{th}$ Ed., W. H. Freeman Pub., New York, N.Y. and Berg et al. (2006) Biochemistry, 6th Ed., W. H. Freeman Pub., New York, N.Y., all of which are herein incorporated in their entirety by reference for all purposes.

BRIEF DESCRIPTION OF THE DRAWINGS

The novel features of the methods, compositions, and kits are set forth with particularity in the appended claims. A better understanding of the features and advantages of the methods, compositions, and kits disclosed herein will be obtained by reference to the following detailed description that sets forth illustrative embodiments, in which the principles of the methods, compositions, and kits are utilized, and the accompanying drawings of which:

FIG. 19 illustrates droplet formation in a droplet generator.

FIG. 21 illustrates qualitatively the effect of DNA digestion upon droplet formation at various DNA loads and flow rates.

FIG. 22 lists examples of allele frequencies and the relative risks of Type 2 diabetes, Crohn's Disease, and rheumatoid arthritis.

FIG. 24 (A&B) illustrates ddPCR detection of wildtype and BRAF V600E in a 0% BRAF V600E DNA sample digested with HaeIII (A) or HaeIII & TspRI (B).

FIG. 26 (A&B) illustrates ddPCR detection of wildtype and BRAF V600E in a 0.005% BRAF V600E DNA sample digested with HaeIII (A) or HaeIII & TspRI (B).

FIG. 31 is a table summarizing BRAF V600E mutant detection in a dilution series.

DETAILED DESCRIPTION

I. General Overview

Figure 1:
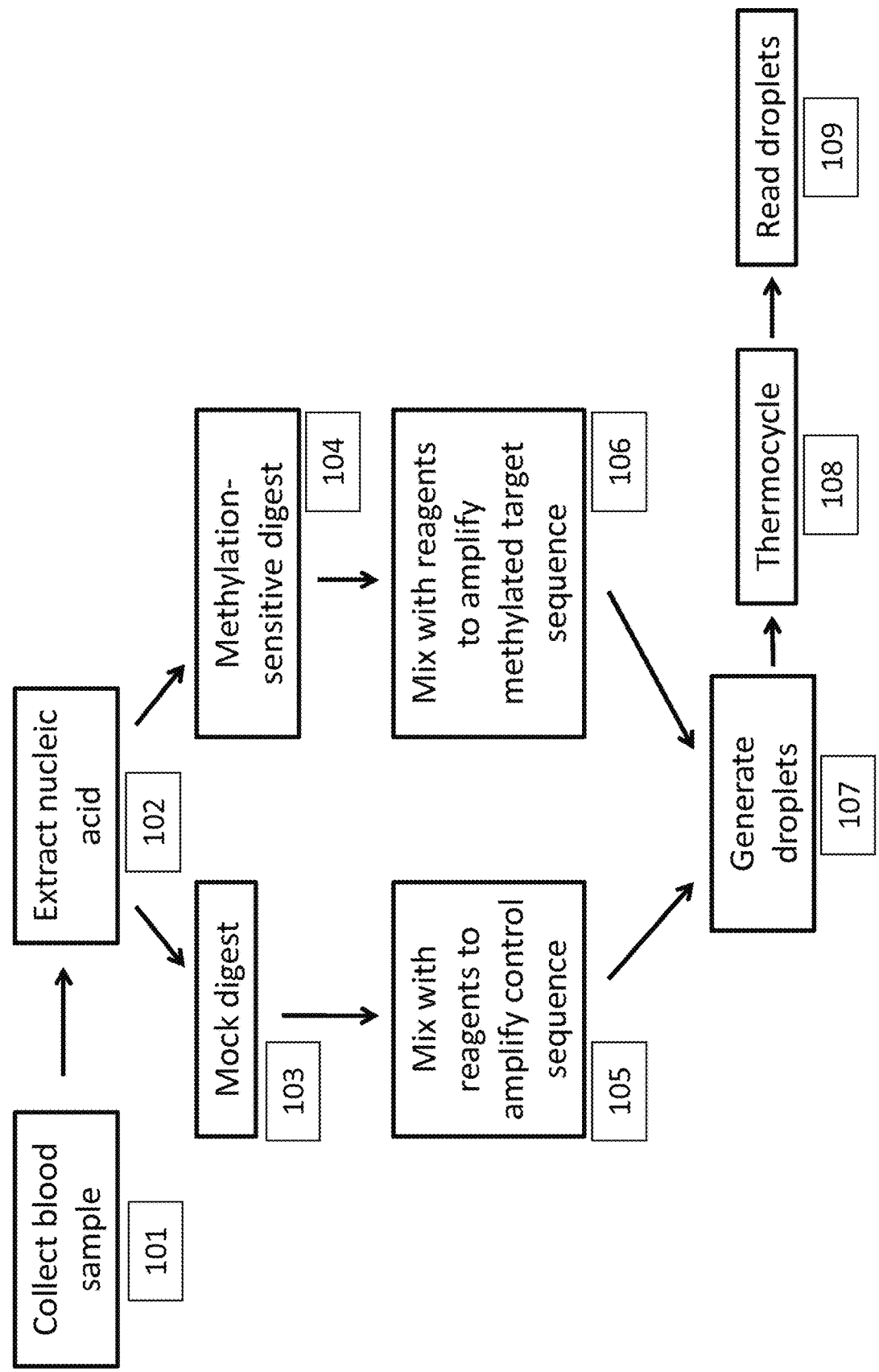
FIG. 1 depicts a workflow of methods of the disclosure.

Provided herein are methods, compositions and kits for detecting, quantifying, and/or analyzing target nucleic acids comprising steps for cleaving and/or removing background nucleic acids. The methods and compositions provided herein can be useful for providing accurate, sensitive, and/or specific quantitative measurements of target nucleic acids. By reducing, digesting, and/or cleaving background nucleic acids, which can inhibit amplification of the background nucleic acids, the methods and compositions disclosed herein can detect rare or low concentrations of target nucleic acids within a larger pool of nucleic acids. The methods disclosed herein can be used in combination with a digital PCR method (e.g., droplet digital PCR). The amplification of the target nucleic acids can produce a detectable signal, which in the case of droplet digital PCR can be read for individual droplets. The digital PCR method can be a multi-plexed digital PCR method, wherein two or more detection reagents are used in a single amplification. The use of multiplexing can further increase the sensitivity of a method comprising a step for cleaving background nucleic acids.

One aspect of the present disclosure relates to methods, compositions, and kits for detecting target nucleic acids in a biological sample wherein the biological sample comprises nucleic acids from two or more subjects. In one example, the biological sample can comprise maternal and fetal nucleic acids. In some embodiments, the biological sample comprises a major population and a minor population of nucleic acids. In some embodiments, the major population comprises maternal DNA and the minor population comprises fetal DNA. The biological sample comprising nucleic acids from two or more subjects can comprise methylated and non-methylated nucleic acids. The methylated nucleic acids can be from a fetal subject; the non-methylated nucleic acids can be of maternal origin. The target nucleic acids can be methylated nucleic acids; for example, the target nucleic acid can be a fetal-specific marker. The background nucleic acids can be non-methylated nucleic acids; for example, the background nucleic acids can comprise maternal nucleic acids. A methylation-specific reagent can be used to digest and/or render non-amplifiable the non-methylated nucleic acids in the biological sample comprising methylated and non-methylated nucleic acids. The methylation-sensitive reagent can be a methylation-sensitive restriction enzyme or a methylation-specific chemical such as a reagent comprising bisulfate, disulfite, hydrogen sulfite or combinations thereof. All or a portion of the nucleic acids extracted from the biological sample can be subjected to the methylation-specific reagent; for example, the nucleic acids can be split into two or more portions and one or more of the portions can be subjected to the methylation-specific reagent. Detection of target nucleic acids (e.g., methylated target nucleic acids) can involve a digital PCR method such as droplet digital PCR. The digital PCR method can comprise a detection probe that produces a detectable signal upon amplification of the target nucleic acids. One or more different detection probes can be used in the digital PCR method; for example, multiplexing using two or more detection probes can be used to increase the sensitivity of the detection methods and/or increase the number of target nucleic acids detected. Any of these methods can be useful, for example, in determining fetal load, diagnosing one or more pregnancy-associated disorders (e.g., preeclampsia (pregnancy induced hypertension), eclampsia, preterm labor, intrauterine growth retardation, gestational diabetes mellitus (GDM), etc.), and/or determining fetal sex.

Another aspect of the present disclosure relates to methods, compositions, and kits for the detection of one or more target nucleic acids wherein the target nucleic acids comprise a genetic variation, genetic mutation, and/or a single nucleotide polymorphism (SNP). The genetic variation, genetic mutation, and/or SNP can be associated with a disease, disorder, or condition. The target nucleic acids can comprise an allele of a genetic marker of interest. The allele of the genetic marker of interest can be a phenotype associated allele of the genetic marker of interest. The background nucleic acids can comprise wild-type polynucleotides (e.g., a wild-type allele of the genetic marker of interest). The background nucleic acids can comprise a non-phenotype associated allele of the genetic marker of interest. Digestion of the background nucleic acids can comprise digestion with a restriction enzyme that specifically targets the background nucleic acid. For example, the restriction enzyme can specifically cleave the wild-type and/or non-phenotype associated allele of the genetic marker of interest while leaving the target nucleic acids undigested.

In another embodiment, digestion of the background nucleic acids can also involve the use of a digestion probe that is designed to form a mismatched dimer with the background nucleic acids. The digestion probe can be perfectly complementary to a portion of the target nucleic acid. The digestion probe can be an unlabeled digestion probe ("Dark" digestion probe). Digestion of the background nucleic acids can further comprise the use of an enzyme that specifically cleaves mismatched dimers (e.g., an endonuclease, e.g., T7 Endonuclease I). Detection and or quantification of the target nucleic acids can comprise a digital PCR method (e.g., droplet digital PCR) to amplify the target nucleic acids. The amplification can comprise a detection probe to produce a detectable signal. The detection probe can comprise the same nucleotide sequence as the digestion probe. The detection probe can comprise modified nucleic acids that protect the detection probe from digestion by an endonuclease. The detection probe can comprise a fluorescer molecule and a quencher molecule. Two or more detection probes can be used in the digital PCR method; for example, multiplexing using two or more detection probes can increase the sensitivity of the detection and/or increase the number of genetic markers detected and/or analyzed. These methods can be useful for diagnosing a disease, disorder, and/or condition.

Another aspect of the present disclosure relates to methods, compositions, and/or kits for the detection of cellular processes such as viability or growth rates. The methods can comprise obtaining biological samples at two or more time points, followed by extraction of nucleic acids and quantitation of one or more target nucleic acids (e.g., biological markers) of interest. The one or more target nucleic acids can be biological markers that are associated with a cell type and/or a microorganism of interest. For example, the biological markers can be associated with a cancer or a pathogen. The quantitation step can comprise a digital PCR method such as droplet digital PCR to amplify, detect, and/or quantify the levels of the nucleic acids of interest. The amplification step can comprise a detectable probe that specifically recognizes the target nucleic acids (e.g., biomarkers of interest). The detectable probe can comprise a fluorescer and a quencher molecule. More than one detectable probe can be used; for example, multiplexing using two or more detection probes can increase the sensitivity and/or increase the number of number of target nucleic acids analyzed. A change in the level of the one or more target nucleic acids over time can be useful in determining viability and/or growth rates. The methods disclosed herein can also be useful to evaluate the efficacy of a drug or treatment. For example, the levels of one or more target nucleic acids in biological specimens obtained prior to and following a drug or treatment can be used evaluate the effect of the drug or treatment upon a cellular population of interest (e.g., a specific cell type or cancer, a specific pathogen, etc.).

Any of the methods disclosed herein can be used singularly or in combination. For example, a method to detect a fetal abnormality can comprise a step to digest or remove background/non-methylated/maternal nucleic acids and a step to digest or remove background/wild-type/non-phenotype associated alleles of one or more genetic markers of interest. In another example, a method to detect fetal growth rates can comprise obtaining two or more biological samples at different timepoints in combination with a step to digest or remove background/non-methylated/maternal nucleic acids. In this example, a change in the fetal load over time can be used to estimate fetal growth rates.

II. Analysis of Methylated DNA

The present disclosure provides methods, compositions, and kits for detecting and quantifying polynucleotides (e.g., DNA, RNA, etc.) in a biological sample. The methods and compositions provided herein are especially useful for providing accurate, sensitive, and/or specific quantitative measurements of polynucleotides in a biological sample. The methods and compositions provided herein can be used to detect low concentrations of polynucleotides (e.g., DNA, RNA, etc.). The methods and compositions provided herein can also be used to distinguish polynucleotides in a biological sample comprising a mixture of two or more polynucleotides derived from a different subject (e.g., maternal-fetal). For example, the methods and compositions provided herein can be used to detect or quantify fetal polynucleotides (e.g., DNA, RNA, etc.) present in a biological sample comprising both fetal and maternal polynucleotides. In some embodiments, the methods and compositions provided herein are used to detect or quantify a modified polynucleotide in a biological sample comprising both modified and non-modified polynucleotides. For example, the methods and compositions provided herein can be used to detect or quantify methylated DNA in a biological sample comprising both methylated and non-methylated DNA. In some embodiments, the methylated DNA represents the presence of fetal DNA. In some embodiments, the methylated DNA is a specific gene that is methylated, e.g., a gene that is known to be highly methylated in fetal DNA but not maternal DNA (e.g., RASSF1A, APC, CASP8, RARB, SCGB3A1, DAB2IP, PTPN6, THY1, TMEFF2, PYCARD, TBX3, SPN, CDC42EP1, MGC15523, SOX14 and the like). In some embodiments, such genes are used as universal fetal markers in non-invasive fetal and pre-natal diagnostics. In some embodiments, the methylated DNA is from a cancer cell.

In some embodiments, the present disclosure provides for a method of detecting methylated target DNA, comprising: a) contacting a DNA sample with a methylation-sensitive enzyme; b) partitioning said DNA sample into a plurality of emulsified droplets; c) amplifying a locus within said DNA sample, wherein the amplification produces a detectable signal; and d) detecting said detectable signal, thereby detecting methylated DNA. Emulsion PCR, digital PCR, or droplet digital PCR (ddPCR) that partition DNA (or other polynucleotide) into a plurality of partitions, can be used to detect polynucleotides present in low concentrations within a nucleic acid sample.

In some embodiments, the present disclosure provides for a method of quantifying methylated DNA, comprising: a) contacting a DNA sample with a methylation-sensitive reagent; b) partitioning said DNA sample into a plurality of emulsified droplets; c) amplifying a first locus within said DNA sample, wherein the amplification produces a first detectable signal; d) amplifying a second locus within said DNA sample, wherein the amplification produces a second detectable signal; and d) comparing said first detectable signal with said second detectable signal, thereby quantifying methylated DNA. In some embodiments, the method further comprises comparing the computed ratio to a ratio determined at an earlier gestational timepoint. In some embodiments, the comparison is used to aid the identification of a prenatal abnormality. In some embodiments, the present disclosure provides for a method of quantifying methylated DNA, comprising: a) contacting a DNA sample with a methylation-sensitive reagent; b) partitioning said DNA sample into a plurality of emulsified droplets; c)

detecting a first detectable signal, wherein the first detectable signal is correlated with the presence of a first locus in said DNA sample; d) detecting a second detectable signal, wherein the second detectable signal is correlated with the presence of a second locus in said DNA sample; and e) computing a ratio between said first detectable signal and said second detectable signal, thereby quantifying methylated DNA. In some embodiments, the method further comprises amplifying the first locus in the DNA sample and amplifying the second locus in the DNA sample.

In some embodiments, the present disclosure provides for a method of quantifying methylated DNA, comprising: a) splitting a DNA sample into a target portion and reference portion; b) contacting the target portion with a methylation-sensitive enzyme; c) partitioning each of the target portion and reference portion into a plurality of partitions; d) amplifying a first locus within the target portion and a second locus within the reference portion, wherein the amplification produces a detectable signal; and e) measuring a ratio of detectable signals from the target and reference portions, thereby quantifying methylated DNA. In some embodiments, the target portion is a portion within a polynucleotide (e.g., DNA, RNA, etc.) of fetal origin. In some embodiments, the reference portion is a portion within a polynucleotide (e.g., DNA, RNA, etc.) of maternal origin.

In some embodiments, the present disclosure provides for a method of quantifying methylated DNA, comprising: a) splitting a DNA sample into a target portion and reference portion; b) contacting the target portion with a methylation-sensitive enzyme; c) partitioning each of the target portion and reference portion into a plurality of partitions; d) amplifying a locus within the target portion and a locus within the reference portion, wherein the amplification produces a detectable signal; and e) measuring a ratio of detectable signals from the target and reference portions, thereby quantifying methylated DNA. In some embodiments, the target portion is a portion within a polynucleotide (e.g., DNA, RNA, etc.) of fetal origin. In some embodiments, the reference portion is a portion within a polynucleotide (e.g., DNA, RNA, etc.) of maternal origin. In some embodiments, the loci are the same locus. In some embodiments, a male-specific fetal marker (e.g., SRY) is compared to a universal fetal marker to determine fetal sex.

The present disclosure provides many different methods, some of which are illustrated in FIG. 1. As shown in FIG. 1, a method can include collecting a blood sample (101), followed by extracting nucleic acids from the sample (102). The nucleic acid sample can then be split, for example, into two equal portions. As used herein, the term equal includes exactly equal, substantially equal, and approximately equal. Alternatively, the nucleic acid sample can be split into unequal portions. One portion can be subjected to a mock digest (103), which can comprise reaction temperature and buffer conditions, but does not include a methyl-sensitive reagent. The second portion undergoes treatment with a methyl-sensitive reagent, such as digestion by a methylation-sensitive restriction enzyme (104). Following mock digest, the first portion is mixed with reagents for amplification of a control sequence (105). Following methylation-sensitive digest, the second portion is mixed with reagents for amplification of a target sequence (106). Each of the two portions is then partitioned into droplets (107) and incubated in a thermocycler (108), to enable amplification of the target or reference sequences. Amplification can produce a detectable signal (or two different signals, one for target and one for reference). Detectable signals can be read for individual droplets, to enumerate droplets containing positive signal representing target and reference sequences (109). The data can be analyzed to produce a determination of fetal load, for example, by taking a ratio of the number of target-positive droplets to reference-positive droplets. If the sample is split into unequal volumes, the ratio of target-positive droplets to reference-positive droplets can be corrected according to volume.

In some embodiments, the present disclosure provides for a method of determining fetal load, comprising: a) isolating a population of nucleic acids from a biological sample comprising a mixture of maternal and fetal nucleic acids; b) splitting said population of nucleic acids into two equal portions; c) contacting the first portion with a methylation-sensitive enzyme; d) partitioning each of the two equal portions into a plurality of partitions; e) amplifying a first locus within the first portion and a second locus within the second portion, wherein the amplification produces a detectable signal; and f) measuring a ratio of detectable signals from the target and reference portions, thereby determining fetal load.

As used herein, fetal load is a general term that refers to the representation of fetal nucleic acid within a biological sample, which can be useful in making quantitative measurements on the biological sample. Fetal load can be represented as a percentage given by the formula $$\text{Fetal load}=(\text{fetal}DNA/(\text{fetal}DNA+\text{maternal}DNA))*100,$$

where fetal DNA is the amount of fetal DNA detected and (fetal DNA+maternal DNA) is the total DNA detected. In some embodiments, an algorithm is used determine the fetal load.

In some embodiments, fetal DNA is determined by analyzing a hypermethylated fetal DNA locus. In some embodiments, the target sequence is preferentially methylated in fetal DNA compared to in maternal DNA. In some embodiments, the target sequence is hypermethylated in fetal DNA compared to in maternal DNA. In some embodiments, the target sequence is RASSF1A, CASP8, RARB, SCGB3A1, DAB2IP, PTPN6, THY1, TMEFF2, TBX3, SPN, CDC42EP1, MGC15523, SOX14 or PYCARD. In some embodiments, multiple target sequences are analyzed. In some embodiments, a first locus is a locus described in Nygren et al. (2010) Clin. Chem. 56: 1627-1635, herein incorporated by reference in its entirety.

In some embodiments, the second locus is not cleaved by restriction enzymes used in the experiment. In some embodiments, the second locus is not methylated in maternal DNA. In some embodiments, the second locus is hypomethylated in maternal DNA. In some, the second locus is hypomethylated in fetal and maternal DNA. In some embodiments, the second locus is RNase P, Tert, ALB (albumin), APOE (apolipoprotein E), or Beta Actin.

In some embodiments, a control locus is analyzed to monitor the completion of the restriction digest. In some embodiments, the control locus is Beta-Actin, LDHA (lactate dehydrogenase A), or POPS (processing of precursor 5, ribonuclease P/MRP subunit). In some embodiments, the digestion control locus comprises a similar number of restriction cleavage sites for one or more restriction enzymes as the target sequence. In some embodiments, a control locus is detected with a probe, e.g., a Taqman probe. In some embodiments, a restriction enzyme digest is about, more than about, or less than about 10%, 20%, 30%, 40%, 50%, 60%, 70%, 80%, 90%, or 100% complete.

In some embodiments, the second locus is a reference sequence. In some embodiments, the total DNA is determined by analyzing multiple reference sequences. In some embodiments, about 1, 2, 3, 4, 5, 6, 7, 8, 9, 10, 11, 12, 13, 14, 15, 16, 17, 18, 19, 20 or more reference sequences are analyzed. In some embodiments, the signals from the more than one reference sequences are averaged to determine total DNA. In some embodiments, a weighted mean of signals from the one or more reference sequences is used to determine total DNA. In some embodiments, the first locus and the second locus are detected in an assay. In some embodiments, the first locus is detected with a probe comprising a label that is different from the label on the probe used to detect the second locus.

Universal fetal markers can be used to measure genetic traits of a fetus. In some embodiments, a universal fetal marker is used in conjunction with a male-specific marker to determine sex of a fetus. One example of a male-specific marker is the SRY gene, located on the Y-chromosome. Because the SRY gene is not found in the maternal genome, it can be detected to determine that a fetus is male. Negative results for this type of analysis can be difficult to interpret, however, because fetal DNA can be present at very low concentrations in a biological sample. Thus, a universal fetal marker can serve as a useful positive control to confirm the presence and indicate the level of fetal DNA in a biological sample. Sex determinations can then be made using a maternal blood sample, e.g., with a higher degree of confidence than can be achieved without the use of a universal fetal marker. In one embodiment, the male-specific marker is ubiquitously transcribed tetratricopeptide repeat gene, Y-linked (UTY).

In some embodiments, a first ratio is computed using detectable signal measured from a first locus versus a second locus. A second ratio can then be computed using detectable signal measured from the first locus and a third locus. A ratio of the first and second ratios can then be calculated to produce a third ratio, indicative of fetal sex. In some embodiments, the first locus is a known diploid gene present in maternal and fetal DNA, such as Beta Actin or RNAse P, Tert, Alb, POPS. In some embodiments, the first locus (e.g., Beta Actin) is not methylated in maternal and fetal DNA. In some embodiments, the first locus (e.g., Beta Actin) is hypomethylated in maternal and fetal DNA. In some embodiments, the first locus (e.g., Beta Actin) is used as a control for the digestion of nonmethylated DNA. In some embodiments, the first locus (e.g., Beta Actin) contains the same or a similar number of restriction sites as the second locus (e.g., RASSF1A). In some embodiments, the second locus is a universal fetal marker, such as methylated RASSF1A. In some embodiments, the second locus is preferentially methylated in fetal DNA compared to maternal DNA. In some embodiments, the second locus is hypermethylated in fetal DNA. In some embodiments, the third locus is a male-specific marker, such as the SRY gene. For example, the third ratio can be given by (RASSF1A/Beta-Actin): (2*SRY/Beta-Actin), where SRY, Beta-Actin, and RASSF1A represent the detectable signals detected for the SRY, Beta-Actin, and methylated RASSF1A genes, respectively. In this example, a measurement of 1:1 or approximately 1:1 indicates the fetus is male, while a 1:0 ratio indicates the fetus is female. Note that the SRY measurement is doubled in the calculation, because it is a haploid gene. This correction can be made for any haploid markers used in the present method.

Methods of the disclosure can also be used to measure a fetal genetic aneuploidy. Trisomy 21 is associated with Down's Syndrome, and can be diagnosed using methods of the disclosure. For example, four loci can be detected, corresponding to a known maternal/fetal diploid marker (e.g., Beta-Actin, "actin"; RNAse P), a presumed diploid universal fetal marker (e.g., methylated RASSF1A, "RASSF1A"), a presumed diploid fetal marker (e.g., a gene on Chromosome 1, "Chr1"), and a suspected aneuploid marker (e.g., a gene on Chromosome 21, "Chr21"). In this example, a ratio given by the formula $$[(Chr21\text{-actin})/RASSF1A]:[(Chr1\text{-actin})/RASSF1A]$$

can be used to determine fetal aneuploidy. A ratio of approximately 3:2 can indicate aneuploidy. A ratio of approximately 1:1 can indicate a normal diploid fetus.

In some embodiments, a methylation-sensitive enzymatic digestion used in the methods provided herein is monitored in order to determine the degree to which the assay contains undigested maternal DNA. In some embodiments, the digestion of a specific gene of maternal origin (e.g., B-actin, etc.) is monitored in order to assess the percentage of undigested maternal DNA. In some embodiments, such percentage can be used to correct the value obtained for the fetal polynucleotides (e.g., DNA, RNA, etc.). In some examples, the sequences of Beta-Actin (or other gene of maternal origin) and the fetal gene of interest (e.g., RASSF1A, APC, etc.) are first evaluated in order to identify regions that contain the identical (or near identical) number of sites susceptible to cleavage by the enzyme (e.g., methylation-sensitive restriction enzyme) used for the digestion step in the methods provided herein. Following the digestion reaction, the relative amount of undigested to digested B-Actin polynucleotides (e.g., DNA, RNA, etc.) can be calculated to obtain a "digestion-completion value". An initial number of copies of the fetal gene of interest (e.g., RASSF1A, APC, etc.) can also be calculated using digital PCR (e.g., droplet digital PCR). This initial number can be corrected using the digestion-completion value, thereby providing more accurate quantification of the fetal DNA.

Fetal methylation markers are described, e.g., in US Patent Application Publication No. 20090155776, which is herein incorporated by reference.

As described further herein, the methods and compositions provided herein can be used to detect a wide variety of conditions and disorders related to pregnancy (e.g., prenatal conditions affecting the mother; fetal aneuploidy and other genetic disorders of the fetus). The methods and compositions provided herein can also be used to detect a wide variety of conditions and disorders not necessarily related to pregnancy or fetal aneuploidy, e.g., certain types of cancer.

As will be appreciated by those of skill in the relevant art, the above-described embodiments can be used not only for the methylation analysis, but also for the quantification of sequence differences in RNA or in DNA.

Additional embodiments of the present disclosure provide a method for the investigation of allele-specific gene expression. In the first step of such embodiments, the RNA to be investigated can be reverse-transcribed, by methods known in the art.

Yet further embodiments of the present disclosure, while distinguishable from those of the above-described methylation analysis, provide methods for investigation of single nucleotide polymorphisms (SNPs) from pooled samples. A pool of samples can be meaningful for different objectives, such as for identifying genes which take part in the emergence of complex disorders (see, e.g., Shifman et al.: Quantitative technologies for allele frequency estimation of SNPs in DNA pools. Mol Cell Probes 16:429-34, 2002, which is herein incorporated by reference in its entirety). A gene duplication event can also be investigated according to these principles (see also, e.g., Pielberg et al.: A sensitive method for detecting variation in copy numbers of duplicated genes. Genome Res 13:2171-7, 2003, which is herein incorporated by reference in its entirety). Additional aspects of the present disclosure provide methods for investigation of strain differences and/or mutations in microorganisms. According to such embodiments, the proportion of wild type and the proportion of mutant strain (or the relative proportions of two different strains) can be determined in a sample. Such applications can be of significant importance for therapeutic decisions.

In alternate embodiments, the methods have substantial utility for predicting subject/drug or subject/treatment interactions (e.g., drug responsiveness, or undesired interactions, etc.), for the differentiation of cell types or tissues, or for the investigation of cell differentiation.

The differential methylation status of maternal versus fetal versions of some genes can allow the fetal and maternal copies to be distinguished using methods that differentially modify methylated or unmethylated DNA. As used herein, the terms methyl-sensitive and methylation-sensitive can be used interchangeably to refer to any reagent, enzyme, process, or treatment whose efficiency is considerably reduced when directed towards methylated nucleic acid substrates compared to unmethylated nucleic acid substrates. The terms methyl-dependent and methylation-dependent can be used interchangeably to refer to any reagent, enzyme, process, or treatment whose efficiency is enhanced for methylated nucleic acid substrates compared to unmethylated nucleic acid substrates.

As used herein, a pregnancy-associated disorder refers to any condition or disease that can affect a pregnant woman, the fetus the woman is carrying, or both the woman and the fetus. Such a condition or disease can manifest its symptoms during a limited time period, e.g., during pregnancy or delivery, or can last the entire life span of the fetus following its birth. Some examples of a pregnancy-associated disorder include preeclampsia, preterm labor, and intrauterine growth retardation (IUGR).

A. Methylation-Specific Reagents

The present disclosure provides methods and compositions that can involve digesting, degrading and/or modifying DNA in a methylation-specific manner. As described herein, enzymes such as methylation-sensitive restriction enzymes are useful in the present disclosure. Other types of methylation-sensitive chemical reagents also can be used, e.g., reagents comprising bisulfite, disulfite, hydrogen sulfite or combinations thereof. Variations of bisulfite conversion are known to persons of ordinary skill in the relevant art (see, e.g., Frommer et al., Proc Natl Acad Sci USA., 89:1827-31, 1992, Olek, Nucleic Acids Res. 24:5064-6, 1996; and PCT/EP2004/011715, each of which is herein incorporated by reference in its entirety). Bisulfite conversion can be facilitated by the presence of denaturing solvents (e.g., dioxane) and a radical trap (see e.g., PCT/EP2004/011715).

In some embodiments, a methylation-sensitive treatment involves treating a sample with bisulfite, such as a bisulfite comprising sodium bisulfite. Bisulfites are generally capable of chemically converting a cytosine (C) to a uracil (U) without chemically modifying a methylated cytosine and therefore can be used to differentially modify a DNA sequence based on the methylation status of the DNA. Unmethylated cytosine is converted to uracil through a three-step process during sodium bisulfite modification. The steps are sulfonation to convert cytosine to cytosine sulfonate, deamination to convert cytosine sulfonate to uracil sulfonate and alkali desulfonation to convert uracil sulfonate to uracil. Conversion on methylated cytosine is much slower and is not observed at significant levels in a 4-16 hour reaction. See Clark et al., Nucleic Acids Res., 22(15):2990-7 (1994), which is herein incorporated by reference in its entirety. If a cytosine is methylated, it can remain cytosine. However, if a cytosine is unmethylated, it can be converted to uracil. When the modified strand is copied, through, for example, extension of a locus specific primer, a random or degenerate primer or a primer to an adaptor, a G can be incorporated in the interrogation position (opposite the C being interrogated) if the C was methylated and an A can be incorporated in the interrogation position if the C was unmethylated. When the double stranded extension product is amplified those C's that were converted to U's and resulted in incorporation of A in the extended primer will be replaced by Ts during amplification. Those C's that were not modified and resulted in the incorporation of G can remain as C.

Kits for DNA bisulfite modification are commercially available from, for example, Human Genetic Signatures' Methyleasy and Chemicon's CpGenome Modification Kit. See also, WO04096825A1, which describes bisulfite modification methods and Olek et al. Nuc. Acids Res. 24:5064-6 (1994), which discloses methods of performing bisulfite treatment and subsequent amplification on material embedded in agarose beads; both of which are herein incorporated by reference in their entireties. In one aspect, a catalyst such as diethylenetriamine can be used in conjunction with bisulfite treatment, see e.g., Komiyama and Oshima, Tetrahedron Letters 35:8185-8188 (1994). Diethylenetriamine can be used to catalyze bisulfite ion-induced deamination of 2'-deoxycytidine to 2'-deoxyuridine, e.g., at pH 5. Other catalysts can include ammonia, ethylene-diamine, 3,3'-diamino-dipropylamine, and spermine. In some aspects deamination is performed using sodium bisulfite solutions of about 3M to about 5 M with an incubation period of about 12 to about 16 hours at about 50° C. In some embodiments, a faster procedure using about 9M to about 10 M bisulfite pH 5.4 for about 10 minutes at 90° C. can be used, see e.g., Hayatsu et al, Proc. Jpn. Acad. Ser. B 80:189-194 (2004), which is herein incorporated by reference in its entirety.

Nucleic acid that contains one or more uracils, e.g., one or more uracils generated via treatment of the nucleic acid with bisulfite to convert one or more non-methylated cytosines to uracil, can be treated with an enzyme that can eliminate uracil from DNA molecules by cleaving the N-glycosylic bond (e.g., uracil-N-glycosylase). An abasic site can result from such cleavage. The nucleic acid can be fragmented at the abasic site by treating with, e.g., heat, NaOH, or an amine (e.g., DMED). See e.g., U.S. Patent Application No. 20040005614, which is herein incorporated by reference in its entirety.

Figure 2:
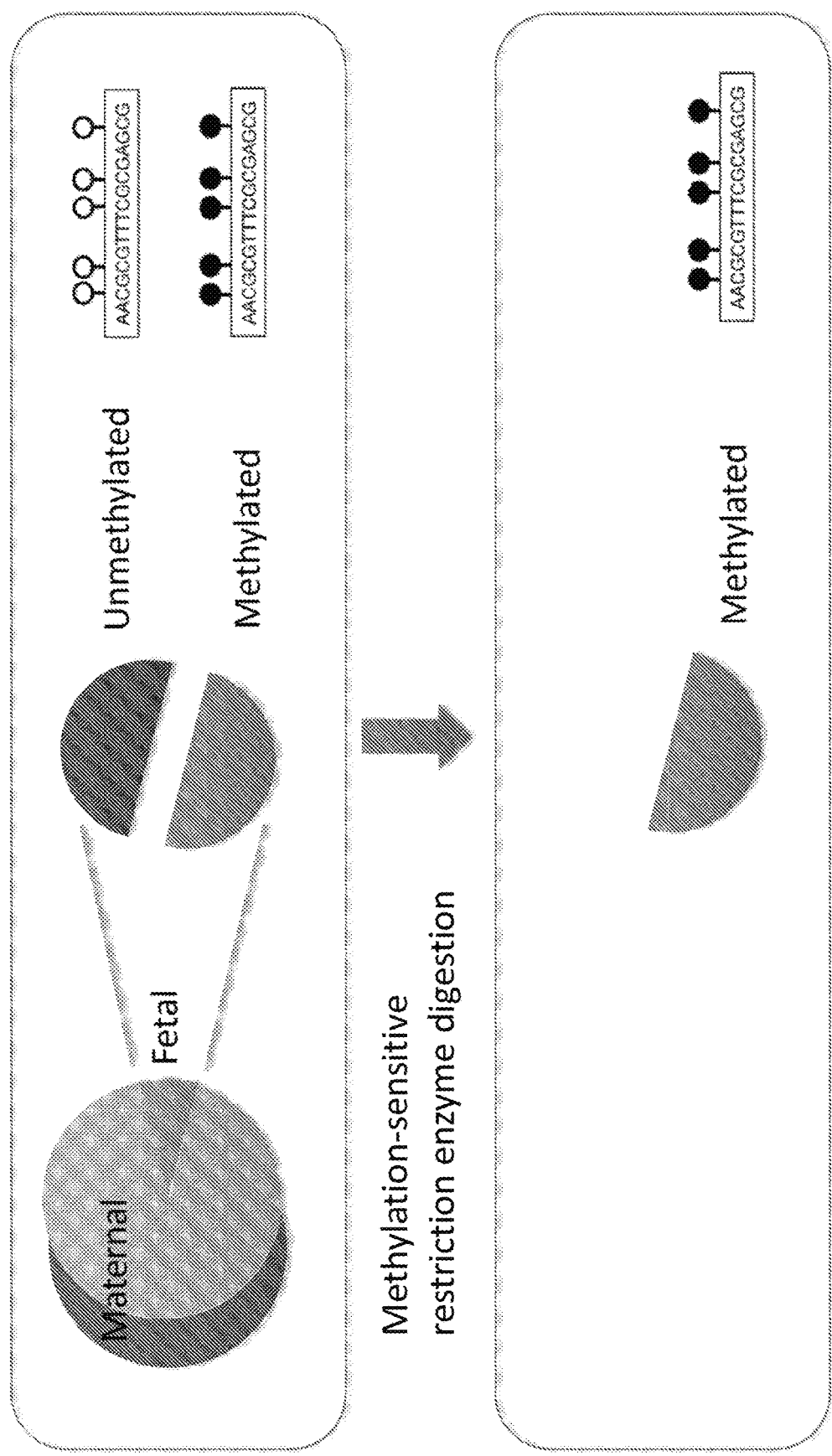
FIG. 2 illustrates a method of the disclosure, in which methylated fetal DNA is isolated from a mixture of methylated fetal and unmethylated maternal DNA.

In some embodiments, nucleic acid samples are digested with enzymes that are methylation-sensitive, for example enzymes that cleave only unmethylated DNA, as illustrated in FIG. 2. In some embodiments, the nucleic acid samples can be digested by enzymes that digest only methylated DNA. In some embodiments, the nucleic acid sample is digested by an enzyme that is methylation-insensitive and that digests both methylated and unmethylated DNA. A sample can be digested in parallel with a methylation-sensitive enzyme and a methylation insensitive enzyme and analyzed to determine which sequences are present following each treatment. Sequences that are present in the first sample but not the second sample indicate that the sequence was methylated. Restriction enzymes that are either sensitive to methylated cytosine or to methylated adenosine can be used in the methods of the disclosure to provide populations of cytosine methylated loci and adenosine methylated loci for comparison.

By selecting appropriate combinations of restriction enzymes (e.g., methylation-sensitive, methylation-dependent, and methylation-insensitive restriction enzymes), the methods of the disclosure can be used to preferentially degrade copies of either fetal or maternal DNA in a mixed sample, depending on the DNA sequence and methylation status.

Suitable methylation-dependent restriction enzymes include, e.g., McrBC, McrA, MrrA, and DpnI. McrBC is an endonuclease which can cleave DNA containing methylcytosine, (e.g., 5-methylcytosine or 5-hydroxymethylcytosine or N4-methylcytosine, reviewed in Raleigh, E. A. (1992) Mol. Microbiol. 6, 1079-1086, which is herein incorporated by reference in its entirety) on one or both strands. In some embodiments, McrBC will not act upon unmethylated DNA (see e.g., Sutherland, E. et al. (1992) J. Mol. Biol. 225, 327-334, which is herein incorporated by reference in its entirety). The recognition site for McrBC can be 5' . . . Pu$^m$C(N$_{40-3000}$)Pu$^m$C . . . 3' where $^m$C designates methylcytosine. Sites on the DNA recognized by McrBC can consist of two half-sites of the form (G/A)$^m$C. These half-sites can be separated by up to 3 kb, but the optimal separation can be 55-103 base pairs (Stewart, F. J. and Raleigh E. A. (1998) Biol. Chem. 379, 611-616 and Panne, D. et al. (1999) J. Mol. Biol. 290, 49-60, each of which is herein incorporated by reference in its entirety). McrBC can use GTP for cleavage, but in the presence of a non-hydrolyzable analog of GTP, the enzyme can bind to methylated DNA specifically, without cleavage (Stewart, F. J. et al. (2000) J. Mol. Biol. 298, 611-622, which is herein incorporated by reference in its entirety). Recombinant McrBC can be available from, for example, New England Biolabs. McrBC can be used to determine the methylation state of CpG dinucleotides. McrBC can act upon a pair of PumCG sequence elements, but can not recognize Hpa II/Msp I sites (CCGG) in which the internal cytosine is methylated. The very short half-site consensus sequence (PumC) can allow a large proportion of the methylcytosines present to be detected.

Suitable methylation-sensitive restriction enzymes include restriction enzymes that do not cut when a cytosine within the recognition sequence is methylated at position C5 such as, e.g., Aat II, Aci I, Acl I, Age I, Alu I, Asc I, Ase I, AsiS I, Bbe I, BsaA I, BsaH I, BsiE I, BsiW L, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mlu I, MapAl I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes include restriction enzymes that do not cut when an adenosine within the recognition sequence is methylated at position N6 such as, e.g., Mbo I. Homologs and orthologs of the restriction enzymes described herein can also be suitable for use in the present disclosure.

In some embodiments, a restriction enzyme is selected from the group consisting of: Aat II, Aci I, Acl I, Afe I, Age I, Asc I, Ava I, BmgB I, BsaA I, BsaH I, BspD I, Eag I, Fse I, Fau I, Hpa II, HinP1 I, Nar I, Hin6I, HapII and SnaB I. Table 1 includes a list of restriction enzymes for which the ability of the restriction enzyme to cleave DNA can be blocked or impaired by CpG methylation.

TABLE 1

List of restriction enzymes whose ability to cleave can be blocked or impeded by CpG methylation.

| Enzyme | Sequence |
|---|---|
| AatII | GACGT/C |
| Acc65I | G/GTACC |
| AccI | GT/MKAC |
| AciI | CCGC(-3/-1) |
| AclI | AA/CGTT |
| AfeI | AGC/GCT |
| AgeI | A/CCGGT |
| AgeI-HF™ | A/CCGGT |
| AhdI | GACNNN/NNGTC |
| AleI | CACNN/NNGTG |
| ApaI | GGGCC/C |
| ApaLI | G/TGCAC |
| AscI | GG/CGCGCC |
| AsiSI | GCGAT/CGC |
| AvaI | C/YCGRG |
| AvaII | G/GWCC |
| BaeI | (10/15)ACNNNNGTAYC(12/7) |
| BanI | G/GYRCC |
| BbvCI | CCTCAGC(-5/-2) |
| BceAI | ACGGC(12/14) |
| BcgI | (10/12)CGANNNNNNTGC(12/10) |
| BcoDI | GTCTC(1/5) |
| BfuAI | ACCTGC(4/8) |
| BfuCI | /GATC |
| BglI | GCCNNNN/NGGC |
| BmgBI | CACGTC(-3/-3) |
| BsaAI | YAC/GTR |
| BsaBI | GATNN/NNATC |
| BsaHI | GR/CGYC |
| BsaI | GGTCTC(1/5) |
| BsaI-HF™ | GGTCTC(1/5) |
| BseYI | CCCAGC(-5/-1) |
| BsiEI | CGRY/CG |
| BsiWI | C/GTACG |
| BslI | CCNNNNN/NNGG |
| BsmAI | GTCTC(1/5) |
| BsmBI | CGTCTC(1/5) |
| BsmFI | GGGAC(10/14) |

TABLE 1-continued

List of restriction enzymes whose ability to cleave can be blocked or impeded by CpG methylation.

| Enzyme | Sequence |
| --- | --- |
| BspDI | AT/CGAT |
| BspEI | T/CCGGA |
| BsrBI | CCGCTC(-3/-3) |
| BsrFI | R/CCGGY |
| BssHII | G/CGCGC |
| BssKI | /CCNGG |
| BstAPI | GCANNNN/NTGC |
| BstBI | TT/CGAA |
| BstUI | CG/CG |
| BstZ17I | GTA/TAC |
| BtgZI | GCGATG(10/14) |
| BtsIMutI | CAGTG(2/0) |
| Cac8I | GCN/NGC |
| ClaI | AT/CGAT |
| DpnI | GA/TC |
| DraIII | CACNNN/GTG |
| DraIII-HF™ | CACNNN/GTG |
| DrdI | GACNNNN/NNGTC |
| EaeI | Y/GGCCR |
| EagI | C/GGCCG |
| EagI-HF™ | C/GGCCG |
| EarI | CTCTTC(1/4) |
| EciI | GGCGGA(11/9) |
| Eco53kI | GAG/CTC |
| EcoRI | G/AATTC |
| EcoRI-HF™ | G/AATTC |
| EcoRV | GAT/ATC |
| EcoRV-HF™ | GAT/ATC |
| FauI | CCCGC(4/6) |
| Fnu4HI | GC/NGC |
| FokI | GGATG(9/13) |
| FseI | GGCCGG/CC |
| FspI | TGC/GCA |
| HaeII | RGCGC/Y |
| HgaI | GACGC(5/10) |
| HhaI | GCG/C |
| HincII | GTY/RAC |

TABLE 1-continued

List of restriction enzymes whose ability to cleave can be blocked or impeded by CpG methylation.

| Enzyme | Sequence |
| --- | --- |
| HinfI | G/ANTC |
| HinP1I | G/CGC |
| HpaI | GTT/AAC |
| HpaII | C/CGG |
| Hpy166II | GTN/NAC |
| Hpy188III | TC/NNGA |
| Hpy99I | CGWCG/ |
| HpyAV | CCTTC(6/5) |
| HpyCH4IV | A/CGT |
| I-CeuI | CGTAACTATAACGGTCCTAAGGTAGCGAA(-9/-13) |
| I-SceI | TAGGGATAACAGGGTAAT(-9/-13) |
| KasI | G/GCGCC |
| MboI | /GATC |
| MluI | A/CGCGT |
| MmeI | TCCRAC(20/18) |
| MspA1I | CMG/CKG |
| MwoI | GCNNNNN/NNGC |
| NaeI | GCC/GGC |
| NarI | GG/CGCC |
| Nb.BtsI | GCAGTG |
| NciI | CC/SGG |
| NgoMIV | G/CCGGC |
| NheI | G/CTAGC |
| NheI-HF™ | G/CTAGC |
| NlaIV | GGN/NCC |
| NotI | GC/GGCCGC |
| NotI-HF™ | GC/GGCCGC |
| NruI | TCG/CGA |
| Nt.BbvCI | CCTCAGC(-5/-7) |
| Nt.BsmAI | GTCTC(1/-5) |
| Nt.CviPII | (0/-1)CCD |
| PaeR7I | C/TCGAG |
| PhoI | GG/CC |
| PI-PspI | TGGCAAAC AGCTATTATGGGTATTATGGGT(-13/-17) |
| PI-SceI | ATCTATGTCGGGTGCGGAGAAAGAGGTAAT(-15/-19) |
| PleI | GAGTC(4/5) |
| PmeI | GTTT/AAAC |
| PmlI | CAC/GTG |

TABLE 1-continued

List of restriction enzymes whose ability to cleave can be blocked or impeded by CpG methylation.

| Enzyme | Sequence |
| --- | --- |
| PshAI | GACNN/NNGTC |
| PspOMI | G/GGCCC |
| PspXI | VC/TCGAGB |
| PvuI | CGAT/CG |
| PvuI-HF™ | CGAT/CG |
| RsaI | GT/AC |
| RsrII | CG/GWCCG |
| SacII | CCGC/GG |
| SalI | G/TCGAC |
| SalI-HF™ | G/TCGAC |
| Sau3AI | /GATC |
| Sau96I | G/GNCC |
| ScrFI | CC/NGG |
| SfaNI | GCATC(5/9) |
| SfiI | GGCCNNNN/NGGCC |
| SfoI | GGC/GCC |
| SgrAI | CR/CCGGYG |
| SmaI | CCC/GGG |
| SnaBI | TAC/GTA |
| StyD4I | /CCNGG |
| TfiI | G/AWTC |
| TliI | C/TCGAG |
| TseI | G/CWGC |
| TspMI | C/CCGGG |
| XhoI | C/TCGAG |
| XmaI | C/CCGGG |
| ZraI | GAC/GTC |

In some embodiments, the DNA sample can be split into equal portions, wherein each portion is submitted to a different amount of partial digestion with McrBC or another methylation-dependent restriction enzyme. The amount of intact locus in the various portions (e.g., as measured by quantitative DNA amplification) can be compared to a control population (either from the same sample representing uncut DNA or equivalent portions from another DNA sample). In embodiments where the equivalent portions are from a second DNA sample, the second sample can have an expected or known number of methylated nucleotides (or at least methylated restriction enzyme recognition sequences) or, alternatively, the number of methylated recognition sequences can be unknown. In the latter case, the control sample will often be from a sample of biological relevance, e.g., from a diseased or normal tissue, etc.

In some embodiments, activation-induced cytidine deaminase (AID) is used as a methylation-sensitive reagent. AID is an enzyme that can deaminate unmethylated cytosines but not methylated cytosines (see Larijani, et al., Mol Immunol. 42(5):599-604 (2005), which is herein incorporated by reference in its entirety). An AID assay can be performed in a short time, about 30 minutes compared to more than 12 hours for a typical bisulfite treatment, there can be fewer steps than the complicated bisulfite treatment, and fewer toxic chemicals can be used. In some aspects DNA can be treated with a combination of AID treatment and bisulfite treatment. This combined approach of the two methods can be used to improve the efficiency of the AID treatment but provide for shorter bisulfite treatment and reduction of the DNA degradation that can be associated with bisulfite treatment.

Repetitive sequences in plant and mammalian genomes are often present in high copy number, have high levels of cytosine and low transcriptional activity (See, e.g., Martienssen, R. A. (1998) Trends Genet. 14:263; Kass, S. U., et al. (1997) Trends Genet. 13:335; SanMiguel, P., et al., (1996) Science 274:765; Timmermans, M. C., et al. (1996) Genetics 143:1771; Martienssen, R. A. and E. J. Richards, (1995) Curr. Opin. Genet. Dev. 5:234-242; Bennetzen, J. L., et al. (1994) Genome 37:565; White, L. F., et al. (1994) Proc. Natl. Acad. Sci. U.S.A. 91:11792; Moore, G., et al. Genomics 15:472, each of which is herein incorporated by reference in its entirety). High copy DNA sequences are frequently methylated and often are not present in areas of expressed genes. Methods that can eliminate or reduce the representation of such high copy methylated DNA from a library or from a nucleic acid sample can be used to enrich for target sequences of interest and result in a sample that has a complexity that is reduced, facilitating further analysis. Often the unmethylated regions are the regions that contain the genes and are of the highest interest for analysis.

A combination of chemical modification and restriction enzyme treatment, e.g., combined bisulfite restriction analysis (COBRA), can be used in the methods disclosed herein.

In another embodiment, methylated DNA can be isolated using chromatin immunoprecipitation. In another embodiment, methylated DNA can be isolated by methylated DNA immunoprecipitation. The methylated DNA immunoprecipitation can comprise use of an antibody. The antibody can be an antibody raised against 5-methylcytosine (5mC) (See e.g., Weber M et al. (2005) Nat. Genet. 37: 853-62).

B. Targets

In some embodiments, a genetic target of interest is detected. In some embodiments, the genetic target is differentially modified in fetal compared to maternal DNA (e.g., the fetal target is hypermethylated while the maternal target is hypomethylated). A genetic target can comprise a genetic locus. In some embodiments, the locus is selected from the group consisting of: RASSF1A, CASP8, RARB, SCGB3A1, DAB2IP, PTPN6, THY1, TMEFF2, and PYCARD. In some embodiments, two loci are analyzed. The first locus can be selected from the group consisting of: RASSF1A, CASP8, RARB, SCGB3A1, DAB2IP, PTPN6, THY1, TMEFF2, and PYCARD. The second locus can be selected from the group consisting of: RNASE P, Beta Actin, SRY, and TERT. In some embodiments, the second locus is hypomethylated. In some embodiments, the genetic target comprises promoter sequence. In some embodiments, the genetic target comprises at least one exon. In some embodiments, the genetic target comprises at least one intron.

In some embodiments, a locus is within ABL1, ABL2, ACSL3, AF15Q14, AF1Q, AF3p21, AF5q31, AKAP9, AKT1, AKT2, ALK, ALO17, APC, ARHGEF12, ARHH, ARNT, ASPSCR1, ASXL1, ATF1, ATIC, ATM, BCL10, BCL11A, BCL11B, BCL2, BCL3, BCLS, BCL6, BCL7A, BCL9, BCR, BHD, BIRC3, BLM, BMPR1A, BRAF, BRCA1, BRCA2, BRD3, BRD4, BRIP1, BTG1, BUB1B, C12 orf9, C15 orf21, CANT1, CARD11, CARS, CBFA2T1, CBFA2T3, CBFB, CBL, CBLB, CBLC, CCND1, CCND2, CCND3, CD74, CD79A, CD79B, CDH1, CDH11, CDK4, CDK6, CDKN2A-p14 ARF, CDKN2A-p16(INK4a), CDKN2C, CDX2, CEBPA, CEP1, CHCHD7, CHEK2, CHIC2, CHN1, CIC, CLTC, CLTCL1, CMKOR1, COL1A1, COPEB, COX6C, CREB1, CREB3L2, CREBBP, CRLF2, CRTC3, CTNNB1, CYLD, D105170, DDB2, DDIT3, DDX10, DDXS, DDX6, DEK, DICER1, DUX4, EGFR, EIF4A2, ELF4, ELK4, ELKS, ELL, ELN, EML4, EP300, EPS15, ERBB2, ERCC2, ERCC3, ERCC4, ERCCS, ERG, ETV1, ETV4, ETVS, ETV6, EVI1, EWSR1, EXT1, EXT2, EZH2, FACL6, FANCA, FANCC, FANCD2, FANCE, FANCF, FANCG, FBXW7, FCGR2B, FEV, FGFR1, FGFR1OP, FGFR2, FGFR3, FH, FIP1L1, FLI1, FLT3, FNBP1, FOXL2, FOXO1A, FOXO3A, FOXP1, FSTL3, FUS, FVT1, GAS7, GATA1, GATA2, GATA3, GMPS, GNAQ, GNAS, GOLGAS, GOPC, GPC3, GPHN, GRAF, HCMOGT-1, HEAB, HEI10, HERPUD1, HIP1, HIST1H4I, HLF, HLXB9, HMGA1, HMGA2, HNRNPA2B1, HOOK3, HOXA11, HOXA13, HOXA9, HOXC11, HOXC13, HOXD11, HOXD13, HRAS, HRPT2, HSPCA, HSPCB, IDH1, IDH2, IGH@, IGK@, IGL@, IKZF1, IL2, IL21R, IL6ST, IRF4, IRTA1, ITK, JAK1, JAK2, JAK3, JAZF1, JUN, KDM5A, KDM5C, KDM6A, KDR, KIAA1549, KIT, KLK2, KRAS, KTN1, LAF4, LASP1, LCK, LCP1, LCX, LHFP, LIFR, LMO1, LMO2, LPP, LYL1, MADH4, MAF, MAFB, MALT1, MAML2, MAP2K4, MDM2, MDM4, MDS1, MDS2, MECT1, MEN1, MET, MHC2TA, MITF, MKL1, MLF1, MLH1, MLL, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYH11, MYH9, MYST4, NACA, NBS1, NCOA1, NCOA2, NCOA4, NF1, NF2, NFIB, NFKB2, NIN, NONO, NOTCH1, NOTCH2, NPM1, NR4A3, NRAS, NSD1, NTRK1, NTRK3, NUMA1, NUP214, NUP98, NUT, OLIG2, OMD, P2RY8, PAFAH1B2, PALB2, PAX3, PAX5, PAX7, PAX8, PBX1, PCM1, PCSK7, PDE4DIP, PDGFB, PDGFRA, PDGFRB, PERI, PHOX2B, PICALM, PIK3CA, PIK3R1, PIM1, PLAG1, PML, PMS1, PMS2, PMX1, PNUTL1, POU2AF1, POU5F1, PPARG, PRCC, PRDM16, PRF1, PRKAR1A, PRO1073, PSIP2, PTCH, PTEN, PTPN11, RAB5EP, RAD51L1, RAF1, RANBP17, RAP1GDS1, RARA, RB1, RBM15, RECQL4, REL, RET, ROS1, RPL22, RPN1, RUNX1, RUNXBP2, SBDS, SDH5, SDHB, SDHC, SDHD, SEPT6, SET, SETD2, SFPQ, SFRS3, SH3GL1, SIL, SLC45A3, SMARCA4, SMARCB1, SMO, SOCS1, SRGAP3, SS18, SS18L1, SSH3BP1, SSX1, SSX2, SSX4, STK11, STL, SUFU, SUZ12, SYK, TAF15, TALI, TAL2, TCEA1, TCF1, TCF12, TCF3, TCL1A, TCL6, TET2, TFE3, TFEB, TFG, TFPT, TFRC, THRAP3, TIF1, TLX1, TLX3 TMPRSS2, TNFAIP3, TNFRSF17, TNFRSF6, TOP1, TP53, TPM3, TPM4, TPR, TRA@, TRB@, TRD@, TRIM27, TRIM33, TRIP11, TSC1, TSC2, TSHR, TTL, USP6, VHL, WAS, WHSC1, WHSC1L1, WRN, WT1, WTX, XPA, XPC, ZNF145, ZNF198, ZNF278, ZNF331, ZNF384, ZNF521, ZNF9, or ZNFN1A1.

C. Measuring Fetal Load and Multiplexing on the Same Fluorescent Channel

When measuring fetal load in cell free plasma, markers of fetal-specific DNA (e.g., Y chromosome markers, paternal SNPs, methyl-digested sequence, etc.) can be measured as well as those of total DNA. Plasma can contain very little DNA and there can be a limit to the amount of blood that can be drawn from a subject; therefore, it can be desirable to use as little DNA as possible to achieve a satisfactory measurement of fetal load.

The amount of plasma used can be decreased by multiplexing several markers of the same type within the same fluorescent channel. Equivalently, the precision of fetal load measurements can be increased if the same volume of plasma is tested using multiplexing techniques disclosed herein. For example, one can simultaneously measure N markers of total DNA on genes of known stable copy number on one channel, and several markers on the Y chromosome on another channel. The concentration of each individual marker does not need to be known, just their combined total, which can be derived directly from the appropriate channel. In one embodiment, the concentration of individual markers is determined. In another embodiment, the combined total concentration of markers on one channel is determined. In another embodiment, the combined total concentration of markers on at least two channels is determined. In another embodiment, the concentration of individual markers is determined, and the total concentration of markers on one or more channels is determined.

D. Amplification and Detection

In aspects of the present disclosure, one or more target sequences are amplified. In some embodiments, one or more of each of a target and reference sequence are amplified. In some embodiments, one or more probes recognizing one or more target and/or reference sequences are amplified. The probes can be, e.g., TaqMan, precircle, padlock, or molecular inversion probes (MIPs) or other probes known in the art or described herein.

An amplification reaction can occur after treatment by the methylation-dependent differential modification process. In some embodiments of this disclosure, the amplification is performed to preferentially amplify a fetal marker of this disclosure that has a particular methylation pattern, such that only the genomic sequence from one particular source, e.g., from the placenta or other tissues of the fetus, is detected and analyzed. In some embodiments, amplification generates a detectable signal that thereby permits detection of the one or more target sequences.

Methods of amplifying specific DNA sequences are known in the art, and include various PCR-based methods of amplification. Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CPPCR) (U.S. Pat. No. 4,437,975), arbitrarily primed polymerase chain reaction (AP-PCR) (U.S. Pat. Nos. 5,413,909, 5,861,245), rolling circle amplification (RCA) (for example, Fire and Xu, PNAS 92:4641 (1995) and Liu et al., J. Am. Chem. Soc. 118:1587 (1996)) and nucleic acid based sequence amplification (NABSA), (See, U.S. Pat. Nos. 5,409,818, 5,554,517, and 6,063,603). Other amplification methods that can be used are described in, U.S. Pat. Nos. 5,242,794, 5,494,810, 4,988,617 and in U.S. Ser. No. 09/854,317, each of which is herein incorporated by reference in its entirety. Other amplification methods are also disclosed in Dahl et al., Nuc. Acids Res. 33(8):e71 (2005) and circle to circle amplification (C2CA) Dahl et al., PNAS 101:4548 (2004), each of which is herein incorporated by reference in its entirety. Locus specific amplification and representative genome amplification methods can also be used.

PCR can be carried out as an automated process with a thermostable enzyme. In this process, the temperature of the reaction mixture is cycled through a denaturing region, a primer annealing region, and an extension reaction region automatically. Machines specifically adapted for this purpose are commercially available. Although PCR amplification of a target polynucleotide sequence (e.g., that of RASSF1A, APC, CASP8, RARB, SCGB3A1, DAB2IP, PTPN6, THY1, TMEFF2, or PYCARD) can be used in practicing the methods of present disclosure, one of skill in the art will recognize that the amplification of a genomic sequence found in a maternal blood sample can be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology can also be used to qualitatively demonstrate the presence of a particular genomic sequence, which represents a particular methylation pattern, or to quantitatively determine the amount of this particular genomic sequence in the maternal blood. For a review of branched-DNA signal amplification for direct quantification of nucleic acid sequences in clinical samples, see Nolte, Adv. Clin. Chem. 33:201-235, 1998, which is herein incorporated by reference in its entirety.

Other techniques for amplification include the methods described in U.S. Pat. No. 7,048,481, which is herein incorporated by reference in its entirety. Briefly, the techniques include methods and compositions that separate samples into small droplets, in some instances with each containing on average less than one nucleic acid molecule per droplet, amplifying the nucleic acid sequence in each droplet and detecting the presence of a particular target sequence. In some embodiments, the sequence that is amplified is present on a probe to the genomic DNA, rather than the genomic DNA itself.

Primers can be designed according to known parameters for avoiding secondary structures and self-hybridization. In some embodiments, different primer pairs will anneal and melt at about the same temperatures, for example, within 1, 2, 3, 4, 5, 6, 7, 8, 9 or 10° C. of another primer pair. In some embodiments, only ligatable probes, and no primers, are initially added to genomic DNA, followed by partitioning the ligated probes, followed by amplification of one or more sequences on the probe within each partition using, for example, universal primers. In some embodiments, greater than 1, 2, 3, 4, 5, 6, 7, 8, 9, 10, 15, 20, 25, 30, 35, 40, 45, 50, 100, 200, 500, 1000, 5000, 10,000 or more probes are initially used. In some embodiments, about 2 to about 10,000, about 2 to about 5,000, about 2 to about 2,500, about 2 to about 1,000, about 2 to about 500, about 2 to about 100, about 2 to about 50, about 2 to about 20, about 2 to about 10, or about 2 to about 6 primers are used. Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Integrated DNA Technologies, Operon Technologies, Amersham Pharmacia Biotech, Sigma, and Life Technologies. The primers can have an identical melting temperature. The melting temperature of a primer can be about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, or 85° C. In some embodiments, the melting temperature of the primer is about 30 to about 85° C., about 30 to about 80° C., about 30 to about 75° C., about 30 to about 70° C., about 30 to about 65° C., about 30 to about 60° C., about 30 to about 55° C., about 30 to about 50° C., about 40 to about 85° C., about 40 to about 80° C., about 40 to about 75° C., about 40 to about 70° C., about 40 to about 65° C., about 40 to about 60° C., about 40 to about 55° C., about 40 to about 50° C., about 50 to about 85° C., about 50 to about 80° C., about 50 to about 75° C., about 50 to about 70° C., about 50 to about 65° C., about 50 to about 60° C., about 50 to about 55° C., about 52 to about 60° C., about 52 to about 58° C., about 52 to about 56° C., or about 52 to about 54° C. The length of a primer can be about, or more than about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases.

Such probes can be able to hybridize to the genetic targets described herein. For example, a mixture of probes can be used, wherein at least one probe targets a specific site on a chromosome and a second probe targets a different site on the same chromosome or a different chromosome. Each set of ligatable probes can have its own universal probe set and be distinguished by the corresponding TaqMan™ probe for each set. Or, all ligatable probe sets can use the same universal primer set and be distinguished by the corresponding TaqMan™ probe for each set.

More particularly, aspects of the present disclosure provide a real-time PCR method for quantitative methylation analysis, comprising producing a non-methylation-specific, conversion-specific target DNA amplification. Products of amplification can be detected by means of the hybridization thereto of two different methylation-specific real-time PCR probes: one specific for the methylated state; and the other specific for the unmethylated state. The two probes can be distinguished, for example, by their bearing different labels (e.g., different fluorescent dyes). A quantification of the degree of methylation is produced within specific PCR cycles employing the ratio of signal intensities of the two probes. Quantification of the degree of methylation is possible without the necessity of determining the absolute DNA quantity.

In some embodiments, methylation-specific primers are used. The design of methylation-specific and non-methylation-specific primers, and the PCR reaction conditions are known in the art (see e.g., U.S. Pat. No. 6,331,393, which is herein incorporated by reference in its entirety; Trinh et al., 2001, which is herein incorporated by reference in its entirety, supra).

In some embodiments, the probes comprise real-time probes (e.g., TaqMan™, etc). Such real-time probes are understood herein to be probes that permit the amplificates to be detected during the amplification process, as opposed to after. Different real-time PCR variants are familiar to persons skilled in the art, and include but are not limited to Lightcycler™, TaqMan™, Sunrise™, Molecular Beacon™ or Eclipse™ probes. The particulars on constructing and detecting these probes are known in the art (see, e.g., U.S. Pat. No. 6,331,393 with additional citations, incorporated by reference herein). The design of the probes is carried out manually, or by means of suitable software (e.g., the "PrimerExpress™" software of Applied Biosystems (for TaqMan™ probes) or via the MGB Eclipse™ design software of Epoch Biosciences (for Eclipse™ probes). In some embodiments, the real-time probes are selected from the probe group consisting of FRET probes, dual-label probe comprising a fluorescence-reporter moiety and fluorescence-quencher moiety, Lightcycler™, TaqMan™, Sunrise™, Molecular Beacon™, Eclipse™, scorpion-type primers that comprise a probe that hybridizes to a target site within the scorpion primer extension product, and combinations thereof. In some embodiments, TaqMan™ probes are used. In some embodiments, TaqMan™ probes are utilized in combination with Minor Groove Binders (MGB).

TaqMan™ probe design can follow the Applied Biosystems design guidelines for the "TaqMan Allelic Discrimination" assay, and both probes have the same 5'-end, which influences the 5'-exonuclease activity of the polymerase. Runs of identical nucleotides (e.g., >4 bases, especially G) can be avoided. In fluorescence based embodiments, a G can be avoided at the probe 5'-end, as G tends to quench the reporter fluorescence). Some embodiments comprise probe sequences containing more Cs than Gs, and the polymorphic site is preferably located approximately in the middle third of the sequence. In some embodiments, the reporter dyes are FAM (carboxyfluorescein) and VIC. A label (fluorophore, dye) used on a probe (e.g., a TaqMan probe) to detect a target nucleic acid sequence or reference nucleic acid sequence in the methods described herein can be, e.g., 6-carboxyfluorescein (FAM), tetrachlorofluorescin (TET), 4,7,2'-trichloro-7'-phenyl-6-carboxyfluorescein (VIC), HEX, Cy3, Cy 3.5, Cy 5, Cy 5.5, Cy 7, tetramethylrhodamine, ROX, and JOE. The label can be an Alexa Fluor dye, e.g., Alexa Fluor 350, 405, 430, 488, 532, 546, 555, 568, 594, 633, 647, 660, 680, 700, and 750. The label can be Cascade Blue, Marina Blue, Oregon Green 500, Oregon Green 514, Oregon Green 488, Oregon Green 488-X, Pacific Blue, Rhodamine Green, Rhodol Green, Rhodamine Green-X, Rhodamine Red-X, and Texas Red-X. The label can be at the 5' end of a probe, 3' end of the probe, at both the 5' and 3' end of a probe, or internal to the probe. A unique label can be used to detect each different locus in an experiment.

A probe, e.g., a Taqman probe, can comprise a quencher, e.g., a 3' quencher. The 3' quencher can be, e.g., TAMARA, DABCYL, BHQ-1, BHQ-2, or BHQ-3. In some cases, a quencher used in the methods provided herein is a black hole quencher (BHQ). In some cases, the quencher is a minor groove binder (MGB, MGBNFQ). In some cases, the quencher is a fluorescent quencher. In other cases, the quencher is a non-fluorescent quencher (NFQ).

A probe can be about, or at least about, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases long. A probe can be about 8 to about 40, about 10 to about 40, about 10 to about 35, about 10 to about 30, about 10 to about 25, about 10 to about 20, about 15 to about 40, about 15 to about 35, about 15 to about 30, about 15 to about 25, about 15 to about 20, about 18 to about 40, about 18 to about 35, about 18 to about 30, about 18 to about 25, or about 18 to 22 bases.

Primers can be prepared by a variety of methods including, but not limited to, cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. In an embodiment, one of the primers of the prime pair is longer than the other primer. In an embodiment, the 3' annealing lengths of the primers, within a primer pair, differ. Also, the annealing position of each primer pair can be designed such that the sequence and length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including, but not limited to, Array Designer Software (Arrayit Inc.), Oligonucleotide Probe Sequence Design Software for Genetic Analysis (Olympus Optical Co.), NetPrimer, and DNAsis from Hitachi Software Engineering.

In some embodiments, the degree of multiplexing to be utilized is informed by the determination of fetal load of the sample and/or the determination of total DNA of the sample. As used herein, the degree of multiplexing is given as a numerical index referring to the number of probes used to detect a single sequence (e.g., a target or reference sequence). In some embodiments, if the fetal load is calculated to be less than 15%, 14%, 13%, 12%, 11%, 10%, 9%, 8%, 7%, 6%, 5%, 4%, 3%, 2%, 1%, 0.5%, 0.4%, 0.3%, 0.2%, or 0.1%, the degree of multiplexing is chosen to be greater than 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 300, 400, 500, or 1000. In some embodiments, if the total DNA is calculated to be less than 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1300, 1400, 1500, 1600, 1700, 1800, 1900, 2000, 3000, 4000, or 5000 genome equivalents, the degree of multiplexing is chosen to be greater than 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 300, 400, 500, or 1000.

A two-color system can be employed for detection of nucleic acids in droplets using universal primers and universal probes without cleavage. A universal probe can comprise two complementary oligonucleotides, one fluorescer probe containing a fluorescent molecule and one quencher probe containing a quenching molecule. Two fluorescer probes can fluoresce at different colors and can be distinguishable in detection. When bound to the quencher probe, the fluorescence intensity of the fluorescer probe is substantially reduced. Additionally, two pairs of universal forward and reverse primers can contain regions that are complementary to the fluorescer probe and promote PCR amplification of a target sequence. In the first round of amplification, the region complementary to the fluorescer probe can be incorporated via the universal primers into the template. In subsequent rounds of amplification, the fluorescer probes can therefore hybridize to this template, rather than to their respective quencher probes. As more of these templates are generated exponentially by amplification reactions, fluorescer-quencher complexes are replaced by fluorescer-template through competitive binding. As a result of this separation between fluorescer probe and quencher probe, fluorescence intensity will increase in the reaction, and can be detected in following steps.

Universal probes can be designed by methods known in the art. In some embodiments, the probe is a random sequence. The universal probe can be selected to ensure that it does not bind the target polynucleotide in an assay, or to other non-target polynucleotides likely to be in a sample (e.g., genomic DNA outside the region occupied by the target polynucleotide).

FRET-based probes (e.g., Lightcycle™, TaqMan™, Sunrise™, Molecular Beacon or Eclipse™ probes) can also be employed.

Following the methylation-dependent differential modification of the DNA, such as chemical modification of DNA in a methylation-specific manner or methylation-sensitive enzymatic digestion, the treated DNA can then subjected to a sequence-based analysis, such that one or more of the relevant genes of the present disclosure (e.g., RASSF1A, APC, CASP8, RARB, SCGB3A1, DAB2IP, PTPN6, THY1, TMEFF2, or PYCARD) from the fetal source can be distinguished from their counterparts from the maternal source, and that the presence and quantity of the fetal gene(s) can be determined and compared to a standard control. Furthermore, once it is determined that one or more of these genes of fetal origin is indeed present in the sample, particularly when the amount of the gene(s) is greater than a predetermined threshold, the sample and its equivalents can be deemed to contain sufficient amount of fetal DNA for further analyses. The quantification of the fetal gene(s) can be used to determine fetal load.

In other embodiments, one can detect and measure the quantity of these particular genes as fetal markers indicative of certain conditions or disorders related to pregnancy, taking advantage of the genes' highly methylated status in contrast to the unmethylated status of their counterparts of maternal origin. For this use, the amount of one or more of the fetal genes selected from RASSF1A, CASP8, RARB, SCGB3A1, DAB2IP, PTPN6, THY1, TMEFF2, and PYCARD in a test sample can be compared to a standard value, where an increase from the standard value indicates the presence or heightened risk of such a pregnancy-associated disorder.

In some embodiments, the degree of methylation of DNA of the biological sample is determined by using one of various means, including, but not limited to, means based on: the fluorescent signal intensities; the first derivative of the fluorescent intensity curves; or the ratio of threshold values at which a given signal intensity will be exceeded. In some embodiments, the degree of methylation of the DNA is determined from the ratio of the signal intensities of two probes.

Signal intensity ratios can be determined during exponential amplification phase of a PCR cycle. Preferably such calculation is carried out close to (or at) the cycle in which the amplification reaches its maximal increase, corresponding to the point of inflection of the fluorescent intensity curve or the maximum of its first derivative. The calculation is thus conducted at a time point which preferably lies at up to five cycles before or after the inflection point, particularly preferably up to two cycles before or after the inflection point, and most particularly preferred up to one cycle before or after the inflection point. In the optimal embodiment, the calculation occurs directly at the inflection point. In embodiments where the inflection points of the two curves (corresponding to the two probes) lie in different cycles, the calculation is preferably conducted at the inflection point of the curve which has the highest signal at this time point.

In some embodiments, the degree of methylation of the DNA can be determined by enumerating the number of partitions (e.g., droplets) emitting a detectable signal above a given threshold intensity.

In particular embodiments, quantification of the degree of methylation is facilitated and optimized by use of standards (standard samples). Specifically, such optimization is conducted using different DNA methylation standards; for example, corresponding to 0%, 5%, 10%, 25%, 50%, 75% and 100% degree of DNA methylation. DNA that covers the entire genomic DNA can be used. Alternately, a representative portion of such DNA can be used as the standard. Standard samples having different degrees of methylation can be obtained by appropriate mixtures of methylated and unmethylated DNA. The production of methylated DNA is relatively simple with the use of SssI methylase, which converts all unmethylated cytosines in the sequence context CG to 5-methylcytosine. Sperm DNA, which provides only a small degree of methylation, can be used as completely unmethylated DNA (see, e.g., Trinh et al., 2001, supra.).

The production of methylation standards is described in great detail, for example, in European Patent Application 04 090 037.5, filed: 5 Feb. 2004; applicant: Epigenomics AG, which is herein incorporated by reference in its entirety). The measured 'methylation rate' can be obtained by calculating the quotient of the signals which are detected for the methylated state and the sum of the signals which are detected for the methylated and the unmethylated state. A 'calibration curve' can be obtained if this quotient is plotted against the theoretical methylation rates (corresponding to the proportion of methylated DNA in the defined mixtures), and the regression line that passes through the measured points is determined. A calibration is conducted preferably with different quantities of DNA; for example, with 0.1, 1 and 10 ng of DNA per batch.

Assays can be suitable for quantification, where the calibration curves for the time point of the exponential amplification provide a y-axis crossing as close as possible to zero. Methylation states that are adjacent should be distinguished by a high Fisher score (preferably greater than 1, and more preferably greater than 3). Additionally, it is advantageous if a y-axis intercept is provided that is as small as possible, and a Fisher score is provided that is as high as possible (preferably greater than 1, and more preferably greater than 3). Preferably, the curves have a slope and a regression close to the value 1. The assays can be optimized in these respects by means of varying the primers, the probes, the temperature program, and the other reaction parameters using standard tests, as will be appreciated by those of skill in the art.

Often, when individual discrete reaction volumes are analyzed for the presence of a genetic abnormality to be tested, the DNA to be analyzed can on average, either be present or absent, permitting so-called digital analysis. The collective number of reaction volumes containing a particular target sequence can be compared to a reference sequence for differences in number. A ratio other than normal (e.g., 1:1) between a target sequence and a reference sequence known to be a diploid sequence is indicative of an aneuploidy. For example, a sample can be partitioned into reaction volumes, such as droplets, such that each droplet contains less than a nominal single genome equivalent of DNA. The relative ratio of the target of interest (e.g., a genetic marker for chromosome 21 trisomy, or related probe) to a reference sequence (e.g., known diploid sequence on chromosome 1, or related probe) can be determined by examining a large number of reaction volumes (e.g., droplets), such as 10,000, 20,000, 50,000, 100,000, 200,000, 500,000 or more. In other embodiments, the reaction volumes, such as droplets, comprise on average one or more target nucleotides (or genomic equivalents) per droplet. In such embodiments, the average copy number of the target nucleotide can be calculated by applying an algorithm, such as that described in Dube et al. (2008) *Plos One* 3(8):

e2876. In some embodiments, the reaction volumes (e.g., dropletse) comprise on average less than 5, 4, 3, 2, or 1 target polynucleotides per droplet.

Bisulfite treatment, AID treatment, and other methods that preferentially mutate an unmethylated nucleotide (e.g., cytosine) allow methylated polynucleotides to be detected by a variety of methods. For example, any method that can be used to detect a SNP can be used; for examples, see Syvanen, Nature Rev. Gen. 2:930-942 (2001), which is herein incorporated by reference in its entirety. Methods such as single base extension (SBE) can be used or hybridization of sequence specific probes similar to allele specific hybridization methods. In another aspect the Molecular Inversion Probe (MIP) assay can be used.

In some embodiments, molecular inversion probes, described in Hardenbol et al., Genome Res. 15:269-275 (2005) and in U.S. Pat. No. 6,858,412, which are herein incorporated by reference in their entiretyies, can be used to determine methylation status after methylation dependent modification. A MIP can be designed for each cytosine to be interrogated. In one aspect, the MIP includes a locus specific region that hybridizes upstream and one that hybridizes downstream of an interrogation site and can be extended through the interrogation site, incorporating a base that is complementary to the interrogation position. The interrogation position can be the cytosine of interest after bisulfite modification and amplification of the region and the detection can be similar to detection of a polymorphism. Separate reactions can be performed for each NTP so extension only takes place in the reaction containing the base corresponding to the interrogation base or the different products can be differentially labeled.

Methods for detection of methylation status are disclosed, for example, in Fraga and Esteller, BioTechniques 33:632-649 (2002) and Dahl and Guldberg Biogerontology 4:233-250 (2003), each of which is herein incorporated by reference in its entirety. Methylation detection using bisulfite modification and target specific PCR have been disclosed, for example, in U.S. Pat. Nos. 5,786,146, 6,200,756, 6,143,504, 6,265,171, 6,251,594, 6,331,393, and 6,596,493, each of which is herein incorporated by reference in its entirety. U.S. Pat. No. 6,884,586 disclosed methods for methylation analysis using nicking agents and isothermal amplification, which is herein incorporated by reference in its entirety.

In some embodiments, the methods and compositions provided herein can be used to identify the blood type of a fetal (or placental) DNA, particularly of the fetal (or placental) DNA in a sample comprising both maternal and fetal (or placental) DNA. In some cases, the blood type is a specific Rh blood type (e.g., RhD, RhC, RhE) or a particular ABO blood type. The RhD status can be RhD positive or RhD negative. If the pregnant woman is RhD positive, there can be no risk of sensitizing the mother due to RhD incompatibility, and no further testing can be required. If the pregnant woman is RhD negative, a test can be performed for the presence of RhD sequence (e.g., exon 7 or exon 10) in the cell-free plasma DNA of the pregnant woman. If RhD signal is detectable in cell-free plasma DNA, the fetus is likely to be RhD positive. No further testing can be required. Prophylatice anti-RhD immunoglobulin or other treatments can be given as clinically indicated. If RhD signal is not detectable in cell-free plasma DNA, RASSF1A and Beta-Actin sequence in an enzyme digested cell-free plasma DNA sample can be detected. If RASSF1A sequence is detectable but Beta-Actin sequence is not detectable, fetal DNA can be present in the cell-free plasma DNA but RhD sequence can be absent. No treatment or anti-RhD can be required. If RASSF1A sequence is not detectable, no fetal DNA can be present in the cell-free plasma DNA, and the process can be repeated with another blood sample. If Beta-Actin signal is positive, an incomplete enzyme digestion can be indicated, and the enzyme digestion of the DNA sample can be repeated and the sample can be tested for RASSF1A and Beta-Actin sequence again.

Anti-RhD treatment can be provided if RhD signal is detectable in cell-free plasma DNA from the pregnant woman and the pregnant woman is RhD negative.

In some embodiments, anti-RhD treatment is not provided where (i) RhD is not detected in cell-free plasma DNA and (ii) RASSF1A is detected when the pregnant woman is RhD negative. In some embodiments, anti-RhD treatment is not provided when (i) RhD signal is not detected in cell-free plasma DNA and (ii) RASSF1A is detected and (iii) Beta-Actin is not detected and (iv) the pregnant woman is RhD negative. In some embodiments, anti-RhD treatment is not provided where (i) RhD signal is not detected in cell free plasma DNA; (ii) RASSF1A is detected; (iii) Beta-Actin is not detected; and (iv) RNAseP is detected and the pregnant woman is RhD negative.

In some embodiments, the methods and compositions provided herein can be used to detect the presence of a particular HLA type, a Y chromosome, or a mutation within a gene in the fetal genome.

In some embodiments, the methods employed herein do not comprise use of mass spectrometry, e.g., MALDI-TOF mass spectrometry.

III. Methods of Detecting Genetic Variations

This disclosure provides methods and compositions for detecting genetic variations, genetic mutations and/or single nucleotide polymorphisms (SNPs) in a biological sample. The methods can involve cleavage of wild-type and/or background nucleic acid.

In one aspect, the present disclosure provides a method for detecting variations in a polynucleotide comprising: (a) incubating a sample with a first restriction enzyme, wherein said sample comprises: (i) a wild-type polynucleotide; and (ii) a mutant polynucleotide that is a mutant form of said wild-type polynucleotide; wherein said first restriction enzyme preferentially digests said wild-type polynucleotide over said mutant polynucleotide; and (b) performing digital PCR on said sample in order to detect said mutant polynucleotide.

In another aspect, the present disclosure provides a method for detecting a target polynucleotide with an allele of interest comprising: (a) incubating a sample with a first restriction enzyme, wherein said sample comprises: (i) a wild-type polynucleotide comprising a target sequence of a first allele of a genetic marker, and (ii) a target polynucleotide comprising a sequence of a second allele of said genetic marker; and wherein the target sequence comprising said first allele forms a recognition sequence of said first restriction enzyme, and the target sequence comprising said second allele does not form a recognition sequence of said first restriction enzyme; and (b) detecting said target polynucleotide by performing digital PCR with said sample to amplify said target sequence.

Figure 8:
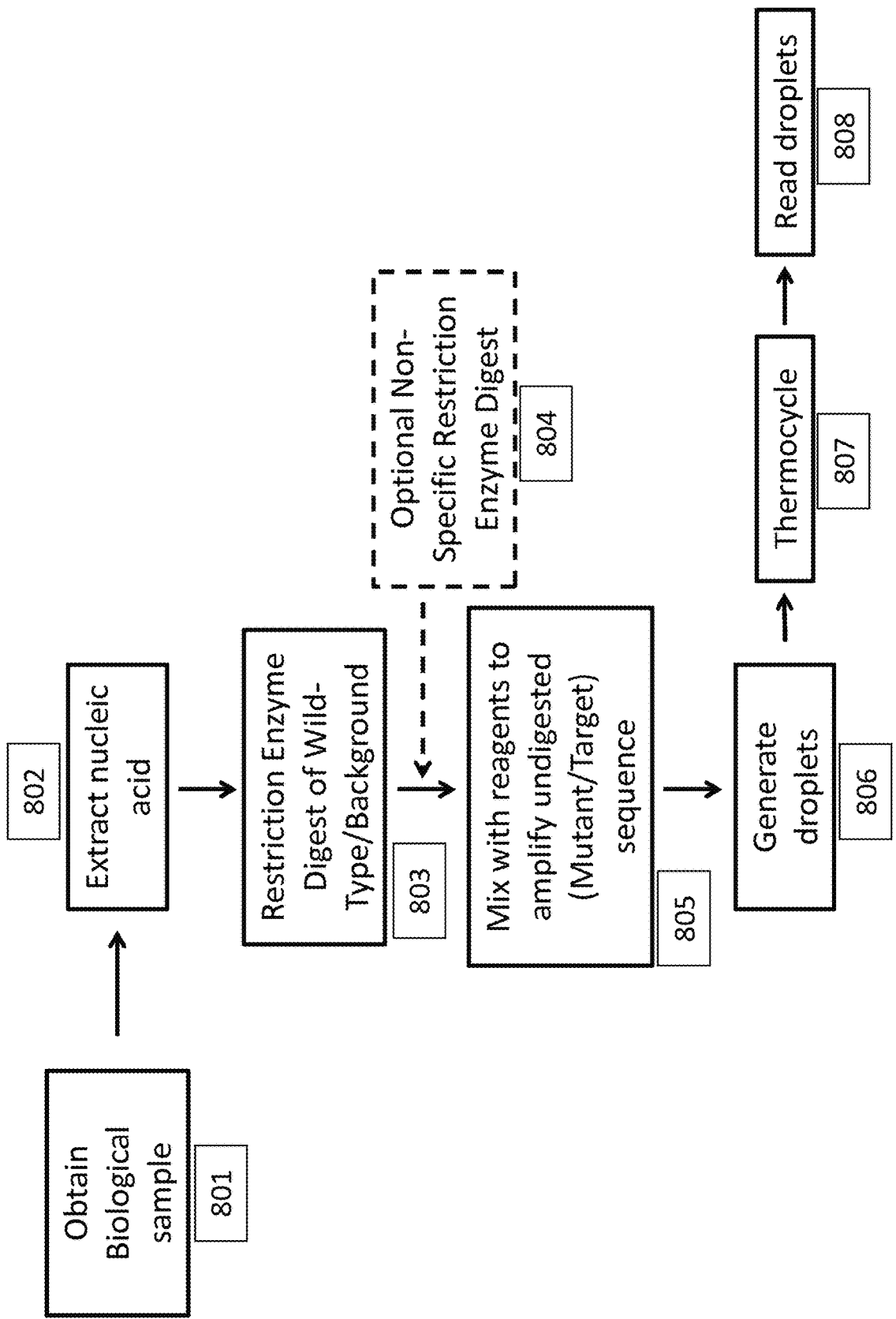
FIG. 8 depicts a workflow of an exemplary method for detecting variants using wild-type targeted restriction enzyme digestion and an optional non-specific restriction enzyme digestion.

The present disclosure provides many different methods for detecting genetic variations, genetic mutations, and/or SNPs, some of which are illustrated in FIG. 8. As shown in FIG. 8, a method can include obtaining a biological sample (801), followed by extraction of nucleic acids (802). The nucleic acid sample can then be subjected to a restriction enzyme digest (803), wherein the restriction enzyme specifically digests the wild-type/background sequence but not the mutant/target sequence. An optional second restriction enzyme digest can be performed (804), wherein the restriction enzyme(s) in the second digest do not digest either the wild-type or background sequence but can digest other nucleic acids in the sample. Following the one or more restriction enzyme digests, the nucleic acids sample can be mixed with reagents for amplification and detection of the undigested mutant/target sequence (805). The detection reagent can be a polynucleotide probe that is complementary to the mutant/target sequence. The detection reagent can be labeled with a fluorescer molecule and a quencher molecule. The nucleic acids sample can then be partitioned into droplets (806) and incubated in a thermocycler (807) to amplify the mutant/target sequence. The amplification can produce a detectable signal, which can be read for individual droplets (808). The presence of a detectable signal can indicate the presence of the mutant/target sequence in the biological sample.

In some embodiments, the restriction enzyme digest of the wild-type DNA occurs before a sample is partitioned, e.g., into droplets. In some embodiments, the restriction enzyme digest of the wild-type DNA occurs after the sample is partitioned, e.g., into droplets. In some embodiments, reagents for restriction enzyme digest and amplification are mixed with a nucleic acid sample. In some embodiments, restriction enzyme digest and amplification occur in a partition, e.g., a droplet.

A single nucleotide polymorphism can generate four alleles of a gene or polynucleotide of interest. In an alternative approach, a sample of nucleic acids extracted from a biological sample can be divided into 4 equal proportions. Each of the portions can be incubated with a restriction enzyme that will specifically digest one of the four alleles. Following the digestion reactions, the portions can be mixed with reagents to amplify the gene or polynucleotide of interest. The four portions can then be partitioned into droplets and incubated in a thermocycler to amplify the gene or polynucleotide of interest. The amplification reaction can produce a detectable signal, which can be read for each of the droplets. In this approach, a decrease in the detectable signal can indicate the presence of the allele targeted by one or the four restriction enzymes. The nucleic acids sample can also be divided into a fifth portion, which can be mock digested. The signal from the mock digested portion can be used as a measure of the total amount of all four alleles of the gene or polynucleotide of interest.

A. Digestion of Background Polynucleotides by Digestion of Mismatched Dimer Pairs The present disclosure provides methods or processes for enzymatically digesting background polynucleotides (e.g., DNA, RNA, etc.) in a sample containing a mixture of background and target polynucleotides. Often, the background polynucleotide comprises a wild-type polynucleotide or sequence (e.g., DNA, RNA) and the target polynucleotide comprises a genetic variation (e.g., SNP, mutation, insertion, transposition, deletion, etc.) of said wild-type sequence. In some cases, the background polynucleotides comprise a first allele of a genetic marker. In some cases, the background polynucleotides comprise two or multiple genetic markers. For example, in some cases, the background polynucleotides comprise a first allele of a first genetic marker, and a first allele of a second genetic marker. In some cases, the background polynucleotides comprise a mixture of alleles of a genetic marker. In some cases, the background polynucleotides comprise a mixture of alleles of a genetic marker; and the target polynucleotides comprise a single allele of said genetic marker. In still other cases, the target polynucleotides comprise two alleles of a genetic marker, or multiple alleles of said genetic marker. In some cases, the target polynucleotides comprise two or more different markers.

Figure 9:
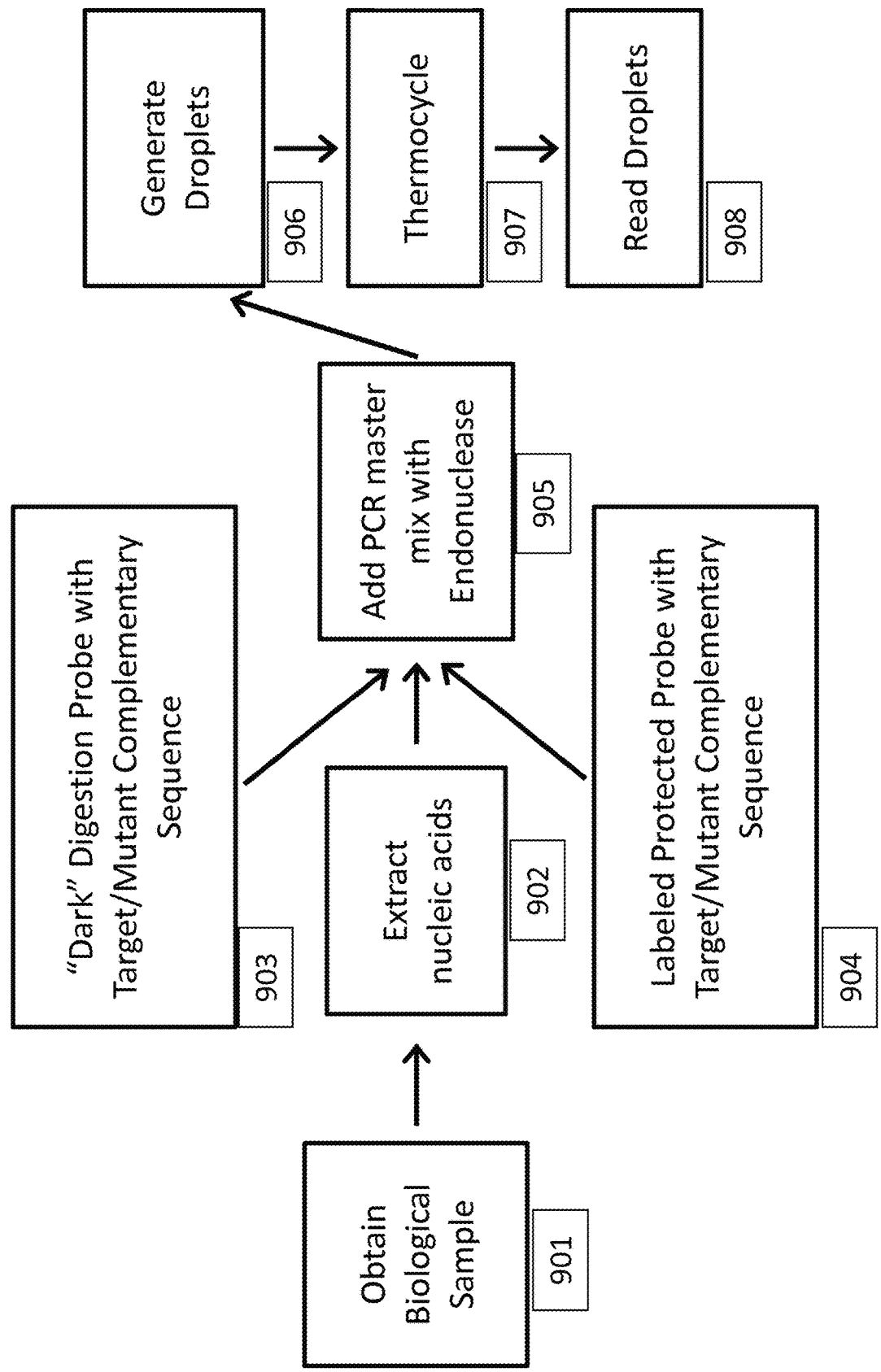
FIG. 9 depicts a workflow of an exemplary method for detecting variants using "dark" and protected labeled probes.

The present disclosure provides many different methods for detecting genetic variations, genetic mutations, and/or SNPs, some of which are illustrated in FIG. 9. As shown in FIG. 9, a method can include obtaining a biological sample (901), followed by extraction of nucleic acids (902). An unlabeled polynucleotide probe ("Dark digestion probe") that is complementary to a target/mutant allele of a genetic marker of interest can be added to the nucleic acids sample (903). The dark digestion probe can form a mismatched dimer with the wild-type/background allele of the genetic marker of interest. In one embodiment, a dark probe can be used to anneal to one strand comprising a target allele and another dark probe can be used to anneal to the complementary strand. A labeled polynucleotide probe that is complementary to the target/mutant allele of the genetic marker of interest can also be added to the nucleic acid sample (904). The labeled polynucleotide probe can have the same sequence as the dark digestion probe. The labeled polynucleotide probe can be protected from digestion by an endonuclease (e.g., by incorporation of Locked Nucleic Acids (LNA) into the probe). An LNA probe can comprise one or more ribose moieties of one or more nucleotides modified with a methylene bridge connecting the 4' carbon and the 2' oxygen, which can lock the ribose in a 3' endo conformation. The labeled polynucleotide probe can be added with the dark digestion probe. Then, the nucleic acids sample can be mixed with reagents for amplification of the target/mutant allele of the genetic marker of interest and an endonuclease (e.g., T7 Endonuclease I) (905). The nucleic acids sample can then be partitioned into droplets (906) and incubated in a thermocycler (907) to amplify the mutant/target sequence. The thermocycling reaction can comprise conditions that allow digestion of mismatched dimers by the endonuclease thus reducing the amount of the wild-type/background allele of the genetic marker of interest in the nucleic acids sample. Alternatively, the endonuclease digestion can be performed prior to droplet generation. The amplification can produce a detectable signal, which can be read for individual droplets (808). The presence of a detectable signal can indicate the presence of the target/mutant allele of the genetic marker of interest in the biological sample. In an alternative method, the dark digestion probe can be added to the nucleic acids sample and the endonuclease reaction performed prior to addition of the labeled probe and downstream processing. In this alternative, a reaction clean up step can be performed to remove the dark digestion probe and/or inactivate/remove the endonuclease before addition of the labeled probe.

In some embodiments, the enzyme digest occurs before the sample is partitioned, e.g., into droplets. In some embodiments, the enzyme digest occurs after the sample is partitioned, e.g., into droplets.

In some embodiments, the detecting step comprises hybridizing a first probe specific to said first allele and a second probe specific to said second allele. In some embodiments, the detecting step comprises hybridizing a first probe specific to said wild-type polynucleotide and a second probe specific to said mutant polynucleotide. In some embodiments, the first probe comprises a first label and the second probe comprises a second label. In some embodiments, the detection probe is a Taqman probe that selectively recognizes the mutant polynucleotide.

Often, the enzymatic digestion method (or process) described herein is used when the target polynucleotides make up a small portion of the total polynucleotides in the sample. In some cases, target polynucleotides make up less than 50%, less than 40%, less than 30%, less than 20%, less than 15%, less than 10%, less than 5%, less than 4%, less than 3%, less than 2%, less than 1%, less than 0.5%, less than 0.1%, less than 0.01%, less than 0.001%, less than 0.0001%, or less than 0.00001% of the sample. In some cases, the target polynucleotide is a rare event.

In some aspects, the enzymatic digestion is an endonuclease digestion (e.g., T7 Endonuclease I digestion). The methods disclosed herein can be used in cases where there is no unique restriction enzyme available that specifically cleaves the background polynucleotides (e.g., DNA) without cleaving the target polynucleotides.

The methods or processes provided herein enable preferential removal of wild-type polynucleotides (or other type of background polynucleotides), thereby enabling or improving detection of mutant target (or genetic variants) that are relatively less represented in the sample.

In some embodiments, the process enables or enhances detection of a specific variant of genetic marker in a sample comprising multiple genetic variants of said genetic marker. In some cases, other types of background polynucleotides can include mutant SNPs and/or a combination of polynucleotides containing mutant SNPs and polynucleotides containing wild-type SNPs. Removal of background polynucleotides that contain a combination of mutant and wild-type SNPs can be useful to identify a specific target genetic variant. A set of background polynucleotides may include: (a) wild-type polynucleotides and (b) two polynucleotides, each with a different SNP variant. (In other cases, the set may include (a) wild-type polynucleotides and (b) either zero or one polynucleotide with a SNP variant.) For example, if the wild-type locus of the SNP comprises an "A" nucleotide and target SNP variant of interest comprises a "G" nucleotide, then the background polynucleotides subject to removal can comprise polynucleotides that contain a wild-type SNP and polynucleotides that comprise two mutant SNPs, such as a SNPs with a T nucleotide variant and a SNP with a C nucleotide variant.

In some embodiments, removal and/or cleavage of background polynucleotides enhances detection of a first allele (or genetic variant) of a genetic marker in samples comprising relatively high quantities of polynucleotides that comprise a second allele (or genetic variant) of a genetic marker.

Figure 10:
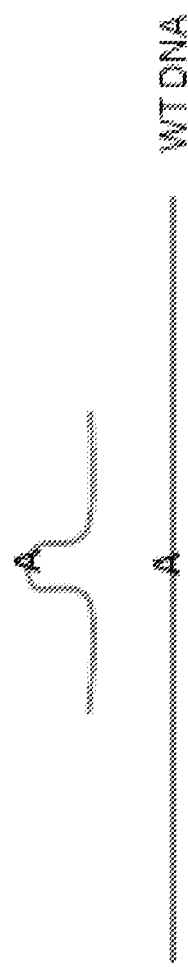
FIG. 10 depicts the hybridization of a "dark" oligonucleotide to the wild-type DNA.

In some embodiments, the digestion probe is an oligonucleotide which is complementary to the background sequence (e.g., a wild-type polynucleotide) except for a single mismatch at the locus of interest (e.g., a SNP site). Once hybridized to a background polynucleotide, the digestion probe forms a duplex with the background polynucleotide that contains a mismatch (e.g., a single base pair mismatch), as illustrated in FIG. 10. In some embodiments, the detection probe is also perfectly complementary to a target sequence. Once hybridized to a target polynucleotide, the digestion probe forms a duplex with the target polynucleotide that is perfectly matched (contains no mismatches).

In general, the digestion probe is not fluorescently labeled (dark oligo; FIG. 10) and does not contribute to fluorescent signal detection (e.g., in droplet digital PCR (ddPCR)). However, in some embodiments, the digestion probe is labeled.

Figure 11:
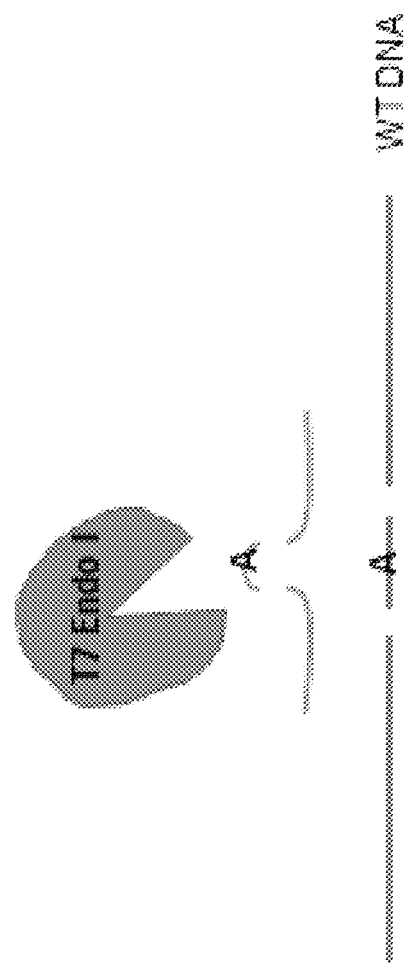
FIG. 11 depicts the digestion of the duplex formed by the "dark" oligonucleotide and the wild-type DNA by an endonuclease. There is a mismatch between the "dark" oligonucleotide and the wild-type DNA that is recognized by the endonuclease.

The methods and process described herein often use an endonuclease that cuts at a single base pair mismatch, such as T7 Endonuclease I, which recognizes and cleaves non-perfectly matched DNA, as illustrated in FIG. 11. The endonuclease (e.g., T7 Endonuclease I) can cleave the detection probe when it is annealed to the background sequence (e.g., wild-type sequence) and contains the mismatch (e.g. a single base pair mismatch). This can result in the cleavage of the wild-type (background) DNA sequence. The cleaved background polynucleotide (e.g., wild-type polynucleotide) can thereby be preferentially removed and thus unlikely to undergo amplification during the amplification process. Also, other enzymes can be substituted for T7 Endonuclease I, such as enzymes that cleave duplexed polynucleotides (e.g., DNA) that comprise at least one mismatched site. The enzyme can be e.g., Surveyor™ nuclease.

The digestion of wild-type DNA (background DNA) can be carried out prior to the PCR reaction. In this scenario, a sample can be prepared by reducing or eliminating the wild-type DNA using restriction enzymes or T7 endonuclease as provided herein, which is then used for a PCR reaction, e.g., droplet digital PCR reaction or digital PCR reaction. However, the digestion reaction can also be combined with the PCR reaction, provided that the activity and specificity of the restriction enzyme or T7 endonuclease can be maintained during the high temperature that is required for the PCR reactions; for example, as illustrated in the exemplary workflow of FIG. 9. For example, for a droplet digital PCR reaction, the digestion reaction may occur prior to partitioning the sample into droplets. In other cases, in a droplet digital PCR reaction, the digestion reaction can occur after the sample is partitioned into droplets. For example, the digestion reaction can occur within the droplets.

In some embodiments, the detecting step comprises performing Taqman or Taqman-type assay with a detection probe that hybridizes to the target polynucleotide with a perfect match. In some cases, the detection probe has the same sequence as the digestion probe. Often, the detection probe is labeled, e.g., fluorescently-labeled.

In general, the detection probe is an oligonucleotide comprising a fluorophore covalently attached to the 5'-end of the oligonucleotide and a quencher at the 3'-end. Different fluorophores (e.g. 6-carboxyfluorescein (FAM), or tetrachlorofluorescin (TET)) and quenchers (e.g. tetramethylrhodamine, (TAMRA), or dihydrocyclopyrroloindole tripeptide minor groove binder (MGB)) can be used in the detection probe. The quencher molecule quenches the fluorescence emitted by the fluorophore when excited by the cycler's light source via FRET (Fluorescence Resonance Energy Transfer). As long as the fluorophore and the quencher are in proximity, quenching inhibits any fluorescence signals.

Figure 12:
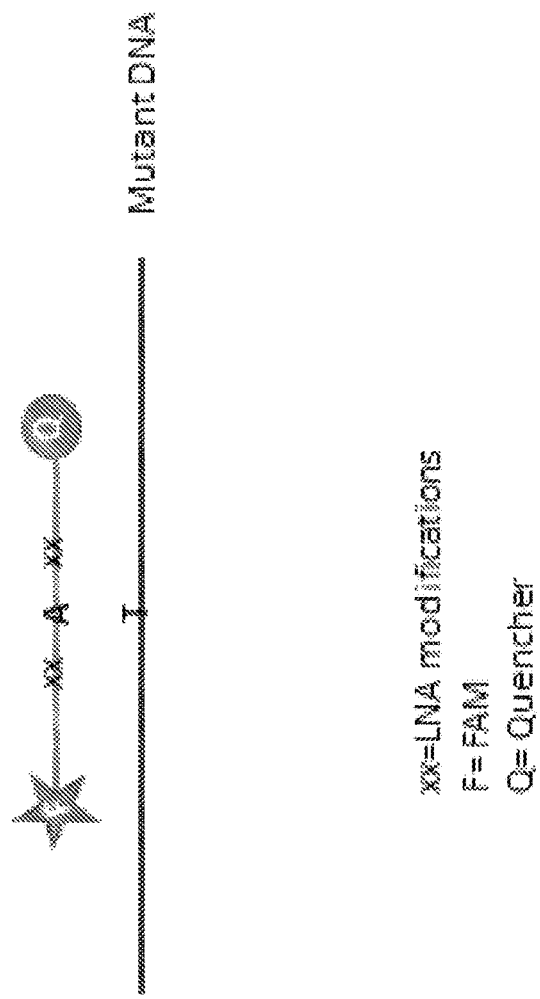
FIG. 12 depicts the hybridization of an LNA modified Taqman mutant probe to the mutant DNA.
Figure 13:
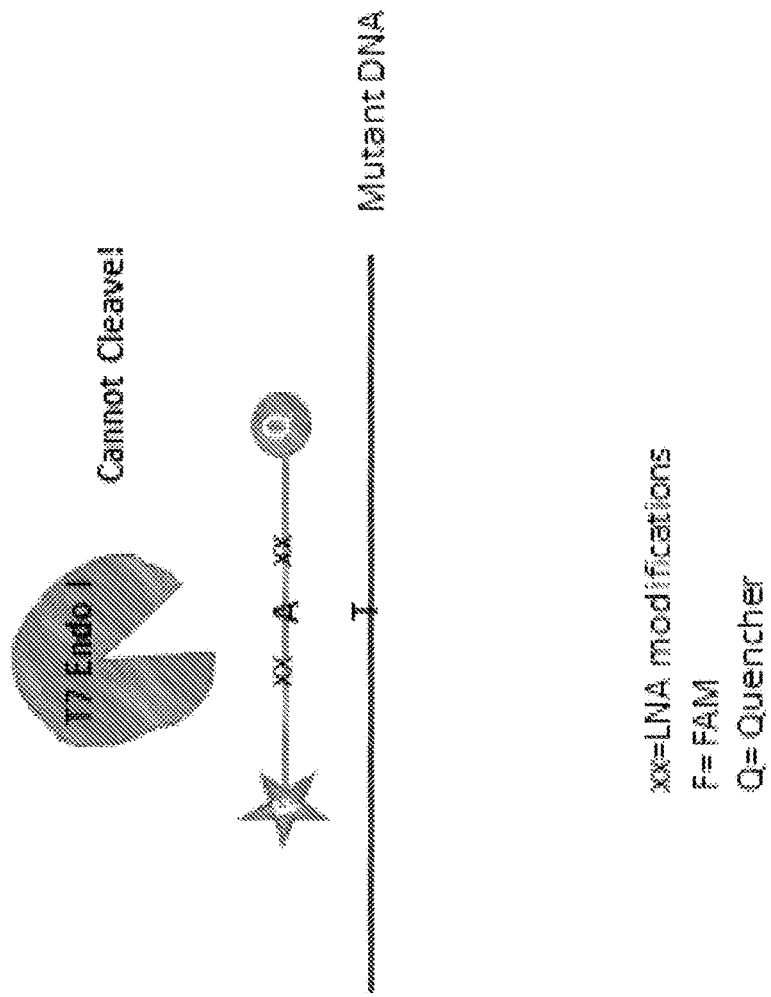
FIG. 13 depicts that an endonuclease cannot digest the duplex formed between an LNA-modified Taqman mutant probe and the mutant DNA. The presence of LNA modifications in the Taqman probe prevent the digestion by the endonuclease.

In some embodiments, the detection probe is modified to be resistant to endonuclease activity. This can be achieved by modifications such as Locked Nucleic Acids (LNA) incorporation in the probe near the SNP base position which would be mismatched with the wild-type sequence. In some cases, the detection probe is resistant to endonuclease cleavage (e.g., T7 Endonuclease I cleavage, etc.). In some cases, the detection probe has the exact sequence of the digestion probe, with the exception of being resistant to T7 Endonuclease I cleavage. The modified detection probe could be used for Taqman detection provided the ends of the probe are not composed of LNA, as illustrated in FIG. 12, which could render the Taqman probe non-cleavable by the Taq polymerase nuclease activity, as illustrated in FIG. 13. The detection probe does not have to necessarily be made with LNA. In some cases, the detection probe is modified in a different manner that renders it resistant to endonuclease cleavage (e.g., T7 Endonuclease I cleavage). In some cases, the detection probe is wholly resistant to endonuclease cleavage (e.g., T7 Endonuclease I cleavage). In some cases, the detection probe is substantially resistant, or partially resistant, to endonuclease cleavage (e.g., T7 Endonuclease I cleavage).

In a Taqman type reaction, the partially LNA-modified detection probe can be combined with the complementary digestion probe ("dark oligo") and an endonuclease (e.g., T7 Endonuclease I). Appropriate PCR primers and reagents for ddPCR may also be included in the reaction. This master mix can then be processed to make droplets and thermal cycled. The droplets are then read for fluorescence resulting from the Taqman partially LNA modified detection probe which is a perfect match for the target sequence and is cleaved via the polymerase in the Taqman reaction.

In some embodiments, the present methods or processes are used to detect a SNP present in sample comprising a relatively large quantity of background DNA. For example, the method may comprise incubating a sample with an endonuclease that recognizes and cleaves non-perfectly matched, double-stranded polynucleotides, wherein said sample comprises: (i) target DNA comprising a SNP of a genetic marker; (ii) background DNA comprising a wild-type version of said genetic marker; and (iii) a digestion probe that perfectly hybridizes to the sequence of said SNP; and (b) detecting said target DNA by performing digital PCR on said sample.

In some aspects, the present disclosure provides a method for detecting a target polynucleotide with an allele of interest, comprising: (a) incubating a sample with an endonuclease that recognizes and cleaves non-perfectly matched, double-stranded polynucleotides, wherein said sample comprises: (i) a polynucleotide comprising a target sequence of a first allele of a genetic marker; (ii) a target polynucleotide comprising a sequence of a second allele of said genetic marker; and (iii) a digestion probe that perfectly hybridizes to the sequence of said second allele within said target polynucleotide; and (b) detecting said target polynucleotide by performing digital PCR with said sample to amplify said target sequence. In one aspect, the present disclosure provides a method for detecting a target polynucleotide with an allele of interest, comprising: (a) incubating a sample with an endonuclease that recognizes and cleaves non-perfectly matched, double-stranded polynucleotides (e.g., DNA), wherein said sample comprises: (i) a wild-type polynucleotide comprising a target sequence of a first allele of a genetic marker; (ii) a target polynucleotide comprising a sequence of a second allele of said genetic marker; and (iii) a digestion probe that hybridizes to said target polynucleotide with perfect match including the sequence of said second allele; and (b) detecting said target polynucleotide by performing digital PCR with said sample to amplify said target sequence.

The methods described herein can have a sensitivity of detection of a mutant sequence about, or at least about 2, 3, 4, 5, 6, 7, 8, 9, 10, 50, 100, 250, 500, 1000, 5000, 10,000, 50,000, 100,000, or 1,000,000 times higher than the sensitivity of detection of the mutant using, e.g., quantitative PCR or real-time PCR. The methods described herein can reduce ambiguity with respect to signal organ in, e.g., a duplex or multiplex reaction. In some embodiments, the methods provided herein can permit sample analysis without the need to reduce the concentration of nucleic acid in a sample by, e.g., 2, 5, 10, 20, 50, 100, 200, 1000, or 10,000 fold.

B. Target Polynucleotide

In one aspect, the present disclosure provides a method for detecting a target nucleic acid molecule.

By "target nucleic acid molecule", "target molecule", "target polynucleotide", "target polynucleotide molecule" or grammatically equivalent thereof, herein is meant a nucleic acid of interest. In one aspect, target nucleic acids disclosed herein can be genomic nucleic acids. DNA derived from the genetic material in the chromosomes of a particular organism is genomic DNA. Target nucleic acids include naturally occurring or genetically altered or synthetically prepared nucleic acids (such as genomic DNA from a mammalian disease model). Target nucleic acids can be obtained from virtually any source and can be prepared using methods known in the art. For example, target nucleic acids can be directly isolated without amplification using methods known in the art, including without limitation extracting a fragment of genomic DNA from an organism (e.g., a cell or bacteria) to obtain target nucleic acids.

"Nucleic acid" or "oligonucleotide" or "polynucleotide" or grammatical equivalents typically refer to at least two nucleotides covalently linked together. A nucleic acid will generally contain phosphodiester bonds, although in some embodiments, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & amp; Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5.235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-0 atom with the 4'-C atom, All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some embodiments. The target nucleic acids can be single stranded or double stranded, as specified, or contain portions of both double stranded or single stranded sequence. Depending on the application, the nucleic acids can be DNA (including genomic and cDNA), RNA (including mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

C. Genetic Markers

In some embodiments, the wild-type polynucleotide is a first allele of a genetic marker and said mutant polynucleotide is a second allele of the genetic marker. Thus, a mutant polynucleotide can be a mutant or variant form of the wild-type polynucleotide with one or more nucleotide sequence changes at a particular locus. The nucleotide sequence changes can comprise a substitution, deletion, and/or insertion of one or more nucleotides. By "genetic marker" herein can be meant a gene or DNA sequence with a known location on a chromosome that can be used to identify cells, individuals or species. A genetic marker can be described as a variation (which may arise due to mutation or alteration in the genomic loci) that can be observed. A genetic marker can be a short DNA sequence, such as a sequence surrounding a single base-pair change (single nucleotide polymorphism, SNP), or a long one, like minisatellites. A genetic marker can be in any gene disclosed herein.

A genetic marker can be associated with a disease, disorder, or condition. The genetic marker can be associated with cancer.

In some embodiments, the wild-type polynucleotide is a portion of a gene. The portion of the gene can be from a coding region or a non-coding region. The wild-type polynucleotide can be a promoter sequence, an exon, or an intron.

In some embodiments, the target sequence is a sequence of a human BRAF gene, EGFR gene, or c-KIT gene. In some embodiments, the wild-type polynucleotide is a sequence of a human BRAF gene, EGFR gene, or c-KIT gene. In some embodiments, the second allele of the genetic marker is V600E of human BRAF. In some embodiments, the mutant polynucleotide is V600E of human BRAF.

FIG. 22 lists examples of allele frequencies and the relative risks of Type 2 diabetes, Crohn's Disease, and rheumatoid arthritis (see U.S. Patent Application Publication No. 20100070455). The SNPs listed in FIG. 22 can be detected using methods described herein. In some embodiments, one or more genetic markers can be a gene disclosed herein, e.g., ABL1, ABL2, ACSL3, AF15Q14, AF1Q, AF3p21, AF5q31, AKAP9, AKT1, AKT2, ALK, ALO17, APC, ARHGEF12, ARHH, ARNT, ASPSCR1, ASXL1, ATF1, ATIC, ATM, BCL10, BCL11A, BCL11B, BCL2, BCL3, BCL5, BCL6, BCL7A, BCL9, BCR, BHD, BIRC3, BLM, BMPR1A, BRAF, BRCA1, BRCA2, BRD3, BRD4, BRIP1, BTG1, BUB1B, C12orf9, C15orf21, CANT1, CARD11, CARS, CBFA2T1, CBFA2T3, CBFB, CBL, CBLB, CBLC, CCND1, CCND2, CCND3, CD74, CD79A, CD79B, CDH1, CDH11, CDK4, CDK6, CDKN2A-p14ARF, CDKN2A-p16(INK4a), CDKN2C, CDX2, CEBPA, CEP1, CHCHD7, CHEK2, CHIC2, CHN1, CIC, CLTC, CLTCL1, CMKOR1, COL1A1, COPEB, COX6C, CREB1, CREB3L2, CREBBP, CRLF2, CRTC3, CTNNB1, CYLD, D105170, DDB2, DDIT3, DDX10, DDXS, DDX6, DEK, DICER1, DUX4, EGFR, EIF4A2, ELF4, ELK4, ELKS, ELL, ELN, EML4, EP300, EPS15, ERBB2, ERCC2, ERCC3, ERCC4, ERCCS, ERG, ETV1, ETV4, ETVS, ETV6, EVI1, EWSR1, EXT1, EXT2, EZH2, FACL6, FANCA, FANCC, FANCD2, FANCE, FANCF, FANCG, FBXW7, FCGR2B, FEV, FGFR1, FGFR1OP, FGFR2, FGFR3, FH, FIP1L1, FLI1, FLT3, FNBP1, FOXL2, FOXO1A, FOXO3A, FOXP1, FSTL3, FUS, FVT1, GAS7, GATA1, GATA2, GATA3, GMPS, GNAQ, GNAS, GOLGAS, GOPC, GPC3, GPHN, GRAF, HCMOGT-1, HEAB, HEI10, HERPUD1, HIP1, HIST1H4I, HLF, HLXB9, HMGA1, HMGA2, HNRNPA2B1, HOOK3, HOXA11, HOXA13, HOXA9, HOXC11, HOXC13, HOXD11, HOXD13, HRAS, HRPT2, HSPCA, HSPCB, IDH1, IDH2, IGH@, IGK@, IGL@, IKZF1, IL2, IL21R, IL6ST, IRF4, IRTA1, ITK, JAK1, JAK2, JAK3, JAZF1, JUN, KDMSA, KDM5C, KDM6A, KDR, KIAA1549, KIT, KLK2, KRAS, KTN1, LAF4, LASP1, LCK, LCP1, LCX, LHFP, LIFR, LMO1, LMO2, LPP, LYL1, MADH4, MAF, MAFB, MALT1, MAML2, MAP2K4, MDM2, MDM4, MDS1, MDS2, MECT1, MEN1, MET, MHC2TA, MITF, MKL1, MLF1, MLH1, MLL, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYH11, MYH9, MYST4, NACA, NBS1, NCOA1, NCOA2, NCOA4, NF1, NF2, NFIB, NFKB2, NIN, NONO, NOTCH1, NOTCH2, NPM1, NR4A3, NRAS, NSD1, NTRK1, NTRK3, NUMA1, NUP214, NUP98, NUT, OLIG2, OMD, P2RY8, PAFAH1B2, PALB2, PAX3, PAX5, PAX7, PAX8, PBX1, PCM1, PCSK7, PDE4DIP, PDGFB, PDGFRA, PDGFRB, PERI, PHOX2B, PICALM, PIK3CA, PIK3R1, PIM1, PLAG1, PML, PMS1, PMS2, PMX1, PNUTL1, POU2AF1, POU5F1, PPARG, PRCC, PRDM16, PRF1, PRKAR1A, PRO1073, PSIP2, PTCH, PTEN, PTPN11, RAB5EP, RAD51L1, RAF1, RANBP17, RAP1GDS1, RARA, RB1, RBM15, RECQL4, REL, RET, ROS1, RPL22, RPN1, RUNX1, RUNXBP2, SBDS, SDH5, SDHB, SDHC, SDHD, SEPT6, SET, SETD2, SFPQ, SFRS3, SH3GL1, SIL, SLC45A3, SMARCA4, SMARCB1, SMO, SOCS1, SRGAP3, SS18, SS18L1, SSH3BP1, SSX1, SSX2, SSX4, STK11, STL, SUFU, SUZ12, SYK, TAF15, TALI, TAL2, TCEA1, TCF1, TCF12, TCF3, TCL1A, TCL6, TET2, TFE3, TFEB, TFG, TFPT, TFRC, THRAP3, TIF1, TLX1, TLX3 TMPRSS2, TNFAIP3, TNFRSF17, TNFRSF6, TOP1, TP53, TPM3, TPM4, TPR, TRA@, TRB@, TRD@, TRIM27, TRIM33, TRIP11, TSC1, TSC2, TSHR, TTL, USP6, VHL, WAS, WHSC1, WHSC1L1, WRN, WT1, WTX, XPA, XPC, ZNF145, ZNF198, ZNF278, ZNF331, ZNF384, ZNF521, ZNF9, and/or ZNFN1A1.

In some embodiments, the copy number ratio between said target polynucleotide and said wild-type nucleotide is less than about 1/10,000, 1/1,000,000, or 1/100,000,000. In some embodiments, the copy number ratio between said target polynucleotide and said wild-type nucleotide is less than about 1/10,000 to 1/100,000,000.

D. Methods of Detection

In another aspect, the present disclosure provides a method for detecting variations in a polynucleotide comprising: (a) incubating a sample with a first restriction enzyme, wherein said sample comprises: (i) a wild-type polynucleotide; and (ii) a mutant polynucleotide that is a mutant form of said wild-type polynucleotide, wherein the number of copies of said mutant polynucleotide is less than 0.1% of the total copies of polynucleotides in the sample; and (b) performing digital PCR on said sample in order to detect said mutant polynucleotide.

In some embodiments, the number of copies of said mutant polynucleotide is less than about 0.0001%, 0.001%, 0.01%, 0.1%, 0.5%, 1%, 5%, or 10% of the total copies of polynucleotides in the sample. The number of copies of the mutant polynucleotide can be about 0.001% to 10%, 0.001% to 10%, 0.001% to 1%, 0.01% to 10%, 0.01 to 1%, or 0.05% to 5% of the total copies of polynucleotides in the sample.

In some embodiments, the mutant polynucleotide is detected with an accuracy of greater than about 60%. In some embodiments, the mutant polynucleotide is detected with an accuracy of greater than about 80%. In some embodiments, mutant polynucleotide is detected with an accuracy of greater than about 90%. The mutant polynucleotide can be detected with an accuracy of greater than about 60, 65, 70, 75, 80, 85, 90, 95, or 100%. The mutant polynucleotide can be detected with an accuracy of about 60-100%, 70-100%, 80-100%, 90-100%, or 95-100%.

In yet another aspect, the present disclosure provides method for detecting variations in a polynucleotide comprising: (a) incubating a sample with a first restriction enzyme, wherein said sample comprises: (i) a wild-type polynucleotide; and (ii) a mutant polynucleotide that is a mutant form of said wild-type polynucleotide, wherein said first restriction enzyme preferentially digests said wild-type polynucleotide over said mutant polynucleotide; and (b) performing digital PCR on said sample in order to detect said mutant polynucleotide.

In another aspect, the present disclosure provides a method for detecting variations in a polynucleotide, comprising: (a) incubating a sample with a reagent, wherein said sample comprises: (i) a wild-type polynucleotide; and (ii) a mutant polynucleotide that is a mutant form of said wild-type polynucleotide, wherein said reagent preferentially digests said wild-type polynucleotide over said mutant polynucleotide; and (b) performing digital PCR on said sample in order to detect said mutant polynucleotide.

In another aspect, the present disclosure provides a population of at least 5,000 emulsified droplets comprising polynucleotides obtained from a maternal sample wherein said maternal sample comprises: (a) fetal DNA comprising a mutant polynucleotide; and (b) maternal DNA comprising a wild-type form of said mutant polynucleotide; and wherein greater than 50% of said emulsified droplets comprise said mutant polynucleotide and wherein each of said emulsified droplets comprises on average one copy of said mutant polynucleotide, or one or fewer copies of said mutant polynucleotide.

The methods described herein provide methods for rare event detection that can yield extremely sensitive results. For example, 1/10,000, up to 1/1,000,000, or up to 1/100,000,000 of the variant/wild-type can be detected. In the total population, at least about 0.1%, 0.05%, 0.01%, 0.005%, or 0.001% of mutant can be detected by the present methods.

When the sample is DNA, which can be viscous, digestion with restriction enzymes can reduce viscosity. Digestion with restriction enzymes can remove the PCR-based competition in the droplet and reduce the cross-reactivity between the probes. The sample for detection can be DNA or RNA (which can be converted to DNA for amplification).

E. Restriction Enzymes

In general a first restriction enzyme recognizes at least one sequence of the target sequence of the wide-type DNA, but does not recognize the target sequence of the mutant DNA to be detected. Thus, when incubating the sample with the first restriction enzyme, the first restriction enzyme can digest the wild-type DNA, including the target sequence. However, the target sequence containing the second allele at the locus of interest is not digested by the first restriction enzyme. Therefore, after the incubation step, only DNA fragments containing the mutant allele (the second allele at the detection locus) are intact, while the wild-type DNA is digested. Preferably, at least about 90%, 95%, 96%, or 100% of the wild-type DNA is digested by the first restriction enzyme. About 90 to 100% of the wild-type DNA can be digested by the first restriction enzyme.

The digestion step can significantly reduce the amount of the wild-type DNA that could be amplified and detected, and thus can increase the sensitivity of the assay.

In some embodiments, the method further comprises incubating said sample with a second restriction enzyme, wherein the wild-type polynucleotide does not contain a recognition site of the second restriction enzyme and wherein the mutant polynucleotide does not contain a recognition site of said second restriction enzyme. In some embodiments, one or more second restriction enzyme is added to an incubation reaction to further increase the sensitivity of the assay. The second restriction enzyme cuts both the wild-type and mutant/variant nucleotide, but only outside the target sequence. This digestion further reduces the amount of wild-type DNA (and nucleotide fragments that are on the same nucleotide as the mutant/variant target sequence but are outside the target sequence to be amplified) that can interfere with the amplification and/or detection step.

In some embodiments, the first restriction enzyme is TspRI. In some embodiments, the second restriction enzyme is Hae III. Other examples of restrictions enzymes that can be used as the first or second restriction enzyme include AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaBI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EaeI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinP1I, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, TaqαI, TfiI, TliI, TseI, Tsp45I, Tsp509I, TspMI, TspRI, Tth111I, XbaI, XcmI, XhoI, XmaI, XmnI, and ZraI.

The one or more restriction enzymes used in the methods, compositions and/or kits described herein can be a component of a hybrid or chimeric protein. For example, a domain of a restriction enzyme comprising an enzymatic activity (e.g., endonuclease activity) can be fused to another protein, e.g., a DNA binding protein. The DNA binding protein can target the hybrid to a specific sequence on a DNA. The nucleic acid cleavage activity of the domain with enzymatic activity can be sequence specific or sequence non-specific. For example, the non-specific cleavage domain from the type IIs restriction endonuclease FoId can be used as the enzymatic (cleavage) domain of the hybrid nuclease. The sequence the domain with the enzymatic activity can cleave can be limited by the physical tethering of the hybrid to DNA by the DNA binding domain. The DNA binding domain can be from a eukaryotic or prokaryotic transcription factor. The DNA binding domain can recognize about, or at least about, 2, 3, 4, 5, 6, 7, 8, 9, 10, 11, 12, 13, 14, 15, 16, 17, 18, 19, 20, 21, 22, 23, 24, or 25 base pairs of continuous nucleic acid sequence. The DNA binding domain can recognize about 9 to about 18 base pairs of sequence. The DNA binding domain can be, e.g., a zinc finger DNA binding domain. The DNA binding domain can be from a naturally occurring protein. The DNA binding domain can engineered to specifically bind any desired nucleotide sequence. The hybrid can be a zinc finger nuclease (e.g., zinc finger nuclease). The hybrid protein can function as a multimer (e.g., dimer, trimer, tetramer, pentamer, hexamer, etc.).

IV. Methods and Compositions for Detecting Cellular Processes.

Described herein are methods and compositions for detecting cellular processes such as viability and growth rates. In some embodiments, the subject methods and compositions relate to detecting polynucleotides in a cellular sample using digital PCR (e.g., droplet digital PCR). Aliquots from the cellular sample can be taken at two time points, or over a period of time with many or several time points. The cellular sample can comprise a variety of cells and/or microbes including organisms, eukaryotic cells, prokaryotic cells, or viruses.

Figure 14:
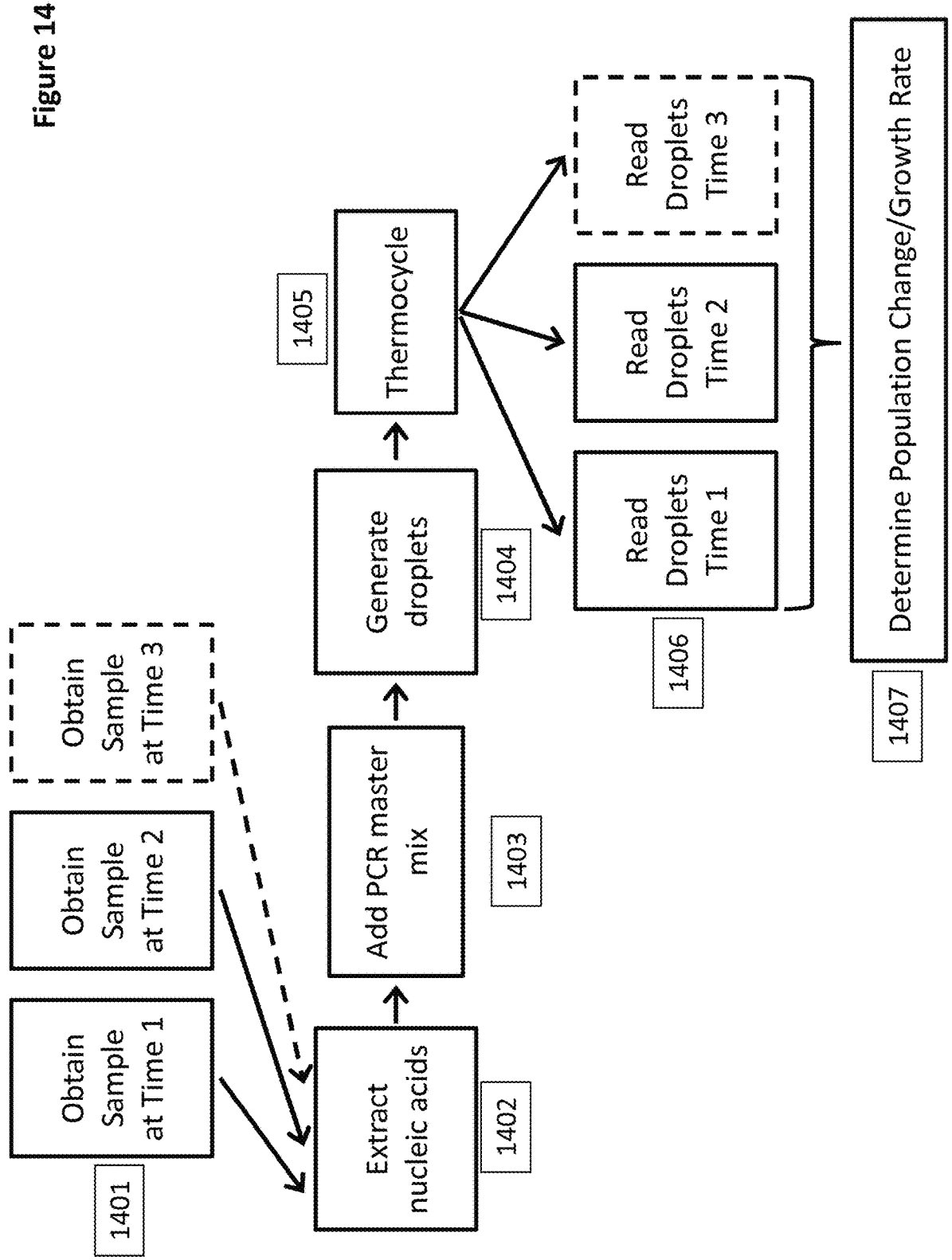
FIG. 14 depicts a workflow of an exemplary method for measuring growth of a cellular population.

The present disclosure provides many different methods for detecting cellular processes such as viability and growth rates, some of which are illustrated in the workflow diagram of FIG. 14. As shown in FIG. 14, a method can comprise obtaining two or more samples at different times (1401). The individual samples can be processed to extract nucleic acids (1402) which can be mixed with reagents to amplify one or more target sequences or biomarkers (1403). The target sequences and or biomarkers can be specific for a particular cell type or organism (e.g., the biomarkers can be specific for a pathogen or a type of cancer). The nucleic acids sample can then be partitioned into droplets (1404) and incubated in a thermocycler (1405) to amplify the one or more target sequences or biomarkers. The amplification can produce a detectable signal which can be read for individual droplets (1406). The change in the level of the one or more target sequences or biomarkers can be used to detect cellular processes such as growth rates or viability (1407).

The subject methods and compositions can be used to determine the quantity or concentration of polynucleotides over time; and the relative differences in polynucleotide quantity or concentration can be monitored, evaluated or quantified. In some embodiments, two or more measurements of polynucleotide quantity or concentration are compared against each other in order to determine whether there is an increase or decrease in polynucleotide quantity or concentration. An increase in polynucleotide quantity or concentration can indicate growth of an organism, and a decrease can indicate a reduction of viability of the organism, or reduction in infection of a patient. A reduction in polynucleotide concentration or quantity can also indicate the efficacy of a test agent, e.g., a test antibiotic, for killing or slowing the growth of a microorganism.

The antibiotic can be, e.g., amanfadine hydrochloride, amanfadine sulfate, amikacin, amikacin sulfate, aminoglycosides, amoxicillin, ampicillin, ansamycins, bacitracin, beta-lactams, candicidin, capreomycin, carbenicillin, cephalexin, cephaloridine, cephalothin, cefazolin, cephapirin, cephradine, cephaloglycin, chloramphenicols, chlorhexidine, chlorhexidine gluconate, chlorhexidine hydrochloride, chloroxine, chlorquinaldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erythromycin stearate, farnesol, floxacillin, gentamicin, gentamicin sulfate, gramicidin, griseofulvin, haloprogin, haloquinol, hexachlorophene, iminocyldline, iodate, iodine, iodochlorhydroxyquin, kanamycin, kanamycin sulfate, lincomycin, lineomycin, lineomycin hydrochloride, macrolides, meclocycline, methacycline, methacycline hydrochloride, methenamine, methenamine hippurate, methenamine mandelate, methicillin, metronidazole, miconazole, miconazole hydrochloride, microcrystalline and nanocrystalline particles of silver, copper, zinc, mercury, tin, lead, bismuth, cadmium and chromium, minocycline, minocycline hydrochloride, mupirocin, nafcillin, neomycin, neomycin sulfate, netilmicin, netilmicin sulfate, nitrofurazone, norfloxacin, nystatin, octopirox, oleandomycin, orcephalosporins, oxacillin, oxytetracycline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, streptomycin, sulfonamide, tetracyclines, tetracycline, tobramycin, tobramycin sulfate, triclocarbon, triclosan, trimethoprim-sulfamethoxazole, tylosin, vancomycin, yrothricin and derivatives, esters, salts and mixtures thereof.

The concentration of any of the antibiotics used in a sample, a clinical sample can be about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 450, 500, 550, 600, 650, 700, 750, 800, 850, 900, 950, 1000, 2000, 3000, 4000, or 5000 μg/ml. The antibiotic concentration can be, e.g., about 1 μg/ml to about 1000 μg/ml, about 1 μg/ml to about 750 μg/ml, about 1 μg/ml to about 500 μg/ml, about 1 μg/ml to about 250 μg/ml, about 1 μg/ml to about 150 μg/ml, about 1 μg/ml to about 100 μg/ml, about 1 μg/ml to about 50 μg/ml, about 1 μg/ml to about 25 μg/ml, about 1 μg/ml to about 15 μg/ml, about 1 μg/ml to about 10 μg/ml, about 1 μg/ml to about 5 μg/ml, about 10 μg/ml to about 1000 μg/ml, about 10 μg/ml to about 750 μg/ml, about 10 μg/ml to about 500 μg/ml, about 10 μg/ml to about 250 µg/ml, about 10 µg/ml to about 150 µg/ml, about 10 µg/ml to about 100 µg/ml, about 10 µg/ml to about 75 µg/ml, about 10 µg/ml to about 50 µg/ml, about 10 µg/ml to about 25 µg/ml, or about 10 µg/ml to about 15 µg/ml. The growth rate of a microorganism at different concentrations of one or more antibiotics in the sample can be determined using methods described herein. The methods can be used to identify one or more antibiotics that reduce or stop growth of a microorganism in, e.g., a clinical sample.

The number of antibiotics that can be added to a sample can be, e.g., at least 1, 2, 3, 4, 5, 6, 7, 8, 9, or 10. If more than one antibiotic is added to a sample, the antibiotics can have the same or different concentrations in the sample.

The cellular sample can be a clinical sample. In some embodiments, a clinical sample is incubated and monitored over time. In other embodiments, clinical samples are obtained from a patient at different points in time in order to monitor the course of disease, or the treatment to the disease. In some embodiments, the cellular sample comprises microbes. For example, the cellular sample can be obtained from a patient suspected of having an infectious disease, or being treated for an infectious disease. The methods and compositions can also be used to detect or monitor free viruses or viral infections, particularly the course of a viral infection over time.

In some embodiments, the methods provided herein are used to monitor an infection. In some embodiments, samples are measured at one or more time-points post infection, e.g., about, or more than about, 6 hrs, 12 hrs, 18 hrs, 24 hrs, 36 hrs, 48 hrs, 60 hrs, 72 hrs, 96 hrs, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 40 days, 50 days, 60 days, 70 days, 80 days, 90 days, 100 days, 120 days, 140 days, 160 days, 180 days, 200 days, 220 days, 240 days, 260 days, 280 days, 300 days, 320 days, 340 days, 360 days, or more post-infection. In some embodiments, the number of samples analyzed from a subject per day can be about, or more than about 1, 2, 3, 4, 5, 6, 7, 8, 9, 10, 11, 12, 13, 14, 15, 16, 17, 18, 19, 20, 21, 22, 23, or 24 samples per day. In some embodiments, the duration of time between samples being taken from a subject is about, or more than about 5 min, 10 min, 15 min, 20 min, 25 min, 30 min, 35 min, 40 min, 45 min, 50 min, 55 min, 60 min, 1 hr, 1.5 hr, 2 hr, 2.5 hr, 3 hr, 3.5 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr, 24 hr, 48 hr, 72 hr, or 96 hr.

In some embodiments, the methods provided herein can be used to determine the presence of a microorganism in a subject within less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 50, 56, 60, 72, 80, 90, 96, 100, 120, 140, 150, 180, 200, or 240 hrs from when the subject is infected with the microorganism. In some embodiments, the methods provided herein can be used to monitor an infection when a subset of the microorganisms to be detected are nonviable or dead, for example when at least 5%, 10%, 20%, 30%, 40%, 50%, 60%, 70%, 80%, 90% of the microorganisms of interest are nonviable or dead.

In some embodiments, the methods provided herein can be used to determine the viability of microorganisms in a sample. In some embodiments, the viability is at least 5%, 10%, 20%, 30%, 40%, 50%, 60%, 70%, 80%, 90% or 100%.

In some embodiments, the presence of nonviable or dead microorganisms does not effect the ability to detect viable microorganisms.

In some embodiments, the methods provided herein are used to monitor a bioterrorist attack. In some embodiments, the methods provided herein are used to monitor a pandemic or an epidemic. In some embodiments, the methods provided herein are used near locations that are anticipated to be bioterrorist targets or locations suspected to be sources of microorganisms that can cause pandemics or epidemics.

The methods and compositions herein enable detection of even small changes in polynucleotide (e.g., DNA, RNA, mitochondrial DNA, etc.) quantity or concentration. Such detection is very sensitive. In some embodiments, the present methods and compositions detect differences of polynucleotide (e.g., DNA, RNA, mitochondrial DNA, etc.) quantity or concentration of less than about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11-fold between two samples. In some embodiments, the present methods and compositions detect differences of polynucleotide (e.g., DNA, RNA, mitochondrial DNA, etc.) quantity or concentration of less than 3, 4, 5, or 6-fold. In some embodiments, the present methods and compositions detect differences of polynucleotide (e.g., DNA, RNA, mitochondrial DNA, etc.) quantity or concentration of less than 1-fold, and other very small changes in quantity or concentration. In some embodiments, a difference of less than 5-fold in polynucleotide concentration or quantity is detected. The difference in quantity or concentration between two time points, e.g., an early and a later time point, can be a fold-decrease or a fold-increase. For example, the present methods and compositions can detect less than about 1.5, 2, 2.5, 3, 3.5, 4, 4.5, 5, 5.5, 6, 6.5, 7, 7.5, 8, 8.5, 9, 9.5, 10, 10.5, 11-fold increase between two samples, or—fold decrease between two samples. In some embodiments, the present methods and compositions detect less than about a 0.1%, 0.2%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, or 25% increase between the first and second sample (or sample from time point one versus time point two). For example, if the first sample has a concentration of 4 copies per µL and the second sample has a concentration of 5 copies per µL, that would be equal to a 25% increase in concentration, and that difference is detected using the present methods and compositions. In some embodiments, the present methods and compositions detect less than a 20% increase in polynucleotide quantity or concentration between the first and second sample. In some embodiments, the present methods and compositions detect less than about a 0.1%, 0.2%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, or 25% decrease between the first and second sample (or sample from time point one versus time point two).

The subject methods and compositions enable rapid measurement of cellular processes, such as cellular viability and or growth rates. In some embodiments, the cellular incubation time needed to obtain a result is relatively low. For example, in some embodiments, the disclosure provides methods that enable detection of a change in polynucleotide quantity or concentration between time point one (early) and time point two (later), wherein time point one occurs less than about 0.1, 0.5, 0.75, 1, 2, 3, 4, 5, 6, 7, 8, 9, 10, 15, 20, 25, 30, 35, 40, 45, 50, 55 or 60 minutes prior to time point two. In some embodiments, the disclosure provides methods that enable detection of a change in polynucleotide quantity or concentration between time point one and time point two, wherein time point one occurs less than about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 15, 16, 17, 18, 19, 20, 21, 22, 23, 24, 25, 26, 27, 28, 29, 30, 35, 40, 42, 44, 46, or 48 hours prior to time point two.

In some embodiments, the subject methods and compositions reduce the total analysis time needed to analyze a change in polynucleotide (e.g., DNA, RNA, mitochondrial DNA, etc.) quantity or concentration. In some embodiments, the period between time point one and obtaining a result indicating a change, is less than about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 15, 16, 17, 18, 19, 20, 21, 22, 23, 24, 25, 26, 27, 28, 29, 30, 35, 40, 42, 44, 46, or 48 hours after time point one or after time point two. For example, ddPCR is coupled with an antibiotic panel (or a single antibiotic) and appropriate PCR assays in order to detect antibiotic susceptibility of a cellular population in less than 4h. In other embodiments, antibiotic susceptibility is detected in less than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 21, 22, 23, 24, 25, 26, 27, 28, 29, 30, 35, 40, 42, 44, 46, or 48 hours.

In some embodiments, the subject methods and compositions involve the use of a small sample size, or small aliquots of a cellular sample. For example, the starting culture can be less than about 0.0000001, 0.000001, 0.00001, 0.0001, 0.001, 0.01, 0.1, 1.5, 2, 2.5, 3, 3.5, 4, 4.5, 5, 5.5, 6, 6.5, 7, 7.5, 8, 8.5, 9, 9.5, or 10 ml in total volume.

In some embodiments, the subject methods and compositions provide highly accurate results (or data) regarding changes in polynucleotide quantity or concentration. In some embodiments, the subject methods and compositions are practiced with a minimal number of replicate samples. For example, the subject methods and compositions can be practiced with less than 1, 2, 3, 4, 5, 6, 7, 8, 9, 10, or 15 replicates of the original sample. In some embodiments, the subject methods and compositions do not require that the original sample undergo a dilution series. In some embodiments, less than 2-, 3-, 4-, 5-, 6-, 7-, 8-, 9-, 10-, 15-, or 20-fold dilution series are used in the subject methods and compositions. In some embodiments, no dilution series are necessary in the subject methods and compositions. In some embodiments, the subject methods and compositions yield results that are very accurate and have a low error rate. For example, the error rate can be less than 0.1%, 0.2%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, or 25%.

The subject methods and compositions can be performed with minimal statistical analysis. For example, the Most-Probable Number (MPV) statistical method may or may not be used in the subject methods and compositions.

A. Applications

The subject methods and compositions can be used in a large variety of applications. In some embodiments, the subject methods and compositions are used in order to monitor cellular growth rates. An increase in quantity and/or concentration of polynucleotide (e.g., DNA, RNA, mitochondrial DNA, etc.) over time can be detected using the subject methods and compositions. Such an increase can indicate that the cellular population (eukaryotic cells, microbial cells, prokaryotic cells, etc.) is growing. Plotting the increase in quantity or concentration of polynucleotides can enable calculation of the rate of growth. Such growth rate studies can be used to monitor the growth of cells growing in culture, or the progress of an infection in a subject. Such growth rate studies can also be used to measure microbial antibiotic susceptibility and resistance. An in vitro sample of microbes (e.g., bacteria) can be treated with an antibiotic of interest; then the growth rate of the microbes is monitored in order to determine the effect, if any, the antibiotic of interest has on the growth rate of the microbes of interest.

Such studies can be performed using high-throughput assays known in the art in order to identify drug candidates as well. For example, a panel of drugs (or test agent) is screened in order to identify a drug of interest that stop or reduces the growth rate of cells (e.g., bacteria, microbes, etc.). In some embodiments, a panel of drugs (or test agents) is screened in order to identify a drug of interest that increases the growth rate of cells, e.g., an effort to identify a compound that promotes healthy gastrointestinal flora. In some embodiments, a panel of drugs (or test agents) is screened against cells (e g., mammalian cells) infected with a virus (or other microbe), in order to identify a drug or test agent that can suppress a viral infection (or other microbial infection). In such viral studies (or microbial studies), a viral polynucleotide (e.g., DNA, RNA, mitochondrial DNA, etc.) (or microbial polynucleotide) is monitored over time in order to determine the growth rate of the virus, or the rate of infection. In yet another example, a panel of drugs can be screened against a specific cell-type (e.g., a cancerous mammalian cell), and then the rate of growth of the cancerous cell can be monitored by detecting cellular polynucleotides over time using the present methods and compositions. In yet another example, a panel of drugs or test agents can be screened against a specific cell-type (e.g., a mammalian cell, mammalian hepatocyte), and then cellular viability can be monitored over time by detecting cellular polynucleotides using the present methods and compositions. In such a manner, drugs or test agents that cause cellular toxicity can be identified. In yet other embodiments, effects on cell growth are measured while altering drug dosages, chemical concentrations and environmental conditions (e.g., temperature and atmosphere) over time.

The subject methods and compositions can also be used to identify microbial susceptibility and/or resistance to a specific drug (e.g., antibiotic). Microbes (e.g., clinical isolates) can be cultured and then treated with a specific drug (e.g., antibiotic). Following treatment, the growth rate of the microbes can be monitored in order to determine whether the microbe is susceptible or resistant to the specific drug. In some embodiments, one sample is taken prior to treatment and one sample is taken following treatment of the sample with the antibiotic or other drug. In other embodiments, one sample is taken prior to treatment and then multiple samples are taken following treatment of the sample with the antibiotic or other drug.

In some embodiments, clinical samples can be obtained from a patient at different time points, for example before and after the patient is treated with an antibiotic or other drug, and then the concentration of microbial polynucleotides can be compared in these samples in order to determine whether the patient is responding to the antibiotic. In some embodiments, one sample is taken prior to treatment and one sample is taken following treatment of the patient with the antibiotic or other drug. In other embodiments, one sample is taken prior to treatment and then multiple samples are taken following treatment of the patient with the antibiotic or other drug. The clinical samples can be obtained from normal patients, patients at risk for having a disease or disorder (e.g., infectious disease), patients with a specific disease, patients with an infectious disease, patients with an infectious disease and undergoing drug treatment. The subject methods and compositions can be used to monitor the course of an infection in a subject who has not been treated with a specific antibiotic, or to monitor the effectiveness of a drug, e.g., an antibiotic, against such infection. The subject methods and compositions can also be used to monitor the course of a viral infection, such as by identifying increases or decreases in viral load.

The subject methods and compositions can also be used to identify the efficacy of spore and cellular decontamination efforts, or sterilization efforts. For example, samples, or swabs from a surface before and after decontamination or sterilization are obtained. Such samples or swabs can then be analyzed using the subject methods and compositions to evaluate the presence of spore or cellular contamination and the extent to which such contamination is eliminated. The subject methods and compositions can also be used to detect whether a release of microbes has occurred, for example an accidental release from an industrial or academic laboratory, or a release resulting from an act of biological terrorism or biowarfare.

B. Cells and Viruses

The cellular sample can comprise a homogenous or heterogeneous population of cells. The cells can be microbial cells, bacterial cells, or eukaryotic cells. Often, the cells are mammalian cells (e.g., human cells). In some embodiments, the cells are non-human mammalian cells. In some embodiments, the cells are microbial cells that can be used in bioterrorism or biowarfare attacks, for example anthrax (or *Bacillus anthracia*). In some embodiments, the present methods and compositions are used to detect cells, or fragments thereof, that are pathogenic (e.g., *Staphylococcus aureus*, Methicillin resistant *Staphylococcus aureus* (MRSA), Methicillin-Sensitive *Staphylococcus Aureus* (MSSA), *Mycobacterium tuberculosis* (MTB), multi-drug resistant strains of *Mycobacterium tuberculosis*). Other bacterial cells (or fragment of such cells) that can be detected include: *Escherichia coli, Salmonella, Shigella, Klebsiella, Pseudomonas, Pseudomonas aeruginosa, Listeria monocytogenes, Mycobacterium aviumintracellulare, Yersinia, Francisella, Pasteurella, Brucella,* Clostridia, *Bordetella pertussis, Bacteroides, Staphylococcus aureus, Streptococcus pneumonia,* B-Hemolytic strep., Corynebacteria, *Legionella, Mycoplasma, Ureaplasma, Chlamydia, Neisseria* gonorrhea, *Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia,* and Acitnomycetes. Fungal infectious agents which can be detected by the present methods and compositions include *Cryptococcus neoformans, Blastomyces dermatitidis, Histoplasma capsulatum, Coccidioides immitis, Paracoccidioides brasiliensis, Candida albicans, Aspergillus fumigautus,* Phycomycetes (*Rhizopus*), *Sporothrix schenckii,* Chromomycosis, and Maduromycosis. Viral infections, or free virus, which can be detected by the present methods and compositions include human immunodeficiency virus (HIV), HIV-1, HIV-2, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses. Parasitic agents which can be detected by the present methods and compositions include malarial parasites, *Plasmodium falciparum, Plasmodium malaria, Plasmodium vivax, Plasmodium ovale, P. knowlesi, Onchoverva volvulus, Leishmania, Trypanosoma* spp., *Schistosoma* spp., *Entamoeba histolytica, Cryptosporidium, Giardia* spp., Trichimonas spp., Balatidium *coli, Wuchereria bancrofti, Toxoplasma* spp., *Enterobius vermicularis, Ascaris lumbricoides, Trichuris trichiura, Dracunculus* medinesis, trematodes, *Diphyllobothrium latum, Taenia* spp., *Pneumocystis carinii,* and *Necator* americanis.

The present methods and compositions are also useful for detection of drug resistance. For example, vancomycin-resistant *Enterococcus faecium,* methicillin-resistant *Staphylococcus aureus,* penicillin-resistant *Streptococcus pneumoniae,* multi-drug resistant *Mycobacterium tuberculosis,* and AZT-resistant human immunodeficiency virus can all be identified with the present methods and compositions.

The subject methods and compositions can be used to detect or monitor cells and viruses potentially associated with a bioterrorist or biowarfare attack, including, but not limited to: Botulinum neurotoxin-producing species, Botulinum neurotoxin producing species of *Clostridium,* Cercopithecine herpesvirus 1 (Herpes B virus), *Clostridium perfringens* epsilon toxin, *Coccidioides posadasii/Coccidioides immitis,* Conotoxins, *Coxiella burnetii,* Crimean-Congo haemorrhagic fever virus, Eastern Equine Encephalitis virus, Ebola virus, *Francisella tularensis,* Lassa fever virus, Marburg virus, Monkeypox virus, reconstructed replication competent forms of the 1918 flu pandemic containing any portion of the coding regions of all eight gene segments (reconstructed 1918 Influenza virus), influenza A H1N1, influenza A H5N1, influenza A H3N2, *Rickettsia prowazekii, Rickettsia rickettsii,* South American Haemorrhagic Fever viruses, Flexal, Guanarito, Junin, Machupo, Sabia, Staphylococcal enterotoxins, Tick-borne encephalitis complex (flavi) viruses, Central European Tick-borne encephalitis Far Eastern Tick-borne encephalitis Kyasanur Forest disease Omsk Hemorrhagic Fever Russian Spring and Summer encephalitis, Variola major virus (Smallpox virus), Variola minor virus (Alastrim), and/or *Yersinia pestis.*

The methods and compositions provided herein can be used to evaluate the quantity of polynucleotides (e.g., DNA, RNA, mitochondrial DNA, genomic DNA, mRNA, siRNA, miRNA, cRNA, single-stranded DNA, double-stranded DNA, single-stranded RNA, double-stranded RNA, tRNA, rRNA, cDNA, etc.). Often, the methods and compositions can be used to evaluate a quantity of a first polynucleotide compared to the quantity of a second polynucleotide. The methods can be used to analyze the quantity of synthetic plasmids in a solution; to detect a pathogenic organism (e.g., microbe, bacteria, virus, parasite, retrovirus, lentivirus, HIV-1, HIV-2, influenza virus, etc.) within a sample obtained from a subject or obtained from an environment. The methods also can be used in other applications wherein a rare population of polynucleotides exists within a larger population of polynucleotides.

The polynucleotides can be measured following lysis of intact cells; or cellular supernatant can be analyzed for polynucleotides that have leaked from cells. Increases in free polynucleotides can indicate disruption of cellular membranes, and therefore decreased cellular viability.

V. Detection of Copy Number Variations and Fetal Aneuploidies

Provided herein are methods and compositions for detecting genetic variations, genetic mutations and/or single nucleotide polymorphisms (SNPs) in a biological sample. In some embodiments, provided herein are methods and compositions for detecting the number of copies of a target polynucleotide (e.g., chromosome, chromosome fragment, gene, etc.) within a biological sample. In some embodiments, methods and compositions for detecting genetic mutations and/or single nucleotide polymorphisms (SNPs) within a biological sample are also provided. The methods herein (e.g., the methods for determining fetal load) are also useful for improving methods of detecting CNV or fetal aneuploidies.

Also provided are compositions and methods for detecting fetal aneuploidy, or other genetic abnormality, in a biological sample derived from maternal tissue. Often such a biological sample comprises a mixture of maternal and fetal nucleic acids (e.g., DNA, RNA). Aneuploidy is a chromosomal abnormality and refers to an aberration in the copy number of a chromosome, or fragment thereof, or portion thereof. The methods and materials described herein apply techniques for analyzing numerous nucleic acids contained in a tissue sample, such as blood (whole blood or peripheral blood), serum or plasma, containing a mixture of DNA (and/or DNA fragments) from both the mother and the fetus, and allowing detection of small differences between target and reference DNA levels that can indicate fetal aneuploidy.

As used herein, copy number variations (CNVs) refer to gains or losses of segments of genetic material. There are large numbers of CNV regions in humans and a broad range of genetic diversity among the general population. CNVs also play a role in many human genetic disorders. The methods disclosed herein are especially useful for detection of a translocation, addition, amplification, transversion, inversion, aneuploidy, polyploidy, monosomy, trisomy (e.g. trisomy 21, trisomy13, trisomy 14, trisomy 15, trisomy 16, trisomy 18, trisomy 22, etc.), triploidy, tetraploidy, and sex chromosome abnormalities including, but not limited to, XO, XXY, XYY, and XXX. These methods also provide non-invasive techniques for determining the sequence of fetal DNA and for identifying mutations within the fetal DNA.

In some embodiments, a single probe can be ligated at its ends following hybridization to a target polynucleotide (e.g., molecular inversion probe). In other embodiments, a ligation probe can comprise two separate molecules that can be ligated together following hybridization to a target polynucleotide.

The following description provides an exemplary overview of the steps that can be taken to detect copy number variations in a sample from a patient through the use of droplet digital PCR (ddPCR) and ligation probes. A sample of genomic nucleic acids (e.g., genomic DNA or RNA) is extracted from a sample obtained from a patient. Probes (such as the ligation probes described herein) are allowed to hybridize to a target nucleotide sequence within the patient sample; following hybridization, the probes are ligated together and then the sample is, optionally, subjected to an enzymatic treatment (e.g., exonuclease) to breakdown genomic nucleic acids and residual unligated probes. PCR reaction components (e.g., primers, fluorescence detection probes, polymerase, dNTPs, etc.) are then added to the sample, which is then partitioned into multiple droplets. After droplet formation, the droplets are subjected to thermocycling to amplify the probes within the sample. The number of positive and negative droplets are then determined, which is used to determine relative copy number of a target polynucleotide. Although droplets are an exemplary means of partitions, other means of partitioning known in the art can be used as well, e.g., partitioning among wells within a nano- or microfluidic device, etc. Other genetic conditions can be detected as well.

The detection of copy number within a sample can involve the detection of chromosomal abnormalities, including aneuploidy. The following is a general overview of steps that can be taken to identify fetal aneuploidy in a maternal sample. A starting tissue sample contains a mixture of maternal and fetal DNA. The DNA is extracted, and mixed with probes for a reference chromosome (e.g., chromosome 1) and a test chromosome (e.g., chromosome 21). Probes are bound to a genetic target and then partitioned into multiple compartments. Probes are detected within the compartments, and the number of compartments containing the test chromosome (e.g., chromosome 21) is compared to the number of compartments containing the reference chromosome (e.g., chromosome 1), followed by calculation of the relative copy number of the test chromosome (e.g., chromosome 21).

The present disclosure provides for the analysis of maternal tissue (e.g., blood, serum or plasma) for a genetic condition, wherein the mixed fetal and maternal DNA in the maternal tissue is analyzed to distinguish a fetal mutation or genetic abnormality from the background of the maternal DNA. Using a combination of steps, a DNA sample containing DNA (or RNA) from a mother and a fetus can be analyzed to measure relative concentrations of cell-free, peripherally circulating DNA sequences. Such concentration differences can be used to distinguish a genetic condition present in a minor fraction of the DNA, which represents the fetal DNA.

The methods disclosed herein can employ digital analysis, in which the DNA in the sample is translated into a plurality of ligated probes that are partitioned to a nominal single ligated probe molecule in a reaction volume to create a sample mixture. For example, the reaction volume can be a droplet, such as a droplet of an aqueous phase dispersed in an immiscible liquid, such as described in U.S. Pat. No. 7,041,481, which is hereby incorporated by reference in its entirety. Each reaction volume has a possibility of having distributed in it zero, one, or more targets (e.g., target polynucleotide, targeting probe or other targeting molecule). The target molecules can be detected in each reaction volume, preferably as target sequences that are amplified, which can include a quantization (or quantification) of starting copy number of the target sequence, that is, 0, 1, 2, 3, etc. A reference sequence can be used to distinguish an abnormal increase in the target sequence, e.g., a trisomy. Thus there can be a differential detection of target sequence to reference sequence that indicates the presence of a fetal aneuploidy. It is not necessary that the reference sequence be maternal sequence.

In addition, the methods disclosed herein can employ a wide range of approaches to capture and detect fetal genetic material, either directly or indirectly. Some embodiments can involve the use of a molecular inversion probe (MIP) (or other oligonucleotide probe) instead of a pair of primers to bind to genomic DNA. This binding can be followed by steps comprising a hybridization step to bind MIP probes to a complementary sequence within a target polynucleotide; a ligation reaction step to circularize bound probes; an exonuclease treatment step to digest residual non-circularized MIP probes; an optional treatment step, where an enzyme such as uracil-N-glycosylase is used to linearize circularized probes; a partitioning step, where the circularized probes, or linearized probes (that were previously circular) are partitioned or subdivided into two or more partitions (e.g., droplets); followed by an amplification step involving amplification of a sequence unique to the oligonucleotide probe through droplet digital PCR.

In some embodiments disclosed herein, multiplexed MIPs (or other oligonucleotide) can be used herein in order to improve sensitivity of detection. For example, a group of two or more MIPs can be used, wherein each of such MIPs binds to a different sequence on the same chromosome (e.g., chromosome 21). In some embodiments, multiple MIPs recognizing, for example, a target and reference sequence, can be differentially detected during amplification using fluorophores of different colors. In some embodiments, binding of a single linear probe to genomic DNA and a subsequent ligation reaction produces a circular molecule. In other embodiments, two linear probes bind to adjacent regions of genomic DNA, and a subsequent ligation reaction produces a ligation-dependent molecule that can be detected in a ligation-detection reaction (LDR).

As used herein, the term ligation refers to a covalent bond or linkage between two or more nucleic acids, e.g., oligonucleotides and/or polynucleotides. Often, a ligation can comprise ligating the 5' terminus of a polynucleotide (e.g., ligation probe) to the 3' terminus of another polynucleotide (e.g., ligation probe), or to the same polynucleotide. The nature of the bond or linkage can vary widely and the ligation can be carried out enzymatically or chemically. In some embodiments, ligations are carried out enzymatically to form a phosphodiester linkage between a 5' carbon of a terminal nucleotide of one oligonucleotide with 3' carbon of another oligonucleotide. A variety of binding-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180, each of which is incorporated by reference in its entirety.

The present disclosure provides methods and compositions for the removal of undesired material (i.e., unbound genomic DNA and unligated probe) and the selection or isolation of desired material (i.e., ligation product). In some embodiments, where the product of ligation is circular, such as in reactions involving a MIP, unbound genomic DNA and unligated probe can be removed using exonuclease treatment. In some embodiments, the circular ligation product can then be released in a treatment involving an enzyme such as uracil-N-glycosylase, which depurinates uracil residues in the probes thus generating an abasic site. In these embodiments, the abasic site can be cleaved upon heating, resulting in a linearized ligation product.

Detection can occur using a variety of methods. In some embodiments, a product of ligation can be detected using a droplet digital PCR reaction in which DNA synthesis proceeds by the extension of at least one detection probe containing a fluorescer-quencher pair within a single molecule. Fluorescer refers to a molecule that emits detectable light after absorbing light or other electromagnetic radiation (i.e., a fluorophore). Quencher refers to a molecule that decreases the fluorescence intensity of a substance, and in the case of a fluorescer-quencher pair, the quencher can reduce detection of a covalently-attached fluorescer by absorbing the detectable light the fluorescer emits. During the process of DNA synthesis, the 5'→3' exonuclease activity of a polymerase enzyme such as Taq polymerase can cleave the detection probe, resulting in release of the fluorescer from the quencher. A variety of fluorescence detection methods can be employed that detect the released fluorescer, but not the fluorescer-quencher pair. In some embodiments, detection of a product of ligation can provide a quantitative measurement of the presence of a specific sequence, such as a target or reference sequence in fetal or maternal genetic material.

The present disclosure further provides compositions and methods for the detection of a nucleic acid molecule of interest using droplet digital PCR, wherein the sample can comprise DNA, RNA, or cDNA from any organism. In some embodiments, the sample can be isolated using a ligation reaction that is followed, in some embodiments, by exonuclease treatment to remove unwanted material. In some embodiments, detection occurs by fluorescence monitoring of droplet digital PCR, wherein a droplet comprises reagents for PCR and zero, one, two, three, or more ligation products detectable by PCR reaction suspended in the aqueous phases of an emulsion.

A. Ligation Probes

In some embodiments, target polynucleotides can be tagged, selected, captured, isolated and/or processed through the use of one or more ligation probes (also, at times, referred to herein as "ligatable probes"). A ligation probe can comprise either: (1) a "circularizable probe", wherein each end (5' and 3') of a single polynucleotide (or oligonucleotide) binds to adjacent or neighboring regions of a target polynucleotide, and where following such binding, a ligation reaction can join the 5' terminus to the 3' terminus of the probe, thereby circularizing the probe; or (2) two polynucleotide (or oligonucleotide) probes wherein, after two probes bind to regions within a target polynucleotide, the 5' end of one probe can be ligated to the 3' end of a different probe. After two of such probes hybridize to neighboring or adjacent sequences of a target polynucleotide, a ligation reaction can result in joining the two probes together into one linear probe.

In some embodiments, a ligation probe can also comprise: an enzymatic cleavage site, a universal primer site, and/or a universal probe-binding site. In some embodiments, the ligation probe is phosphorylated at its 5' terminus. In other embodiments, the ligation probe is not phosphorylated at it 5' terminus. Such phosphorylation at the 5' terminus can enable ligation of the 5' terminus to the 3' terminus of the same (or different) ligation probe that is bound to an adjacent region of target polynucleotide, without the need of a gap-fill reaction. In other embodiments, a probe is synthesized without phosphorylation at the 5' end. In such embodiments, the probe is designed so that the 5' end binds to a region neighboring, but not directly adjacent to, the binding site of the 3' end of the same (or different) probe. Ligation of such probe can additionally require a gap-fill, or extension reaction.

In some embodiments, a ligation probe is a molecular inversion probe. U.S. Pat. No. 7,368,242, which is hereby incorporated by reference in its entirety, describes a molecular inversion probe and how it can be used to generate an amplicon after interacting with a target polynucleotide in a sample. A linear version of the probe is combined with a sample containing target polynucleotide under conditions that permit neighboring regions in the genetic target to form stable duplexes with complementary regions of the molecular inversion probe (or other ligation probe). In general, the 5' terminus of the probe binds to one of the target sequences, and the 3' terminus of the probe binds to the adjacent sequence, thereby forming a loop structure. The ends of the target-specific regions can abut one another (being separated by a nick) or there can be a gap of several (e.g., 1-10 nucleotides) between them. In some embodiments, the gap can be greater than about 5, 10, 20, 30, 40, 50, 100, 200, 300, 400, 500, or more nucleotides. In some embodiments, the target-specific regions are directly adjacent (e.g., separated by 0 nucleotides). In some embodiments, after hybridization of the target-specific regions, the ends of the two target specific regions can be covalently linked by way of a ligation reaction or a multiextension reaction followed by a ligation reaction, using a gap-filling reaction.

The following is an exemplary description of the use of Molecular Inversion Probes (MIPs) to detect two genetic targets. One genetic target is recognized by one probe (MIP1-1), and a second genetic target is recognized by a second probe (MIP2-1). After binding of a MIP to a genetic target, a ligation reaction is conducted to ligate the 5'-terminus of a bound MIP probe to the 3'-terminus of the same MIP probe, thereby forming a circular MIP. In some embodiments, a MIP probe binds two sequences of neighboring DNA that are separated by one or more nucleotides. In such embodiments, a gap-fill (or extension) reaction can be performed to fill in the gap using the target DNA as a template. After a MIP binds its target sequences, the MIP forms a loop, and the sequence of the probe can be inverted. This inversion can be followed by a ligation reaction, in which the ends of the inverted molecule are ligated to form a circularized probe.

Following the binding of the MIP probe to the DNA (and, optionally the gap-fill reaction), a ligation reaction can be conducted with a ligase enzyme to circularize the MIP probe. The circular MIP probe can then be retained during exonuclease digestion, which digests unused, linear, single-stranded probe and single-stranded linear genomic DNA and double-stranded linear genomic DNA. The circular MIPs can then be combined with PCR reagents into droplets for analysis by droplet digital PCR. In some embodiments, the circular probes can be linearized prior to, or during the PCR reaction. A probe can contain a site that comprises an enzymatic cleavage site (e.g., a series of uracil residues that are susceptible to enzymatic cleavage by uracil N-glycosylase enzyme). In some embodiments, there is an enzymatic cleavage step, wherein the polynucleotide can be cleaved to form a linear molecule. In other embodiments, there is no enzymatic cleavage step at this step, and the polynucleotide remains in a circular state. Next, the ligated MIP probes (either circularized, linear, or a mixture of both) can be subdivided among one of more partitions. In some embodiments, the partitions are droplets (e.g., aqueous droplets within an oil phase). The droplets are then subjected to a thermal cycling reaction. During the thermal cycling reaction, a linearized MIP (or in some embodiments, a circular MIP) serves as the template for a reaction primed by a universal forward primer (UF1 or UF2) and a universal reverse primer (UR1 or UR2). During amplification, a universal probe that hybridizes to a sequence in each MIP (UP1 or UP2) can be cleaved such that the fluorescent side of the probe is separated from the quencher side of the probe. As a result of this cleavage, fluorescence from the fluorescer side of the probe increases.

In some embodiments, a gap-fill reaction is performed by a polymerase with a 5'→3' polymerization activity. Polymerases useful in this method include those that will initiate 5'-3' polymerization at a nick site. The polymerase can also displace the polymerized strand downstream from the nick.

In some embodiments, the polymerase used for the gap-fill reaction lacks any 5'→3'exonuclease activity. A polymerase ordinarily having such exonuclease activity can lack such activity if that activity is blocked, e.g., by the addition of a blocking agent; if a domain or fragment of the polymerase where such domain or fragment performs 5'→3'exonuclease activity is deleted, mutated, or otherwise modified; if the polymerase is chemically modified; or any other method known in the art.

In some embodiments, the polymerase used for the gap-fill reaction comprises a 3'→5' editing exonuclease activity. Examples of suitable polymerases include the klenow fragment of DNA polymerase I and the exonuclease deficient klenow fragment of DNA polymerase I and a similar fragment from the Bst polymerase (Bio-Rad, Richmond, Calif.). SEQUENASE 1.0 and SEQUENASE 2.0 (US Biochemical), T5 DNA polymerase and Phi29 DNA polymerases also work, as does Stoffel Fragment of AmpliTaq DNA Polymerase (Life Technologies, Carlsbad, CA).

Although the present disclosure describes ligation probes (e.g., MIP probes) comprising DNA, the ligation probes described herein can contain any other nucleic acid (e.g., RNA, mRNA, cDNA, rRNA, tRNA, siRNA, miRNA, etc.), polypeptide, synthetic nucleic acid, or synthetic polypeptide. In some embodiments, the ligation probes can comprise a two or more different types of polynucleotides (e.g., comprising both RNA and DNA) or the ligation probe can comprise a polynucleotide and a polypeptide (e.g., RNA plus polypeptide; DNA plus polypeptide). In certain other applications, the ligation probe (e.g., MIP probe) can be conjugated to a fluorescent dye, solid support, or bead in the methods described herein.

Nucleic acid refers to naturally occurring and non-naturally occurring nucleic acids, as well as nucleic acid analogs that function in a manner similar to the naturally occurring nucleic acids. The nucleic acids can be selected from RNA, DNA or nucleic acid analog molecules, such as sugar- or backbone-modified ribonucleotides or deoxyribonucleotides. Other nucleic analogs, such as peptide nucleic acids (PNA) or locked nucleic acids (LNA), are also suitable. Examples of non-naturally occurring nucleic acids include, but are not limited to: halogen-substituted bases, alkyl-substituted bases, hydroxy-substituted bases, and thiol-substituted bases, as well as 5-propynyl-uracil, 2-thio-5-propynyl-uracil, 5-methylcytosine, isoguanine, isocytosine, pseudoisocytosine, 4-thiouracil, 2-thiouracil and 2-thiothymine, inosine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine), 2-amino-6-"h"-purines, 6-amino-2-"h"-purines, 6-oxo-2-"h"-purines, 2-oxo-4-"h"-pyrimidines, 2-oxo 6-"h"-purines, 4-oxo-2-"h"-pyrimidines. Those will form two hydrogen bond base pairs with non-thiolated and thiolated bases; respectively, 2,4 dioxo and 4-oxo-2-thioxo pyrimidines, 2,4 dioxo and 2-oxo-4-thioxo pyrimidines, 4-amino-2-oxo and 4-amino-2-thioxo pyrimidines, 6-oxo-2-amino and 6-thioxo-2-amino purines, 2-amino-4-oxo and 2-amino-4-thioxo pyrimidines, and 6-oxo-2-amino and 6-thioxo-2-amino purines.

In some embodiments, the method comprises selection, tagging, capture and/or isolation of a desired sequence from genomic DNA by selectively protecting the desired sequence from enzymatic digestion (e.g., protecting from enzymes such as endonucleases and exonucleases). For example, circularization of a MIP probe (after it has bound its target) protects the probe from digestion by certain enzymes (e.g., exo I, exo III). Other methods of protecting the probe after it has bound its target can also be used.

In some embodiments, the ligation reaction can then be followed by enzymatic digestion, such as exonuclease treatment (e.g., exonuclease I, exonuclease III), to digest unbound genomic DNA and unbound probe but not circular DNA, thereby isolating the circular MIP representing the desired sequence. In some embodiments, MIPs allow for multiplexing, when more than one probe binds a desired genetic target and undergoes ligation to form a circular MIP. Multiple MIPs can thereby represent a given genetic target, enhancing the sensitivity of detection.

In some embodiments wherein circular MIPs are generated to represent sequences of interest, these circular MIPs can be linearized prior to (or during) detection by PCR reaction. In some embodiments, the MIPs contain uracil bases that can be depurinated by treatment with an enzyme such as uracil-N-glycosylase, and the circular molecule can become linearized at the abasic sites upon heating. In other embodiments, the MIPs can contain restriction enzyme sites that are targeted by site-specific restriction enzymes, cleaving the circular probes to form linear DNA molecules. In some embodiments in which circular MIPs are linearized, enzymes that occupy the solution containing MIPs, including exonucleases, can be inactivated by such methods as heat-inactivation, pH denaturation, or physical separation prior to MIP linearization. In some embodiments, DNA can be purified from proteins using gel purification or ethanol precipitation, or proteins can be removed from the solution using precipitation with organic solutions such as trichloroacetic acid.

Other types of probes, and other methods of selecting a genetic probe, can also be used in the methods and compositions described herein. For example, although use of MIP probes generally involves circularization of a single ligation probe; a circularization step is not always necessary. For example, ligation detection PCR techniques can be used, where two different probes, each of which hybridizes to neighboring DNA (or adjacent DNA), are ligated together followed by addition of universal primers and probes to detect the ligated fragments.

The following is description of an exemplary method for detecting two genetic targets with two colors using a ligation-detection reaction (LDR) followed by PCR in droplets. Two linear oligonucleotides bind to adjacent or neighboring regions on a genetic target. These regions can be directly adjacent or separated by a gap. Alternatively, the regions can be separated by a gap that can be filled-in using a polymerase reaction, that extends the length of the 3' end of the first probe so that its 3' end is directly adjacent to the 5' end of the second probe. The two probes are then ligated to each other. During ligation, the two linear oligonucleotides are ligated to form a single template oligonucleotide (LDR1-1 or LDR2-1). This single template oligonucleotide, but not the pairs of oligonucleotides from which it was formed, can produce a product in a PCR reaction using universal forward (UF1 or UF2) and reverse (UR1 or UR2) primers. Additionally, the PCR reaction contains a universal probe (UP1 or UP2) comprising a fluorescer-quencher pair that hybridizes to a portion of the template oligonucleotide. During the PCR reaction, a 5'→3' exonuclease activity of a DNA polymerase (such as Taq) cleaves the probe, resulting in detachment of the fluorescer end from the quencher end of the molecule. As a result of this separation between fluorescer probe and quencher probe, fluorescence intensity will increase in the reaction, and can be detected in following steps. This analysis can be performed using two universal probes (UP1 and UP2) containing fluorescers of two different colors that can be distinguished during detection. For example, LDR1-1 can recognize a target sequence such as a suspected aneuploid chromosome, while LDR2-1 recognizes a reference sequence such as a presumed diploid chromosome, allowing detection of aneuploidy.

The ligation probes used in ligation detection reactions described herein can be protected from exonuclease treatment once they are bound to a target polynucleotide. For example, addition of a protective group, a chemical blocking unit, or a phosphorothiate modification can protect a hybridized ligation probe from being digested by certain exonucleases capable of digesting unbound probe and/or unbound target polynucleotides (e.g., genomic DNA). Phosphorothioate-modification can protect a ligation probe from the activity of exo III, a 3' to 5' exonuclease. Similarly, phosphorothioate-modification can protect a ligation probe from the activity exo T7, a 5' to 3' exonuclease. In some embodiments, exo T, a 3' to 5' exonuclease, and RecJf, a 5' to 3' exonuclease can be used. Disclosure of phosphorothioate providing protection against exo T activity is provided in Putney et al. (1981) PNAS 78(12):7350-54, which is herein incorporated by reference in its entirety. For RecJf, see also Tosch et al, (2007) *J. of Physics: Conference Series* 61 (2007) 1241-1245; doi:10.1088/1742-6596/61/1/245 International Conference on Nanoscience and Technology (ICN&T 2006), which is herein incorporated by reference in its entirety. Both exo T and RecJF digest ssDNA and can be blocked by phosphorothioates. The phosphorothioate modification can be located at the ends of the universal PCR primer sequences in the probes, or at tails upstream of the universal PCR primer sequences.

In some embodiments, a probe comprises a mixture of different linear oligonucleotides, wherein the 5' region of one of the linear oligonucleotides is able to be ligated to the 3' region of a different linear oligonucleotide, after each probe hybridizes to a target polynucleotide. In some embodiments, two identical (or substantially identical) oligonucleotides can each bind to a region of adjacent or neighboring target polynucleotide in a manner such that the 5' end of one such probe can then be ligated to the 3' end of another such probe. Such ligation can occur following hybridization of each probe to the target polynucleotide.

In other embodiments, the method comprises capture of a desired sequence without subsequent isolation. In some embodiments, more than one linear probe recognizes the desired sequence and binds to it. Following the binding of probe, a ligation reaction can be performed to ligate one or more probes to one another. In some embodiments, the desired sequence is captured as a result of the ligation, which can allow PCR detection of ligated probe (known as ligase detection reaction-PCR, or LDR-PCR) in subsequent steps, while unligated probe is not detectable by PCR. In some embodiments, multiple probes can bind a genetic target and undergo ligation, enhancing the sensitivity of detection of the genetic target by LDR-PCR.

Ligation probes (e.g., MIP probes) can be designed to satisfy certain criteria in order to minimize sample to sample variation in assay performance, or to otherwise optimize an assay. Some criteria of use in the design of a ligation probe can include: (1) target sequences that do not contain any known SNPs (e.g., all the SNPs in dbSNP); 2) target sequences within conserved regions of genomic DNA; (3) target sequences that do not overlap any known CNV regions (e.g., all the CNVs present in CNV tracks in the UCSC genome database); 4) target sequences within in regions of a target polynucleotide (e.g., genomic DNA, RNA) that are conserved across species (e.g., as assessed by conservation tracks in the UCSC genome database). Additionally, to optimize universal and consistent performance of the probes, several criteria can be applied to the selection of the target sequences. Target sequences can be chosen so that they are unique in the human genome. Target sequences can be chosen so that both termini of the MIP probes contain G/C nucleotides, so that they are near 40 nucleotides in length, so that combined homer arms have similar melting temperatures (e.g., within 2 of 67 degrees using default parameters from Primer3 software) and so that individual homer arms have similar melting temperatures (e.g., within 2 degrees of 50 degrees using default parameters from Primer3 software). (The 5'- and 3'-ends of the probe, which are complementary to genomic DNA are called homer arms: H2 and H1, respectively.)

The MIPs and the targets can also be screened to discard MIPs and targets that form secondary structures because they may not bind well to their counterparts. Additionally, MIPs can be compared to each other to reduce the possibility of reactions between MIP probes in solution. Some generic rules for avoiding secondary structure can be found in Hyman et al. (2010), Applied and Environmental Microbiology 76: 3904-3910, which is hereby incorporated by reference in its entirety. Secondary structure screening can be aided by building distributions of dG scores and removing outliers.

The methods provided herein include methods for assessing multiple abnormalities simultaneously, for example on chromosomes 13, 18, and 21. For such studies, the chromosomes can be used as references for each other, and therefore an extra reference sample or reference probe (e.g., to Chromosome 1) can be unnecessary.

The sample containing the genetic target can comprise genomic DNA in the form of whole chromosomes, chromosomal fragments, or non-chromosomal fragments. In some embodiments, the average length of the genomic DNA fragment can be less than about 100, 200, 300, 400, 500, or 800 base pairs, or less than about 1, 2, 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some embodiments, the fragments range from 10 to 500, 10-1000, or 100-150 bases (or nucleotides) in length, and, in some embodiments, preferably between 100-150 bases.

In some embodiments in which fetal genomic DNA is enriched compared to maternal DNA, the fragment size can be an average of about 300 base pair or 100 or 150 base pairs. In some embodiments, the sample can comprise at least one genome equivalent. In other embodiments, the sample can comprise less than one genome equivalent, but include enough genomic DNA to make a determination of the ratios of target and reference sequences in fetal or maternal samples. In still other embodiments, the sample will comprise about half of one genome equivalent. The term genome equivalent is used to refer to the calculated distribution of sample DNA based on a calculated genome size and DNA weight, wherein the haploid genome weighs about 3.3 pg, and the genomic content of a diploid normal cell (46 chromosomes) weighs about 6.6 pg and corresponds to two genomic equivalents (GE)("genomic equivalent" and "genome equivalent" are used interchangeably herein). In practice, there can be some variation in DNA sample size. Also, due to random fragment distribution, a given genome equivalent may not contain exactly the DNA fragments corresponding only to a single complete diploid genome.

B. Multiplexing

The amplification methods (e.g., PCR) described herein, and known in the art, can be multiplexed, that is, run with multiple primers and probes in each reaction volume. In some embodiments of the methods and compositions provided herein, there are at least about 1, 2, 3, 4, 5, 6, 7, 8, 9, 10, 15, 20, 25, 30, 35, 40, 45, 50, 100, 200, 500, 1000, 5000, 10,000, 20,000, 30,000, 40,000, 50,000, 60,000, 70,000, 100,000, 2,000,000, 3,000,000, 4,000,000, 5,000,000, 6,000,000, 7,000,000, 8,000,000, 9,000,000 or 10,000,000 or more different probes in a given sample volume. In some embodiments, there are at least about 1, 2, 3, 4, 5, 6, 7, 8, 9, 10, 15, 20, 25, 30, 35, 40, 45, 50, 100, 200, 500, 1000, 5000, 10,000, 20,000, 30,000, 40,000, 50,000, 60,000, 70,000, 100,000, 2,000,000, 3,000,000, 4,000,000, 5,000,000, 6,000,000, 7,000,000, 8,000,000, 9,000,000 or 10,000,000 or more primers in a given sample volume.

In some embodiments, a plurality of probes (or primer sets) is used, and the probes (or primer sets) differ with respect to one or more aspects. The probes can bind identical target polynucleotides; or different target polynucleotides (e.g., different chromosomes; or identical chromosomes, but different regions within said chromosomes). For example, greater than about 1, 2, 3, 4, 5, 6, 7, 8, 9, 10, 11, 12, 13, 14, 15, 16, 17, 18, 19, or 20 probes directed to different targets can be used. In some embodiments, greater than about 20, 30, 40, 50, 100, 500, 1000, 5000, 10000, 50000, 100000, 500000, 1000000, or more probes directed to different targets are used. In other embodiments, the probes differ as to the type of cleavage site that is present within said probe. In some embodiments, the plurality of probes comprises a plurality of different types of probes (e.g., ligation probes, MIPs, padlock probes, sets of PCR primers, universal primers, universal probes, and any combination thereof). In some embodiments, said plurality of different types of probes differs in that each probe is conjugated to a different signaling agent (e.g., green fluorophore vs. red fluorophore, etc.). In some embodiments, the probes differ in that they comprise different primer binding sites. In other embodiments, the same set of universal primers can be used to bind all, or most of, the probes within a plurality of probes.

Multiplexing in reaction volumes, such as droplets, can allow for detection of small changes in DNA ratio between a target and reference sequence from the expected ratio of 1:1 for diploid sequences. Multiplexing can allow for a large number of sequences to be counted for any set of target and reference sequences, despite samples where the GE/mL is low (e.g., 1000 GE/mL), such as in maternal plasma. The intact target and reference chromosomes are large molecules and have multiple conserved and unique regions that can be recognized and amplified by specific primer sets. In plasma, the circulating DNA can be present as small fragments (~300 bp). By designing multiplexed primers that produce small products (e.g., 100 base pairs), small fragments (e.g., 300 base pairs) of the target or reference sequence can be efficiently amplified.

Multiplexing can increase the likelihood that a target isolated in a reaction volume, such as a droplet, can be recognized by one of the multiplexed primers. Multiplexing can also increase the likelihood that amplification will occur and can permit a positive measurement of a target sequence that would be counted as negative in a single-plex assay. The same can be done for a reference sequence. In some embodiments, the degree of multiplexing can include more than one primer set to a target sequence, such as at least about 2, 3, 4, 5, 10, 15, 20, 25, or more primer sets, each to a particular target sequence. In some embodiments, the degree of multiplexing can include more than one reference primer set to a reference sequence, such as at least about 2, 3, 4, 5, 10, 15, 20, 25, or more primer sets, each to a particular reference sequence. In some embodiments, the degree of multiplexing can include more than one primer set to a target sequence and more than one reference primer set to a reference sequence, such as at least about 2, 3, 4, 5, 10, 15, 20, 25, or more primer sets to particular target or reference sequences. In some embodiments, the number of primer sets to a target sequence is not the same as the number of primer sets to a reference sequence. In other embodiments, the number of primer sets to a target sequence is the same as the number of primer sets to a reference sequence. In some embodiments, the degree of multiplexing can be less than about 500, 250, 200, 150, or 100 primer sets for each target and reference sequence. In some embodiments, the target and reference sequence multiplexes can be combined into a single reaction volume.

The different primer pair amplified sequences can be differentiated based on spectrally distinguishable probes (e.g., 2 different dye-labeled probes such as Taqman or Locked Nucleic Acid Probes (Universal Probe Library, Roche)). In such approach, all probes can be combined into a single reaction volume and distinguished based on the differences in the color emitted by each probe. For example, the probes targeting one polynucleotide (e.g., a test chromosome, chr. 21) can be conjugated to a dye with a first color and the probes targeting a second polynucleotide (e.g., a reference chromosome, chr. 1) in the reaction can be conjugated to a dye of a second color. The ratio of the colors then reflects the ratio between the test and the reference chromosome.

In some embodiments, a set of probes (e.g., a set of probes targeting a test chromosome, e.g., Chromosome 21), can target different regions of a target polynucleotide, yet each probe within the set has the same universal primer binding sites. In some embodiments, each probe has the same probe-binding site. In some embodiments, two or more probes in the reaction can have different probe-binding sites. In some embodiments, the probes added to such reactions are conjugated to the identical signal agent (e.g., fluorophore of same color). In some embodiments, different signal agents (e.g., two different colors) are conjugated to one or more probes.

Alternatively, the set of reaction volumes (e.g., droplets) can be split into two sample sets, with amplification of target sequence in one set and reference sequence in the other set. The target and reference sequences are then measured independently of each other. This can allow the use of a single fluorescence probe, such as SYBR Green. In some instances, this requires splitting the sample and potentially doubling the number of primers in each multiplex set to achieve an equivalent sensitivity. In some embodiments, the sample is split and a plurality of ligation probes to a test chromosome is added to one half of the sample, and a plurality of ligation probes to a reference chromosome is added to the second half of the sample. In such examples, the ligation probes can then be hybridized to a universal probe conjugated to the same signaling agent (e.g., fluorophore of the same color spectrum).

The multiplexing provided by the instant disclosure can also be accomplished using a probe for a target, instead of using a primer pair, at an early step. An example of a probe that can be used is a linear oligonucleotide with two ends specifically designed to hybridize to adjacent, or neighboring, sequences within a target polynucleotide. A non-limiting example of such a probe is a padlock probe, which is a linear oligonucleotide with two ends specifically designed to hybridize to adjacent target sequences. Once hybridized, the two ends can be joined by ligation and the padlock probe becomes circularized. Padlock probes are disclosed in, e.g., Lizardi et al. (1998) Nat Genetics 19:225-232; U.S. Pat. Nos. 5,871,921; 6,235,472; and 5,866,337, each of which is hereby incorporated by reference in its entirety. In some embodiments, the probe (e.g., oligonucleotide) binds to adjacent sequences of genomic DNA and the ends can then be directly ligated via a ligase reaction. In other embodiments, there is a gap of one or more bases between the two ends. In such embodiments, an extension, or gap fill, reaction can be performed. For the gap fill reaction, any known method in the art will suffice. For example, a mix of nucleotides (dATP, dCTP, dGTP, dTTP, dUTP) can be added to a reaction mix, as well as a polymerase, ligase and other reaction components and incubating at about 60° C. for about 10 minutes, followed by incubation at 37° C. for about 1 minute. Following binding to a target polynucleotide, and ligation, a ligation probe (e.g., molecular inversion probe, padlock probe, etc.) can become circularized.

In some embodiments, the probe is an oligonucleotide probe that binds to a genetic target, as described herein. In other embodiments, the probe is an oligonucleotide probe that binds to a reference target. An example of a reference target is Chromosome 1, or other Chromosome unlikely to be associated with fetal aneuploidy. In some embodiments, the oligonucleotide or reference oligonucleotide comprises a site cleavable by an enzyme. For example, the oligonucleotide can be a DNA oligonucleotide that comprises a series of one or more uracil residues, e.g., at least 1, 2, 3, 4, 5, 6, 7, 10, 15, 20, or more uracil residues, and can be cleavable by an enzyme such as uracil-N-glycosylase (UNG). In other embodiments, the oligonucleotide can comprise one or more restriction sites. The oligonucleotide can comprise one or more of the same restriction sites, or one or more different restriction sites. Examples of restriction sites are well known in the literature. In general, a site cleavable by a restriction enzyme can be used. The restriction enzymes can be any restriction enzyme (or endonuclease) that can cut at a specific site. In some embodiments, the restriction enzymes are blunt cutters; in others, the restriction enzymes cut at an asymmetrical site to create an overhang. Non-limiting examples of restriction enzymes are provided herein.

The oligonucleotide probe can further comprise sites that hybridize to forward and reverse primers, e.g., universal primers. As used herein, universal primers include one or more pairs of 5' and 3' primers that recognize and hybridize to sequences flanking a region to be amplified. The region to be amplified can be within a genetic target such as a suspected fetal aneuploid chromosome, with non-limiting examples of such chromosomes including chromosome 21, chromosome 13, chromosome 18, and the X chromosome. In some embodiments, the region to be amplified is within a genetic target of a presumed diploid chromosome.

In some embodiments, the region to be amplified is not within a genetic target, but within a probe to a genetic target, such as a molecular inversion probe. Primer pairs can be directed to a genetic target, or they can be universal primers that recognize sequences flanking a multitude of amplification targets. For example, probes to a genetic target can comprise one or more segments that recognize and bind to a specific sequence in a genetic target, and the probes can additionally comprise a universal sequence common to all of a set of probes. A single pair of universal primers can therefore be employed to amplify any probes within such a set. In some embodiments, the universal pair of primers only produces a detectable PCR product when the molecular inversion probe has been inverted. Inversion of a molecular inversion probe can be induced by cleavage of a site within a circular molecular inversion probe that results in an inverse orientation of a primer with respect to its primer pair. In some embodiments, a universal pair of primers only produces a detectable PCR product when amplifying the product of a ligation reaction, such as in a ligation detection reaction.

The oligonucleotide probe can also comprise a sequence that is complementary to a probe attached to a marker, such as a dye or fluorescent dye (e.g., TaqMan probe). In some embodiments, the TaqMan probe is bound to one type of dye (e.g., FAM, VIC, TAMRA, ROX). In other embodiments, there are more than one TaqMan probe sites on the oligonucleotide, with each site capable of binding to a different TaqMan probe (e.g., a TaqMan probe with a different type of dye). There can also be multiple TaqMan probe sites with the same sequence of the oligonucleotide probe described herein. Often, the TaqMan probe can bind only to a site on the oligonucleotide probe described herein, and not to genomic DNA, but in some embodiments a TaqMan probe can bind genomic DNA.

Using oligonucleotide probes described herein, the signal-to-background noise can be improved greater than 1-, 2-, 5-, 10-, 15-, 20-, 30-, 40-, 50-, 75-, or 100-fold over as compared to using conventional PCR techniques, such as techniques that use a primer set. One reason is that, potentially, only one probe is needed for all the oligonucleotide probes to a specific target, e.g., a chromosome. For example, there can be a large number of oligonucleotide probes (e.g., greater than 50), wherein each binds to a separate site on a chromosome, but wherein each also comprises a TaqMan site that is universal or the same, and therefore will fluoresce at the same wavelength when a TaqMan probe bound to a specific fluorescent dye is annealed to the probe.

The methods provided herein include methods with the following steps: a denaturation and annealing step in order to permit hybridization of one or more oligonucleotide probes with genomic DNA. An optional gap fill reaction, if the 5' and 3' ends of the probes do not target directly adjacent sequences of genomic DNA, followed by a ligase reaction to circularize the probe. The method can further comprise an exonuclease treatment step wherein the sample is treated with exonuclease enzymes, e.g., exonuclease I and/or III, that digest linear probes (in other words, probes that did not successfully hybridize) as well as ssDNA and dsDNA (e.g., genomic DNA), followed by an inversion step. The method can further comprise an amplification step wherein PCR reagents are added to the samples, e.g., Taq polymerase, universal primers, fluorescence probes (e.g., TaqMan probe), and other PCR reaction components, in order to amplify one or more sites on the oligonucleotide probe. The method can further comprise a partitioning step, wherein the sample is emulsified into monodisperse water-in-oil droplets, e.g., greater than 1,000, 10,000, 20,000, 50,000, 100,000, 200,000, 500,000 or more water-in-oil droplets (also referred to as reaction volumes, herein), followed by thermal cycling, and detecting the fluorescence of each droplet at a wavelength corresponding to the fluorescent probes that were used. In some embodiments, on average, about 1, 2, 3, 4, or 5 copies of DNA are present in each droplet. In some embodiments, on average, no more than about 1, 2, 3, 4, or 5 copies of DNA (e.g., target polynucleotide) are present in each droplet. In some embodiments, an average of about 0.001, 0.005, 0.01, 0.05, 0.1, 0.5, 1, 2, 3, 4, or 5 oligonucleotide probes are present in each droplet. The methods described herein can function at high multiplex depths.

When a high multiplex depth is coupled with ddPCR counting it can provide a large number of target counts to enable high resolution for relative chromosome dosage. This multiplex approach can be coupled with ddPCR fetal load quantification using paternally inherited SNPs, Y chromosome targets or fetal-specific methylation markers, to protect against false negatives. The fetal load measurement can be performed separately on an aliquot of the extracted sample, or can be conducted after the inversion step of the assay by multiplexing the two orthogonal assays (universal MIP PCR+fetal specific quantitation assay).

In some embodiments, ligation is coupled with universal PCR methods in order to achieve multiplexing. Examples include, but are not limited to: a Molecular Inversion Probe (MIP) strategy (see Hardenbol et al., (2003) Nature Biotechnology, 21(6): 673-78); U.S. Patent Application Publication No. 2004/0101835; Multiplex Ligation-dependent Probe Amplification (MLPA) (see Schouten J P, McElgunn C J, Waaijer R, Zwijnenburg D, Diepvens F, Pals G (2002), Nucleic Acids Res. 30 (12); Ligation Detection Reaction (LDR); and Ligase Chain Reaction. The Figures of the instant specification provide a summary of different multiplex strategies using different types of probes or probe/primer combinations.

Multiplexing of the MIP approach can be used to increase sensitivity of detection of genetic targets. For example, a MIP recognizing a particular genetic target can be combined with a second MIP recognizing a different portion of the same genetic target. This process can be repeated, generating many MIPs to recognize the same genetic target. Similarly, a collection of MIPs can be generated to recognize a second genetic target. These MIPs can be employed in analysis to compare two genetic targets.

The ligation, padlock or other oligonucleotide probe described herein can be mixed with genomic DNA. In some embodiments, a plurality of oligonucleotide probes are used, comprising greater than 1, 2, 3, 4, 5, 6, 7, 8, 9, 10, 15, 20, 25, 30, 35, 40, 45, 50, 100, 200, 500, 1000, 5000, or 10,000 oligonucleotide probes to a specific site on a chromosome or different chromosomes.

Multiplexed oligonucleotides for LDR-PCR in droplets can be used to enhance sensitivity of this approach to detect genetic targets in droplets. For example, a single pair of linear oligonucleotides can be designed to recognize neighboring regions of a genetic target. A different pair can be designed to recognize a second genetic target. Multiple pairs of oligonucleotides can be designed to recognize different portions of a genetic target. These pairs of oligonucleotides bind a portion of the genetic target and undergo ligation. Two different colors are used to detect the two different genetic targets depicted. For example, half the LDR probes can recognize a target sequence such as a suspected aneuploid chromosome, while the other half recognize a reference sequence such as a presumed diploid chromosome, allowing detection of aneuploidy with improved sensitivity.

In some embodiments, a target and reference sequence can be pre-amplified prior to analysis using digital droplet detection. Methods of amplification are known in the art, and include a self-sustained sequence reaction, ligase chain reaction, rapid amplification of cDNA ends, polymerase chain reaction and ligase chain reaction, Q-beta phage amplification, strand displacement amplification, isothermal amplification or splice overlap extension polymerase chain reaction. The pre-amplification product can then be used in the methods described in the present disclosure.

VI. Role of Devices

A. Droplet Generation

The present disclosure includes compositions and methods for the detection and quantification of genetic material (e.g., fetal genetic material) using droplet digital PCR. The droplets described herein include emulsion compositions (or mixtures of two or more immiscible fluids) described in U.S. Pat. No. 7,622,280, and droplets generated by devices described in International Application Publication No. WO/2010/036352, first inventor: Colston, each of which is hereby incorporated by reference in its entirety. The term emulsion, as used herein, refers to a mixture of immiscible liquids (such as oil and water). Oil-phase and/or water-in-oil emulsions allow for the compartmentalization of reaction mixtures within aqueous droplets. In preferred embodiments, the emulsions comprise aqueous droplets within a continuous oil phase. In other embodiments, the emulsions provided herein are oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

In some embodiments, the aqueous phase can also comprise additives including, but not limited to, non-specific background/blocking nucleic acids (e.g., salmon sperm DNA), biopreservatives (e.g., sodium azide), PCR enhancers (e.g., Betaine, Trehalose, etc.), and inhibitors (e.g., RNAse inhibitors). In some embodiments a GC-rich additive comprising, e.g., Betaine and DMSO, is added to samples assayed in the methods provided herein.

The mixtures or emulsions described herein can be stable or unstable. In preferred embodiments, the emulsions are relatively stable and have minimal coalescence. Coalescence occurs when small droplets combine to form progressively larger ones. In some embodiments, less than about 0.00001%, 0.00005%, 0.00010%, 0.00050%, 0.001%, 0.005%, 0.01%, 0.05%, 0.1%, 0.5%, 1%, 2%. 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Splitting a sample into small reaction volumes as described herein, can enable the use of reduced amounts of reagents, thereby lowering the material cost of the analysis. Reducing sample complexity by partitioning also improves the dynamic range of detection, since higher-abundance molecules are separated from low-abundance molecules in different compartments, thereby allowing lower-abundance molecules greater proportional access to reaction reagents, which in turn enhances the detection of lower-abundance molecules.

In some embodiments, droplets can be generated having an average diameter of about 0.001, 0.01, 0.05, 0.1, 1, 5, 10, 20, 30, 40, 50, 60, 70, 80, 100, 120, 130, 140, 150, 160, 180, 200, 300, 400, or 500 microns. Microfluidic methods of producing emulsion droplets using microchannel cross-flow focusing or physical agitation are known to produce either monodisperse or polydisperse emulsions. In some embodiments, the droplets are monodisperse droplets. In some embodiments, the droplets are generated such that the size of said droplets does not vary by more than plus or minus 5% of the average size of said droplets. In some embodiments, the droplets are generated such that the size of said droplets does not vary by more than plus or minus 2% of the average size of said droplets. In some embodiments, a droplet generator can generate a population of droplets from a single sample, wherein none of the droplets vary in size by more than plus or minus 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Both the flow rate in a droplet generator and the length of nucleic acids in a sample can have an impact on droplet generation. One way to decrease extension is to decrease flow rate; however, this has the undesirable side effects of lower throughput and also increased droplet size. Long nucleic acids can disrupt droplet formation, in extreme cases, resulting in a steady flow rather than discrete droplets. Reducing nucleic acid size in a sample can improve droplet formation when nucleic acid loads are high (e.g., in experiments directed toward fetal aneuploidy detection). Samples with high nucleic acid loads (e.g., high DNA loads, high RNA loads, etc.) can be used in fetal aneuploidy detection experiments because fetal nucleic acids can be rare in a maternal sample compared to the amount of maternal nucleic acids. Reducing the length of nucleic acids in the maternal sample (e.g., by digestion, heat treatment, or shearing) can improve droplet formation.

Higher mechanical stability is useful for microfluidic manipulations and higher-shear fluidic processing (e.g., in microfluidic capillaries or through 90 degree turns, such as valves, in fluidic path). Pre- and post-thermally treated droplets or capsules can be mechanically stable to standard pipette manipulations and centrifugation.

In some embodiments, the droplet can be formed by flowing an oil phase through an aqueous sample. In some embodiments, the aqueous phase comprises a buffered solution and reagents for performing a PCR reaction, including nucleotides, primers, probe(s) for fluorescent detection, template nucleic acids, DNA polymerase enzyme, and optionally, reverse transcriptase enzyme.

In some embodiments, the aqueous phase comprises a buffered solution and reagents for performing a PCR reaction without solid-state beads, such as magnetic-beads. In some embodiments, the buffered solution can comprise about 1, 5, 10, 15, 20, 30, 50, 100, or 200 mM Tris. In some embodiments, the concentration of potassium chloride can be about 10, 20, 30, 40, 50, 60, 80, 100, 200 mM. In one embodiment, the buffered solution comprises 15 mM Tris and 50 mM KCl. In some embodiments, the nucleotides comprise deoxyribonucleotide triphosphate molecules, including dATP, dCTP, dGTP, dTTP, in concentrations of about 50, 100, 200, 300, 400, 500, 600, or 700 µM each. In some embodiments, dUTP is added within the aqueous phase to a concentration of about 50, 100, 200, 300, 400, 500, 600, or 700, 800, 900, or 1000 µM. In some embodiments, magnesium chloride (MgCl2) is added to the aqueous phase at a concentration of about 1.0, 2.0, 3.0, 4.0, or 5.0 mM. In one embodiment, the concentration of MgCl2 is 3.2 mM.

A non-specific blocking agent such as BSA or gelatin from bovine skin can be used, wherein the gelatin or BSA is present in a concentration range of approximately 0.1-0.9% w/v. Other possible blocking agents can include beta-lactoglobulin, casein, dry milk, or other common blocking agents. In some embodiments, preferred concentrations of BSA and gelatin are 0.1% w/v.

Primers for amplification within the aqueous phase can have a concentration of about 0.1, 0.2, 0.3, 0.4, 0.5, 0.6, 0.7, 0.8, 0.9, or 1.0 µM. In one embodiment, the concentration of primers is 0.5 µM. In some embodiments, the aqueous phase comprises one or more probes for fluorescent detection, at a concentration of about 0.1, 0.2, 0.3, 0.4, or 0.5 µM. In one embodiment, the concentration of probes for fluorescent detection is 0.25 µM. Amenable ranges for target nucleic acid concentrations in PCR are between about 1 pg and about 500 ng.

In some embodiments, a non-ionic Ethylene Oxide/Propylene Oxide block copolymer is added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. In one preferred embodiment, Pluronic F-68 is present at a concentration of 0.5% w/v.

In some embodiments magnesium sulfate can be substituted for magnesium chloride, at similar concentrations. A wide range of common, commercial PCR buffers from varied vendors can be substituted for the buffered solution.

The oil phase can comprise a fluorinated base oil which can be additionally stabilized by combination with a fluorinated surfactant such as a perfluorinated polyether. In some embodiments, the base oil can be one or more of HFE 7500, FC-40, FC-43, FC-70, or another common fluorinated oil. In some embodiments, the anionic surfactant is Ammonium Krytox (Krytox-AM), the ammonium salt of Krytox FSH, or morpholino derivative of Krytox-FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% w/w. In some embodiments, the concentration of Krytox-AS is 1.8%. In other embodiments, the concentration of Krytox-AS is 1.62%. Morpholino derivative of Krytox-FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% w/w. In some embodiments, the concentration of morpholino derivative of Krytox-FSH is 1.8%. In some embodiments, the concentration of morpholino derivative of Krytox-FSH is 1.62%.

The oil phase can further comprise an additive for tuning the oil properties, such as vapor pressure or viscosity or surface tension. Nonlimiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 1.00%, 1.25%, 1.50%, 1.75%, 2.00%, 2.25%, 2.50%, 2.75%, or 3.00% w/w. In some embodiments, 1H,1H,2H,2H-Perfluorodecanol is added to a concentration of 0.18% w/w.

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50, 60, 70, 80, 90, or 95 degrees Celsius. In some embodiments this heating occurs using a thermocycler. During the heating process, a fluid or mineral oil overlay can be used to prevent evaporation. Excess continuous phase oil may or may not be removed prior to heating. The biocompatible capsules can be resistant to coalescence and/or flocculation across a wide range of thermal and mechanical processing.

Following conversion, the capsules can be stored at about 3, 4, 5, 6, 7, 8, 9, 10, 15, 20, 25, 30, 35, or 40 degrees, with one embodiment comprising storage of capsules at less than about 25 degrees. In some embodiments, these capsules are useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more nucleic acid probes (e.g., molecular inversion probe, ligation probe, etc.) and can resist coalescence, particularly at high temperatures. Accordingly, PCR amplification reactions can occur at a very high density (e.g., number of reactions per unit volume). In some embodiments, greater than 100,000, 500,000, 1,000,000, 1,500,000, 2,000,000, 2,500,000, 5,000,000, or 10,000,000 separate reactions can occur per ml. In some embodiments, the reactions occur in a single well, e.g., a well of a microtiter plate, without inter-mixing between reaction volumes. The microcapsules can also contain other components necessary to enable a PCR reaction to occur, e.g., primers, probes, dNTPs, DNA or RNA polymerases, etc. These capsules exhibit resistance to coalescence and flocculation across a wide range of thermal and mechanical processing.

The compositions described herein include compositions comprising mixtures of two or more immiscible fluids such as oil and water that contain a type of nucleic acid probe (e.g., TaqMan probe, molecular inversion probe, ligation probe, etc.). In some cases, the composition comprises a restriction enzyme described herein, e.g., a droplet comprising a restion enzyme (e.g., methylation-sensitive enzyme). In other embodiments, the compositions described herein comprise microcapsules that contain a type of nucleic acid (e.g., TaqMan probe, molecular inversion probe, ligation probe, etc.). Such microcapsules can resist coalescence, particularly at high temperatures, and therefore enable amplification reactions to occur at a very high density (e.g., number of reactions per unit volume).

B. Performance/Accuracy/Sensitivity/Speed

The methods and compositions provided herein can quantify polynucleotides (e.g., fetal polynucleotides) in a sample with a high degree of accuracy. For example, the methods and compositions provided herein can quantify the amount of polynucleotides (e.g., fetal polynucleotides) in a sample with an accuracy of greater than 20%, 30%, 40%, 1%, 50%, 55%, 60%, 65%, 70%, 75%, 80%, 85%, 90%, 95%, 96%, 97%, 98%, 99%, 99.2%, 99.5%, 99.7%, or 99.9%. The methods and compositions provided herein can quantify the amount of polynucleotides (e.g., fetal polynucleotides) in a sample with a sensitivity of greater than 20%, 30%, 40%, 1%, 50%, 55%, 60%, 65%, 70%, 75%, 80%, 85%, 90%, 95%, 96%, 97%, 98%, 99%, 99.2%, 99.5%, 99.7%, or 99.9%. The methods and compositions provided herein can quantify the amount of polynucleotides (e.g., fetal polynucleotides) in a sample with superior confidence intervals. The methods and compositions provided herein can quantify the amount of polynucleotides (e.g., fetal polynucleotides) in a sample with a confidence interval of greater than 20%, 30%, 40%, 1%, 50%, 55%, 60%, 65%, 70%, 75%, 80%, 85%, 90%, 95%, 96%, 97%, 98%, 99%, 99.2%, 99.5%, 99.7%, or 99.9%.

In some embodiments, the methods and compositions provided herein can quantify polynucleotides originating from a female fetus within a maternal sample with the sensitivity that is at least 20%, 30%, 40%, 1%, 50%, 55%, 60%, 65%, 70%, 75%, 80%, 85%, 90%, 95%, 96%, 97%, 98%, 99%, 99.2%, 99.5%, 99.7%, or 99.9% of the sensitivity of the same assay for determining the load a fetal polynucleotide in a sample of maternal blood or plasma, wherein the origin of said fetal polynucleotide is a male fetus.

In some embodiments, the droplets described herein are generated at a rate of greater than about 1, 2, 3, 4, 5, 10, 50, 100, 200, 300, 400, 500, 600, 700, 800, 900, or 1000 droplets/second. The droplet rate can be about 1-1000, 1-500, 1-250, or 1-100 droplets/second.

The present disclosure provides means for rapid, efficient and sensitive detection of cellular processes such as cellular viability and growth rates. In some embodiments, less than about 0.00001, 0.00005, 0.00010, 0.00050, 0.001, 0.005, 0.01, 0.05, 0.1, 0.5, 1, 2, 2.5, 3, 3.5, 4, 4.5, 5, 6, 7, 8, 9, or 10 copies of target polynucleotide are detected. In some embodiments, less than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide are detected.

C. Processes/Systems

A variety of devices can be used to effectuate the methods described herein, either alone or in combination with other devices. In some embodiments, the device or devices are used to perform digital PCR. The digital PCR can be any appropriate microfluidic-based digital PCR. In some embodiments, the digital PCR is droplet digital PCR.

For example, following extraction of DNA from a maternal tissue sample containing maternal and fetal genetic material, and treatment of a portion of the sample with a methylation-specific chemical modification, a sample can be introduced to a droplet generator, which partitions the nucleic acids into multiple droplets within a water-in-oil emulsion. Examples of some droplet generators useful in the present disclosure are provided in International Application Publication No. WO/2010/036352, first inventor: Colston. Droplets can then be incubated in a thermocycler to allow amplification of target sequences. During the amplification reaction, a droplet comprising an amplified probe can experience an increase in fluorescence relative to droplets that do not contain amplified probe. The droplets can then be processed individually through a droplet reader, and data can be collected to detect fluorescence. Examples of some droplet readers useful in the present disclosure are provided in International Application Publication No. WO/2010/036352, first inventor: Colston, which is herein incorporated by reference in its entirety.

Often, data obtained from the devices as described is analyzed using an algorithm applied by a device such as a computer. In some embodiments, the droplet generator, thermocycler, droplet reader, and computer are each a separate device. In other embodiments, one device comprises two or more of such devices, in any combination. For example, one device can comprise a droplet generator in communication with a thermocycler. In other embodiments, a device can comprise a droplet generator, thermocycler, and droplet reader.

Following acquisition of fluorescence detection data, a computer is used in some embodiments to store and process the data. A computer-executable logic can be employed to perform such functions as subtraction of background fluorescence, assignment of target and/or reference sequences, and quantification of the data. For example, the number of droplets containing fluorescence corresponding to the presence of a fetal genetic element (such as methylated RASSF1A) in the sample can be counted and compared to the number of droplets containing fluorescence corresponding to the presence of genetic element common to fetal and maternal DNA (such as Beta Actin). A computer can be useful for displaying, storing, retrieving, or calculating diagnostic results from the molecular profiling; displaying, storing, retrieving, or calculating raw data from genomic or nucleic acid expression analysis; or displaying, storing, retrieving, or calculating any sample or patient information useful in the methods of the present disclosure.

In some embodiments, an integrated, rapid, flow-through thermal cycler device is used. See, e.g., International Application Publication No. WO/2010/036352, first inventor: Colston, which is herein incorporated by reference in its entirety. In such an integrated device, a capillary is wound around a cylinder that maintains 2, 3, or 4 temperature zones. As droplets flow through the capillary, they are subjected to different temperature zones to achieve thermal cycling. The small volume of each droplet results in an extremely fast temperature transition as the droplet enters each temperature zone. In one embodiment, viability testing is performed by moving droplets through the integrated thermal cycler to achieve rapid thermal cycling. In another embodiment, automated viability testing is performed by integrating cell suspension sampling, cell lysis, mixing lysate with PCR master mix, droplet generation, flow-through PCR, and detection. In another embodiment, the integrated ddPCR system automatically monitors small changes in cell-growth over the course of time by periodic autosampling and ddPCR analysis of the suspension. In another embodiment, the integrated ddPCR system measures the effects of treatment on cell growth.

Using the instant methods and compositions, ddPCR can be implemented for rapid, accurate cell viability determination, while reducing the cell incubation times, reducing the total analysis time, minimizing the sample size, and reducing the complexity of the testing. In addition, ddPCR for viability testing can be performed in an integrated system that allows in-line sampling and viability analysis of incubating cells.

The following is a description of an exemplary method for diagnosing fetal aneuploidy and highlights some devices that can be used in the methods herein. A maternal tissue sample containing maternal and fetal genetic material can be obtained. DNA can then be extracted from the sample, and bound to probes recognizing, for example, chromosome 1 and 21, which then can undergo a ligation reaction. A sample comprising ligated probes (as well as components necessary for a PCR reaction) can be introduced into a droplet generator, which partitions the probes into multiple droplets within a water-in-oil emulsion. Droplets can then be incubated in a thermocycler to allow amplification of the probes. During the amplification reaction, a droplet comprising an amplified probe can experience an increase in fluorescence relative to droplets that do not contain amplified probe. The droplets can then be processed individually through a droplet reader, and data is collected to detect fluorescence.

Data relating to the copy number of chromosome 1 and 21 can then compared in order to detect fetal aneuploidy. Often, the data is analyzed using an algorithm applied by a device such as a computer. In some embodiments, the droplet generator, thermocycler, droplet reader, and computer are each a separate device. In other embodiments, one device comprises two or more of such devices, in any combination. For example, one device can comprise a droplet generator in communication with a thermocycler. In other embodiments, a device can comprise a droplet generator, thermocycler, and droplet reader.

In some embodiments, the digital PCR is performed for less than about 15, 16, 17, 18, 19, 20, 21, 22, 23, 24, 25, 26, 27, 28, 29 or 30 cycles. In some embodiments, the digital PCR is performed for less than about 30 cycles. In some embodiments, digital PCR is performed in droplets with a size that is about or less than 1 nL.

D. Exemplary Digital PCR for CNV Analysis

This disclosure provides methods for the detection of genetic variations (e.g., CNV, fetal aneuploidy, SNPs), for example, by the use of digital PCR (e.g., droplet digital PCR), as well as specialized probes, often referred to herein as detection probes capable of hybridizing to a target polynucleotide. In the methods provided herein, a sample comprising a target nucleotide, or probes to said target nucleotide is partitioned into a plurality of compartments (e.g., droplets). The compartments (e.g., droplets) are then subjected to a thermocycling reaction to encourage PCR reactions within compartments that contain either a target nucleotide, or a probe to said target nucleotide, resulting in amplified products (e.g., amplified DNA, RNA or other nucleic acid).

The method can employ digital analysis, in which the DNA in the sample is partitioned to a nominal single molecule in a reaction volume to create a sample mixture. For example, the reaction volume can be a droplet, such as a droplet of an aqueous phase dispersed in an immiscible liquid, such as described in U.S. Pat. No. 7,041,481, which is hereby incorporated by reference in its entirety. Each reaction volume has a possibility of having distributed in it less than 1 target (e.g., target polynucleotide, targeting probe, or other target molecule) or one or more targets (e.g., target polynucleotide, targeting probe or other targeting molecule). The target molecules can be detected in each reaction volume, preferably as target sequences which are amplified, which can include a quantization (or quantification) of starting copy number of the target sequence, that is, 0, 1, 2, 3, etc.

E. Amplification Reaction

Techniques and devices for amplification of target and reference sequences (as well as sequences within ligation probes) are known in the art, and include the methods and devices described in U.S. Pat. No. 7,048,481. Briefly, the techniques include methods and compositions that separate samples into small droplets, in some instances with each containing on average less than one nucleic acid molecule per droplet, amplifying the nucleic acid sequence in each droplet and detecting the presence of a particular target sequence. In some embodiments, the sequence that is amplified is present on a probe to the genomic DNA, rather than the genomic DNA itself.

Primers are designed according to known parameters for avoiding secondary structures and self-hybridization. In some embodiments, different primer pairs will anneal and melt at about the same temperatures, for example, within 1, 2, 3, 4, 5, 6, 7, 8, 9 or 10° C. of another primer pair. In some embodiments, only ligatable probes, and no primers, are initially added to genomic DNA, followed by partitioning the ligated probes, followed by amplification of one or more sequences on the probe within each partition using, for example, universal primers. In some embodiments, greater than 1, 2, 3, 4, 5, 6, 7, 8, 9, 10, 15, 20, 25, 30, 35, 40, 45, 50, 100, 200, 500, 1000, 5000, 10,000 or more probes are initially used. Such probes can hybridize to the genetic targets described herein. For example, a mixture of probes can be used, wherein at least one probe targets a specific site on a chromosome and a second probe targets a different site on the same chromosome or a different chromosome. Each set of ligatable probes can have its own universal probe set and be distinguished by the corresponding TaqMan probe for each set. Or, all ligatable probe sets can use the same universal primer set and be distinguished by the corresponding TaqMan probe for each set. Exemplary sequences for universal primers bearing no homology to human genomic DNA are disclosed in US 2011-0159499, which is hereby incorporated by reference in its entirety.

While many embodiment disclosed herein are described in terms of PCR, some embodiments disclosed herein are primarily directed to the use of multiple individual genetic sequence detections. In some embodiments, the method of amplification can be, for example, a self-sustained sequence reaction, ligase chain reaction, rapid amplification of cDNA ends, and polymerase chain reaction, Q-beta phage amplification, strand displacement amplification, isothermal amplification or splice overlap extension polymerase chain reaction.

Primers can be prepared by a variety of methods including, but not limited to, cloning of appropriate sequences and direct chemical synthesis using methods well known in the art (Narang et al., Methods Enzymol. 68:90 (1979); Brown et al., Methods Enzymol. 68:109 (1979), both of which are herein incorporated by reference in its entirety). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. In one embodiment, one of the primers of the prime pair is longer than the other primer. In another embodiment, the 3' annealing lengths of the primers, within a primer pair, differ. Also, the annealing position of each primer pair can be designed such that the sequence and length of the primer pairs yield the desired melting temperature. The simplest equation for determining the melting temperature of primers smaller than 25 base pairs is the Wallace Rule ($Td=2(A+T)+4(G+C)$). Computer programs can also be used to design primers, including, but not limited to, Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Net Primer (free web based program at http://premierbio soft.com/netprimer/netprlaunch/netprlaunch.html; internet address as of Apr. 17, 2002).

In another embodiment, the annealing temperature of the primers can be recalculated and increased after any cycle of amplification, including, but not limited to, cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers is incorporated into the products from each loci of interest, thus the TM can be recalculated based on both the sequences of the 5' half and the 3' half of each primer.

In some embodiments, desired sequences that can include target and reference sequences are represented by template MIPs, which are formerly-circularized MIPs that have been isolated and linearized as described above. Template MIPs serve as template molecules in PCR. In some embodiments, template MIPs are produced prior to droplet generation, and in other embodiments, template MIPs are produced during or following droplet generation. In an example of the last case, a circular MIP containing abasic sites resulting from uracil-N-deglycosylase treatment of uracil bases undergoes a spontaneous ring-opening reaction upon heating in a melting step of a PCR reaction in a thermocycler. In some embodiments, template MIPs serve as DNA templates for droplet digital PCR, wherein amplification of the template MIP corresponds to detection of the desired sequence that the MIP represents (e.g., a target or reference sequence). In some embodiments, the method involves producing a droplet for a droplet digital PCR reaction by flowing an immiscible liquid in a sample fluid, wherein the sample fluid comprises one or more MIPs or one or more template MIPs, and a master mix containing reagents necessary for PCR. In some embodiments, a master mix for PCR comprises a thermostable polymerase enzyme, universal primers for template MIP amplification, free DNA nucleotides for incorporation, and buffer components for the reaction. The thermostable polymerase enzyme can retain activity when exposed to temperatures greater than 99, 98, 97, 96, 95, 94, 93, 92, 91, 90, 80, 70 degrees or less. In some embodiments, the sample fluid additionally comprises digested genomic DNA or inactivated enzymes such as endonucleases and/or deglycosylases retained from MIP template generation. In some embodiments, the method involves generating droplets comprising less than one, one, or more than one genome equivalents of DNA represented by MIPs or MIP templates.

In some embodiments, desired sequences that can include target and reference sequences are present as part of a mixture containing unwanted background genomic DNA. In some embodiments, only desired sequences, and not background genomic DNA sequences, are detected using ligation detection reaction and droplet digital PCR (e.g., in embodiments where only ligation products are competent to form detectable products in PCR using a master mix comprising universal primers). In other embodiments, desired sequences are detected in droplet digital PCR using sequence-specific primers.

In some embodiments, the present disclosure involves compositions comprising emulsions comprising an average of about one genome equivalent of DNA that can be used to detect fetal genetic material. In some embodiments, one or more MIPs or MIP templates represent a sequence of interest (such as a region of chromosome 21) whose detection can enable determination of fetal aneuploidy. In some embodiments, a composition containing a sequence of interest representing a genetic target that can be associated with a genetic abnormality (such as trisomy) can be compared to a composition containing a sequence representing a reference sequence that may not be associated with a genetic abnormality. In some embodiments, sensitivity of detection can be enhanced through multiplexing of probes directed to a genetic target. Furthermore, multiple genetic targets can be examined in parallel using multiple simultaneous detection modes, such as different colors in the fluorescence detection methods detailed below.

In some embodiments, genetic targets can include any nucleic acid molecules that can be represented by ligation products such as MIPs, MIP templates, or ligated probes. These ligation products are present in a sample fluid in which an immiscible liquid is flowed to generate a droplet. Reagents necessary for PCR can also be contained in the droplet, for subsequent droplet digital PCR. Examples of genetic targets that can be analyzed herein include genetic variations, such as aneuploidy, mutations, insertions, additions, deletions, translocation, point mutation, trinucleotide repeat disorders and/or single nucleotide polymorphisms (SNPs), that may not be associated with fetal genetic abnormalities.

The annealing temperature of the primers can be recalculated and increased after any cycle of amplification, including, but not limited to, cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers is incorporated into the products from each loci of interest, thus the TM can be recalculated based on both the sequences of the 5' half and the 3' half of each primer. Any DNA polymerase that catalyzes primer extension can be used including, but not limited to, E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™. Genomic DNA polymerase, or sequenase. Preferably, a thermostable DNA polymerase is used. A hot start PCR can also be performed wherein the reaction is heated to 95° C. for two minutes prior to addition of the polymerase or the polymerase can be kept inactive until the first heating step in cycle 1. Hot start PCR can be used to minimize nonspecific amplification. Any number of PCR cycles can be used to amplify the DNA, including, but not limited to, 2, 5, 10, 15, 20, 25, 30, 35, 40, or 45 cycles.

Amplification of target nucleic acids (e.g., ligation probes, MIP probes) can be performed by any means known in the art. In some embodiments, target nucleic acids are amplified by polymerase chain reaction (PCR). Examples of PCR techniques that can be used include, but are not limited to, quantitative PCR, quantitative fluorescent PCR (QF-PCR), multiplex fluorescent PCR (MF-PCR), real time PCR(RT-PCR), single cell PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938. In some embodiments, amplification of target nucleic acids can occur on a bead. In other embodiments, amplification does not occur on a bead.

In some embodiments, thermocycling reactions are performed on samples contained in droplets. In some embodiments, the droplets remain intact during thermocycling. Droplets can remain intact during thermocycling at densities of greater than about 10,000 droplets/mL, 100,000 droplets/mL, 200,000 droplets/mL, 300,000 droplets/mL, 400,000 droplets/mL, 500,000 droplets/mL, 600,000 droplets/mL, 700,000 droplets/mL, 800,000 droplets/mL, 900,000 droplets/mL or 1,000,000 droplets/mL. In other embodiments, two or more droplets can coalesce during thermocycling. In other embodiments, greater than 100 or greater than 1,000 droplets can coalesce during thermocycling.

F. Detection and Analysis

Detection of PCR products can be accomplished using fluorescence techniques. DNA-intercalating dyes such as ethidium bromide or SYBR green that increases fluorescence upon binding DNA can provide a quantitative readout of the amount of DNA present in a reaction volume. As this amount of DNA increases over the course of a reaction, the fluorescence intensity increases. Methods involving DNA-intercalating dyes can be susceptible to background fluorescence since they do not measure DNA in a sequence-specific manner, and do not distinguish between reaction products and other molecules such as primer dimers. A method for detecting PCR products that provides sequence specificity involves probes that contain a fluorescer-quencher pair and hybridize to a specific sequence. The fluorescer can be any molecule emitting detectable light such as a fluorophore, and the quencher can be any molecule that absorbs this emission, reducing the intensity of emission by the fluorescer. When present in a solution containing a complementary sequence, the fluorescer-quencher probe binds to the sequence. During a PCR reaction, a polymerase such as Taq can use this probe as a primer, and the probe is cleaved by a 5'→3' exonuclease activity that functions in cells to excise RNA primers. In the case of PCR reactions using synthetic fluorescer-quencher probes as primers, the 5'→3' exonuclease activity causes the probes to be cleaved, resulting in separation of the fluorescer from the quencher. Once it is no longer covalently attached to the quencher, the fluorescence emission from the fluorescer can be detected.

An aspect of the present disclosure involves detecting droplet digital PCR products produced using MIP templates. In some embodiments, detection occurs via cleavage of a fluorescer-quencher probe that binds a sequence that is specific to the MIP, distinct from the genetic target. This strategy allows the use of universal fluorescer-quencher probes that detect MIPs without requiring sequence specificity to the genetic target represented by the MIP.

In some embodiments, molecular beacon (MB) probes, which become fluorescent on binding to the target sequence (s) can be used. MB probes are oligonucleotides with stem-loop structures that contain a fluorescer at the 5' end and a quencher at the 3' end. The degree of quenching via fluorescence energy resonance transfer can be inversely proportional to the 6th power of the distance between the quencher and the fluorescer. After heating and cooling, MB probes reform a stem-loop structure, which quenches the fluorescent signal from the fluorescer. If a PCR product whose sequence is complementary to the loop sequence is present during the heating/cooling cycle, hybridization of the MB to one strand of the PCR product will increase the distance between the quencher and the fluorescer, resulting in increased fluorescence.

In some embodiments, detection occurs through the use of universal probes. A universal fluorescer probe (UFP) can contain a fluorescent molecule that emits a detectable electromagnetic radiation upon absorbing electromagnetic radiation in a range of wavelengths. A universal quencher probe (UQP) can contain a quencher molecule that reduces the intensity of fluorescent emission of a proximal fluorescer probe. In some cases, a universal fluorescer probe contains a nucleic acid segment that hybridizes to a complementary nucleic acid segment on a universal quencher probe or a complementary nucleic acid segment within a target sequence, such as a MIP. During PCR, amplification of such a target sequence results in increased binding of a universal fluorescer probe to a target sequence, compared to a quencher probe, which results in increased detectable fluorescence. In some embodiments, the length of complementary sequence between a universal fluorescer probe and a universal quencher probe can be varied to modulate the melting temperature of the complex of universal fluorescer probe bound to universal quencher probe. In some embodiments, the length of the complementary sequence can be 15 base pairs. In some embodiments, the length of the complementary sequence can be more than about 5, 10, 15, 20, 25, 30, 35, 40, 45, 50, 55, 60, 70, or 80 base pairs. The melting temperature of the complex of universal fluorescer probe bound to universal quencher probe can be greater than about 40, 45, 50, 55, 60, 65, 70, 75, 80, 85, 90, or 95 degrees Celsius.

An exemplary two-color system for detection of nucleic acids in droplets using universal primers and universal probes without cleavage is described here. A universal probe comprises two complementary oligonucleotides, one fluorescer probe containing a fluorescent molecule and one quencher probe containing a quenching molecule. The two complementary oligonucleotides can comprise fluorescer probes that fluoresce at different colors and are distinguishable in detection. When bound to the quencher probe, the fluorescence intensity of the fluorescer probe can be substantially reduced. Additionally, two pairs of universal forward and reverse primers contain regions that are complementary to the fluorescer probe and promote PCR amplification of a target sequence. In the first round of amplification, the region complementary to the fluorescer probe is incorporated via the universal primers into the template. In subsequent rounds of amplification, the fluorescer probes can therefore hybridize to this template, rather than to their respective quencher probes. As more of these templates are generated exponentially by amplification reactions, fluorescer-quencher complexes are replaced by fluorescer-template complexes through competitive binding. As a result of this separation between fluorescer probe and quencher probe, fluorescence intensity will increase in the reaction, and can be detected in following steps.

Universal probes can be designed by methods known in the art. In some embodiments, the probe is a random sequence. The universal probe can be selected to ensure that it does not bind the target polynucleotide in an assay, or to other non-target polynucleotides likely to be in a sample (e.g., genomic DNA outside the region occupied by the target polynucleotide). Exemplary sequences for universal probes are disclosed in US 2011-0159499, which is hereby incorporated by reference in its entirety.

Fluorescence detection can be achieved using a variety of detector devices equipped with a module to generate excitation light that can be absorbed by a fluorescer, as well as a module to detect light emitted by the fluorescer. In some embodiments, samples (such as droplets) can be detected in bulk. For example, samples can be allocated in plastic tubes that are placed in a detector that measures bulk fluorescence from plastic tubes. In some embodiments, one or more samples (such as droplets) can be partitioned into one or more wells of a plate, such as a 96-well or 384-well plate, and fluorescence of individual wells can be detected using a fluorescence plate reader.

In some embodiments, the detector further comprises handling capabilities for droplet samples, with individual droplets entering the detector, undergoing detection, and then exiting the detector. For example, a flow cytometry device can be adapted for use in detecting fluorescence from droplet samples. In some embodiments, a microfluidic device equipped with pumps to control droplet movement is used to detect fluorescence from droplets in single file. In some embodiments, droplets are arrayed on a two-dimensional surface and a detector moves relative to the surface, detecting fluorescence at each position containing a single droplet.

Following acquisition of fluorescence detection data, a computer is used in some embodiments to store and process the data. A computer-executable logic can be employed to perform such functions as subtraction of background fluorescence, assignment of target and/or reference sequences, and quantification of the data. For example, the number of droplets containing fluorescence corresponding to the presence of an suspected aneuploid chromosome (such as chromosome 21) in the sample can be counted and compared to the number of droplets containing fluorescence corresponding to the presence of chromosome not suspected to be aneuploidy (such as chromosome 1). A computer can be useful for displaying, storing, retrieving, or calculating diagnostic results from the molecular profiling; displaying, storing, retrieving, or calculating raw data from genomic or nucleic acid expression analysis; or displaying, storing, retrieving, or calculating any sample or patient information useful in the methods of the present disclosure. In one embodiment, a computer readable medium is provided.

Following digital PCR of samples having primers to amplify a target and a reference sequence, the number of positive samples having a target sequence and the number of positive samples having a reference sequence can be compared. Since this is a comparison of sequences present in the maternal tissue, there is no need to differentiate between maternal and fetal DNA. When a target sequence contains the same number of copies as a reference sequence known to be diploid, then the sample can be determined to be diploid as well. When the target sequence differs from the reference sequence, then the sample possibly contains an aneuploidy.

In some embodiments, the genomic DNA obtained from a maternal tissue as described above is partitioned into multiple reaction volumes (e.g., droplets), so that there is, on average, less than one genome equivalent (GE) per droplet. In some embodiments, the droplets contain much more than, on average, one GE per droplet, such as, on average, 1, 2, 3, 4, 5, 6, 7, 8, 9, 10, 15, 20, 25, 30, 35, 30, 45, or 50 GE/droplet. In some embodiments, a sample will produce greater than on average 1, 5, or 10 GE/droplet, but, nonetheless some of the droplets will contain no GE, or no target polynucleotide. In such embodiments, it can be necessary to apply an algorithm to calculate the average number of copies/droplet of a particular genetic target. In some embodiments, the genetic target is actually an entire chromosome (or fragment), that is then fragmented and therefore one copy can appear in multiple droplets.

Often, when individual discrete reaction volumes are analyzed for the presence of a genetic abnormality to be tested, the DNA (chromosomal) to be analyzed can on average, either be present or absent, permitting so-called digital analysis. The collective number of reaction volumes containing a particular target sequence can be compared to a reference sequence for differences in number. A ratio other than normal (e.g., 1:1) between a target sequence and a reference sequence known to be a diploid sequence is indicative of an aneuploidy. For example, a sample can be partitioned into reaction volumes, such as droplets, such that each droplet contains less than a nominal single genome equivalent of DNA. The relative ratio of the target of interest (e.g., a genetic marker for chromosome 21 trisomy, or related probe) to a reference sequence (e.g., known diploid sequence on chromosome 1, or related probe) can be determined by examining a large number of reaction volumes (e.g., droplets), such as 10,000, 20,000, 50,000, 100,000, 200,000, 500,000 or more. In other embodiments, the reaction volumes, such as droplets, comprise on average one or more target nucleotides (or genomic equivalents) per droplet. In such embodiments, the average copy number of the target nucleotide can be calculated by applying an algorithm, such as that described in Dube et al. (2008) *Plos One* 3(8): e2876.

By analyzing a large number of reaction volumes, a change in the relative ratio from 1:1 resulting from the fetal aneuploidy can be measured from a mixture of fetal and maternal DNA in the starting sample, where the relative concentration of fetal DNA is low compared to the maternal DNA. This is termed a digital analysis, because each reaction volume will have, on average, one genome equivalent per reaction volume, and furthermore, the dilution can be read as a binary "yes-no" result as to the presence of the sequence (e.g., target or reference) to be counted.

The methods and compositions described herein can be used in a wide range of applications. In some embodiments, the methods and compositions related to methods for diagnosing, detecting, identifying, predicting, evaluating, or prognosing a condition associated with a genetic disorder. Such condition can due to genetic causes, including genetic disorders, variations, mutations, SNPs, deletions, amplifications, translocations, inversions, or any other abnormality within a specific genetic locus (including any locus provided herein).

The methods and compositions provided herein can be used to evaluate the relative copy number of a first polynucleotide (e.g., DNA, RNA, genomic DNA, mRNA, siRNA, miRNA, cRNA, single-stranded DNA, double-stranded DNA, single-stranded RNA, double-stranded RNA, tRNA, rRNA, cDNA, etc.) compared to a second polynucleotide. The methods can be used to analyze the quantity of synthetic plasmids in a solution; to detect the sequence of a pathogenic organism (e.g., bacteria, virus, retrovirus, lentivirus, HIV-1, HIV-2, influenza virus, etc.) within a sample obtained from a subject. The methods also can be used in other applications wherein a rare population of polynucleotides exists within a larger population of polynucleotides.

VII. Sample Acquisition and Preparation

This starting material (e.g., biological sample) for use in the methods and compositions disclosed herein can be obtained in some embodiments from a hospital, laboratory, clinical or medical laboratory. In some embodiments, the sample is taken from a subject (e.g., a patient, a person suspected of exposure to an infectious agent, a person having an infectious disease). In some embodiments, the sample is obtained from a swab of a surface, such as a door or bench top.

The present disclosure involves methods of obtaining a biological sample comprising fetal DNA. In certain embodiments, fetal DNA can be obtained from maternal blood, maternal urine, maternal sweat, maternal cells, or cell free DNA from the mother. In some embodiments, the biological sample can be biological fluid. In some embodiments, the biological sample can be a maternal biological sample. In some embodiments, samples can be whole blood, bone marrow, blood spots, blood serum, blood plasma, buffy coat preparations, saliva, cerebrospinal fluid, buccal swabs, solid tissues such as skin and hair, body waste products, such as feces and urine. In other embodiments, samples can be lysates, homogenates, or partially purified samples of biological materials. In other embodiments, biological materials can include crude or partially purified mixtures of nucleic acids. In some embodiments, the biological sample is serum, urine, sweat, cells, or cell free DNA.

In some embodiments, the methods and compositions of the present disclosure provide a means for obtaining fetal or maternal genetic material. The methods and compositions can provide for detecting a difference in copy number of a target polynucleotide without the need of an invasive surgical procedure, amniocentesis, chorionic villus sampling, etc. In other embodiments, the methods and compositions can provide for detecting a difference in copy number of a target polynucleotide from a sample (e.g., blood sample), to be used in addition to, as supplementary to, a preliminary step to, or as an adjunct to a more invasive test such as a surgical procedure. Often, the fetal/maternal genetic material can be obtained via a blood draw, or other method provided herein. In some embodiments, the starting material can be maternal plasma or peripheral blood, such as maternal peripheral venous blood. The peripheral blood cells can be enriched for a particular cell type (e.g., mononuclear cells; red blood cells; CD4+ cells; CD8+ cells; B cells; T cells, NK cells, or the like). The peripheral blood cells can also be selectively depleted of a particular cell type (e.g., mononuclear cells; red blood cells; CD4+ cells; CD8+ cells; B cells; T cells, NK cells, or the like). The starting material can also be bone marrow-derived mononuclear cells. The starting material can also include tissue extracted directly from a placenta (e.g., placental cells) or umbilical cord (e.g., umbilical vein endothelial cells, umbilical artery smooth muscle cell, umbilical cord blood cells). The starting material can also derive directly from the fetus in the form, e.g., of fetal tissue, e.g., fetal fibroblasts or blood cells. The starting material can also be from an infant or child, including neonatal tissue.

This starting material can be obtained in some embodiments from a hospital, laboratory, clinical or medical laboratory. In some embodiments, the sample can be taken from a subject (e.g., an expectant mother) after at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or more weeks of gestation. In some embodiments, the subject is affected by a genetic disease, a carrier for a genetic disease or at risk for developing or passing down a genetic disease, where a genetic disease can be any disease that can be linked to a genetic variation such as mutations, insertions, additions, deletions, translocation, point mutation, trinucleotide repeat disorders and/or single nucleotide polymorphisms (SNPs). In other embodiments, the sample can be taken from a female patient of childbearing age and, in some embodiments, the female patient is not pregnant or of unknown pregnancy status. In still other embodiments, the subject can be a male patient, a male expectant father, or a male patient at risk of, diagnosed with, or having a specific genetic abnormality. In some embodiments, a female patient is known to be affected by, or is a carrier of, a genetic disease or genetic variation, or is at risk of, diagnosed with, or has a specific genetic abnormality. In some embodiments, the status of the female patient with respect to a genetic disease or genetic variation is not known. In other embodiments, the sample can be taken from any child or adult patient of known or unknown status with respect to copy number variation of a genetic sequence. In some embodiments, the child or adult patient is known to be affected by, or is a carrier of, a genetic disease or genetic variation.

An advantage of the methods and compositions provided herein is that they can enable detection of fetal nucleic acids (e.g., DNA, RNA) at a relatively early stage of gestation and at stages when the total concentration of fetal nucleic acids (e.g., DNA, RNA) in the maternal plasma is low. The starting material (e.g., biological sample) can have a fetal concentration that is at least about 0.0001%, 0.001%, 0.01%, 0.1%, 0.2%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, or more of the total maternal genomic DNA load in a maternal sample, and preferably at least about 3% of the total maternal genomic DNA load. In some embodiments, the fetal DNA concentration can be less than about 0.1%, 0.2%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, or 25%, of the total maternal genomic DNA load in a maternal sample. In embodiments where the starting material (e.g., biological sample) comprises a type of polynucleotide (e.g., DNA, RNA) present in one quantity (H) and a type of polynucleotide (e.g., DNA, RNA, etc.) present at a lower quantity (L) compared to H, the starting material (e.g., biological sample) can have a concentration of L that is at least about 0.1%, 0.2%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, or more of the total concentration of H in the sample, and preferably at least about 3% of the H. In some embodiments, the L can be less than about 0.1%, 0.2%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, or more of the total quantity of H in the sample.

In some embodiments, in order to obtain sufficient nucleic acid for testing, a blood volume of at least about 1, 2, 3, 4, 5, 10, 20, 25, 30, 35, 40, 45, 50, or more mL is drawn. The blood volume can be about 1-50, 1-40, 1-30, 1-20, or 1-10 mL. This blood volume can provide at least 1,000 genome equivalents (GE) of total DNA. Total DNA can be present at roughly 1,000 GE/mL of maternal plasma in early pregnancy, with a fetal DNA concentration of about 3.5% of total plasma DNA. However, less blood can be drawn for a genetic screen where less statistical significance is required, or the DNA sample is enriched for fetal DNA. Also, the fetal DNA concentration can vary according to the gestational age of the fetus. In some embodiments, fetal DNA or RNA can be enriched by isolating red blood cells, in particular fetal nucleated red blood cells, which differ from anucleate adult red blood cells as described below. In other embodiments, red blood cells can be removed from a maternal blood sample, and genetic material can be obtained from maternal plasma.

In some embodiments, the starting material (e.g., biological sample) can be a tissue sample comprising a solid tissue. Non-limiting examples of solid tissue include brain, liver, lung, kidney, prostate, ovary, spleen, lymph node (including tonsil), thyroid, pancreas, heart, skeletal muscle, intestine, larynx, esophagus, and stomach. In other embodiments, the starting material (e.g., biological sample) can be cells containing nucleic acids, including, but not limited to, connective tissue, muscle tissue, nervous tissue, and epithelial cells, and in particular exposed epithelial cells such as skin cells and hair cells. In yet other embodiments, the starting material (e.g., biological sample) can be a sample containing nucleic acids from any organism from which genetic material can be obtained and detected by droplet digital PCR, as outlined herein.

A. Enrichment of Fetal Material

Fetal cells can be enriched from a maternal sample containing a mixture of fetal and maternal cells. In some embodiments, such enrichment can occur where fetal nucleic acid concentration is at least about 0.1%, 0.2%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25% or more of the total maternal genomic DNA (or RNA) load.

In some embodiments, fetal cells can be enriched by affinity methods, which can include collection of fetal cells on a solid structure conjugated with molecules that have a greater affinity for fetal cells than non-fetal cells (e.g., fetal-specific antibodies). Non-limiting examples of a solid structure can include, but are not limited to, a polymer surface, magnetic beads, polymer beads, or the surface of a microfluidic channel. In some embodiments, a biological sample is not enriched for fetal cells prior to, or as part of, the methods or compositions described herein. In some embodiments, the fetal cells in a sample are not enriched by affinity methods. In some embodiments, the fetal cells in a sample are not enriched by the use of fetal-specific antibodies. In some embodiments, the fetal cells in a sample are not enriched via the introduction of the sample to a microfluidic device.

Flow cytometry techniques can also be used to enrich fetal cells (Herzenberg et al., PNAS 76: 1453-1455 (1979); Bianchi et al., PNAS 87: 3279-3283 (1990); Bruch et al., Prenatal Diagnosis 11: 787-798 (1991)). U.S. Pat. No. 5,432,054, which is hereby incorporated by reference in its entirety, also describes a technique for separation of fetal nucleated red blood cells, using a tube having a wide top and a narrow, capillary bottom made of polyethylene. In some embodiments, flow cytometry is not used to enrich fetal cells in samples analyzed using the present methods or compositions. Centrifugation using a variable speed program can result in a stacking of red blood cells in a capillary based on the density of the molecules. The density fraction containing low-density red blood cells, including fetal red blood cells, can be recovered and then differentially hemolyzed to preferentially destroy maternal red blood cells. A density gradient in a hypertonic medium can be used to separate red blood cells, now enriched in the fetal red blood cells, from lymphocytes and ruptured maternal cells. A hypertonic solution can optionally be employed to shrink the red blood cells, which can increase their density, and facilitate purification from the more dense lymphocytes. After the fetal cells have been isolated, fetal DNA can be purified using standard techniques in the art, detailed herein.

In some embodiments, the maternal blood can be processed to enrich the fetal DNA concentration in the total DNA, as described in Li et al., (2005) J. Amer. Med. Assoc. 293:843-849, which is hereby incorporated by reference in its entirety. Briefly, circulatory DNA can be extracted from 5- to 10-mL of maternal plasma using commercial column technology (e.g., Roche High Pure Template DNA Purification Kit; Roche) in combination with a vacuum pump. After extraction, the DNA can be separated by agarose gel electrophoresis using, e.g., a gel containing less than, about, or more than 1% agarose w/v). The gel fraction containing circulatory DNA with a size of approximately 300 nucleotides can be carefully excised. The DNA can be extracted from this gel slice by using an extraction kit (e.g., QIAEX II Gel Extraction Kit; Qiagen) and eluted into a final volume of 40-μL sterile 10-mM TRIS-hydrochloric acid, pH 8.0.

In some embodiments, free fetal DNA can be isolated from a maternal blood sample containing whole cells. In some embodiments, free fetal DNA can be isolated from a sample of maternal plasma. In some embodiments, the plasma sample can be at least about 50%, 75%, or 95% free of intact cells. In some embodiments, the plasma can be completely free of intact cells.

United States Patent Application 20040137470 to Dhallan, Ravinder S, published Jul. 15, 2004, entitled "Methods for detection of genetic disorders," is herein incorporated by reference in its entirety. This application describes an enrichment procedure for fetal DNA, that can be utilized along with the methods and compositions disclosed herein. Blood can be collected into 9 ml EDTA Vacuette tubes (catalog number NC9897284) and 0.225 ml of a 10% neutral buffered solution containing formaldehyde at less than, equal to, or greater than 4% w/v can be added to each tube, followed by gentle inversion. The tubes can be stored at 4° C. until ready for processing. Agents that impede cell lysis or stabilize cell membranes can be added to the tubes including, but not limited to, crosslinkers (e.g., primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, etc.); formaldehyde, and derivatives of formaldehyde; formalin; glutaraldehyde, and derivatives of glutaraldehyde; etc. Any concentration of agent that stabilizes cell membranes or impedes cell lysis can be added. In one embodiment, the agent that stabilizes cell membranes or impedes cell lysis is added at a concentration that does not impede or hinder subsequent reactions.

In another embodiment, DNA can be isolated using techniques and/or protocols that substantially reduce the amount of maternal DNA in the sample including, but not limited to, techniques involving density gradient centrifugation. This technique can be used to separate a blood sample into three layers: a top layer of clear fluid (i.e., plasma), a bottom layer of red fluid that is enriched with red blood cells, and a whitish or green middle layer (i.e., buffy coat) that is enriched, e.g., with white blood cells and platelets. In one embodiment, a sample can be centrifuged with the braking power for the centrifuge set to zero (i.e., the brake on the centrifuge is not used) after which the entire supernatant, or a portion of the supernatant, can be transferred to a new tube with minimal or no disturbance of the "buffy-coat". In one embodiment, both acceleration power and braking power for the centrifuge are set to zero. In another embodiment, the DNA can be isolated using techniques and/or protocols that substantially reduce the amount of maternal DNA in the sample including, but not limited to, centrifuging the samples with the acceleration power for the centrifuge set to zero, transferring the supernatant to a new tube with minimal or no disturbance of the "buffy-coat," and transferring only a portion of the supernatant to a new tube. In another embodiment, the "buffy-coat" is removed from the tube prior to removal of the supernatant using any applicable method including, but not limited to, using a syringe or needle to withdraw the "buffy-coat." In another embodiment, the braking power for the centrifuge is set at a percentage including, but not limited to, 1-5%, 5-10%, 1-10%, 10-20%, 20-30%, 30-40%, 40-50%, 50-60%, 60-70%, 70-80%, 80-90%, 90-95%, 95-99%, or any included sub-range of the maximum braking power of a centrifuge. In another embodiment, the acceleration power for the centrifuge is set at a percentage including, but not limited to, about 1-5%, 5-10%, 1-10%, 10-20%, 20-30%, 30-40%, 40-50%, 50-60%, 60-70%, 70-80%, 80-90%, 90-95%, 95-99%, or any included sub-range of the maximum acceleration power of a centrifuge.

In another embodiment, the present disclosure is directed to a composition comprising free fetal DNA and free maternal DNA, wherein the composition comprises a relationship of free fetal DNA to free maternal DNA including, but not limited to, at least about 1% free fetal DNA, at least about 2% free fetal DNA, at least about 3% free fetal DNA, at least about 4% free fetal DNA, at least about 5% free fetal DNA, at least about 6% free fetal DNA, at least about 7% free fetal DNA, at least about 8% free fetal DNA, at least about 9% free fetal DNA, at least about 10% free fetal DNA, at least about 11% free fetal DNA, at least about 12% free fetal DNA, at least about 13% free fetal DNA, at least about 14% free fetal DNA, at least about 15% free fetal DNA, at least about 20% free fetal DNA, at least about 30% free fetal DNA, at least about 40% free fetal DNA, at least about 50% free fetal DNA, at least about 60% free fetal DNA, at least about 70% free fetal DNA, at least about 80% free fetal DNA, at least about 90% free fetal DNA, at least about 91% free fetal DNA, at least about 92% free fetal DNA, at least about 93% free fetal DNA, at least about 94% free fetal DNA, at least about 95% free fetal DNA, at least about 96% free fetal DNA, at least about 97% free fetal DNA, at least about 98% free fetal DNA, at least about 99% free fetal DNA, and at least about 99.5% free fetal DNA.

In some embodiments, a cell membrane stabilizing agent can be added to a maternal blood sample to reduce maternal cell lysis during DNA purification. Suitable stabilizing agents can include, but are not limited to, aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, *ginkgo Biloba* extract, diphenylhydantoin, perftoran, polyvinylpyrrolidone, phosphatidylserine, tegretol, PABA, disodium cromglycate, nedocromil sodium, phenyloin, zinc citrate, mexitil, dilantin, sodium hyaluronate, or polaxamer 188. In another embodiment, an agent that preserves or stabilizes the structural integrity of cells can be used to reduce the amount of cell lysis.

Any protocol that reduces the amount of free maternal DNA in the maternal blood can optionally be used prior to obtaining a sample. In one embodiment, prior to obtaining a sample, a pregnant female can abstain from physical activity for a period of time including, but not limited to, about 0-5, 5-10, 10-15, 15-20, 20-25, 25-30, 30-35, 35-40, 40-45, 45-50, 50-55, 55-60, 60-120, 120-180, 180-240, 240-300, 300-360, 360-420, 420-480, 480-540, 540-600, 600-660, 660-720, 720-780, 780-840, 840-900, 900-1200, 1200-1500, 1500-1800, 1800-2100, 2100-2400, 2400-2700, 2700-3000, 3000-3300, 3000-3600, 3600-3900, 3900-4200, 4200-4500, or greater than 4500 minutes. In another embodiment, a sample can be obtained from a pregnant female after her body has reached a relaxed state. The period of rest prior to obtaining the sample can reduce the amount of maternal nucleic acid in the sample. In another embodiment, a sample can be obtained from a pregnant female at any time in the a.m., including, but not limited to 1 am, 2 am, 3 am, 4 am, 5 am, 6 am, 7 am, 8 am, 9 am, 10 am, 11 am, 12 am, or any intervening time. In another embodiment, a sample can be obtained from a pregnant female after she has slept for a period of time including, but not limited to, about 0-1, 1-2, 2-3, 3-4, 4-5, 5-6, 6-7, 7-8, 8-9, 9-10, 10-11, 11-12, or greater than 12 hours. In another embodiment, prior to obtaining a sample, a pregnant female can exercise for a period of time followed by a period of rest. In another embodiment, the period of exercise can include, but is not limited to, about 0-15, 15-30, 30-45, 45-60, 60-120, 120-240, or greater than 240 minutes. In another embodiment, agents that can prevent the destruction of DNA, including, but not limited to, a DNase inhibitor, zinc chloride, ethylenediaminetetraacetic acid, guanidine-HCl, guanidine isothiocyanate, N-lauroylsarcosine, or Na-dodecylsulphate can be added to a blood sample. In another embodiment, fetal DNA can be obtained from a fetal cell, wherein the fetal cell can be isolated from a source including, but not limited to, maternal blood, umbilical cord blood, chorionic amniotic fluid, embryonic tissues or mucous obtained from the cervix or vagina of the mother.

Cell lysis can contribute to the amount of cell free DNA in a sample. Fetal cells are likely destroyed in the maternal blood by the mother's immune system; however, a large portion of maternal cell lysis can occur during sample collection and/or processing. Thus, methods that prevent or reduce cell lysis can reduce the amount of maternal DNA in a sample, and thereby increase the relative percentage of free fetal DNA. In one embodiment, any blood drawing technique, method, protocol, or equipment that reduces the amount of cell lysis can be used in the methods disclosed herein, including, but not limited to, a large boar needle, a shorter length needle, a needle coating that increases laminar flow (e.g., Teflon), a modification of the needle bevel to increase laminar flow, or techniques that reduce the rate of blood flow.

A protocol for processing a blood sample can include the following steps: the blood can be stored at 4° C. prior to processing; a tube containing the blood can be spun at 1000 rpm for ten minutes in a centrifuge, the centrifuge can have the braking power set at zero; the tube can be spun a second time at 1000 rpm for ten minutes; the supernatant (i.e., plasma) of the sample can be transferred to a new tube and spun at 3000 rpm for ten minutes in a centrifuge with the brake set at zero; the supernatant can be transferred to a new tube and stored at −80° C.; the buffy coat, which contains maternal cells, can optionally be placed into a separate tube and stored at −80° C.

In some embodiments, a sample can be obtained from maternal blood or plasma.

In some embodiments, a sample is not processed to reduce the level of maternal DNA relative to the level of fetal DNA.

B. Extraction of DNA or RNA

In some embodiments, DNA or RNA can be extracted from a biological sample prior to analysis using methods of the disclosure.

Extraction can be by means that are standard to one skilled in the art, including, but not limited to, the use of detergent lysates, sonication, or vortexing with glass beads. In particular embodiments, DNA can be extracted according to standard methods from blood, e.g., with the use of the Qiagen UltraSens DNA extraction kit. In particular embodiments, isolated DNA can be fragmented (e.g., by reaction with restriction enzymes). Reaction conditions and enzymes that can be employed for such isolation and fragmentation/restriction are known to a person of ordinary skill in the relevant art (e.g., from the protocols supplied by the manufacturers), and could be optimized thereby for such uses.

Some embodiments disclosed herein are directed to methods for isolating free fetal DNA. In one embodiment, a method can comprise (a) obtaining a sample containing nucleic acid; (b) adding a cell lysis inhibitor, cell membrane stabilizer or cross-linker to the sample of (a); and (c) isolating the DNA. In another embodiment, DNA can be isolated using any technique suitable in the art including, but not limited to, techniques using gradient centrifugation (e.g., cesium chloride gradients, sucrose gradients, glucose gradients, etc.), centrifugation protocols, boiling, DNA purification kits (e.g., Qiagen purification systems, e.g., QIA DNA blood purification kit, HiSpeed Plasmid Maxi Kit, QIAfilter plasmid kit, etc.; Promega DNA purification systems, e.g., MagneSil Paramagnetic Particle based systems, Wizard SV technology, Wizard Genomic DNA purification kit, etc.; Amersham purification systems, e.g., GFX Genomic Blood DNA purification kit, etc.; Invitrogen Life Technologies Purification Systems, e.g., CONCERT purification system, etc.; Mo-Bio Laboratories purification systems, e.g., Ultra-Clean BloodSpin Kits, UltraClean Blood DNA Kit, etc.).

Some embodiments disclosed herein are directed to methods for isolating free fetal DNA from a sample containing nucleic acid to which a cell lysis inhibitor, cell membrane stabilizer or cross-linker has been added. In one embodiment, the free fetal DNA can be isolated from a sample (e.g., plasma or serum) obtained from the blood of a pregnant female.

In another embodiment, DNA can be isolated from a sample using techniques and/or protocols that substantially reduce the amount of maternal DNA in the sample including, but not limited, techniques involving density gradient centrifugation. In one embodiment, a sample can be centrifuged with the braking power for the centrifuge set to zero (i.e., the brake on the centrifuge is not used) after which the entire supernatant, or a portion of the supernatant, can be transferred to a new tube with minimal or no disturbance of the "buffy-coat". In one embodiment, both acceleration power and braking power for the centrifuge are set to zero.

Genomic DNA can be isolated from plasma (e.g., maternal plasma) using techniques known in the art, such as using the Qiagen Midi Kit for purification of DNA from blood cells. DNA can be eluted in 100 µl of distilled water. The Qiagen Midi Kit can also be used to isolate DNA from the maternal cells contained in the buffy coat. A QIAamp Circulating Nucleic Acid Kit can also be used for such purposes, see, e.g., http://www.qiagen.com/products/qiaampcirculatingnucleicacidkit.aspx.

Methods of extracting polynucleotides (e.g., DNA) can also include the use of liquid extraction (e.g., Trizol, DNA-zol) techniques.

In some embodiments, a sample (e.g., blood or plasma) can have a starting volume of at least about 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, 26 mL, 27 mL, 28 mL, 29 mL, 30 mL, 31 mL, 32 mL, 33 mL, 34 mL, 35 mL, 36 mL, 37 mL, 38 mL, 39 mL, 40 mL, 41 mL, 42 mL, 43 mL, 44 mL, 45 mL, 46 mL, 47 mL, 48 mL, 49 mL, 50 mL, or more. In some embodiments, at least about 10 µL, 20 µL, 30 µL, 40 µL, 50 µL, 60 µL, 70 µL, 80 µL, 90 µL, 100 µL, 110 µL, 120 µL, 130 µL, 140 µL, 150 µL, 160 µL, 170 µL, 180 µL, 190 µL, 200 µL, 210 µL, 220 µL, 230 µL, 240 µL, 250 µL, 260 µL, 270 µL, 280 µL, 290 µL, 300 µL, 350 µL, 400 µL, 450 µL, 500 µL, 600 µL, 700 µL, 800 µL, 900 µL, 1000 µL, or more of DNA or other polynucleotide can be extracted from a sample. In one embodiment, 100-200 µL of DNA can be extracted from a sample. An extracted DNA sample can then be converted (i.e., concentrated) into a final sample with a smaller final volume, e.g., at least about 1 µL, 2 µL, 3 µL, 4 µL, 5 µL, 6 µL, 7 µL, 8 µL, 9 µL, 10 µL, 11 µL, 12 µL, 13 µL, 14 µL, 15 µL, 16 µL, 17 µL, 18 µL, 19 µL, 20 µL, 21 µL, 22 µL, 23 µL, 24 µL, 25 µL, 26 µL, 27 µL, 28 µL, 29 µL, 30 µL, or more. In one embodiment, a final volume can be 5 µL. In another embodiment, a final volume can be 10 µL. In some embodiments, the volume of the starting sample can be greater than 2-, 5-, 10-, 20-, 30-, 40-, 50-, 75-, 100-, 500-, 1000-, 5000-, 10,000-, 50,000-, 100,000-, 500,000-, 1,000,000-fold, or more than the volume of the final sample. The final sample can also be a sample that is introduced into a device for droplet generation.

The final sample can be from about 1 to 20 µL in volume. In some embodiments, the final sample is greater than about 1, 5, 10, 15, 20, 25, 30, 35, 40, 45, 50, 75, or 100 µL. In some embodiments, the final sample is less than about 1, 5, 10, 15, 20, 25, 30, 35, 40, 45, 50, 75, or 100 µL. In some embodiments, the final sample is greater than about 1, 5, 10, 15, 20, 25, 30, 35, 40, 45, 50, 75, or 100 nL. In some embodiments, the final sample is less than about 1, 5, 10, 15, 20, 25, 30, 35, 40, 45, 50, 75, or 100 nL. In some embodiments, the final sample is greater than about 1, 5, 10, 15, 20, 25, 30, 35, 40, 45, 50, 75, or 100 pL. In some embodiments, the final sample is less than about 1, 5, 10, 15, 20, 25, 30, 35, 40, 45, 50, 75, or 100 pL.

In some embodiments, DNA can be concentrated by known methods and such methods can include centrifugation and the use of various enzyme inhibitors (e.g., a DNase inhibitor). The DNA can be bound to a selective membrane (e.g., silica) to separate it from contaminants. The DNA can also be enriched for fragments circulating in the plasma which are between 1 and 1000, 1 and 500, 1 and 400, 1 and 300, 1 and 200, 1 and 100 base pairs in length, or any included sub-ranges. Size selection can be done on a DNA size separation medium, such as an electrophoretic gel or chromatography material (Huber et al. (1993) Nucleic Acids Res. 21:1061-6), gel filtration chromatography, TSK gel (Kato et al. (1984) J. Biochem, 95:83-86). In some embodiments, a polynucleotide (e.g., DNA, RNA) can be selectively precipitated, concentrated (e.g., sample can be subjected to evaporation), or selectively captured using a solid-phase medium. Following precipitation, DNA or other polynucleotide can be reconstituted or dissolved into a small volume. A small volume can enable hybridization, or enable improved hybridization, of a probe with target polynucleotide.

In some embodiments, the starting material (e.g., biological sample) can comprise cells or tissue, including connective tissue, muscle tissue, nervous tissue, blood cells, or epithelial cells. In some embodiments, non-nucleic acid materials can be removed from the starting material (e.g., biological sample) using enzymatic treatments (such as protease digestion). Other non-nucleic acid materials can be removed, in some embodiments, by treatment with membrane-disrupting detergents and/or lysis methods (e.g., sonication, French press, freeze/thaw, dounce homogenation, etc.), which can be followed by centrifugation to separate nucleic acid-containing fractions from non-nucleic acid-containing fractions. The extracted nucleic acid can be from any appropriate sample including, but not limited to, nucleic acid-containing samples of tissue, bodily fluid (e.g., blood, serum, plasma, saliva, urine, tears, peritoneal fluid, ascitic fluid, vaginal secretion, breast fluid, breast milk, lymph fluid, cerebrospinal fluid, mucosa secretion, etc.), umbilical cord blood, chorionic villi, amniotic fluid, an embryo, a two-celled embryo, a four-celled embryo, an eight-celled embryo, a 16-celled embryo, a 32-celled embryo, a 64-celled embryo, a 128-celled embryo, a 256-celled embryo, a 512-celled embryo, a 1024-celled embryo, embryonic tissues, lymph fluid, cerebrospinal fluid, mucosa secretion, or other body exudate, fecal matter, an individual cell or extract of the such sources that contain the nucleic acid of the same, and subcellular structures such as mitochondria, using protocols well established within the art.

In some embodiments, blood can be collected into an apparatus containing a magnesium chelator including, but not limited to, EDTA, and is stored at 4° C. Optionally, a calcium chelator, including, but not limited to, EGTA, can be added. In another embodiment, a cell lysis inhibitor is added to the maternal blood including, but not limited to, formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sultydryl addition or disulfide reduction, carbohydrate reactive crosslinkers, carboxyl reactive crosslinkers, photoreactive crosslinkers, or cleavable crosslinkers.

Plasma RNA extraction is described in Enders et al. (2003), Clinical Chemistry 49:727-731, which is hereby incorporated by reference for such purposes. Briefly, plasma harvested after centrifugation steps can be mixed with Trizol LS reagent (Invitrogen) and chloroform. The mixture can be centrifuged, and the aqueous layer transferred to new tubes. Ethanol can be added to the aqueous layer. The mixture can then be applied to an RNeasy mini column (Qiagen) and processed according to the manufacturer's recommendations.

In some embodiments, when the extracted material comprises single-stranded RNA, double-stranded RNA, or DNA-RNA hybrid, these molecules can be converted to double-stranded DNA using techniques known in the field. In a non-limiting example, reverse transcriptase can be employed to synthesize DNA from RNA molecules. In some embodiments, conversion of RNA to DNA can require a prior ligation step, to ligate a linker fragment to the RNA, thereby permitting use of universal primers to initiate reverse transcription. In other embodiments, the poly-A tail of an mRNA molecule, for example, can be used to initiate reverse transcription. Following conversion to DNA, the methods detailed herein can be used, in some embodiments, to further capture, select, tag, or isolate a desired sequence.

Wherever the methods and compositions disclosed herein refer to fetal DNA, fetal RNA found in maternal blood (as well as RNA in general) can optionally be analyzed as well as or instead of said fetal DNA. As described previously, "mRNA of placental origin is readily detectable in maternal plasma," (Ng et al. (2003) Proc. Nat. Acad. Sci. 100:4748-4753, which is hereby incorporated by reference in its entirety), hPL (human placental lactogen) and hCG (human chorionic gonadotropin) mRNA transcripts are detectable in maternal plasma, as analyzed using the respective real-time RT-PCR assays. In the present method, mRNA encoding genes expressed in the placenta and present on a chromosome of interest can be used. In a non-limiting example, DSCR4 (Down syndrome critical region 4) is found on chromosome 21 and is mainly expressed in the placenta. Its mRNA sequence can be found at GenBank NM_005867, which is herein incorporated by reference in its entirety. In some embodiments, RNase H minus (RNase$^{H-}$) reverse transcriptases (RTs) can be employed to prepare cDNA for detection. RNase$^{H-}$ RTs are available from several manufacturers, such as SuperScript™ II (Invitrogen). Reverse transcriptase PCR can be used as described herein for chromosomal DNA. The RNA can include siRNA, miRNA, cRNA, tRNA, rRNA, mRNA, or any other type of RNA.

VIII. Diseases and Disorders/Genetic Targets

This disclosure provides methods and compositions useful for diagnosing, prognosing, detecting, and/or identifying a wide variety of diseases and disorders in a subject.

In some embodiments, the methods and compositions described herein are used to detect certain forms of cancer (e.g., breast cancer, cancer derived from hematopoietic (blood-forming) cells (e.g., lymphoma or leukemia), blastoma, cancer derived from connective tissue or mesenchymal cells (sarcoma), cancers of epithelial origin (carcinoma), prostate cancer, testicular cancer, ovarian cancer, bladder cancer, skin cancer, uterine cancer, colon cancer, lung cancer, pancreatic cancer, stomach cancer, liver cancer, thyroid cancer, brain cancer, a cancer listed in NCCN Clinical Practice Guidelines in Oncology, etc.). Hypermethylation of genes and regulatory regions of genes including RASSF1A, RAR-beta2, GSTP1, MGMT, DAPK has been reported in primary breast tumors and epithelial origin tumors (see U.S. Pat. No. 7,718,364). The present methods and compositions can be used to detect and/or quantify genes known to be hypermethylated in cancer (e.g., RASSF1A, RAR-beta2, GSTP1, MGMT, DAPK).

In some embodiments, blood samples are analyzed to detect changes in the methylation pattern of tumor cells that are sloughed-off into the blood stream (i.e., circulating tumor cells or CTCs). Patterns of aberrant methylation or demethylation that are characteristic of a tumor type can be identified by analysis of a blood sample. Aberrant methylation patterns can be correlated with cancer, imprinting defects and aging. In some embodiments, the sample is divided into two substantially equal portions, and the first portion is contacted with a methylation-sensitive enzyme. Following enzymatic treatment, each portion can be amplified and detected, e.g., by PCR. Prior to PCR, the portions can be partitioned into partitions such as emulsified droplets.

Other genetic diseases can be diagnosed using methods of the disclosure including, but not limited to, polycystic kidney disease, cystic fibrosis, Wilson's Disease, Gaucher's Disease, and Huntington's Disease, amyotrophic lateral sclerosis (or ALS or Lou Gehrig's Disease), Duchenne muscular dystrophy, Becker muscular dystrophy, Gaucher's disease, Parkinson's disease, Alzheimer's disease, Huntington's disease, Charcot-Marie-Tooth syndrome, Zellweger syndrome, autoimmune polyglandular syndrome, Marfan's syndrome, Werner syndrome, adrenoleukodystrophy (or ALD), Menkes syndrome, malignant infantile osteopetrosis, spinocerebellar ataxia, spinal muscular atrophy (or SMA), or glucose galactose malabsorption.

Genetic diseases can be associated with mutated forms of genes known to be associated with a genetic disease including, but not limited to, the CFTR gene, the ATP7B gene, the SOD1 gene, the gene that encodes the protein dystrophin, the gene that encodes the protein glucocerebrosidase, the ASYN gene, the HD gene, the gene that encodes the protein PMP22, the PKD1 gene, the PXR1 gene, the ARE gene, the FBN1 gene, the WRN gene, the ALD gene, the CLCN7 gene, the OSTM1 gene, the TCIRG1 gene, the SCA1 gene, the SMA gene, or the SGLT1 gene.

In some embodiments, any disease associated with a modification of the methylation state can be diagnose or prognosed according to methods of the disclosure. These diseases include, among others, CNS malfunctions; symptoms of aggression or behavioral disturbances; clinical, psychological and social consequences of brain damage; psychotic disturbances and personality disorders; dementia and/or associated syndromes; cardiovascular diseases, malfunction and damage; malfunction, damage or disease of the gastrointestinal tract; malfunction, damage or disease of the respiratory system; lesion, inflammation, infection, immunity and/or convalescence; malfunction, damage or disease of the body as a consequence of an abnormality in the development process; malfunction, damage or disease of the skin, the muscles, the connective tissue or the bones; endocrine and metabolic malfunction, damage or disease; headaches or sexual malfunction. The method according to the disclosure is also suitable for predicting undesired drug effects and for distinguishing cell types or tissues or for investigating cell differentiation. The relationship between DNA methylation and human disease is described, e.g., in Robertson K. D. (2005) *Nature Reviews Genetics* 6: 597-610, which is herein incorporated by reference in its entirety.

In some cases, the methods and compositions provided herein can be used to diagnose, detect, predict, identify, or otherwise evaluate the risk that a fetus has a genetic abnormality (e.g., Down's Syndrome, fetal aneuploidy, etc.). The methods can also be used to identify, quantify, diagnose, prognose, evaluate, or analyze the risk that an expectant mother will experience issues in pregnancy including miscarriage within the first trimester, second trimester, or third trimester; still birth; birth defects in her infant; pre-term labor, or other issues with labor; and any other condition associated with pregnancy, labor, or the birth of a child.

Often the methods and compositions described herein can enable detection of extra or missing chromosomes, particularly those typically associated with birth defects or miscarriage. For example, the methods and compositions described herein enable detection of autosomal trisomies (e.g., Trisomy 13, 15, 16, 18, 21, or 22). In some embodiments the trisomy can be associated with an increased chance of miscarriage (e.g., Trisomy 15, 16, or 22). In other embodiments, the trisomy that is detected is a liveborn trisomy that can indicate that an infant will be born with birth defects (e.g., Trisomy 13 (Patau Syndrome), Trisomy 18 (Edwards Syndrome), and Trisomy 21 (Down Syndrome)). The abnormality can also be of a sex chromosome (e.g., XXY (Klinefelter's Syndrome), XYY (Jacobs Syndrome), or XXX (Trisomy X). In certain preferred embodiments, the genetic target is one or more targets on one or more of the following chromosomes: 13, 18, 21, X or Y. For example, the genetic target can be 50 sites on chromosome 21 and/or 50 sites on chromosome 18, and/or 50 sites on chromosome 13.

Further fetal conditions that can be determined based on the methods and systems herein include monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g., XXXX, XXYY, XXXY, XYYY, XXXXX, XXXYY, XXXYY, XYYYY and XXYYY), monoploidy, triploidy (three of every chromosome, e.g., 69 chromosomes in humans), tetraploidy (four of every chromosome, e.g., 92 chromosomes in humans), pentaploidy and multiploidy.

In some embodiments, the genetic target comprises more than 1, 2, 3, 4, 5, 6, 7, 8, 9, 10, 11, 12, 13, 14, 15, 16, 17, 18, 19, 20, 21, 22, 23,24, 25, 26, 27, 28, 29, 30, 31, 32, 33, 34, 35, 36, 37, 38, 39, 40, 41, 42, 43,44,45, 46, 47, 48, 49, 50, 75, 100, 125, 150, 175, 200, 225, 250, 300, 350, 400, 450, 500, 1,000, 5,000, 10,000, 20,000, 30,000, 40,000, 50,000, 60,000, 70,000, 80,000, 90,000 or 100,000 sites on a specific chromosome. In some embodiments, the genetic target comprises targets on more than 1, 2, 3, 4, 5, 6, 7, 8, 9, 10, 11, 12, 13, 14, 15, 16, 17, 18, 19, 20, 21, or 22 different chromosomes. In some embodiments the genetic target comprises targets on less than 2, 3, 4, 5, 6, 7, 8, 9, 10, 11, 12, 13, 14, 15, 16, 17, 18, 19, 20, 21, 22, or 23 chromosomes. In some embodiments, the genetic target comprises a gene that is known to be mutated in an inherited genetic disorder, including autosomal dominant and recessive disorders, and sex-linked dominant and recessive disorders. Non-limiting examples include genetic mutations that give rise to autoimmune diseases, neurodegenerative diseases, cancers, and metabolic disorders. In some embodiments, the method detects the presence of a genetic target associated with a genetic abnormality (such as trisomy), by comparing it in reference to a genetic target not associated with a genetic abnormality (such as a gene located on a normal diploid chromosome).

The methods or compositions herein can also comprise primer sets and/or probes targeting separate regions of a chromosome. For example, a plurality of probes (e.g., MIP probes, ligation probes) can include at least one first probe that targets a first specific region of a chromosome and at least one second probe that targets a second specific region of a chromosome. In some embodiments, the first probe is tagged with a signaling molecule or agent (e.g., fluorophore), and the second probe is tagged with a second signaling molecule (e.g., a fluorophore of a color/wavelength distinguishable from that of the fluorophore conjugated to the first probe). The plurality of probes can then bind to the target polynucleotide. Following a selection protocol (e.g., ligation, circularization followed by exonuclease, etc.), the selected probes are partitioned into multiple partitions (e.g., droplets) followed by analysis of the number of partitions (e.g., droplets) containing a selected probe. The ratio between the number of first probes and the number of second probes can then be used to evaluate whether a target polynucleotide contains partial deletions, translocations, or amplifications. For example, such method can be used to detect a partial deletion of a chromosome, where probe 1 is directed to the intact chromosome and probe 2 is directed to a sequence within the deleted portion of the chromosome. In some embodiments, greater than 1, 2, 3, 4, 5, 6, 7, 8, 9, 10, 11, 12, 13, 14, 15, 16, 17, 18, 19, or 20 probes directed to different targets can be used. In some embodiments, this number can be greater than 20, 30, 40, 50, 100, 500, 1000, 5000, 10000, 50000, 100000, 500000, 1000000, or more.

In a non-limiting example, a ligation probe (or primer set) targets the q arm of chromosome 21 and a second ligation probe (or primer set) targets the p arm. If both are giving answers that are reasonably close (e.g., within some pre-defined confidence interval) to each other, this can provide validation of the measurement of chromosome 21 concentration. If, on the other hand, the measurement made with the targets on the p arm is significantly different from the measurement made with those on the q arm, this can indicate a partial aneuploidy (fragment of a chromosome), or it can indicate that the assay requires further optimization or validation.

The actual measurement of the target sets can be performed simultaneously by using one color for 21q targets and another color for 21p targets. Alternatively, the sample can be split so that the 21q measurements are made in one portion and the 21p measurement in the other. Also, chromosomes can be partitioned into more than two primer sets (or oligonucleotide probes) to have a more fine-grained assessment of the chromosomal copy number.

Examples of diseases where the target sequence exist in one copy in the maternal DNA (heterozygous) disease in a fetus (homozygous), include sickle cell cystic fibrosis, hemophilia, and Tay Sachs disease. Accordingly, using the methods described here, one can distinguish genomes with one specific mutation at a certain site from genomes with two specific mutations at a certain site.

Sickle-cell anemia is an autosomal recessive disease. Nine-percent of US blacks are heterozygous, while 0.2% are homozygous recessive. The recessive allele causes amino acid substitution in the beta chains of hemoglobin.

Tay-Sachs Disease is an autosomal recessive resulting degeneration of the nervous system. Symptoms manifest after birth. Children homozygous recessive for this allele rarely survive past five years of age. Sufferers lack the ability to make the enzyme N-acetyl-hexosaminidase, which breaks down the GM2 ganglioside lipid.

Another example is phenylketonuria (PKU), a recessively inherited disorder whose sufferers lack the ability to synthesize an enzyme to convert the amino acid phenylalanine into tyrosine. Individuals homozygous recessive for this allele have a buildup of phenylalanine and abnormal breakdown products in the urine and blood.

Hemophilia is a group of diseases in which blood does not clot normally. Factors in blood are involved in clotting. Hemophiliacs lacking the normal Factor VIII are said to have Hemophilia A, and those who lack Factor IX have hemophilia B. These genes are carried on the X chromosome, so primers and probes can be used in the present method to detect whether or not a fetus inherited the mother's defective X chromosome, or the father's normal allele.

In some embodiments, the genetic target is a gene, or portion of a gene, e.g., CFTR, Factor VIII (F8 gene), beta globin, hemachromatosis, G6PD, neurofibromatosis, GAPDH, beta amyloid, or pyruvate kinase gene.

In some embodiments, the genetic target is any sequence whose copy number variation can be associated with a disease or disorder. Other diseases arising from genetic abnormalities include Achondroplasia, Adrenoleukodystrophy, X-Linked, Agammaglobulinemia, X-Linked, Alagille Syndrome, Alpha-Thalassemia X-Linked Mental Retardation Syndrome, Alzheimer Disease, Alzheimer Disease, Early-Onset Familial, Amyotrophic Lateral Sclerosis Overview, Androgen Insensitivity Syndrome, Angelman Syndrome, Ataxia Overview, Hereditary, Ataxia-Telangiectasia, Becker Muscular Dystrophy also The Dystrophinopathies), Beckwith-Wiedemann Syndrome, Beta-Thalassemia, Biotinidase Deficiency, Branchiootorenal Syndrome, BRCA1 and BRCA2 Hereditary Breast/Ovarian Cancer, Breast Cancer, CADASIL, Canavan Disease, Cancer, Charcot-Marie-Tooth Hereditary Neuropathy, Charcot-Marie-Tooth Neuropathy Type 1, Charcot-Marie-Tooth Neuropathy Type 2, Charcot-Marie-Tooth Neuropathy Type 4, Charcot-Marie-Tooth Neuropathy Type X, Cockayne Syndrome, Colon Cancer, Contractural Arachnodactyly, Congenital, Craniosynostosis Syndromes (FGFR-Related), Cystic Fibrosis, Cystinosis-Deafness and Hereditary Hearing Loss, DRPLA (Dentatorubral-Pallidoluysian Atrophy), DiGeorge Syndrome (also 22q11 Deletion Syndrome), Dilated Cardiomyopathy, X-Linked, Down Syndrome (Trisomy 21), Duchenne Muscular Dystrophy (also The Dystrophinopathies), Dystonia, Early-Onset Primary (DYT1), Dystrophinopathies, The, Ehlers-Danlos Syndrome, Kyphoscoliotic Form, Ehlers-Danlos Syndrome, Vascular Type, Epidermolysis Bullosa Simplex, Exostoses, Hereditary Multiple, Facioscapulohumeral Muscular Dystrophy, Factor V Leiden Thrombophilia, Familial Adenomatous Polyposis (FAP), Familial Mediterranean Fever, Fragile X Syndrome, Friedreich Ataxia, Frontotemporal Dementia with Parkinsonism-17, Galactosemia, Gaucher Disease, Hemochromatosis, Hereditary, Hemophilia A, Hemophilia B, Hemorrhagic Telangiectasia, Hereditary 55, Hearing Loss and Deafness, Nonsyndromic, DFNA (Connexin 26), Hearing Loss and Deafness, Nonsyndromic, DFNB 1 (Connexin 26), Hereditary Spastic Paraplegia, Hermansky-Pudlak Syndrome, Hexosaminidase A Deficiency (also Tay-Sachs), Huntington Disease, Hypochondroplasia, Ichthyosis, Congenital, Autosomal Recessive, Incontinentia Pigmenti, Kennedy Disease (also Spinal and Bulbar Muscular Atrophy), Krabbe Disease, Leber Hereditary Optic Neuropathy, Lesch-Nyhan Syndrome Leukemias, Li-Fraumeni Syndrome, Limb-Girdle Muscular Dystrophy, Lipoprotein Lipase Deficiency, Familial, Lissencephaly, Marfan Syndrome, MELAS (Mitochondrial Encephalomyopathy, Lactic Acidosis, and, Stroke-Like Episodes), Monosomies, Multiple Endocrine Neoplasia Type 2, Multiple Exostoses, Hereditary Muscular Dystrophy, Congenital, Myotonic Dystrophy, Nephrogenic Diabetes Insipidus, Neurofibromatosis 1, Neurofibromatosis 2, Neuropathy with Liability to Pressure Palsies, Hereditary, Niemann-Pick Disease Type C, Nijmegen Breakage Syndrome Norrie Disease, Oculocutaneous Albinism Type 1, Oculopharyngeal Muscular Dystrophy, Ovarian Cancer, Pallister-Hall Syndrome, Parkin Type of Juvenile Parkinson Disease, Pelizaeus-Merzbacher Disease, Pendred Syndrome, Peutz-Jeghers Syndrome Phenylalanine Hydroxylase Deficiency, Prader-Willi Syndrome, PROP 1-Related Combined Pituitary Hormone Deficiency (CPHD), Prostate Cancer, Retinitis Pigmentosa, Retinoblastoma, Rothmund-Thorns on Syndrome, Smith-Lemli-Opitz Syndrome, Spastic Paraplegia, Hereditary, Spinal and Bulbar Muscular Atrophy (also Kennedy Disease), Spinal Muscular Atrophy, Spinocerebellar Ataxia Type 1, Spinocerebellar Ataxia Type 2, Spinocerebellar Ataxia Type 3, Spinocerebellar Ataxia Type 6, Spinocerebellar Ataxia Type 7, Stickler Syndrome (Hereditary Arthroophthalmopathy), Tay-Sachs (also GM2 Gangliosidoses), Trisomies, Tuberous Sclerosis Complex, Usher Syndrome Type I, Usher Syndrome Type II, Velocardiofacial Syndrome (also 22q11 Deletion Syndrome), Von Hippel-Lindau Syndrome, Williams Syndrome, Wilson Disease, X-Linked Adreno leukodystrophy, X-Linked Agammaglobulinemia, X-Linked Dilated Cardiomyopathy (also The Dystrophinopathies), and X-Linked Hypotonic Facies Mental Retardation Syndrome.

The term polynucleotide refers to any nucleic acid molecule containing more than one nucleotide, and can include, but is not limited to lengths of 2, 3, 5, 10, 20, 30, 50, 100, 200, 300, 400, 500, or 900 nucleotides, or 1, 2, 3, 5, 10, 20, 30, 50, 100, 200, 300, 400, 500, or 900 kilobases, or 1, 2, 3, 5, 10, 20, 30, 50, 100, 200, 300, 400, 500, or 900 megabases. A polynucleotide can also refer to the coding region of a gene, or non-coding regions of DNA, or a whole chromosome.

As used herein, an allele can be one of several alternate forms of a gene or non-coding regions of DNA that occupy the same position on a chromosome. The term allele can be used to describe DNA from any organism including, but not limited to, bacteria, viruses, fungi, protozoa, molds, yeasts, plants, humans, non-humans, animals, and archeabacteria. For example, bacteria typically have one large strand of DNA. The term allele with respect to bacterial DNA refers to the form of a gene found in one cell as compared to the form of the same gene in a different bacterial cell of the same species.

Alternate forms of a gene (e.g., alleles) can include one or more single nucleotide polymorphisms (SNPs) in which a single nucleotide varies between alternate forms. Alternate forms of a gene or noncoding region can encompass short tandem repeats (STR), adjacent repeated patterns of two or more nucleotides.

Alleles can have the identical sequence or can vary by a single nucleotide or more than one nucleotide. With regard to organisms that have two copies of each chromosome, if both chromosomes have the same allele, the condition is referred to as homozygous. If the alleles at the two chromosomes are different, the condition is referred to as heterozygous.

In some embodiments, extracted DNA or RNA can be processed to select, tag, capture and/or isolate target sequence polynucleotides, which can particularly include genetic targets described herein. In some embodiments, capture and isolation involves physical separation of target sequences from bulk genetic material, and removal of unwanted genetic material. In some embodiments, physical separation can be achieved by hybridizing desired sequences to complementary sequences immobilized on a solid structure such as a polymer surface, polymer beads, magnetic beads, or surface of a microfluidic channel. In other embodiments, physical separation is achieved by affinity methods, such as capturing a desired sequence using a probe of complementary sequence conjugated with an affinity tag, non-limiting examples of affinity interactions including streptavidin-biotin, antibody-antigen, enzyme-substrate, receptor-ligand, and protein-small molecule interactions having a binding affinity of greater than micromolar, nanomolar, picomolar, femtomolar, or greater than femtomolar strength. Following capture, desired sequences can in some embodiments be isolated from bulk genetic material using wash methods that are well-known in the arts, including washing with buffered saline solutions comprising mild ionic or non-ionic detergents, protease inhibitors, and DNase inhibitors. In some embodiments, the droplets described herein do not comprise beads, polymer beads, or magnetic beads.

The targets for the assays and probes described herein can be any genetic target associated with fetal genetic abnormalities, including aneuploidy as well as other genetic variations, such as mutations, insertions, additions, deletions, translocation, point mutation, trinucleotide repeat disorders and/or single nucleotide polymorphisms (SNPs), as well as control targets not associated with fetal genetic abnormalities. Other assays unrelated to fetal aneuploidy are also described herein.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

EXAMPLES

Example 1: Extraction of DNA from Maternal Plasma 10 to 20 maternal plasma samples each with volume of 1 mL-2 mL, drawn from pregnancies between 10 and 20 weeks of gestational age, can be analyzed using a noninvasive method of the disclosure.

Plasma is extracted using Qiagen's QIAamp circulating nucleic acid kit with the QiaVac manifold. Samples are extracted in batches of 20. The samples are eluted in 150 µl of the supplied AVE buffer. Carrier RNA is prepared by dissolving the lyophilized carrier RNA thoroughly in 310 µL of elution buffer. 20° C. QIAvac vacuum manifold is prepared by connecting the QIAvac 24 Plus to the vacuum pump. Next, a VacConnector is inserted into each luer slot of the QIAvac 24 Plus that is to be used, ensuring that unused luer slots are closed with luer plugs. The QIAamp mini columns are placed into the VacConnectors on the manifold. A tube extender is inserted into each QIAamp mini column.

After equilibrating samples to room temperature, QIAGEN Proteinase K is pipette into a 50 mL centrifuge tube. The plasma is added to the tube. Next, Buffer ACL (containing carrier RNA) is added to the tube, which is mixed by pulse vortexing for 30s. The tube is then incubated at 60° C. in water bath for 30 min. During the incubation, the QIAvac is set up as described above. Following incubation, the tube is briefly centrifuged to remove drops from inside the lid. Buffer ACB is added to the lysate in the tube, which is mixed by pulse vortexing for 15-30s. Then the tube is incubated on ice for 5 min. The lysate is carefully applied into the tube extender of the QIAamp Mini column. The vacuum pump is switched on to draw lysate through the columns Buffer ACW1 is then applied to the QIAamp Mini column, leaving the lid of the column open, and the vacuum pump is switched on. When all ACW1 has been drawn through the columns, the vacuum pump is switched off to release the pressure. Buffer ACW2 is then applied to the QIAamp Mini columns and drawn through the columns Ethanol (96-100%) is applied to the QIAamp Mini columns and drawn through. The column is then removed from the vacuum manifold, and the VacConnector is discarded. The QIAamp mini column is placed in a clean 2 ml collection tube and centrifuged at full speed (20,000×g; 14,000 rpm) for 3 min. The QIAamp mini Column is then dried at 56° C. for 10 min and placed in a new collection tube, followed by centrifugation at full speed (20,000×g; 14,000 rpm) for 3 min Buffer AVE is applied to the center of the column and centrifuged in a microcentrifuge at full speed (20,000×g; 14,000 rpm) for 1 min to elute the DNA. The extracted DNA can be stored at −20° C.

Example 2: Assaying of QIAamp-Purified Fetal DNAs to Determine Fetal Sex

Figure 3:
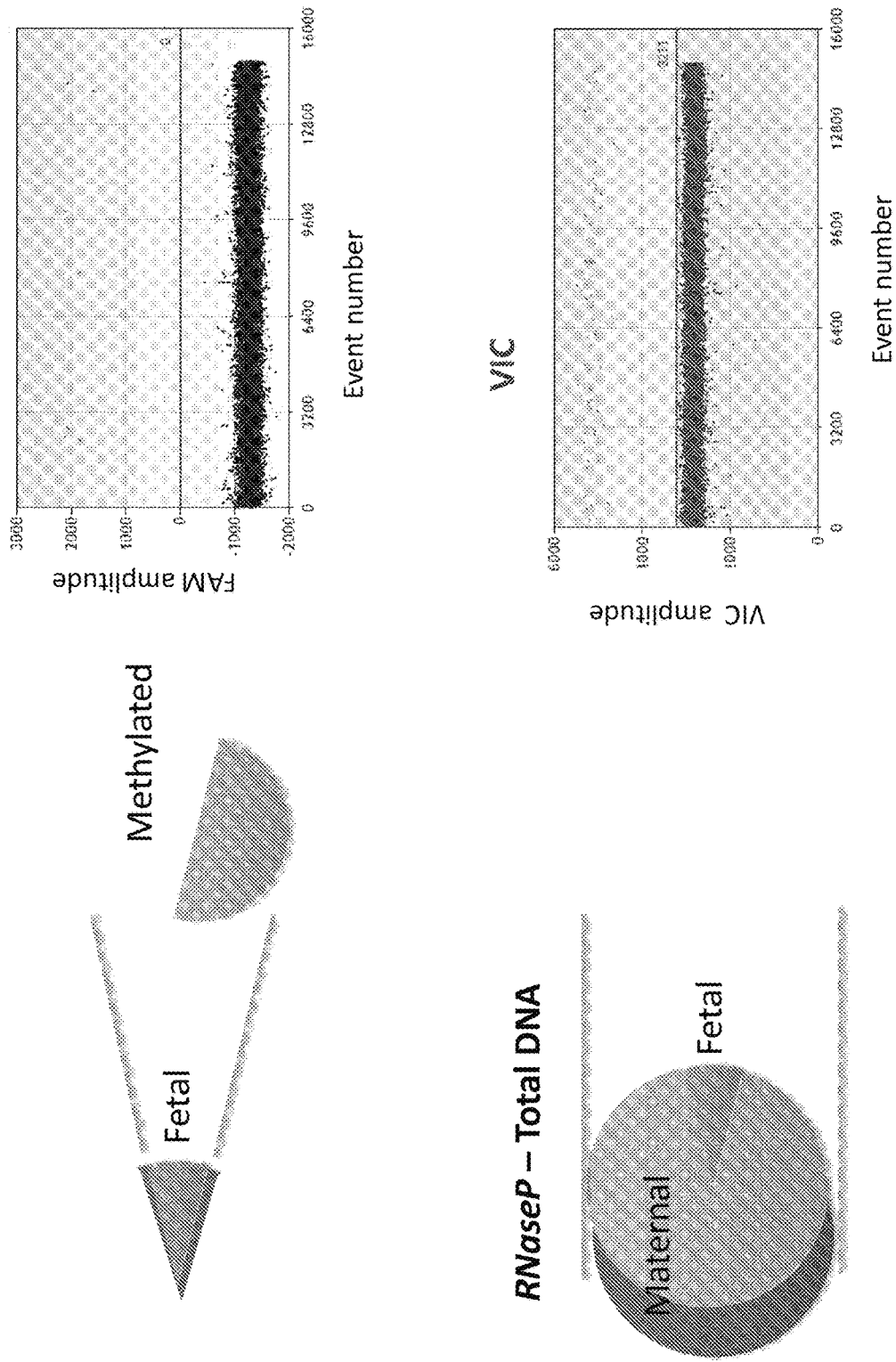
FIG. 3 shows data obtained from detection of methylated fetal DNA (top panel) and total DNA (bottom panel).
Figure 4:
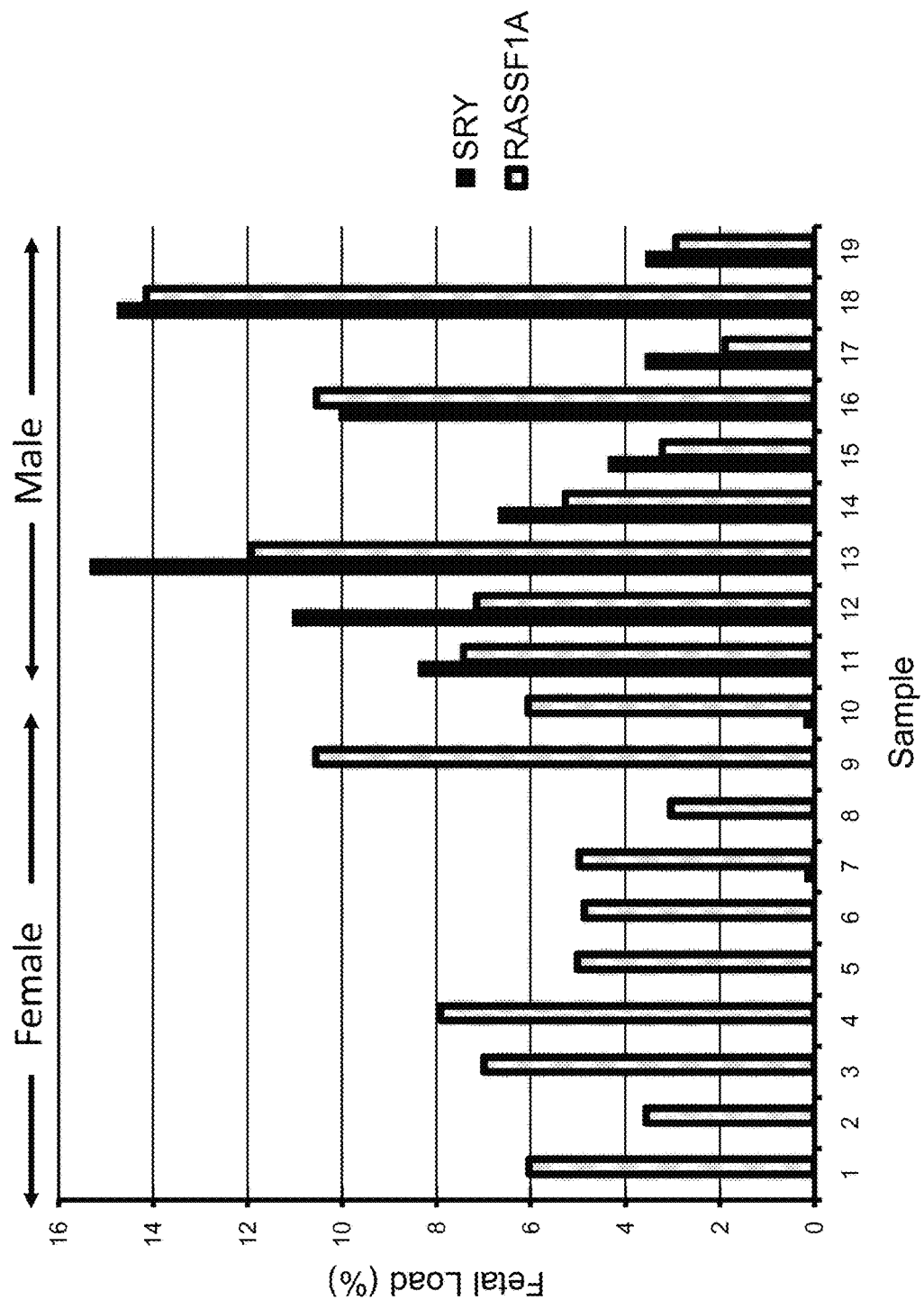
FIG. 4 is a graph showing detected SRY and RASSF1A DNA from DNA samples comprising female and male fetal DNA.
Figure 5:
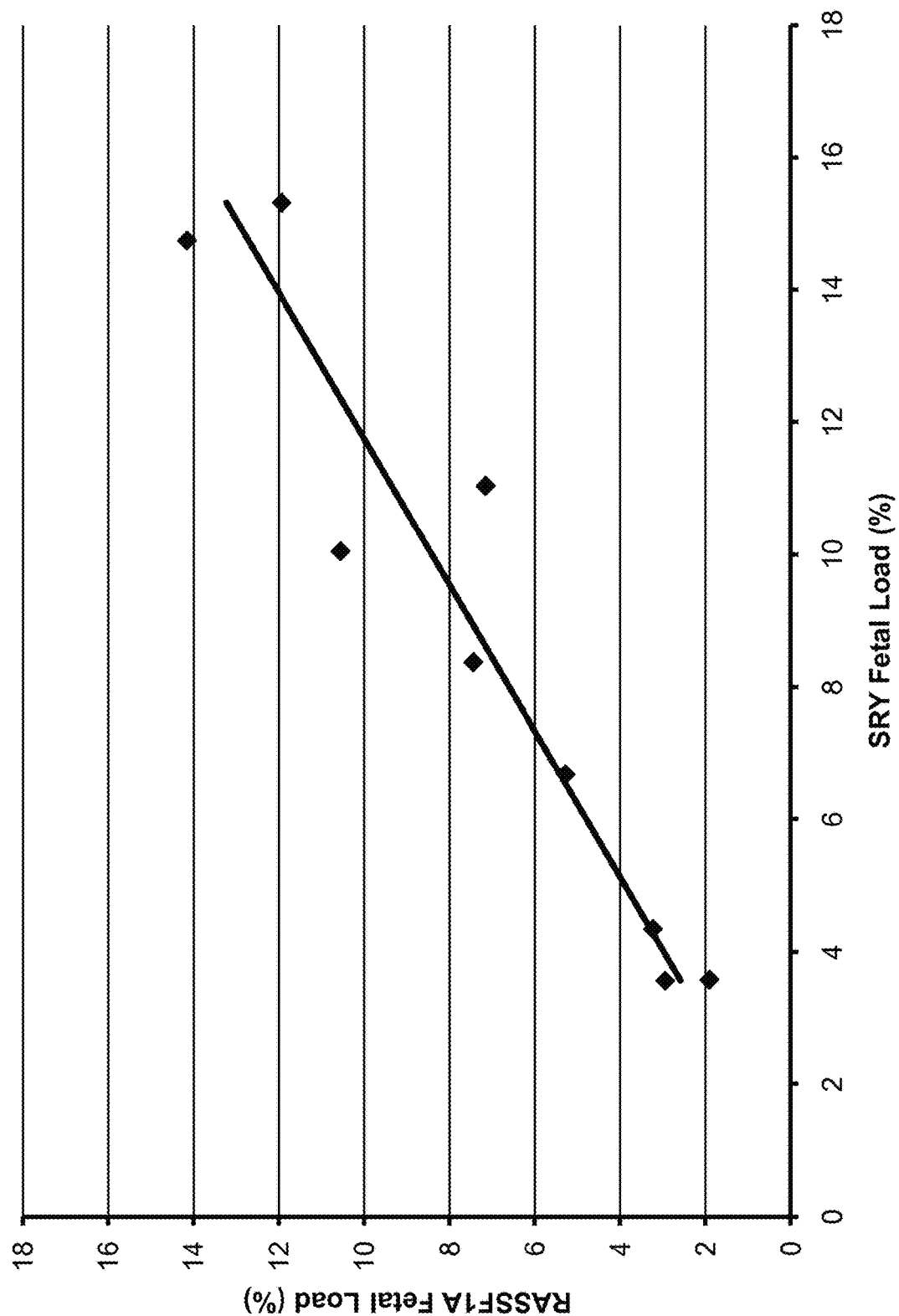
FIG. 5 is a graph showing the correlation between fetal load as determined by analysis of RASSF1A and SRY DNA.

Data showing detection of RASSF1A in male fetal DNA and RNASE P (representative of total DNA) is shown in FIG. 3. Data comparison for a female and male fetus collected using a method of the disclosure is shown in FIG. 4. Comparison of fetal load as determined by RASSF1A versus SRY is shown in FIG. 5, and shows that measurements using the two markers are highly correlated.

Figure 6:
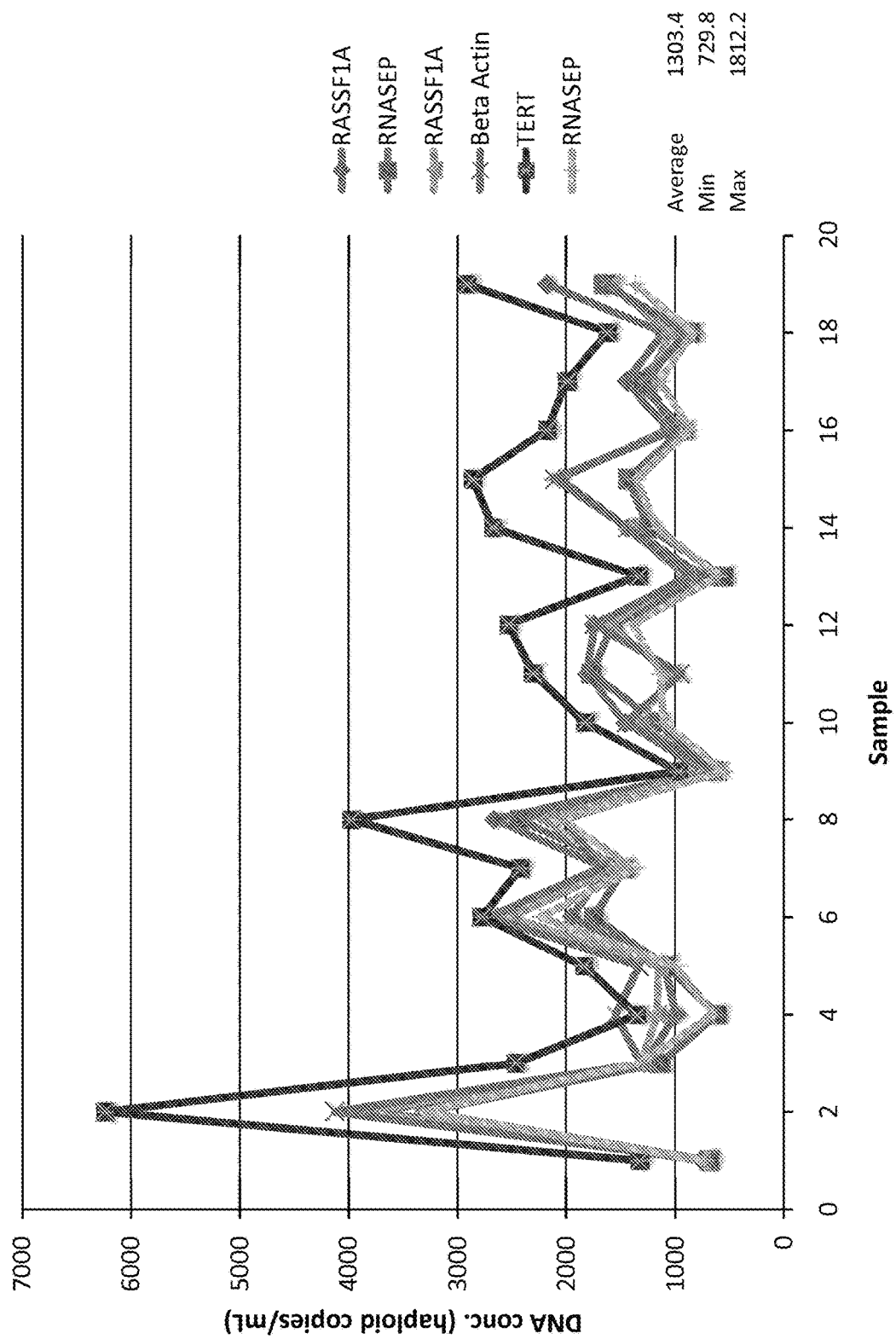
FIG. 6 shows DNA concentration, as measured for 19 samples using the genetic loci as indicated in the legend.

Total DNA concentration was measured for 19 plasma samples using the various markers shown in FIG. 6. The different assays reported similar total DNA concentrations, though quantification for TERT was consistently higher.

Figure 7:
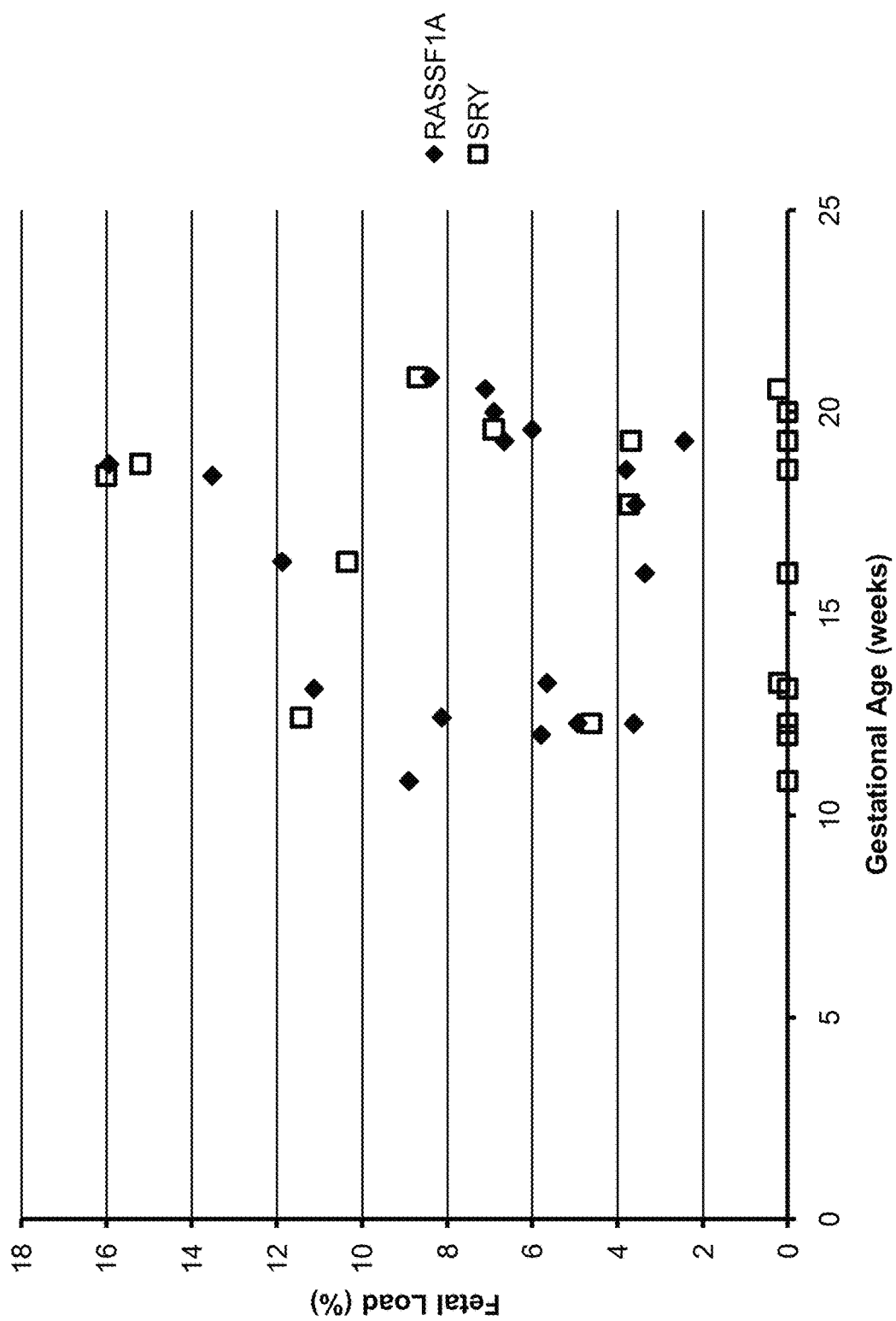
FIG. 7 is a graph showing that fetal load, as measured using RASSF1A or SRY DNA, did not correlate with gestational age using a method of the disclosure.

FIG. 7 shows that there is no obvious correlation between fetal load and gestational age, when determining fetal load in healthy pregnancies using a method of the disclosure.

Materials & Methods:
1. Reagents:
   a. New England Biolabs:
      i. Restriction Enzymes:
         1. HpaII, P/N R0171S, 10U/uL
         2. HhaI, P/N R0139S, 20U/uL
         3. BstUI, P/N R0518S, 10U/uL
      ii. NEBuffer 4, P/N B7004S, 10X
   b. Ambion nuclease free water, P/N AM9937, 10×50 mL
   c. QuantaLife's real time PCR master mix, v0.2
   d. Primers (forward and reverse) & TaqMan Probes: (See Appendix)
      i. SRY(84 bp)
      ii. RASSF1A (96 bp)
      iii. Beta-actin (123 bp)
   e. Primer/Probe Mixes:
      i. ABI's RNase P VIC, P/N 4403328
2. Instruments:
   a. Rainin LT pipettors and pipet tips
   b. Microcentrifuge
   c. Vortexer
   d. Thermocycler with block for 0.5 mL tubes DNA Assay Protocol
3. Restriction Digestions:
   a. Thaw 20 QIAamp-purified plasma DNAs.
   b. Formulate the following 25 reaction bulks without DNA:

SRY No-Restriction Controls

| Component | [Starting] | [Final] in Rxn | 1.0 rxn | 25.0 rxn |
|---|---|---|---|---|
| Water | | | 3.0 | 75.0 uL |
| NEBuffer 4 | 10.0 X | 1.0 X | 4.0 | 100.0 uL |
| QIAamp-purified plasma or positive control DNAs | varies ng/uL | varies ng varies copies/ddPCR | 33.0 | |
| HpaII | 10.0 U/uL | 0.0 Units | 0.00 | |
| HhaI | 20.0 U/uL | 0.0 Units | 0.00 | |
| BstUI | 10.0 U/uL | 0.0 Units | 0.00 | |
| Total Volume | | | 40.0 | 175.0 uL |

| Component | [Starting] | [Final] in Rxn | 1.0 rxn | 25.0 rxn |
|---|---|---|---|---|
| Water | | | 39.0 | 975.0 uL |
| NEBuffer 4 | 10.0 X | 1.0 X | 8.0 | 200.0 uL |
| QIAamp-purified plasma or positive control DNAs | varies ng/uL | varies ng varies copies/ddPCR | 33.0 | |
| HpaII | 10.0 U/uL | 0.0 Units | 0.00 | |
| HhaI | 20.0 U/uL | 0.0 Units | 0.00 | |
| BstUI | 10.0 U/uL | 0.0 Units | 0.00 | |
| Total Volume | | | 80.0 | 1175.0 uL |

Restriction Digestions

| Component | [Starting] | [Final] in Rxn | 1.0 rxn | 25.0 rxn |
|---|---|---|---|---|
| Water | | | 0.0 | |
| NEBuffer 4 | 10.0 X | 1.0 X | 8.0 | 200.0 |
| QIAamp-purified plasma or positive control DNAs | varies ng/uL | varies ng varies copies/ddPCR | 66.0 | |
| HpaII | 10.0 U/uL | 20.0 Units | 2.00 | |
| HhaI | 20.0 U/uL | 40.0 Units | 2.00 | |
| BstUI | 10.0 U/uL | 20.0 Units | 2.00 | |
| Total Volume | | | 80.0 | 200.0 uL | a. Pipet 7 uL of reaction mix to each of 20-0.5 mL tubes for the "SRY no-restriction controls."
b. Pipet 47 uL of reaction mix to each of 20-0.5 mL tubes for the "other no-restriction controls."
c. Pipet 8 uL of NEBuffer 4 to each of 20-0.5 mL tubes for the "restriction digestions."
d. Add 33 uL of the appropriate DNA per tube for the no restriction samples.
e. Add 66 uL of the appropriate DNA per tube for the restriction samples.
f. Add 2.0 uL of each restriction enzyme for the "restriction digestion" samples.
g. Mix by vortexing gently; spin-down; repeat.
h. Subject to thermal cycling:
  i. 37° C. for 120 minutes; 60° C. for 120 minutes; 65 for 20 min; 4° C. infinitely.

4. Digital Droplet Polymerase Chain Reaction, (ddPCR) Reaction Mixes:

Samples

| Restricted? | FAM Assay | VIC Assay | | 1 | 2 | 3 | 4 | 5 | 6 | 7 | 8 | 9 | 10 | 11 | 12 |
|---|---|---|---|---|---|---|---|---|---|---|---|---|---|---|---|
| No | SRY | ABI's | A | 1 | 2 | 3 | 4 | 5 | 6 | 7 | 8 | 9 | 10 | 11 | 12 |
| | | RNase P | B | 13 | 14 | 15 | 16 | 17 | 18 | 19 | 20 | | | NTC | NTC |
| | RASSF1A | ABI's | C | 1 | 2 | 3 | 4 | 5 | 6 | 7 | 8 | 9 | 10 | 11 | 12 |
| | | RNase P | D | 13 | 14 | 15 | 16 | 17 | 18 | 19 | 20 | | | NTC | NTC |
| | RASSF1A | B-Actin | E | 1 | 2 | 3 | 4 | 5 | 6 | 7 | 8 | 9 | 10 | 11 | 12 |
| | | | F | 13 | 14 | 15 | 16 | 17 | 18 | 19 | 20 | | | NTC | NTC |
| | | | G | | | | | | | | | | | | |
| | | | H | | | | | | | | | | | | |

Samples

| Restricted? | FAM Assay | VIC Assay | | 1 | 2 | 3 | 4 | 5 | 6 | 7 | 8 | 9 | 10 | 11 | 12 |
|---|---|---|---|---|---|---|---|---|---|---|---|---|---|---|---|
| | SRY | ABI's | A | 1 | 2 | 3 | 4 | 5 | 6 | 7 | 8 | 9 | 10 | 11 | 12 |
| | | RNase P | B | 13 | 14 | 15 | 16 | 17 | 18 | 19 | 20 | | | NTC | NTC |
| Yes | RASSF1A | ABI's | C | 1 | 2 | 3 | 4 | 5 | 6 | 7 | 8 | 9 | 10 | 11 | 12 |
| | | RNase P | D | 13 | 14 | 15 | 16 | 17 | 18 | 19 | 20 | | | NTC | NTC |
| | RASSF1A | B-Actin | E | 1 | 2 | 3 | 4 | 5 | 6 | 7 | 8 | 9 | 10 | 11 | 12 |
| | | | F | 13 | 14 | 15 | 16 | 17 | 18 | 19 | 20 | | | NTC | NTC |
| | | | G | | | | | | | | | | | | |
| | | | H | | | | | | | | | | | | |

Formulate the following 25 and 50 bulk reaction mixes without DNA:

i.
PCR Reaction Mix: SRY/ABI's RNase P

| Component | [Starting] | [Final] in Rxn | 1.0 rxn | 25.0 rxns |
|---|---|---|---|---|
| Water | | | 45.9 | 1147.5 uL |
| QL Master Mix, v0.2 | 2.0 X | 1.0 X | 100.0 | 2500.0 uL |
| Forward Primer (SRY) | 100.0 uM | 900.0 nM | 1.80 | 45.0 uL |
| Reverse Primer (SRY) | 100.0 uM | 900.0 nM | 1.80 | 45.0 uL |
| Probe (SRY), BHQ | 100.0 uM | 25.0 nM | 0.50 | 12.5 uL |
| ABI's RNase P primer probe mix | 20.0 X | 1.0 X | 10.00 | 250.0 uL |
| Non-restricted DNA | varies copies | varies copies | 40.00 | uL |
| Total Volume | | | 200.0 | 4000.0 uL |

PCR Reaction Mix: RASSF1A/ABI's RNase P

| Component | [Starting] | | [Final] in Rxn | | 1.0 rxn | 50.0 rxns | |
|---|---|---|---|---|---|---|---|
| Water | | | | | 5.9 | 295.0 | uL |
| QL Master Mix, v0.2 | 2.0 | X | 1.0 | X | 100.0 | 5000.0 | uL |
| Roche's GC Rich Additive | 5.0 | X | 1.0 | X | 40.0 | 2000.0 | uL |
| Forward Primer (RASSF1A 96) | 100.0 | uM | 900.0 | nM | 1.80 | 90.0 | uL |
| Reverse Primer (RASSF1A 96) | 100.0 | uM | 900.0 | nM | 1.80 | 90.0 | uL |
| Probe (RASSF1A 96), MGB | 100.0 | uM | 250.0 | nM | 0.50 | 25.0 | uL |
| ABI's RNase P primer probe mix | 20.0 | X | 1.0 | X | 10.00 | 500.0 | uL |
| Non-restricted or restricted DNA | varies | copies | varies | copies | 40.0 | | |
| Total volume | | | | | 200.0 | 8000.0 | uL |

PCR Reaction Mix: RASSF1A/B-Actin

| Component | [Starting] | | [Final] in Rxn | | 1.0 rxn | 50.0 rxns | |
|---|---|---|---|---|---|---|---|
| Water | | | | | 11.8 | 590.0 | uL |
| QL Master Mix, v0.2 | 2.0 | X | 1.0 | X | 100.0 | 5000.0 | uL |
| Roche's GC Rich Additive | 5.0 | X | 1.0 | X | 40.0 | 2000.0 | uL |
| Forward Primer (RASSF1A 96) | 100.0 | uM | 900.0 | nM | 1.80 | 90.0 | uL |
| Reverse Primer (RASSF1A 96) | 100.0 | uM | 900.0 | nM | 1.80 | 90.0 | uL |
| Probe (RASSF1A 96), MGB | 100.0 | uM | 250.0 | nM | 0.50 | 25.0 | uL |
| Forward Primer (B-Actin 123) | 100.0 | uM | 900.0 | nM | 1.80 | 90.0 | uL |
| Reverse Primer (B-Actin 123) | 100.0 | uM | 900.0 | nM | 1.80 | 90.0 | uL |
| Probe (B-Actin 123), MGB | 100.0 | uM | 250.0 | nM | 0.50 | 25.0 | uL |
| Non-restricted or restricted DNA | varies | copies | varies | copies | 40.00 | | |
| Total Volume | | | | | 200.0 | 8000.0 | uL | b. Aliquot 160 uL of PCR reaction mix to 1.5 mL tubes per sample labeled 1-20 per the following:
  i. No Digestion Controls:
    1. a=SRY/RNase P
    2. b=RASSF1A/RNase P
    3. c=RASSF1A/B-Actin
  ii. Restriction Digested:
    1. B=RASSF1A/RNase P
    2. C=RASSF1A/B-Actin
c. Add 40 uL of each non-restricted or restricted DNA sample per labeled tube.
d. Mix by gentle vortexing. Spin down. Repeat.
5. ddPCR, (Digital Droplet Polymerase Chain Reaction):
  a. Follow QuantaLife's protocol for executing ddPCR.
Additional Information:
1. Primer & Probe Sequences:

a. RASSF1A (96 bp) forward:
  5'-AGCTGGCACCCGCTGG-3' b. RASSF1A (96 bp) reverse:
  5'-GTGTGGGGTTGCACGCG-3' c. RASSF1A (96 bp) probe:
  5'-FAM-ACCCGGCTGGAGCGT-MGBNFQ-3' d. SRY (84 bp) forward:
  5'-CGCTTAACATAGCAGAAGCA-3' e. SRY (84 bp) reverse:
  5'-AGTTTCGAACTCTGGCACCT-3' f. SRY (84 bp) probe:
  5'-FAM-TGTCGCACTCTCCTTGTTTTTGACA-BHQ1-3' g. Beta-Actin (123 bp) forward:
  5'-GCAAAGGCGAGGCTCTGT-3' h. Beta-Actin (123 bp) reverse:
  5'-CGTTCCGAAAGTTGCCTTTTATGG-3' i. Beta-Actin (123 bp) probe:
  5'-VIC-ACCGCCGAGACCGCGTC-MGBNFQ-3'

2. Fetal Load Assay Amplicon Nicks Table:

| | | # Nicks w/in Amplicon? | | | Total # of Amplicon |
|---|---|---|---|---|---|
| Assay Name | Purpose | Hpa II | Hha I | BstU I | Nicks |
| RASSF1A (96 bp) | Fetal DNA quantification ("fetal load") | 2 | 8 | 8 | 18 |
| SRY (84 bp) | Sex determination and fetal load | 0 | 0 | 0 | 0 |
| B-Actin (123 bp) | Maternal digestion completion control | 0 | 7 | 10 | 17 |
| ABI's RNase P | Total DNA quantitation | 0 | 0 | 0 | 0 |

Example 3: Bisulfite Treatment

Sodium bisulfite modification can be performed as described previously (Agathanggelou et al., 2001). Briefly, 0.5-1.0 mg of genomic DNA is denatured in 0.3M NaOH for 15 min at 37° C. Unmethylated cytosine residues are then sulfonated by incubation in 3.12M sodium bisulfite (pH 5.0) (Sigma) and 5 mM hydroquinone (Sigma) in a thermocycler for 15s at 99° C. and 15 min at followed by amplification and/or detection to confirm methylation status and quantify the methylated DNA. Exemplary PCR conditions for amplifying bisulfite-treated DNA include: initial denaturation for 10 min at 95° C., followed by 30 cycles of 1 min at 94° C., 1 min at 57° C. and 2 min at 74° C. with a final extension for 10 min at 72° C.

Example 4: Clinical Isolates of S. Aureus

Figure 15:
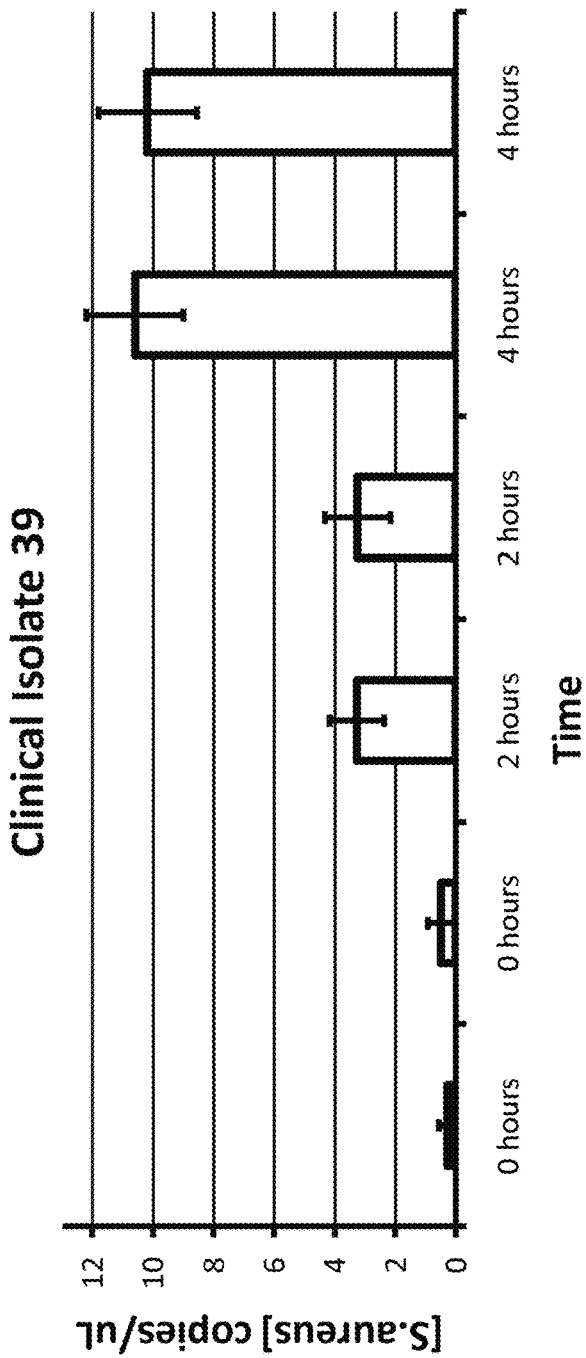
FIG. 15 provides a graphical representation of the results from tests using a clinical isolate of *S. aureus* (referred to in the Figure as "clinical isolate 39").

Cultures of S. aureus were set up in 4 ml volumes. About 0.5 ml of culture was removed at three time points (0, 2, and 4 hours). Cells were then centrifuged for 5 minutes at 14,000 rpm. The supernatant of the cells was removed and frozen at −20° C. DNA was isolated using a Qiagen mini DNA kit, followed by droplet digital PCR (ddPCR) to quantify DNA concentration. FIG. 15 provides a graphical representation of the results from tests using a clinical isolate of S. aureus (referred to in the Figure as "clinical isolate 39"). The y-axis of the figure depicts the concentration of S. aureus as copies/ul, and the x-axis indicates the time course. As shown, the DNA concentration of S. aureus rose at the two-hour and at the four-hour time points.

Example 5: Clinical Isolates of S. Aureus

Figure 16:
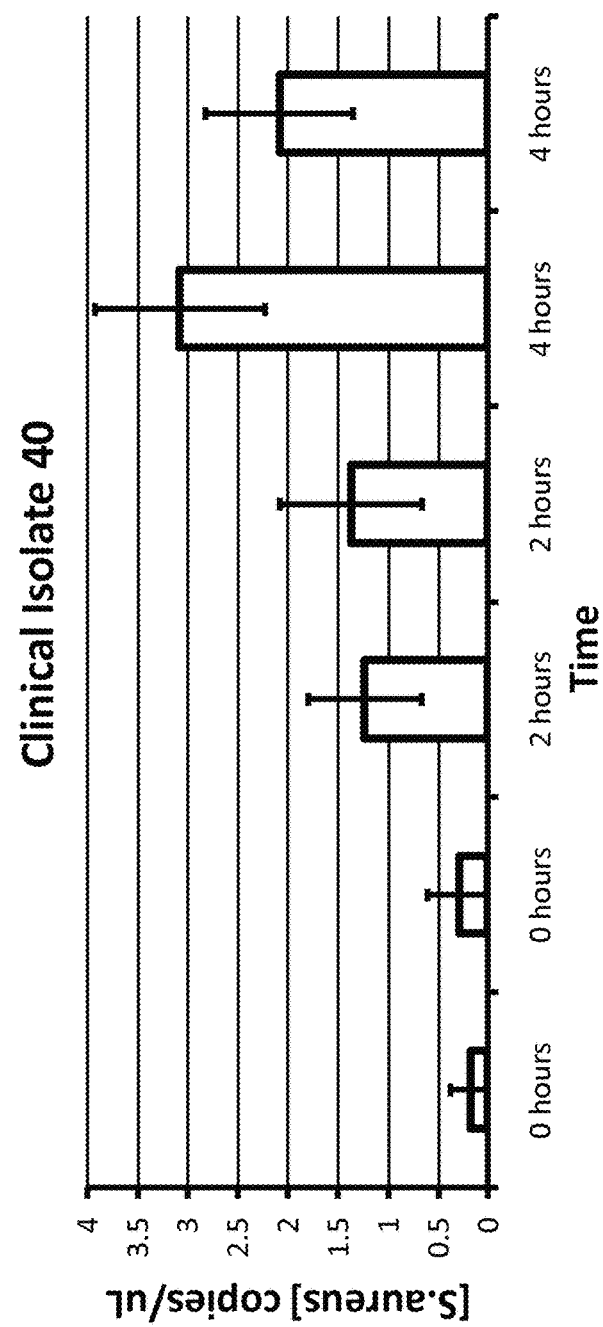
FIG. 16 provides a graphical representation of the results from tests using a clinical isolate of *S. aureus*.

In this example, the methods of example 8 were used to detect a second clinical isolate of S. aureus. FIG. 16 provides a graphical representation of the results from tests using a clinical isolate of S. aureus (referred to in the Figure as "clinical isolate 40") and using the methods described in Example 8. The y-axis of the figure depicts the concentration of S. aureus as copies/ul, and the x-axis indicates the time course. As shown, the DNA concentration of S. aureus rose at the two-hour and at the four-hour time points.

Example 6: MRSA

Figure 17:
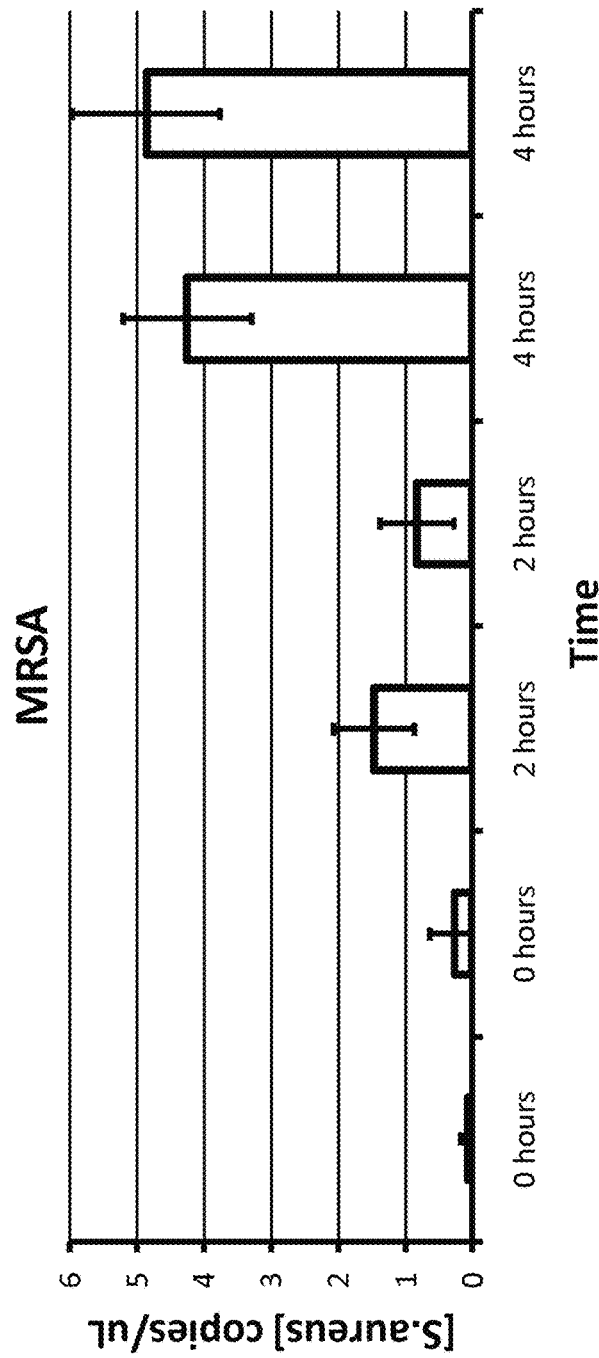
FIG. 17 provides a graphical representation of the results from tests using methicillin resistant *Staphylococcus aureus* (MRSA).

FIG. 17: provides a graphical representation of the results from tests using Methicillin resistant Staphylococcus aureus (MRSA), using the methods described in Example 8. The y-axis of the figure depicts the concentration of MRSA as copies/ul, and the x-axis indicates the time course. As shown, the DNA concentration of MRSA rose at the two-hour and at the four-hour time points.

Example 7: MSSA

Figure 18:
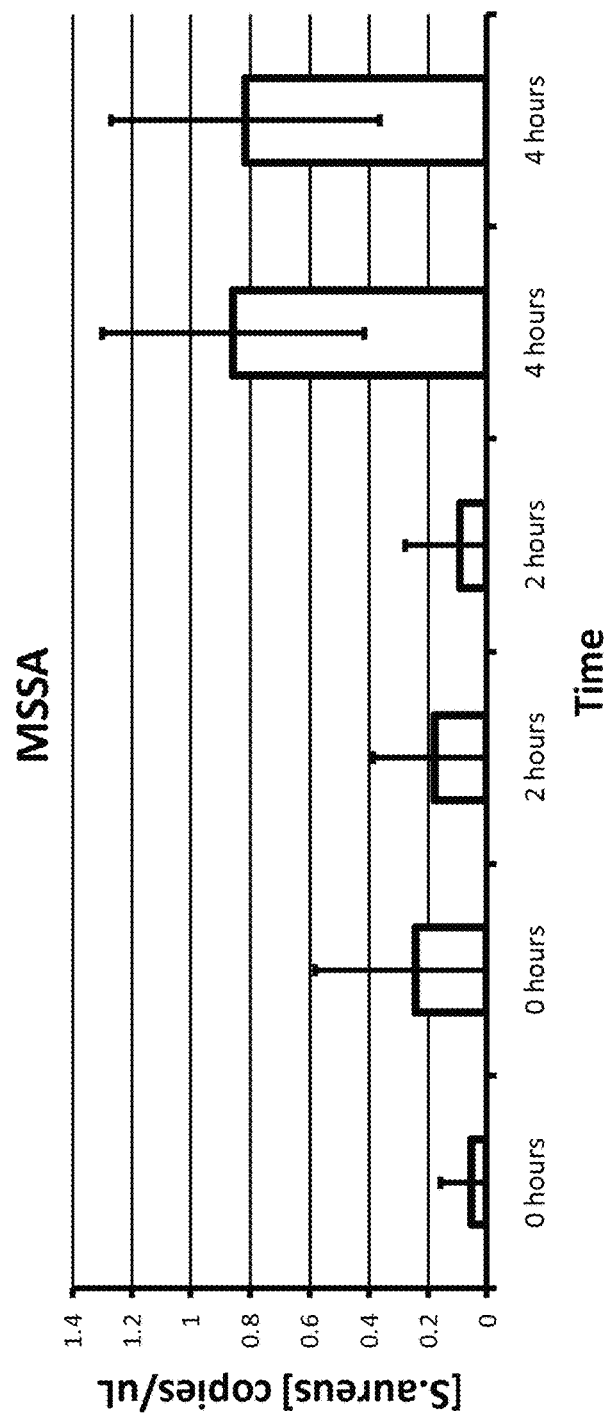
FIG. 18 provides a graphical representation of the results from tests using methicillin sensitive *Staphylococcus aureus* (MSSA).

FIG. 18 provides a graphical representation of the results from tests using Methicillin Sensitive Staphylococcus aureus (MSSA) using the methods of Example 8. The y-axis of the figure depicts the concentration of MSSA as copies/ul, and the x-axis indicates the time course. As shown, the DNA concentration of MSSA rose at the two-hour and at the four-hour time points.

Example 8: Prophetic Example

Aliquots of a cell culture are removed at time 0 and time 4 hrs. The aliquots are lysed (e.g., heat lysis), and TaqMan PCR reactions are prepared in triplicate for each aliquot. The reactions are loaded into a droplet generator to convert each 20 µL reaction to 20,000 1-nl droplets in an oil emulsion. Each set of 20,000 droplets is loaded in the well of a 96-well PCR plate. The plate is placed in a conventional thermal cycler (not a real-time PCR thermal cycler) to perform PCR. Droplets that contain a target DNA molecule will generate PCR product and a cleaved TaqMan probe, resulting in a bright fluorescent signal within those droplets. Droplets that don't contain a target DNA molecule will generate a weak, baseline fluorescent signal. The 96-well PCR plate is loaded on a ddPCR detector platform. In this platform, the droplets in each well are aspirated and flowed in single file passed a fluorescent detector. Total positive and negative fluorescent droplets are counted, and the concentration of the target DNA can be precisely calculated. Unlike real-time PCR, this is accomplished without the use of a standard curve generated from a dilution series of a sample of known concentration. Differences in DNA concentrations as determined by ddPCR between time 0 and time 4 hrs determines the rate of growth. The growth rate can be used to determine differences in rate of growth between untreated and treated cells, such as cells treated with an antibiotic, chemical compound, or test agent.

Example 9: Droplet Generation

FIG. 19 shows images of droplet formation. Droplets form as the droplet gets pinched by the inflow of oil from the sides. As the droplet pulls away from the bulk fluid, stretching/necking can be seen.

Figure 20:
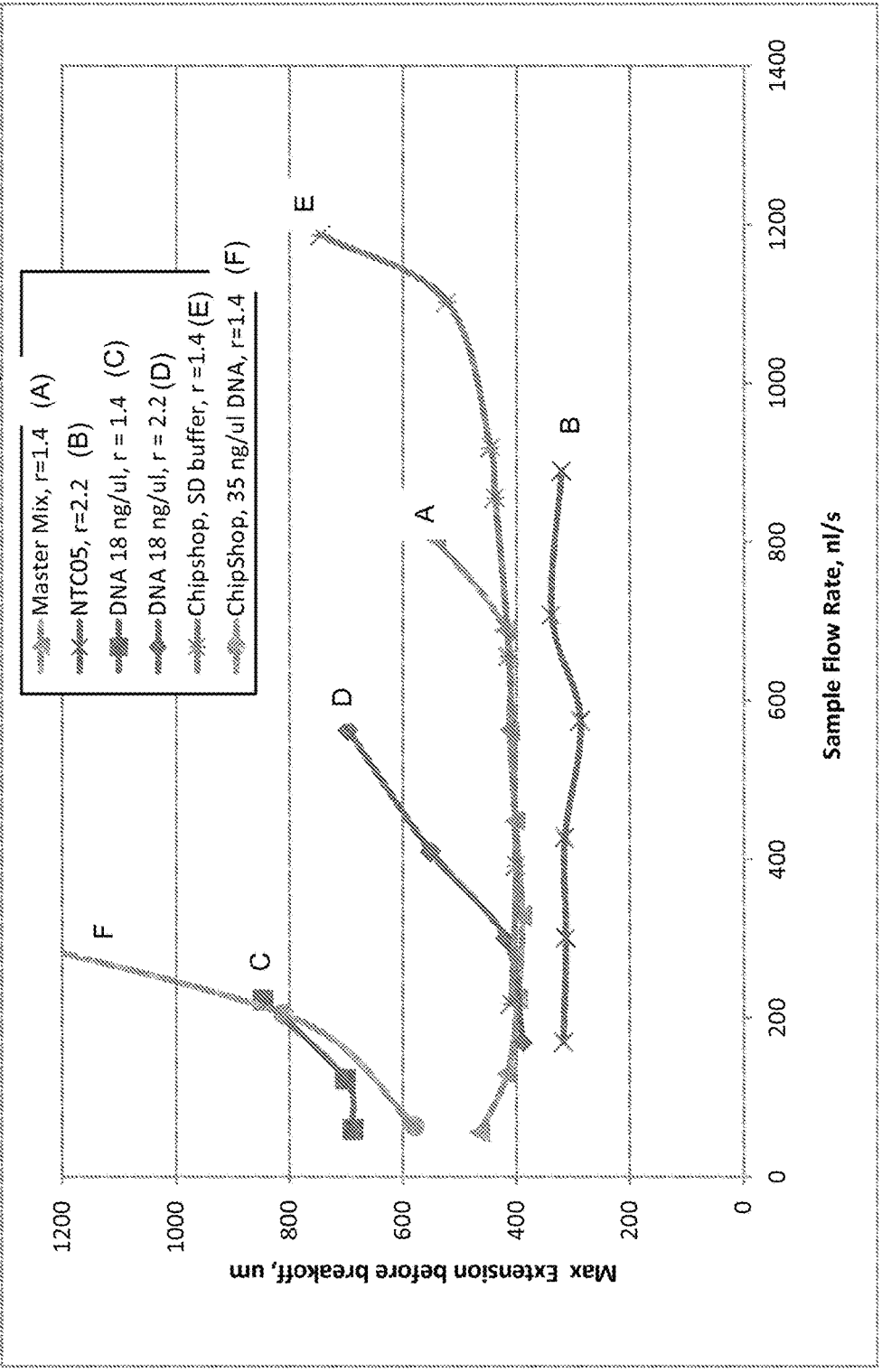
FIG. 20 illustrates droplet extension as a function of flow rate and DNA load.

FIG. 20 is a graph illustrating the effect of increasing DNA load upon the maximum extension of a droplet before the droplet breaks away from the bulk fluid. The graph plots maximum extension versus flow rate. Extension is measured from the center of the cross to the farthest extent of the droplet just as it breaks off Some droplet extension is tolerable, but if it becomes excessive, a long "thread" is drawn that connects the droplet to the bulk fluid. As the droplet breaks off, this thread may collapse to microdroplets, leading to undesirable polydispersity. In extreme cases, the droplet does not break off; instead the aqueous phase flows as a continuous phase down the center of the channel, while the oil flows along the channel walls, and no droplets are formed. Curve B, curve E, and curve A correspond to samples containing zero DNA. These samples can tolerate high flow rates without substantially increasing their extension into the channel. Curve D, curve F, and curve C correspond to samples higher DNA loads. For these conditions, higher flow rates cause droplet extension into the channel. Low flow rates are necessary to avoid excessive droplet extension One way to decrease extension is to decrease flow rate. This has the undesirable side effects of lower throughput and also increased droplet size.

FIG. 21 summarizes qualitatively the effect of DNA digestion upon droplet formation. Samples 1-10 are undigested; samples 11-20 contain digested DNA. DNA load is shown in the right-most column; pressure (roughly proportional to flow rate) is shown in the $2^{nd}$ row. The table is letter coded: J indicates jetting, E indicates extension, and N indicates normal (no jetting or extension) droplet generation. As can be seen, digestion (with restriction enzymes) resulted in improved droplet generation, even at high DNA loads and high flow rates.

Example 10. Detection of Fetal DNA Using a Two-Color Detection Scheme

In this example, detection of a trisomy 21 fetal aneuploidy is described, where there is 3% fetal DNA in a maternal plasma sample. There are 1000 genome equivalents (GE) per mL in the maternal plasma, and a maternal blood volume of 20 mL is collected.

Plasma is isolated from the maternal blood sample by centrifugation, and the nucleic acids are purified and concentrated to a volume of 50 µL. The sample is mixed with an equal volume of PCR reagent containing the multiplexed assay components. The entire 100 µL sample is partitioned into 100,000 aqueous droplets having a volume of 1 nL per droplet. For an ideal positive droplet percentage for quantitation of 75%, this would mean 1.47 copies of target sequence per droplet, based on Poisson distribution, which translates to 147,000 targets that need to be compartmentalized into 100,000 lnL droplets. The number of primer sets required to reach this is 147,000GE/10,000GE, which is a 15 plex. Thus, in each droplet, there would be a 15 plex for each target and reference sequence, or a total of 30 primer sets per droplet. The samples are analyzed using a two-color detection scheme, where the target sequence probes fluoresce using a green emitter and the reference sequence probes fluoresce using a yellow, orange or red emitter. Detection is performed over the 100,000 droplets and the ratio of target (green) to reference (yellow, orange or red) sequence is calculated.

Example 11. Detection of Fetal DNA Using a One-Color Detection Scheme

The conditions for Example 1 are used here, except that rather than using different colored target and reference probes, the sample is split (e.g., in half), then two set of droplets are generated, amplified and separately analyzed, with one half using a target probe and the other half using a reference probe.

Example 12. Detecting Fetal DNA Using MIP-ddPCR

Cell-free plasma is isolated from a maternal blood sample by centrifugation. The nucleic acids are then purified and concentrated using a cell free DNA kit (Qiagen). The purified genomic DNA is then mixed with 1000 chromosome-sequence specific oligonucleotide probes (e.g., MIP probe) to Chromosome 21 (MIP-21Chr), and 1000 chromosome-sequence specific oligonucleotide probes (e.g., MIP probe) to Chromosome 1 (MIP-1Chr). Ligase, polymerase and other reaction components are added to the mix. The sample is incubated at 20° C. for 4 minutes. The sample is then incubated at 95° C. for 5 minutes to promote denaturation, and then at 60° C. for 15 minutes in order to promote annealing of the MIP probes to the genomic DNA. A gap fill reaction is then performed in order to circularize the MIP probes. (In some embodiments, the ends can be directly ligated without a gap fill reaction). Nucleotides are added to the sample, which is then incubated at 60° C. for 10 minutes in order to allow binding of the ligase and polymerase to the gap in the MIP probes. The sample is then incubated at 37° C. for 1 minute. Next, the sample is treated with Exonuclease I and III in order to digest remaining linear probes and ssDNA such as genomic DNA that is not hybridized to a probe, followed by incubation at 37° C. for 14 minutes to promote exonuclease activity, an incubation at 95° C. for 2 minutes to inactivate the exonucleases, and, finally, an incubation at 37° C. for 1 minute. Uracil-N-glycosylase is next added to the sample, which is incubated at 37° C. for 10 minutes in order to promote enzymatic depurination, followed by incubation at 95° C. for 20 minutes in order to allow cleavage of abasic depurinated uracil residues in the MIP probes. The linearized probes now have an inverted primer orientation.

Next, droplet digital PCR is performed on the sample. Taq polymerase, universal primers, Taqman fluorescence probes, and PCR reaction components are added to the sample. The Taqman fluorescent probes complementary to the universal probe binding sequence on the MIP-21Chr probe are tagged with a FAM dye; and the Taqman fluorescent probes complementary to the universal probe binding sequence on the MIP-1Chr probe are tagged with a VIC dye. The sample is then emulsified into 100,000 monodisperse-water-in-oil droplets stabilized by surfactant additives into emulsification oil phase and/or aqueous PCR reaction phase. As a result, the sample is partitioned into 100,000 droplets. The sample then undergoes 15-50 thermal cycles under conditions to drive each PCR reaction in each droplet to endpoint. The droplets are then analyzed by using a two-color detection scheme to detect the emission of the FAM and VIC dyes. The number of targets counted for Ch21 is determined by identifying the fraction of positive and negative droplets for FAM fluorescence. Similarly, the number of targets counted for the reference sample (Ch1) is determined by identifying the fraction of positive and negative droplets for VIC fluorescence. The number of positive and negative droplets are then used as input in a Poisson distribution to determine the number of copies per droplet (lambda) for both the target and reference chromosomes. The relative copy number of Ch21 is then determined using equations known in the art, e.g., as described in Dube et al. (2008) Plos ONE 3(8):e2876. doi:10.1371/journal.pone.0002876, which is herein incorporated by reference in its entirety. The confidence of the estimate is also determined using such equations.

Example 13. Separation of Positive and Negative Droplet Signals and Sensitivity of ddPCR to Template Copy Number in MIP Reaction Circularization Reactions Multiplexed MIP circularization products were generated using either 3-plex or 12-plex probe pools containing 100 attomoles (amol) of each MIP species in the multiplex per 10 µL annealing mixture. One attomole is equivalent to $10^{-18}$ mole. 100 amol equals approximately ~60M copies of each MIP probe sequence. The volume of the annealing reactions was 20 µL.

(Note that in the current experiment, all volumes cited in this protocol were doubled, beginning with a 20 ul annealing reaction; however, all DNA, buffer and enzyme concentrations were maintained the same as in the standard 10 ul annealing reaction protocol). The probe pools were formulated from mass-dilutions of selected MIP probes (the IDT Ultramers, purified by PAGE) from among either the Chromosome 1 Reference set of 24 nucleic acids (SEQ ID NOS: 1-24); detected by SEQ ID NO: 81, or from the Chromosome 21 Test set of 24 nucleic acids (SEQ ID NOS: 25-48); detected by the SEQ ID NO: 82.

MIP probes were combined with varying numbers of copies of Raji human gDNA (0; 100; 1,000; or 10,000 copies, 3 pg gDNA/copy) in 1×Ampligase buffer in 96-well PCR plates, denatured for 5 minutes at 95° C. in a thermocycler (Eppendorf Mastercycler Pro.S or ABI 9700), then cooled to 58° C. and allowed to incubate and anneal at this temperature for >12h.

After annealing, while remaining in the thermocycler at 58° C., 0.75 U of Ampligase was added to each reaction in 5 µL of 1×Ampligase buffer with mixing to provide mixtures with a total volume of 15 µL, and the plates were resealed and allowed to incubate for 15 additional minutes at 58° C.

Digestion of Uncircularized Materials

Immediately following the circularization reaction, the temperature of the thermocycler was ramped down to 4° C., and exonuclease digestion of uncircularized excess MIP probes and gDNA was carried out by adding to each reaction well a 5 µL mixture of 6U Exo I & 30U Exo III in 1×Exo III buffer (EpiCentre) with mixing and plate resealing (total reaction volume=20 µL). Digestion proceeded for 20 minutes at 37° C. on the thermocycler, followed by heat denaturation at 95° C. for 10 minutes.

MIP reaction products were analyzed by qPCR (4 µL of circularization reaction mixture per 20 µL qPCR reaction) and subsequently frozen at −20° C. and stored for use in droplet digital PCR (ddPCR) experiments.

Preparation of a General 2X Stock Solution

The general stock solution (10 mL) was formulated as follows.

| Component | Volume per 10 µL aliquot (µL) | Volume per 10 mL solution (µL) |
| --- | --- | --- |
| FastStart Taq polymerase (Roche) (5 U/µL) | 0.16 | 160 |
| 10× Buffer | 2 | 2000 |
| 10 mM dNTP/ 20 mM dUTP | 0.4 | 400 |
| Glycerol (50% w/v) | 3.2 | 3200 |
| BSA (20 mg/mL) | 1 | 1000 |
| Pluronic ® 10% | 1 | 1000 |
| Water | 2.24 | 2240 |
| Total Volume | 10.0 | 10,000 |

The general stock solution was stored at 4° C., and was used for multiple experiments.

Preparation of 2× Hb_pr1 ddPCR stock solution

The 2× Hb_pr1 ddPCR stock solution (520.5 µL) was formulated as follows.

| Component | Volume per 520.5 µL aliquot (µL) | Volume per 520.5 µL solution (µL) |
| --- | --- | --- |
| General stock solution | 50 | 500 |
| Primer Hb_Fwd (100 µM) CCGAATAGGAACGTTGAGCCGT (SEQ ID NO: 79) | 0.9 | 9 |
| Primer Hb_Rev (100 µM) GCAAATGTTATCGAGGTCCGGC (SEQ ID NO: 80) | 0.9 | 9 |
| Taqman Hb_pr1 (FAM-BHQ) (100 µM) ttggcagcctttgccgcggc (SEQ ID NO: 81) | 0.25 | 2.5 |
| Total Volume | 52.05 | 520.5 |

Preparation of 1.25× Hb_pr1 ddPCR stock solution

The 1.25× HB_PR1 ddPCR stock solution (800 µL) was formulated as follows.

| Component | Volume per 800 µL solution (µL) |
| --- | --- |
| 2× Hb_pr1 ddPCR stock solution | 520.5 |
| Aqueous MgCl$_2$ (25 mM) | 80 |
| Water | 199.5 |
| Total Volume | 800 |

The 1.25× Hb_pr1 ddPCR stock solution was partitioned among 4 centrifuge tubes (1.5 mL capacity) in 160 µL aliquots.

Preparation of 2× Hb_pr2 ddPCR stock solution

The 2× Hb_pr2 ddPCR stock solution (936.9 µL) was formulated as follows.

| Component | Volume per 52.05 µL aliquot (µL) | Volume per 936.9 µL solution (µL) |
| --- | --- | --- |
| General stock solution | 50 | 900 |
| Primer Hb_Fwd (100 µM) CCGAATAGGAACGTTGAGCCGT (SEQ ID NO: 79) | 0.9 | 16.2 |
| Primer Hb_Rev (100 µM) GCAAATGTTATCGAGGTCCGGC (SEQ ID NO: 80) | 0.9 | 16.2 |
| Taqman Hb_pr2 (FAM-BHQ) (100 µM) tctgccacctaagcggccgcag (SEQ ID NO: 82) | 0.25 | 4.5 |
| Total Volume | 52.05 | 936.9 |

Preparation of 1.25× Hb_pr2 ddPCR stock solution

The 1.25× Hb_pr2 ddPCR stock solution (1440 µL) was formulated as follows.

| Component | Volume per 1440 µL solution (µL) |
| --- | --- |
| 2× Hb2 ddPCR stock solution | 936.9 |
| Aqueous MgCl$_2$ (25 mM) | 144 |
| Water | 359.1 |
| Total Volume | 1440 |

The 1.25× Hb_pr2 ddPCR stock solution was partitioned among 8 centrifuge tubes (1.5 mL capacity) in 160 µL aliquots.

ddPCR Procedure

The products of the MIP circularization experiments were thawed and centrifuged (2,000 rpm for 2 min). 40 µL aliquots of MIP products, i.e. 2×20 µL aliquots from duplicate assay reactions, were combined with 160 µL of either 1.25× Hb_pr1 ddPCR stock solution for MIPs designed to contain the Taqman Assay Hb_pr1, or 1.25× Hb2 ddPCR stock solution for MIPs designed to contain the Taqman Assay Hb_pr2. The reaction mixtures were partitioned into 1 nL droplets using a ChipShop droplet generation system with a syringe pump system.

Droplet samples were transferred to thermocycler plates (3×30 µL aliquots per droplet sample), sealed with a foil seal, then thermocycled for about 1.25 h. Thermocycling began by holding the plates at 94° C. for 10 minutes, subsequently cycling the plates through 35 or 40 cycles of (94° C., 20 s/65° C., 60s), and finally cooling and holding the plates at 4° C. Thermocycled plates were stored at that temperature.

Leftover droplet aliquots were visualized under a Nikon light microscope to assess uniformity and proper size.

Thermocycled samples were placed on a QuantaLife Box 2 Alpha detector system, where droplet samples were automatically withdrawn from one well at-a-time, and passed single-file by a detector, which was used to assess both droplet size and fluorescence intensity from reacted FAM Taqman probes.

Droplets in each well of the appropriate size were scored as either positive or negative droplets, depending upon their fluorescence amplitude, and these distributions were used to compute the concentration of the assayed sample target according to Poisson statistics.

These data indicate that increasing numbers of positive droplets (or counts) is correlated with increasing input copies of template DNA. Here, Raji genomic DNA was used (derived from Raji cancer cells) for the experiments. For these experiments, 0 copies (or no template control "NTC") of input copies of DNA were used in the sample; 100 copies in the next set of three; 1000 copies in the next set of three; and for the last three, 10,000 copies were used. All MIP reactions were carried out with a MIP three-plex, using three different MIP probes, each directed to a different site on the test chromosome (which is Chromosome 21, also corresponding to hb_pr2). 10605 RFUs (relative fluorescent units) was used as the threshold between positive and negative droplets. Experiments are conducted in triplicate.

An identical experiment was conducted with a larger set of MIP probes. A MIP 12-plex was used, wherein each of 12 MIP probes is directed to a different region within chromosome 21. A roughly 4-fold greater number of positive droplets at a given input number (e.g., NTC, 100, 1000, 10000) of DNA template was achieved.

Similar results obtained when MIP probe pools are derived from probes to the reference polynucleotide (hb_pr1, or chromosome 1).

The hybridization efficiency is similar whether a thousand copies or 10,000 copies of template are present in the reaction, as evidenced by the 10-fold increase in counts when going from 1,000 to 10,000 copies of template. For a given number of copies of genomic DNA, the number of counts can be increased by increasing the degree of multiplexing of the MIP probes. MIP probes enable multiplexing across a given chromosome, providing a large number of counts from a small number of genomic equivalents, which can be important for differentiation of small copy number changes between a target and reference. Experiments as shown are conducted in triplicate.

Example 14 (Prophetic): Digesting Wild-Type DNA with a Restriction Enzyme

A tumor sample is obtained from a subject suspected of having melanoma. A health care provider seeks to determine the presence or absence of mutation that can result in encoding of BRAF V600E in the sample. It is suspected that the mutation, if present, is not an inherited mutation. DNA is extracted from the tumor sample. The DNA sample is contacted with a restriction enzyme to digest sequence that comprises wild type BRAF sequence, but not sequence encoding the V600E mutation. The nucleic acid sample is mixed with amplification reagents, including a probe comprising a fluorescer and a quencher, and the nucleic acid sample is separated into a plurality of emulsified droplets. The emulsified droplets are subjected to droplet digital PCR. From the droplet digital PCR, it is determined that the subject has a mutation that can result in encoding of BRAF V600E. The presence of the mutation suggests that the subject will not be responsive to panitumumab or cetuximab, and the subject is not provided these drugs. The presence of the mutation encoding V600E suggests that the subject will be responsive to Vemurafenib (PLX4032, RG7204, R05185426, Zelboraf), and the subject can be administered Vemurafenib.

Example 15 (Prophetic): Detecting Mutations by Digesting Wild-Type Sequence Using "Dark" Probes and Endonuclease A tumor sample is obtained from a subject suspected of having melanoma. A health care provider seeks to determine the presence or absence of a mutation that can result in encoding of BRAF V600E in the sample. It is suspected that the mutation, if present, is not an inherited mutation. DNA is extracted from the tumor sample. The DNA is mixed with two "dark" probes that have no label and comprise sequence complementary to each strand of sequence encoding BRAF V600E. The DNA is also mixed with a labeled probe with a 5' fluorescer and 3' quencher that comprises sequence complementary to sequence encoding BRAF V600E. The labeled probe also comprises locked nucleic acids. The sample is mixed with T7 endonuclease I, which can cleave both strands of a duplex with a mismatched sequence. The two dark probes anneal to either strand of the wildtype BRAF sequence and form a mismatch in the position of the sequence encoding the V600E amino acid. T7 endonuclease cleaves each strand of the duplexes of the wild-type sequence near the mismatches. Labeled probe that happens to anneal to the wild-type BRAF sequence is not cleaved, because although there is a mismatch, the T7 endonuclease I cannot cleave the locked nucleic acids. The sample can also be mixed with reagents for PCR amplification. The sample can be separated into a plurality of emulsified droplets, and the droplets can be subjected to droplet digital PCR. The labeled probe can be used to detect the presence of nucleic acids encoding BRAF V600E. From the droplet digital PCR, it is determined that the subject has a mutation that can result in encoding of BRAF V600E. The presence of the mutation suggests that the subject will not be responsive to panitumumab or cetuximab, and the subject is not provided these drugs. The presence of the mutation encoding V600E suggests that the subject will be responsive to Vemurafenib, and the subject can be administered Vemurafenib.

Example 16: Rare Allele Detection Using Droplet Digital PCR

This example demonstrates the ability of droplet digital PCR (ddPCR) to detect rare mutations that are present in a sample comprising a 100,000 fold excess of the wildtype allele (0.001% mutant fraction). By comparison, an optimized real time PCR assay can detect down to 1% mutant fraction.

Digital PCR amplification of the BRAF V600E mutation was performed at 0.001%, 0.005%, 0.01%, 0.1%, and 1% of BRAF V600E in a final assay concentration of wild type DNA background of about 5,000 copies per µL. The dilution series was made by combining DNA extracted from a mutant (HT-29 cell line; ATCC #HTB-38) and wildtype (Corielle #19205) cell line in the appropriate ratios. The HT-29 cell line is heterogeneous for the V600E mutation, and a ratio of 1/3 mutant to 2/3 wild type copies per genome was determined by ddPCR prior to performing the dilution series. The ratio of 3.3 pg/copy of genomic DNA was used to calculate the ratios of mutant to wild type DNA for the titration series. No template control and mutant cell line DNA samples were also analyzed.

Restriction endonuclease digestion of the titration series prior to ddPCR amplification were performed as a single digest with HaeIII (NE Biolabs), or as a double digest with both HaeIII and TspRI (NE Biolabs). The digests were performed in a 100 uL digest volume, using a final 1× concentration of NEBuffer 4, 1×BSA (NE Biolabs), at 37° C. for 1 hour. The purpose of the HaeIII digestion was to reduce the average size of the genomic DNA in the samples, which can reduce the viscosity of the samples and enable more uniform droplet formation at high DNA concentrations. The TspRI restriction enzyme specifically cleaves the wildtype BRAF allele, thus rendering it non-amplifiable.

The ddPCR work flow was performed according to the following steps. Assembled PCR reactions, each comprising template, ddPCR Mastermix and TaqMan reagents, are loaded into individual wells of a single-use injection molded cartridge. Next, droplet generation oil containing stabilizing surfactants is loaded and the cartridge placed into the droplet generator. By application of vacuum to the outlet wells, sample and oil are drawn through a flow-focusing junction where monodisperse droplets are generated at a rate of ~1,000 per second. The surfactant-stabilized droplets flow to a collection well where they quickly concentrate due to density differences between the oil and aqueous phases, forming a packed bed above the excess oil. The densely packed droplets are pipet transferred to a conventional 96-well PCR plate and thermal cycled to end-point. After thermal cycling, the plate is transferred to a droplet reader. Here, droplets from each well are aspirated and streamed toward the detector where, en route, the injection of a spacer fluid separates and aligns them for single-file simultaneous two-color detection. TaqMan assays provide specific duplexed detection of target and reference genes. All droplets are gated based on detector peak width to exclude rare outliers (e.g., doublets, triplets). Each droplet has an intrinsic fluorescence signal resulting from the imperfect quenching of the fluorogenic probes enabling detection of negative droplets. For droplets that contain template, specific cleavage of TaqMan probes generates a strong fluorescence signal. On the basis of fluorescence amplitude, a simple threshold assigns each droplet as positive or negative. As the droplet volume is known, the fraction of positive droplets is then used to calculate the absolute concentration of the target sequence. For 20,000 droplets, the dynamic range for absolute quantitation spans from a single copy up to ~100,000 copies. For human genomic DNA, this equates to an input DNA mass ranging from 3.3 fg to 330 ng per 20 μL reaction. As templates are randomly distributed across the droplet partitions, a Poisson correction extends the dynamic range into the realm where on average there are multiple copies per droplet. Statistical models are applied to calculate confidence limits of the concentration estimates and their ratios.

In this example, the BRAF V600E/wildtype duplex TaqMan assay used common primers and specific probes; the sequences of which are:

```
forward primer:
5'-CTACTGTTTTCCTTTACTTACTACACCTCAGA-3';

reverse primer:
5'-ATCCAGACAACTGTTCAAACTGATG-3';

BRAF V600E probe:
6FAM-TAGCTACAGAGAAATC-MGBNFQ;
and wildtype probe:
VIC-CTAGCTACAGTGAAATC-MGBNFQ.
```

The PCR reaction mix was prepared as 20 uL volumes per well, using QuantaLife's v1.1 mastermix and final assay concentrations of PCR primers at 900 nM and 250 nM probe, respectively. Eight droplet digital PCR (ddPCR) wells were used for each sample. The thermal cycling conditions were as follows: 1 cycle at 95° C. for 10 minutes; 55 cycles at 94° C. for 30 seconds and 62.7° C. for 60 seconds; and a temperature hold at 12° C.

Figure 23:
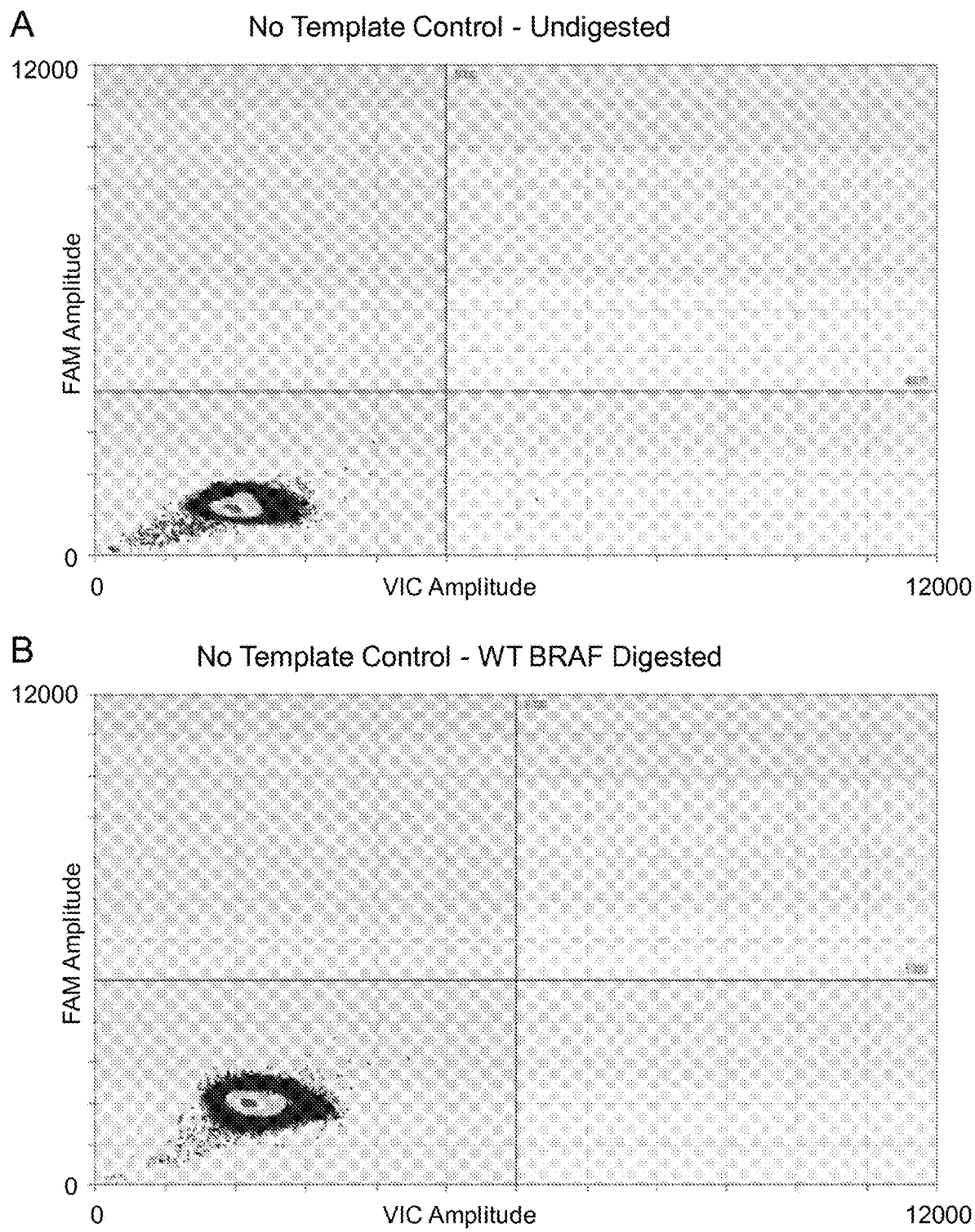
FIG. 23 (A&B) illustrates ddPCR detection of wildtype and BRAF V600E in a no template control sample digested with HaeIII (A) or HaeIII & TspRI (B).
Figure 25:
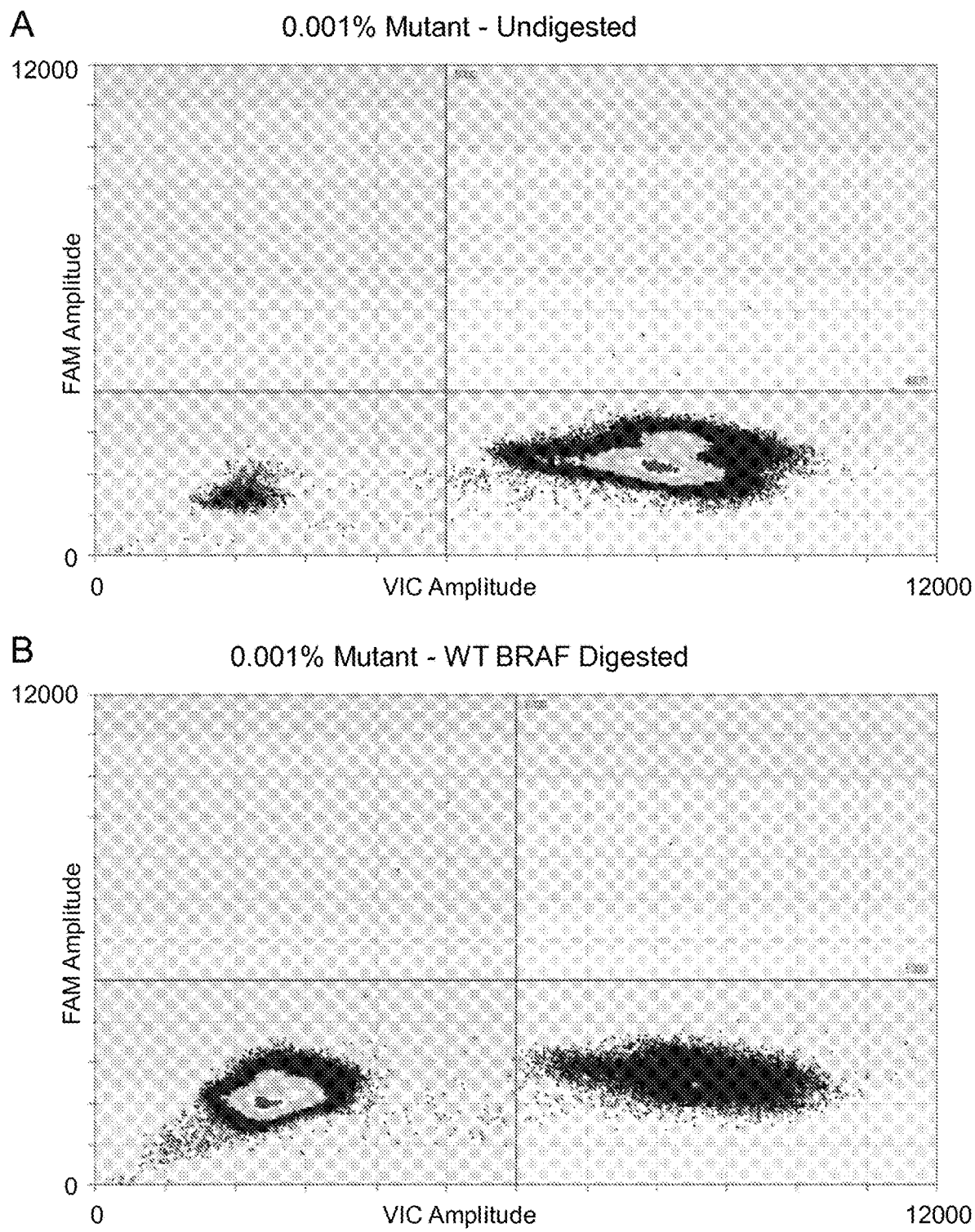
FIG. 25 (A&B) illustrates ddPCR detection of wildtype and BRAF V600E in a 0.001% BRAF V600E DNA sample digested with HaeIII (A) or HaeIII & TspRI (B).
Figure 27:
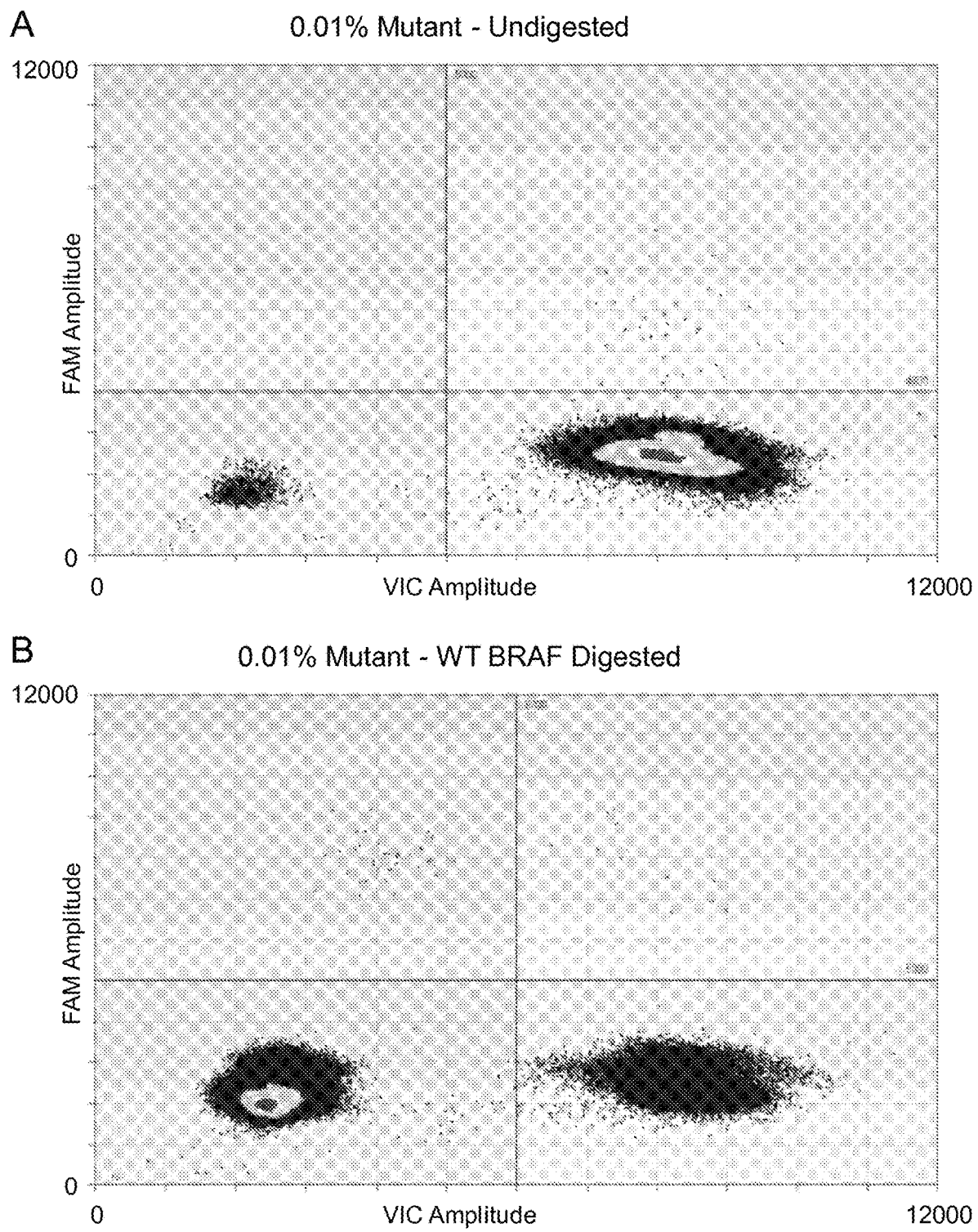
FIG. 27 (A&B) illustrates ddPCR detection of wildtype and BRAF V600E in a 0.01% BRAF V600E DNA sample digested with HaeIII (A) or HaeIII & TspRI (B).
Figure 28:
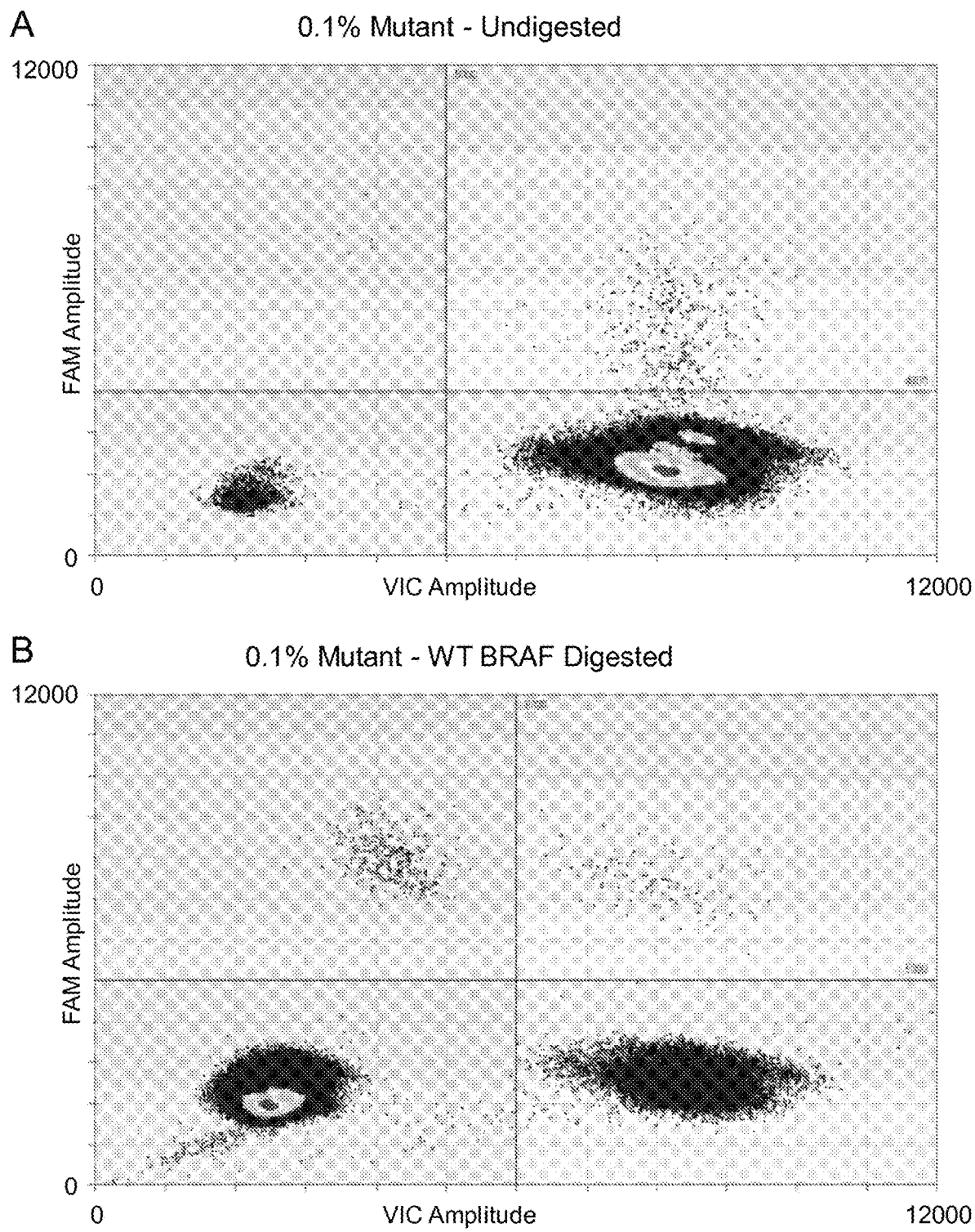
FIG. 28 (A&B) illustrates ddPCR detection of wildtype and BRAF V600E in a 0.1% BRAF V600E DNA sample digested with HaeIII (A) or HaeIII & TspRI (B).
Figure 29:
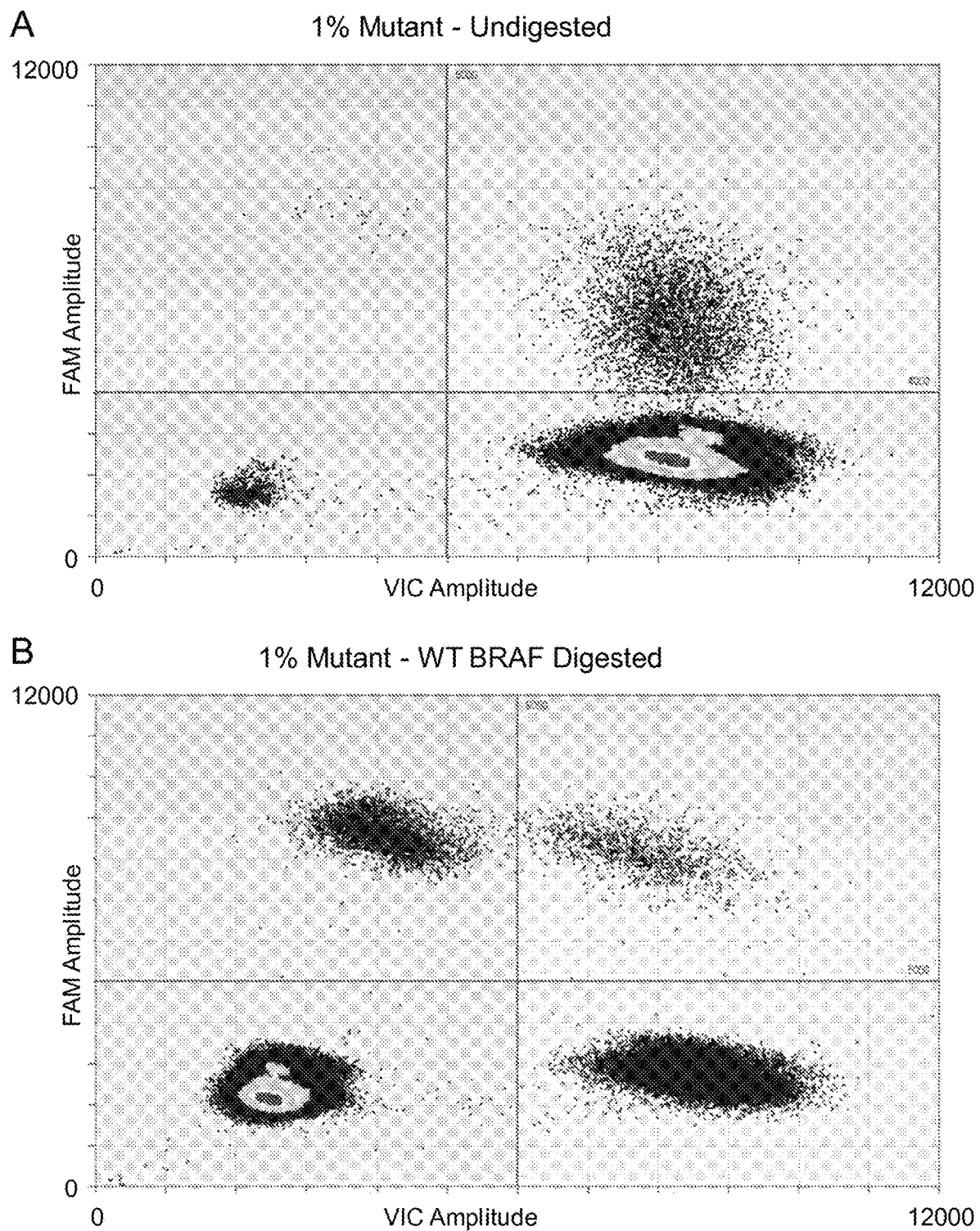
FIG. 29 (A&B) illustrates ddPCR detection of wildtype and BRAF V600E in a 1% BRAF V600E DNA sample digested with HaeIII (A) or HaeIII & TspRI (B).
Figure 30:
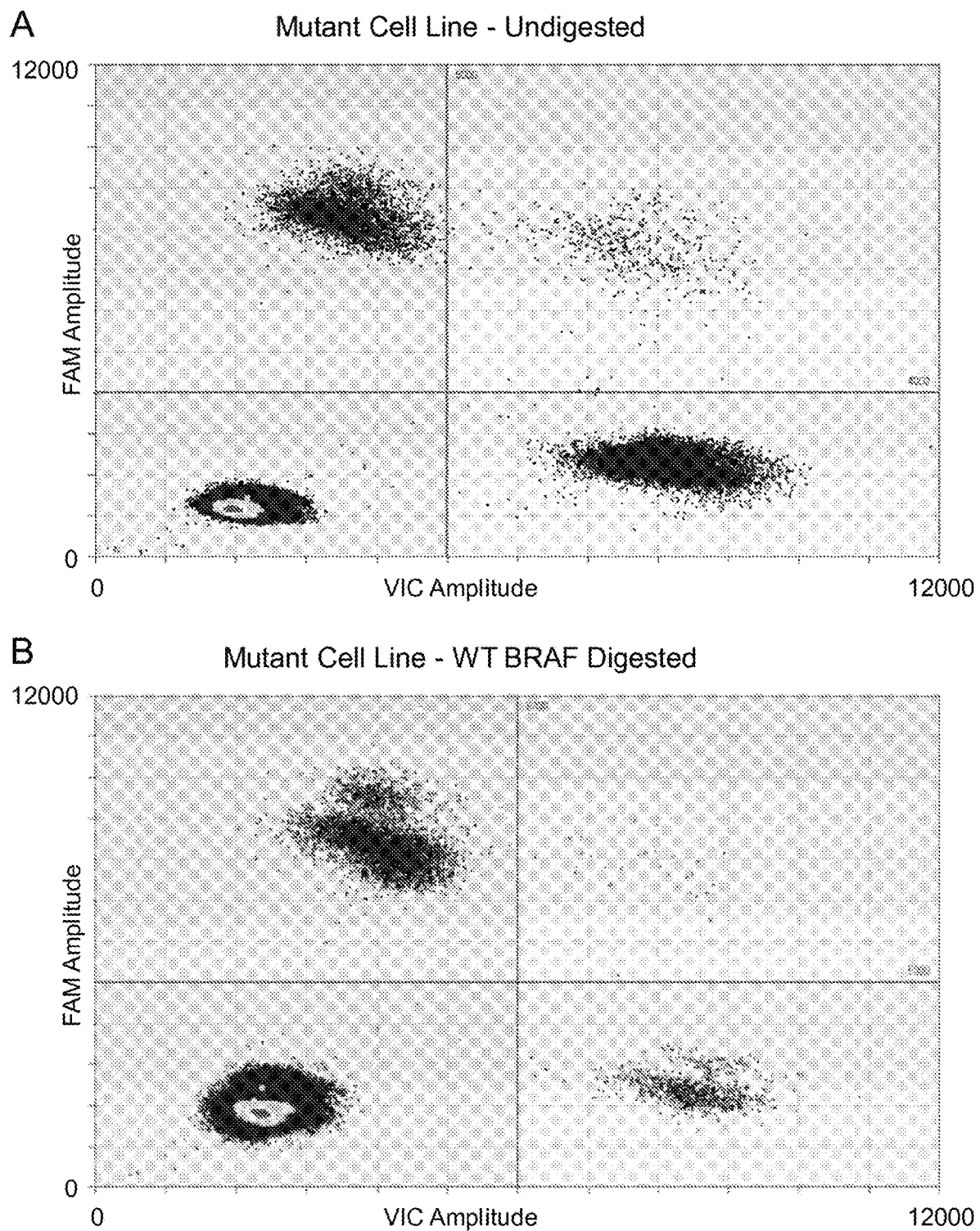
FIG. 30 (A&B) illustrates ddPCR detection of wildtype and BRAF V600E in a DNA sample obtained from a mutant cell line and digested with HaeIII (A) or HaeIII & TspRI (B).

The results for the individual dilutions are shown in FIG. 23 (no template control), FIG. 24 (0% mutant), FIG. 25 (0.001% mutant), FIG. 26 (0.005% mutant), FIG. 27 (0.01% mutant), FIG. 28 (0.1% mutant), FIG. 29 (1% mutant), FIG. 30 (mutant cell line), and summarized in the table found in FIG. 31. Each of the graphs in FIGS. 23-30 display the fluorescent intensity in the FAM (mutant) and VIC (wildtype) channels for the individual droplets analyzed. Each graph can be divided into four quadrants. The lower left hand quadrant represents droplets that contain neither wildtype nor mutant alleles of the BRAF gene. As expected, all of the droplets in the no template control sample are in the lower left quadrant (FIG. 23). The detectable signal in these droplets is most likely due to incomplete quenching in the probes. The lower right hand quadrant represents droplets that contain only wildtype alleles of the BRAF gene. As expected, the droplets in the 0% mutant samples are located in only the lower left and lower right quadrants (FIG. 24). The upper left quadrant represents droplets that contain only V600E alleles of the BRAF gene and the upper right quadrant represents droplets that contain both V600E and wildtype alleles of the BRAF gene. As expected, the number of droplets in the upper quadrants increases as the percentage of mutant DNA in the samples increases (FIGS. 25-30; summarized in FIG. 31). In each graph, with the exception of the no template control, digestion of the wildtype allele shifted the droplets from the right two quadrants to the left two quadrants, reflecting the decrease in the number of wildtype alleles in the samples. As can be appreciated from the data shown, specific removal of at least a portion of the wildtype alleles improves the separation of the wildtype and mutant signals and can make the resulting analysis easier.

Example 17: Quantitation of Cell-Free Fetal and Total DNA in Maternal Plasma

The ability of ddPCR to quantitate DNA in clinical samples was evaluated. Circulating DNA in cell-free plasma (Lo Y M et al. (1997) *Lancet* 350: 485-487) can be used as a sample for developing noninvasive prenatal (Wright CF (2009) *Hum. Reprod. Update* 15: 139-151) and oncology diagnostics (Pathak A K (2006) *Clin. Chem.* 56: 1833-1842). The cell-free DNA in plasma can be highly fragmented (Fan H C et al (2010) *Clin. Chem.* 56: 1279-1286) and present at low levels, which can present challenges for quantitation. We enumerated fetal and total DNA in maternal cell-free plasma. For 19 maternal plasma samples taken between 10 and 20 weeks gestational age, the level of fetal (FIG. 32) and total DNA (FIG. 33) were measured for both male and female fetuses. A selective methylation-sensitive digest enabled the low-levels of hypermethylated RASSF1 fetal DNA (Tong Y K et al. (2010) *Clin. Chem.*56: 90-98) to be accurately quantified using the ddPCR system. With an absolute measure of SRY, RASSF1, and total DNA concentrations, the fetal load for each sample was calculated (FIG. 34). For male fetuses, a correlation of 93.7% between the hypermethylated RASSF1 fetal DNA and SRY fetal loads provided confidence in the estimates for female fetuses. On the basis of RASSF1 alone, fetal loads ranged from 2.1 to 11.9% and were in general agreement with those data collected by next-generation sequencing (Fan et al. (2008) *PNAS* 105: 16266-16271) that is currently limited to estimating fetal loads from male fetuses. This application demonstrates the capability of absolute quantitation of highly fragmented cell-free DNA in clinical samples.

Figure 32:
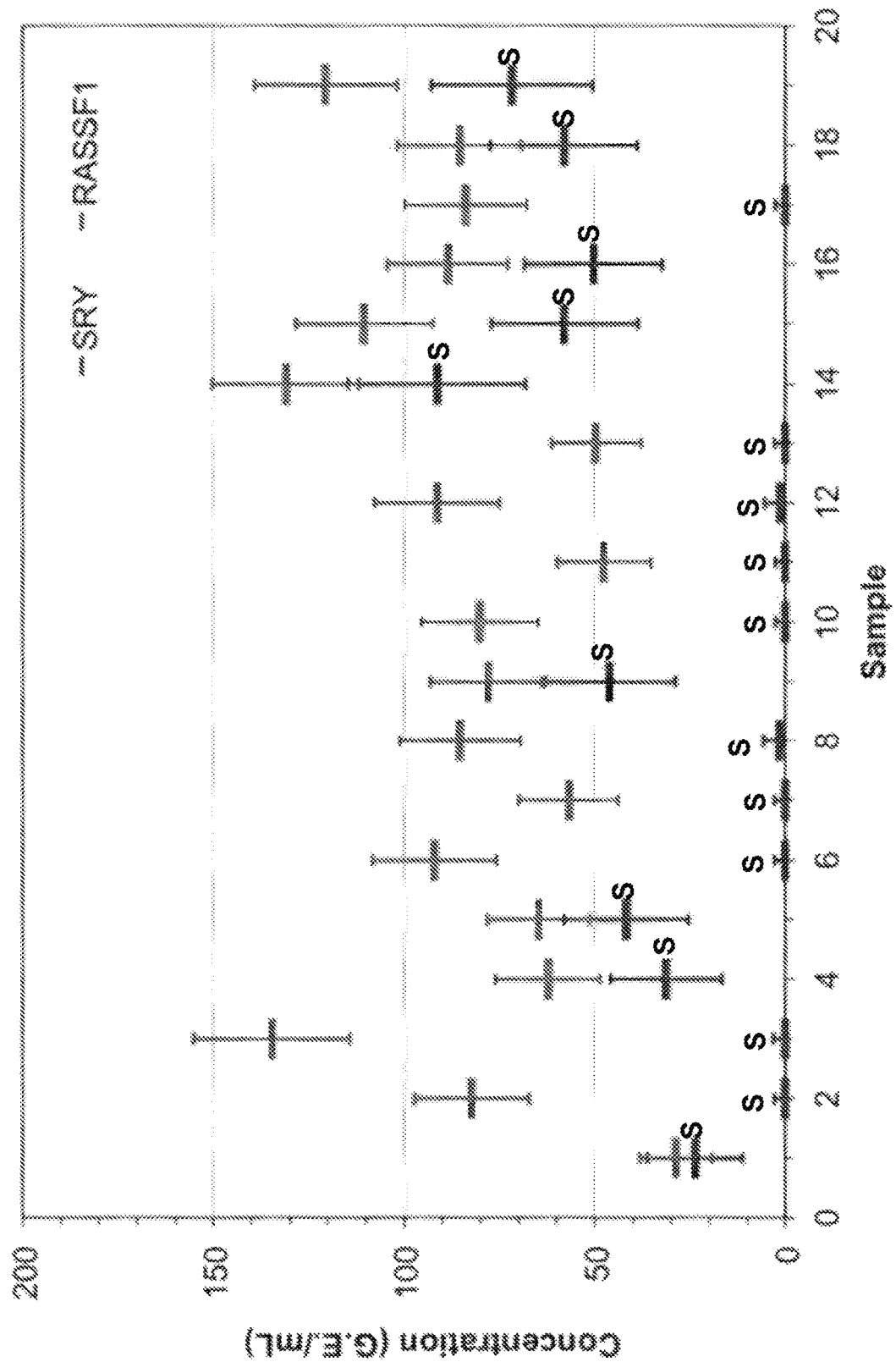
FIG. 32 illustrates levels of fetal DNA for 19 maternal plasma samples.
Figure 33:
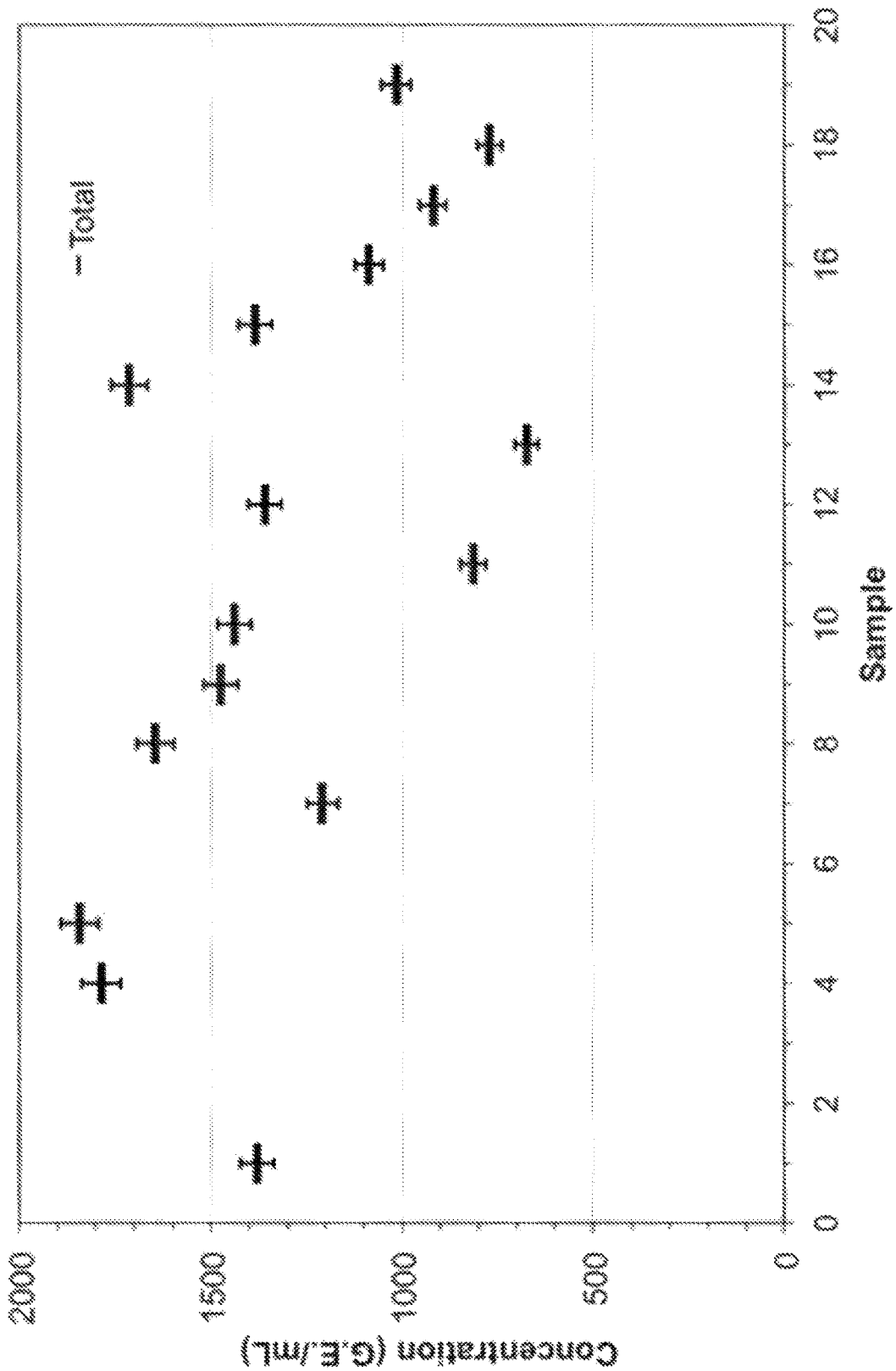
FIG. 33 illustrates levels of total DNA for 19 maternal plasma samples.
Figure 34:
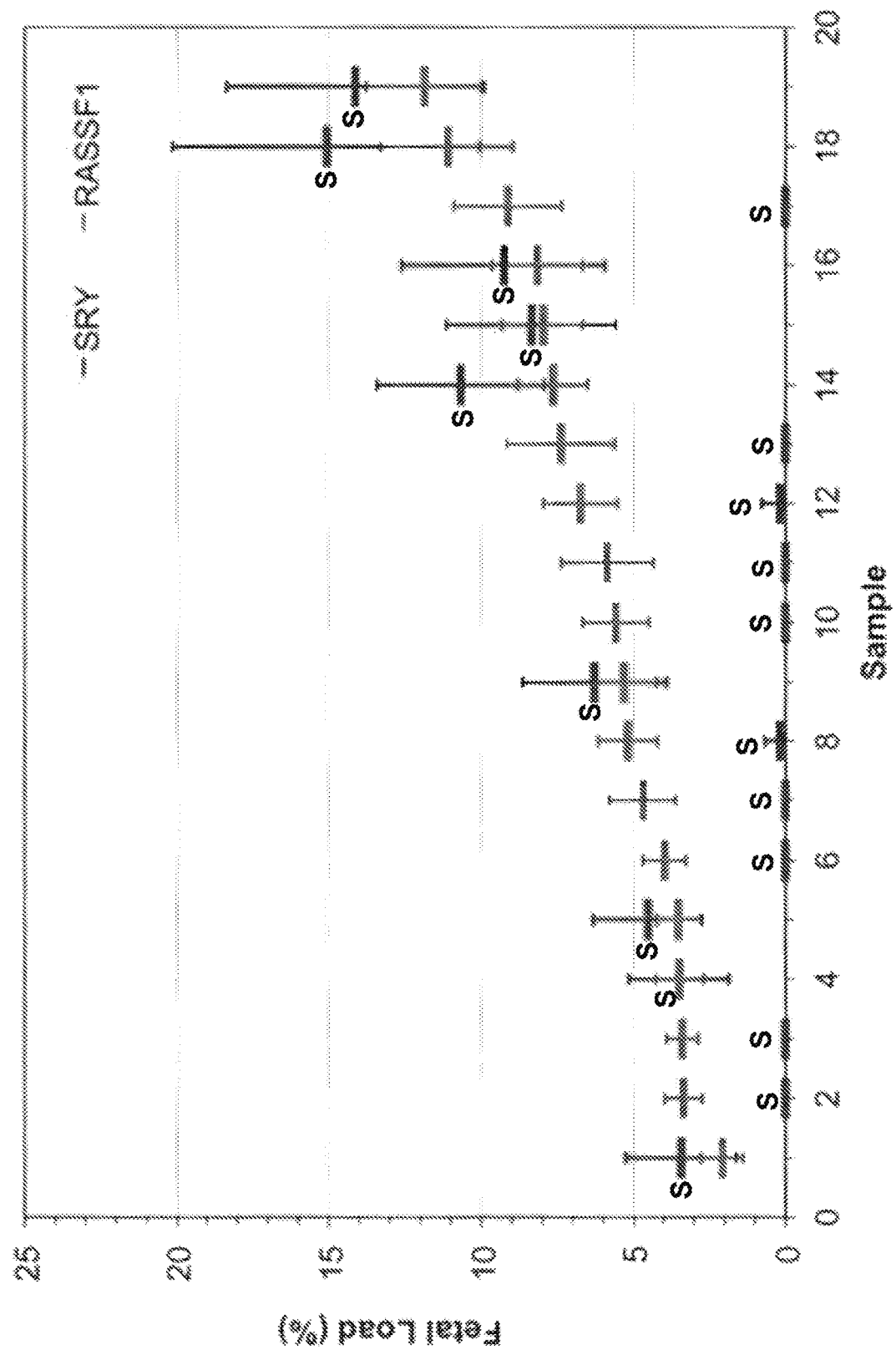
FIG. 34 illustrates fetal load calculations for 19 maternal plasma samples.

FIGS. 32-34 illustrate absolute quantitation of circulating fetal and maternal DNA from cell-free plasma for male and female fetuses. FIG. 32: Quantitation of fetal DNA concentration using SRY (bars labeled "S") and hypermethylated RASSF1 (unlabeled bars). The RASSF1 gene of circulating fetal DNA is hypermethylated whereas maternal DNA is hypomethylated. Methylation sensitive restriction enzymes selectively digested away the hypomethylated fraction, leaving the hypermethylated fetal DNA that was quantified. FIG. 33: Quantitation of total DNA concentration represented as the weighted average from six independent assay measurements including undigested RASSF1 and β-actin as well as RNaseP and TERT. FIG. 34: Fetal loads as determined from the ratio of SRY to total (male fetuses only) and RASSF1 to total (male and female fetuses). For male fetuses, the Pearson's correlation coefficient between SRY and RASSF1 fetal loads was 97.3%. SRY bars are labeled "S"; RASSF1 bars are unlabeled. Fetal DNA is not completely hypermethylated; therefore, the RASSF1 fetal loads measured for some samples are lower than those determined using SRY. Error bars represent the Poisson 95% confidence intervals of the concentration or the ratio in the case of fetal load estimates.

Materials and Methods

Whole blood (3×10 mL) was collected (ProMedDx) from healthy pregnant donors, between 10 and 20 weeks of gestational age, by venipuncture into cell-free DNA BCT tubes (Streck) according to the manufacturer's instructions. Fetus gender was determined by ultrasound within 6 weeks of sample collection. The tubes were stored for up to 48 h at room temperature then shipped overnight at 4° C. to Bio-Rad where they were processed upon receipt. The whole blood was centrifuged for 10 min at 1600 g, the supernatant removed and transferred to a new tube, centrifuged for 10 min at 16,000 g, the supernatant removed, and transferred to a new tube, then the cell-free plasma was stored at −80° C. Cell-free plasma (5 mL) was thawed and cell-free DNA isolated using the QIAmp Circulating Nucleic Acid Kit (Qiagen) according to the manufactuer's protocol and eluted in AVE buffer (150 μL). A portion of the eluate (99 μL) was subjected to a single-tube digest containing HhaI (30 U), HpaII (60 U), and BstUI (30 U) in 1×NEB buffer 4 in a total volume of 120 μL. A second portion of the eluate (33 μL) was used in a no-digest control mixture where restriction enzymes were substituted for water. The mixtures were incubated for 37° C. for 2 h, 60° C. for 2 h, then 65° C. for 20 min. The restriction enzyme digested mixture was split and subjected to three ddPCR duplexed assays of SRY/TERT, RASSF1/RNaseP, and RASSF1/β-actin. The restriction enzyme mixture cuts unmethylated RASSF1 and β-actin TaqMan templates but not SRY, RNaseP, or TERT. The no-digest control mixture was split and subjected to two ddPCR duplexed assays of RASSF1/RNaseP and RASSF1/β-actin. β-Actin is hypomethylated in both fetal and maternal DNA and is completely digested by the enzyme cocktail.

RASSF1 and SRY assays were reported previously (Tong et al. (2010) *Clin. Chem.* 56: 90-98; Fan et al. (2009) *Am. J. Obstet. Gynecol.* 200 (543): e541-547). RNaseP and TERT copy number reference assays were purchased commercially (Applied Biosystems). The β-actin assay was modified from Chan et al. (forward primer) 5'-GCAAAGGCGAGGCTCTGT-3', (reverse primer) 5'-CGTTCCGAAAGTTGCCTTTTATGG-3', and (probe) VIC-ACCGCCGAGACCGCGTC-MGBNFQ. For RASSF1/RNaseP and RASSF1/β-actin duplexes, 1× GC-Rich Solution (Roche) was used as a component of the assembled ddPCR reaction mixtures. Thermal cycling conditions were 95° C.×10 min (1 cycle), 95° C.×30 s and 60° C.×60 s (45 cycles), and 4° C. hold.

For each sample, six independent assay measurements of total DNA concentration (G.E/mL) were made from one TERT, one β-actin, two RASSF1, and two RNaseP assays. Each assay measurement comprised data from seven replicate ddPCR wells. The droplet counts were combined (positive and negative) from all seven replicate wells to yield a single "metawell". The concentration and confidence intervals for each of the 6 measurement metawells were computed (Dube S et al. (2008) *PLos One* 3: e2876). The appropriate dilution factors were applied to yield total cell-free DNA concentration (G.E./mL) and the confidence interval is scaled accordingly. The weighted mean of the six total measurements was calculated, where weights are inverses of confidence interval variances of these measurements. For digested RASSF1, there are two independent assay measurements, which are also combined in the same manner. For SRY, there is one measurement that was used directly, with scaling by a factor of 2 to account for haploidy. Fetal load is then computed as a ratio with the associated Poisson 95% confidence intervals. See Hindson et al. (2011) *Anal. Chem.*83: 8604-8610, While embodiments have been shown and described herein, it will be obvious to those skilled in the art that such embodiments are provided by way of example only. Numerous variations, changes, and substitutions will now occur to those skilled in the art without departing from the methods, compositions, and kits described herein. It should be understood that various alternatives to the embodiments of the methods, compositions, and kits described herein can be employed in practicing the methods, compositions, and kits. It is intended that the following claims define the scope of the methods, compositions, and kits and that methods and structures within the scope of these claims and their equivalents be covered thereby.

What is claimed is:

1. A method of detecting methylated DNA, comprising:
a) contacting a DNA sample comprising a major population and a minor population with a methylation-sensitive reagent;
b) partitioning said DNA sample into a plurality of spatially-isolated partitions;
detecting a first locus within said DNA sample, wherein said-first locus is c) hypermethylated in the minor population and wherein the first locus is selected from the group consisting of CASP8, RARB, SCGB3A1, DAB2IP, PTPN6, THY1, TMEFF2, and PYCARD; and
d) quantifying a first quantity of said first locus, thereby detecting methylated DNA.

2. The method of claim 1, further comprising detecting a second locus within said DNA sample, wherein said second locus is present in both the major population and the minor population and wherein said second locus is not significantly cleaved by said methylation-sensitive reagent.

3. The method of claim 1, further comprising detecting a third locus within said DNA sample, wherein said third locus is present in both the major population and the minor population and wherein said third locus is significantly cleaved by said methylation-sensitive reagent.

4. The method of claim 1, further comprising amplifying a sequence associated with said first locus to produce a detectable signal.

5. The method of claim 4, wherein said signal is a fluorescence signal.

6. A The method claim 1, further comprising:
e) detecting a second quantity of a second locus within said DNA sample; and
f) comparing said first and second quantities, to obtain a value indicative of a percentage of methylated DNA in the sample.

7. The method of claim 6, wherein said major population comprises maternal DNA and said minor population comprises fetal DNA.

8. The method of claim 6, wherein said second locus does not comprise a restriction site recognized by said methylation-sensitive reagent.

9. The method of claim 6, wherein said second locus is methylated in (a) the major population and (b) the minor population.

10. The method of claim 6, further comprising detecting a signal associated with a third locus within said DNA sample.

11. The method of claim 10, wherein said value indicative of the percentage of methylated DNA in said sample is adjusted by a value associated with the presence of said third locus within said DNA sample.

12. The method of claim 6, further comprising calculating the amount of total DNA in said sample.

13. The method of claim 6, wherein said detecting of said first and second quantities comprises an amplification reaction.

14. The method of claim 7, further comprising comparing said value indicative of the percentage of methylated DNA in said DNA sample with a value at an earlier gestational timepoint, thereby detecting a pregnancy-associated disorder.

15. The method of claim 6, wherein said value indicative of the percentage of methylated DNA in the sample is calculated using a detectable signal from at least a third locus within said DNA sample, wherein said third locus comprises a sequence that is not significantly cleaved by said methylation-sensitive reagent.

16. The method of claim 1, wherein said spatially-isolated partitions are wells.

17. The method of claim 6, wherein said spatially-isolated partitions are wells.

18. The method of claim 1, wherein said methylation-sensitive reagent is a methylation-sensitive enzyme.

* * * * *